United States Patent
Wu et al.

(10) Patent No.: US 10,435,723 B2
(45) Date of Patent: Oct. 8, 2019

(54) ADIPATE (ESTER OR THIOESTER) SYNTHESIS

(71) Applicant: Genomatica, Inc., San Diego, CA (US)

(72) Inventors: Liang Wu, Delft (NL); Axel Christoph Trefzer, Leidschendam (NL); Stefaan Marie Andre De Wildeman, Maasmechelen (BE); Marco Alexander Van Den Berg, Poeldijk (NL)

(73) Assignee: Genomatica, Inc., San Diego, CA (US)

( * ) Notice: Subject to any disclaimer, the term of this patent is extended or adjusted under 35 U.S.C. 154(b) by 0 days.

(21) Appl. No.: 15/140,384

(22) Filed: Apr. 27, 2016

(65) Prior Publication Data

US 2017/0073708 A1 Mar. 16, 2017

Related U.S. Application Data

(63) Continuation of application No. 14/082,000, filed on Nov. 15, 2013, now abandoned, which is a continuation of application No. 13/841,142, filed on Mar. 15, 2013, now abandoned, which is a continuation of application No. 13/572,346, filed on Aug. 10, 2012, now abandoned, which is a continuation of application No. 12/921,547, filed as application No. PCT/NL2009/050115 on Mar. 11, 2009, now Pat. No. 9,096,873.

(30) Foreign Application Priority Data

Mar. 11, 2008 (EP) ..................... 08152595

(51) Int. Cl.
C12P 7/44 (2006.01)
C12P 7/62 (2006.01)
C12P 17/10 (2006.01)
C12N 15/70 (2006.01)

(52) U.S. Cl.
CPC ............... *C12P 7/44* (2013.01); *C12N 15/70* (2013.01); *C12P 7/62* (2013.01); *C12P 17/10* (2013.01)

(58) Field of Classification Search
CPC .... C12P 7/44; C12P 17/10; C12P 7/62; C12N 15/70
See application file for complete search history.

(56) References Cited

U.S. PATENT DOCUMENTS

| | | |
|---|---|---|
| 5,487,987 A | 1/1996 | Frost et al. |
| 6,194,572 B1 | 2/2001 | Buijs et al. |
| 6,365,376 B1 | 4/2002 | Brzostowicz et al. |
| 6,372,939 B1 | 4/2002 | Bunel et al. |
| 7,799,545 B2 | 9/2010 | Burgard et al. |
| 8,062,871 B2 | 11/2011 | Burgard et al. |
| 8,216,814 B2 | 7/2012 | Burgard et al. |
| 2003/0087403 A1 | 5/2003 | Cheng et al. |
| 2007/0111294 A1 | 5/2007 | Burgard et al. |
| 2012/0264179 A1 | 10/2012 | Burgard et al. |

FOREIGN PATENT DOCUMENTS

| | | |
|---|---|---|
| CN | 1021815 C | 8/1993 |
| DE | 4322065 A1 | 1/1995 |
| EP | 0628535 A1 | 12/1994 |
| TW | I289473 B | 11/2007 |
| WO | WO 2004/106347 A1 | 12/2004 |
| WO | WO 2005/068643 A2 | 7/2005 |
| WO | WO 2008/000632 A1 | 1/2008 |
| WO | WO 2009/151728 A2 | 12/2009 |

OTHER PUBLICATIONS

Witkowski et al., Biochemistry 38:11643-11650, 1999.*
Tang et al., Phil Trans R Soc B 368:20120318, 1-10, 2013.*
Seffernick et al., J. Bacteriol. 183(8):2405-2410, 2001.*
Branden et al., Introduction to Protein Structure, Garland Publishing Inc., New York, p. 247, 1991.*
Sadowski et al., Current Opinion in Structural Biology 19:357-362, 2009.*
Becker et al., "Characterization of Wild-Type and an Active-site Mutant in *Escherichia coli* of Short-Chain Acyl-CoA Dehydrogenase from Megashaera Elsdenil," Database Uniprot:Q06319, pp. 1-2, Oct. 1, 1996.
Cao et al., "Bacterial Polypeptide #546," Database Uniprot:ADN17893, pp. 1-2, Dec. 2, 2004.
Donaldson et al., "Fermentative Production of four Carbon Alcohols," Database Uniprot:CS620067, p. 1, Jul. 2, 2007.
Fedorova et al., "Genomic Islands in the Pathogenic Filamentous Fungus *Aspergillus fumigatus*," Database Uniprot:A1C497, p. 1 Jul. 23, 2007.
Finocchiaro et al., "cDNA Cloning and Mitochondrial Import of the Beta-Subunit of the Human Electron-Transfer Flavoprotein," Database Uniprot:P38117, pp. 1-5, Jan. 23, 2007.
Fontaine et al., "Molecular Characterization and Transcriptional Analysis of AdhE2, the Gene Encoding the NADH-dependent Aldehyde/Alcohol Dehydrogenase Responsible for Butanol Production in Alcohologenic Cultures of Clostridium Acetobutylicum A TCC 824," Database Uniprot:Q9ANR5, pp. 1-2, Jun. 1, 2001.
Gerischer et al., "PcaU, a Transcriptional Activator of Genes for Protocatechuate Utilitation in Acinetobacter," Database Uniprot:Q937T0, pp. 1-3, Dec. 1, 2001.
Gerischer et al., "PcaU, a transcriptional activator of genes for protocatechuate utilization in Acinetobacter," GenBank accession No. Q937T0, Oct. 2006.

(Continued)

*Primary Examiner* — Delia M Ramirez
(74) *Attorney, Agent, or Firm* — Jones Day

(57) ABSTRACT

The present invention relates to a method for preparing an adipate ester or thioester. The invention further relates to a method for preparing adipic acid from said ester or thioester. Further the invention provides a number of methods for preparing an intermediate for said ester or thioester. Further the invention relates to a method for preparing 6-amino caproic acid (6-ACA), a method for preparing 5-formyl valeric acid (5-FVA), and a method for preparing caprolactam. Further, the invention relates to a host cell for use in a method according to the invention.

20 Claims, 4 Drawing Sheets

Specification includes a Sequence Listing.

(56) References Cited

OTHER PUBLICATIONS

Harris et al., "Engineering of Pencillium Chrysogenum for Fermentative Production of a Novel Carbamoylated Cephem Antiobiotic Precursor,"*Metabol. Eng.*, 11:125-137 (2009).
International Search Report for PCT/NL2009/050115, dated Oct. 2, 2009.
Kale, "From 5-Carboxy-2-Pentenoyl-CoA to (3s)-3-hydroxyadiphl-CoA," Database Uniprot p. 1, Oct. 2008.
Miinalainen et al., "Characterization of 2-enoyl thioester reductase from mammals. An ortholog of YBR026p/MRF1'p of the yeast mitochondrial fatty acid synthesis type II," *J. Biol. Chem.*, 278(22):20154-20161 (2003).
Nelson et al., "Complete Genome Sequence of the Oral Pathogenic Bacterium Porphyromonas Gingivalis Strain W83," Database Uniprot:Q7MWD5, p. 1, Dec. 15, 2003.
Seedorf et al., "The Genome of Clostridium Kluyveri, a Strict Anaeroble with Unique Metabolic Features," Database Uniprot:A5N735, p. 1, Jul. 10, 2007.
Seedorf et al., "The Genome of Clostridium Kluyveri, a Strict Anaerobe with Unique Metabolic Features," Database Uniprot: A5N8M5, pp. 1-2, Jul. 10, 2007.
Seedorf et al., "The Genome of Clostridium Kluyveri, a Strict Anaerobe with Unique Metabolic Features," Database Uniprot:A5N5C9 p. 1, Jul. 10, 2007.
Seffernick et al., "Melamine deaminase and atrazine chlorohydrolase: 98 percent identical but functionally different," *J. Bacteriol.*, 183(8):2405-2410 (2001).
Seshadri et al., "Genome Sequence of Aeromonas Hydrophila ATCC 7966T: jack of all trades," Database Uniprot:A0KL17, p. 1, Dec. 12, 2006.
Witkowski et al., "Conversion of a beta-ketoacyl synthase to a malonyl decarboxylase by replacement of the active-site cysteine with glutamine," *Biochem.*, 38:11643-11650 (1999).
Altschul et al., "Basic local alignment search tool," *J. Mol. Biol.*, 215:403-410 (1990).
Appel et al., "A P450 BM-3 mutant hydroxylates alkanes, cycloalkanes, arenes and heteroarenes," *J. Biotechnol.*, 88(2):167-171 (2001).
Ayorinde et al., "Syntheses of 12-Aminododecanoic and 11-Aminoundecanoic Acids from Vernolic Acid," *J. Am. Oin Chem. Soc.*, 74:531-538 (1997).
Balzer et al., "KorB protein of promiscuous plasmid RP4 recognizes inverted sequence repetitions in regions essential for conjugative plasmid transfer," *Nucleic Acids Res.*, 20(8):1851-1858 (1992).
Becker et al., "Characterization of wild-type and an active-site mutant in *Escherichia coli* of short-chain acyl-CoA dehydrogenase from Megasphaera elsdenii," *Biochemistry*, 32(40):10736-10742 (1993).
Becker et al., "Three-dimensional structure of butyryl-CoA dehydrogenase from Megasphaera elsdenii," Database Uniprot: Q06319, pp. 1-2, Oct. 31, 2014.
Birren et al., "Annotation of the Aspergillus terreus NIH2624 genome," Database Uniprot:Q0C7P0, Oct. 17, 2006.
Birren et al., "Annotation of the Aspergillus terreus NIH2624 genome," Database Uniprot:Q0CP00, Oct. 17, 2006.
Coleman et al., "Cloning of the debranching-enzyme gene from Thermoanaerobium brockii into *Escherichia coli* and Bacillus subtilis," *J. Bacteriol.*, 169(9):4302-4307 (1987).
Copeland et al., "Complete sequence of Clostridium beijerinckii NCIMB 8052," Database Uniprot: A6LV73, pp. 1-6, Oct. 31, 2014.
Daeschner et al., "Purification, characterization and cloning of isovaleryl-CoA dehydrogenase from higher plant mitochondria," Database Uniprot: Q9SWG0, pp. 1-2, Oct. 31, 2014.
Das et al., "Molecular cloning and expression of mammalian peroxisomal trans-2-enoyl-coenzyme A reductase cDNAs," *J. Biol. Chem.*, 275(32):24333-24340 (2000).
Dujon et al., "Genome evolution in yeasts," Database Uniprot: Q6CBE4, pp. 1-7, Oct. 31, 2014.
Elvidge et al., "Polyene acids. Part VII. Half methyl esters and amides of the muconic acids," *J. Chem. Soc.*, 1793-1799 (1953).
Emanuelsson et al., "Locating proteins in the cell using TargetP, SignalP and related tools," *Nat. Protoc.*, 2(4):953-971 (2007).
Finocchiaro et al., "cDNA cloning and mitochondrial import of the beta-subunit of the human electron-transfer flavoprotein," *Eur. J Biochem.*, 213(3):1003-1008 (1993).
Finocchiaro et al., "cDNA cloning and mitochondrial import of the beta-subunit of the human electron-transfer flavoprotein," Database Uniprot: P38117, pp. 1-3, Oct. 31, 2014.
Finocchiaro et al., "Molecular cloning and nucleotide sequence of cDNAs encoding the alpha-subunit of human electron transfer flavoprotein," Database Uniprot: P13804, pp. 1-16, Oct. 31, 2014.
Fontaine et al., "Molecular Characterization and Transcriptional Analysis of adhE2, the Gene Encoding the NADH-Dependent Aldehyde/Alcohol Dehydrogenase Responsible for Butanol Production in Alcohologenic Cultures of Clostridium acetobutylicum ATCC 824," *J. Bacteriol.*, 184(3):821-830 (2002).
Furste et al., "Molecular cloning of the plasmid RP4 primase region in a multi-host-range tacP expression vector," *Gene*, 48(1):119-131 (1986).
GenBank Accession No. KZN94317.1, "Acyl-coenzyme A thioesterase [Penicillium chiysogenum]" URL: https://www.ncbi.nlm.nih.gov/protein/KZN94317.1 (Apr. 22, 2016).
GenBank Accession No. WP_048769853.1, "aldehyde dehydrogenase EutE [Propionibacterium freudenreichii]" URL: https://www.ncbi.nlm.nih.gov/protein/WP_048769853.1 (May 13, 2017).
GenBank Accession No. XP_002557199.1, "Pc12g03130 [Penicillium rubens Wisconsin 54-1255]" URL: https://www.ncbi.nlm.nih.gov/protein/XP_002557199.1 (Aug. 14, 2009).
GenBank Accession No. XP_002558313.1, "Pc12g15100 [Penicillium rubens Wisconsin 54/1255]" URL: https://www.ncbi.nlm.nih.gov/protein/XP_002558313.1 (Aug. 14, 2009).
GenBank Accession No. XP_002560053.1, "Pc14g00590 [Penicillium rubens Wisconsin 54/1255]" URL: https://www.ncbi.nlm.nih.gov/protein/XP_002560053.1 (Aug. 14, 2009).
GenBank Accession No. XP_002560061.1, "Pc14g00670 [Penicillium rubens Wisconsin 54/1255]" URL: https://www.ncbi.nlm.nih.gov/protein/XP_002560061.1 (Aug. 14, 2009).
GenBank Accession No. XP_002564753.1, "Pc22g07280 [Penicillium rubens Wisconsin 54/1255]" URL: https://www.ncbi.nlm.nih.gov/protein/XP_002564753.1 (Aug. 14, 2009).
GenBank Accession No. XP_002565728.1, "Pc22g18230 [Penicillium rubens Wisconsin 54/1255]" URL: https://www.ncbi.nlm.nih.gov/protein/XP_002565728.1 (Aug. 14, 2009).
Goodman et al., "Pork and human cDNAs encoding glutaryl-CoA dehydrogenase," Database Uniprot: Q92947, pp. 1-3, Oct. 31, 2014.
Guest et al "Enzymological and physiological consequences of restructuring the lipoyl domain content of the pyruvate dehydrogenase complex of *Escherichia coli*,"*Microbiology*, 143:457-466 (1997).
Hartnett et al., "DNA sequences of genes encoding Acinetobacter calcoaceticus protocatechuate 3,4-dioxygenase: evidence indicating shuffling of genes and of DNA sequences within genes during their evolutionary divergence," Database Uniprot: Q937T0, pp. 1-8, Oct. 2, 2014.
Haygood et al., "Peroxisomal trans-2-enoyl-CoA reductase," Database Uniprot: A1ZFB1, pp. 1-5, Nov. 3, 2014.
Hoffmeister et al., "Mitochondrial trans-2-enoyl-CoA reductase of wax ester fermentation from Euglena gracilis defines a new family of enzymes involved in lipid synthesis," Database Uniprot: Q5EU90, pp. 1-6, Oct. 31, 2014.
Jantama et al., "Combining Metabolic Engineering and Metabolic Evolution to Develop Nonrecombinant Strains of *Escherichia coli* C That Produce Succinate and Malate," *Biotech. Bioeng.*, 99(5):1140-1153 (2007).
Kippenberger et al., "Determination of higher carboxylic acids in snow samples using solid-phase extraction and LC/MS-TOF," *Anal. Bioanal. Chem.*, 392(7-8):1459-1470 (2008).
Lehrbach et al., "Enzyme recruitment in vitro: use of cloned genes to extend the range of haloaromatics degraded by *Pseudomonas* sp. strain B13," *J. Bacteriol.*, 158:1025-1032 (1984).
Liu et al., "Synthesis of a new conformation-constrained L-tyrosine analogue as a potential scaffold for SH2 domain ligands," *J. Org. Chem.*, 68(17):6679-6684 (2003).

(56) References Cited

OTHER PUBLICATIONS

Nelson et al., "Complete genome sequence of the oral pathogenic Bacterium porphyromonas gingivalis strain W83," *J. Bacteriol.*, 185(18):5591-5601 (2003).

Nolling et al., "Genome sequence and comparative analysis of the solvent-producing bacterium Clostridium acetobutylicum," *J. Bacteriol.*, 183(16):4823-4838 (2001).

Oku et. al., "Biosynthesis of branched-chain fatty acid in bacilli: FabD (malonyl-CoA:ACP transacylase) is not essential for in vitro biosynthesis of branched-chain fatty acids," *Biosci. Biotechnol. Biochem.*, 67(10):2106-2114 (2003).

Pel et al., "Genome sequencing and analysis of the versatile cell factory Aspergillus niger CBS 513.88," Database Uniprot:A2R2J8, Mar. 6, 2007.

Pel et al., "Genome sequencing and analysis of the versatile cell factory Aspergillus niger CBS 513.88," Database Uniprot:A2RB23, Mar. 6, 2007.

Peters et al., "Regio- and enantioselective alkane hydroxylation with engineered cytochromes P450 BM-3,"*J. Am. Chem. Soc.*, 125(44):13442-13450 (2003).

Rahman et al., "Enzymatic synthesis of methyl adipate ester using lipase from Candida rugosa immobilised on Mg, Zn and Ni of layered double hydroxides (LDHs)," *J. Mol. Catalys. B Enzym.*, 50:33-39 (2008).

Reeves et al., "Alteration of the substrate specificity of a modular polyketide synthase acyltransferase domain through site-specific mutations," *Biochemistry*, 40(51):15464-15470 (2001).

Seedorf et al., "he genome of Clostridium kluyveri, a strict anaerobe with unique metabolic features," Database Uniprot: A5N5D0, pp. 1-6, Oct. 31, 2014.

Seedorf et al., "The genome of Clostridium kluyveri, a strict anaerobe with unique metabolic features," *Proc. Natl. Acad. Sci. USA*, 105(6):2128-2133 (2008).

Seedorf et al., "The genome of Clostridium kluyveri, a strict anaerobe with unique metabolic features," Database Uniprot: A5N5C9, pp. 1-6, Oct. 31, 2014.

Seshadri et al., "Genome sequence of Aeromonas hydrophila ATCC 7966T: jack of all trades," Database Uniprot: A0KL17, pp. 1-6, Oct. 31, 2014.

Shiba et al., "Engineering of the pyruvate dehydrogenase bypass in *Saccharomyces cerevisiae* for high-level production of isoprenoids," *Metabol. Eng.*, 160-168 (2007).

Sohling et al., "Molecular Analysis of the Anaerobic Succinate Degradation Pathway in Clostridium kluyveri," *J. Bacteriol.*, 178(3):871-880 (1996).

Song et al., "Production of succinic acid by bacterial fermentation," *Enzym. Microbial Tech.*, 352:361 (2006).

Stern et al., "Enzymes of fatty acid metabolism. II. Properties of crystalline crotonase," *J. Biol. Chem.*, 218(2):985-1002 (1956).

Torkko et al., "Candida tropicalis Etrlp and *Saccharomyces cerevisiae* Ybr026p (Mrfl'p), 2-enoyl thioester reductases essential for mitochondrial respiratory competence," Database Uniprot: Q8WZM3, pp. 1-6, Nov. 3, 2014.

White et al., "Genome sequence of the radioresistant bacterium Deinococcus radiodurans R1," Database Uniprot: Q9RVV0, pp. 1-8, Oct. 2, 2014.

Smith et al., "The type I fatty acid and polyketide synthases: a tale of two megasynthases," *Nat. Prod. Rep.*, 24:1041-1072 (2007).

* cited by examiner

SEQUENCE LISTING

```
<160> NUMBER OF SEQ ID NOS: 148

<210> SEQ ID NO 1
<211> LENGTH: 419
<212> TYPE: PRT
<213> ORGANISM: Penicillium chrysogenum

<400> SEQUENCE: 1

Met Ser Asn Ala Gln Gln Arg Leu Ser Gln Val Ser His Phe Gly
1               5                   10                  15

Pro Gly Gly Lys Lys Gly Ala Ala Ile Thr Glu Lys His Pro Asp
                20                  25                  30

Asp Ile Val Val Thr Cys Ala Leu Arg Thr Ala Leu Thr Lys Gly Gly
                35                  40                  45

Lys Gly Gly Phe Lys Asp Thr Ala Gly Ala Asp Leu Leu Ala Gly Val
    50                  55                  60

Phe Lys Ala Val Leu Asn Lys Ser Gly Val Asp Pro Ser Ser Val Gln
65                  70                  75                  80

Asp Ile Ala Val Gly Ser Val Leu Ala Pro Gly Gly Gly Ala Thr Glu
                85                  90                  95

Phe Arg Ala Ala Ala Leu Val Ala Gly Phe Pro Glu Ser Thr Ala Val
                100                 105                 110

Lys Ser Leu Asn Arg Gln Cys Ser Ser Gly Leu Gln Ala Ile Ala Asp
                115                 120                 125

Ile Ala Asn Ala Ile Gln Ser Gly Met Ile Asp Val Gly Ile Gly Ala
                130                 135                 140

Gly Val Glu Ser Met Ser Ser Gln Tyr Gly Pro Gly Ala Val Thr Glu
145                 150                 155                 160

Phe Ser Asp Leu Leu Glu Ser His Pro Glu Ser Ala Asn Cys Lys Val
                165                 170                 175

Pro Met Gly Val Leu Ser Glu Asn Met Ala Lys Asp Arg Gly Val Thr
                180                 185                 190

Arg Ala Ser Gln Asp Ser Phe Ala Ala Gln Ser Tyr Gln Lys Ala Val
                195                 200                 205

Ala Ala Gln Lys Ala Gly Leu Phe Asn Glu Glu Ile Ala Pro Leu Asp
                210                 215                 220

Val Lys Trp Thr Asp Pro Lys Thr Gly Glu Glu Lys Thr Ile Thr Val
225                 230                 235                 240

Lys Ala Asp Asp Gly Val Arg Gln Gly Ile Thr Ala Glu Ser Leu Gly
```

```
                    245                 250                 255
Lys Ile Lys Pro Ala Phe Ala Lys Asp Gly Ser Ile His Ala Gly Asn
            260                 265                 270

Ala Ser Gln Ile Ser Asp Gly Ala Ala Val Leu Leu Met Lys Arg
    275                 280                 285

Ser Thr Ala Glu Arg Leu Gly Gln Lys Ile Leu Gly Lys Tyr Val Thr
    290                 295                 300

Ala Ser Val Val Gly Val Lys Pro Leu Leu Met Gly Val Gly Pro Trp
305                 310                 315                 320

Lys Ala Ile Pro Val Ala Leu Glu Lys Ala Gly Ile Thr Lys Asp Asp
                325                 330                 335

Val Asp Ile Tyr Glu Ile Asn Glu Ala Phe Ala Ser Gln Cys Val Trp
                340                 345                 350

Cys Val Asn Glu Leu Gly Ile Pro Ala Glu Lys Val Asn Pro Lys Gly
            355                 360                 365

Gly Ala Ile Ala Phe Gly His Pro Leu Gly Cys Thr Gly Ala Arg Gln
    370                 375                 380

Val Ser Thr Leu Phe Thr Glu Leu Lys Arg Thr Asn Lys Lys Ile Gly
385                 390                 395                 400

Val Thr Ser Met Cys Val Gly Thr Gly Met Gly Met Ala Ala Val Trp
                405                 410                 415

Val Ser Glu

<210> SEQ ID NO 2
<211> LENGTH: 418
<212> TYPE: PRT
<213> ORGANISM: Penicillium chrysogenum

<400> SEQUENCE: 2

Met Ser Ser Pro Gln Arg Leu Asn Ser Val Ala Asn Gln Leu Ala
1               5                   10                  15

Pro Gly Ser Ala Arg Gln Lys Ile Leu Ala Lys Asn Pro Asp Asp Val
            20                  25                  30

Val Ile Thr Tyr Leu Ala Arg Thr Pro Leu Thr Lys Ala Arg Lys Gly
        35                  40                  45

Gly Leu Lys Asp Thr Thr Val Asp Asp Leu Leu Ile Ser Leu Leu Thr
    50                  55                  60

Thr Val Arg Glu Lys Ser Asn Leu Asp Pro Asn Leu Val Glu Asp Val
65                  70                  75                  80

Cys Val Gly Asn Val Leu Cys Pro Gly Ser Ala Tyr Val Ala Arg Ser
                85                  90                  95

Ala Val Leu Ala Ala Gly Tyr Pro Val Thr Ala Ala Ser Ile Ala
            100                 105                 110

Asn Arg Phe Cys Ser Ser Gly Leu Leu Ala Val Gln Asn Ile Ala Asn
        115                 120                 125

Gln Ile Ile Ala Gly Ser Ile Asp Val Gly Val Ala Val Gly Ala Glu
    130                 135                 140

Ser Met Ser Lys Asn Ala Asp Gly Gly Ala Pro Glu Met Ser Glu Arg
145                 150                 155                 160

Ile Thr Lys His Pro Ile Ala Ser Gln Asn Ser Gln Pro Met Gly Gln
                165                 170                 175

Thr Ser Glu Asn Val Ala Asn Gln Phe Asn Ile Ser Arg Glu Gln His
            180                 185                 190

Asp Arg Phe Ala Ala Asn Ser Phe Gln Lys Ala Glu Arg Ala Gln Lys
```

```
                195                 200                 205
Ala Gly Trp Leu Glu Asp Glu Ile Val Pro Val Arg Thr Gln Ile Lys
210                 215                 220
Asp Pro Lys Thr Gly Glu Val Lys Asp Ile Val Val Arg Asp Asp
225                 230                 235                 240
Gly Ile Arg Tyr Gly Thr Thr Pro Glu Ser Leu Gly Lys Val Arg Ala
            245                 250                 255
Ala Phe Pro Gln Trp Ala Pro Ser Ala Thr Thr Gly Gly Asn Ala Ser
            260                 265                 270
Gln Ile Thr Asp Gly Ala Ala Ala Leu Val Leu Met Lys Arg Ser Arg
            275                 280                 285
Ala Gln Gln Leu Gly Gln Pro Ile Val Ala Lys Phe Cys Gly Ala Thr
290                 295                 300
Val Ser Gly Leu Glu Pro Arg Ile Met Gly Ile Gly Pro Ser Leu Ala
305                 310                 315                 320
Ile Pro Lys Ile Leu Ser Lys Phe Asn Leu Ser Lys Asp Asp Ile Asp
            325                 330                 335
Ile Phe Glu Ile Asn Glu Ala Phe Ser Ser Met Gly Val Tyr Cys Val
            340                 345                 350
Asn Lys Leu Gly Leu Asp Glu Ser Lys Val Asn Pro Arg Gly Gly Ala
            355                 360                 365
Ile Ala Phe Gly His Pro Leu Gly Ala Thr Gly Ala Arg Gln Val Val
370                 375                 380
Thr Ala Leu Ser Glu Leu Arg Arg Gln Asp Lys Arg Val Ala Val Thr
385                 390                 395                 400
Ser Met Cys Val Gly Thr Gly Met Gly Met Ala Gly Ile Phe Val Ser
                405                 410                 415
Glu His

<210> SEQ ID NO 3
<211> LENGTH: 418
<212> TYPE: PRT
<213> ORGANISM: Penicillium chrysogenum

<400> SEQUENCE: 3

Met Ala Ala Asp Arg Leu Ser Ser Leu Leu Ser His Leu Lys Pro Gly
1               5                   10                  15
Ala Thr Asn Gly Leu Ala Ala Ile Thr Gln Lys Asn Pro Asp Asp Val
            20                  25                  30
Val Ile Thr Leu Ala Ile Arg Thr Pro Leu Thr Lys Ala Arg Lys Gly
        35                  40                  45
Gly Phe Lys Asp Thr Glu Leu Asp Tyr Met Ile Tyr Ala Leu Leu Lys
    50                  55                  60
Glu Thr Leu Ala Lys Ser Gln Ile Asp Pro Ala Leu Ile Glu Asp Val
65                  70                  75                  80
Cys Leu Gly Asn Val Asn Glu Val Lys Ala Ala Tyr Met Val Arg Ala
                85                  90                  95
Ala Ala Leu Ala Ala Gly Ile Pro His Thr Ala Gly Ala Ser Ser Val
            100                 105                 110
Asn Arg Phe Cys Ser Ser Gly Leu Lys Ala Val Gln Asp Ile Ala Asn
            115                 120                 125
Gln Ile Gln Leu Gly Ala Ile Asp Val Gly Val Ala Leu Gly Ala Glu
        130                 135                 140
Leu Met Ser Ala Ser Gly Asp Arg Leu Asp Arg Pro Phe Asn Glu Glu
```

```
145                 150                 155                 160
Val Leu Arg Asn Gln Glu Ala Ala Asp Cys Met Gln Pro Met Gly Gln
                165                 170                 175

Thr Ser Glu Asn Val Gly Lys Asp Phe Asp Ile Pro Arg Glu Gln Gln
            180                 185                 190

Asp Arg Tyr Ala Ala Glu Ser Phe Arg Arg Ala Glu Ala Ala Gln Asn
        195                 200                 205

Asn Gly Trp Leu Asp Asp Glu Ile Ala Pro Ile Ala Val Lys Val Lys
    210                 215                 220

Asp Pro Lys Thr Gly Glu Val Lys Glu Val Thr Leu Ser Arg Asp Asp
225                 230                 235                 240

Gly Ile Arg Pro Gly Thr Thr Phe Glu Ser Leu Ser Lys Ile Arg Pro
                245                 250                 255

Ala Phe Pro Gln Phe Gly Asp Lys Ser Thr Gly Gly Asn Ser Ser Gln
            260                 265                 270

Val Thr Asp Gly Ala Ala Ser Val Leu Leu Met Arg Arg Ser Lys Ala
        275                 280                 285

Ile Glu Leu Asn Gln Pro Ile Leu Ala Lys Phe Cys Gly Ala Thr Val
    290                 295                 300

Ala Gly Val Pro Pro Arg Val Met Gly Ile Gly Pro Thr Ala Ala Ile
305                 310                 315                 320

Pro Lys Leu Leu Ser Lys Phe Gln Leu Asp Lys Asn Asp Ile Asp Ile
                325                 330                 335

Tyr Glu Ile Asn Glu Ala Phe Ala Ser Met Ala Val Tyr Cys Val Lys
            340                 345                 350

Asn Leu Gly Leu Asp His Ala Lys Val Asn Pro Arg Gly Gly Ala Ile
        355                 360                 365

Ala Leu Gly His Pro Leu Gly Ala Thr Gly Ala Arg Gln Ile Ala Thr
    370                 375                 380

Ile Leu Ser Glu Ala Arg Arg Thr Lys Ser Lys Ile Leu Val Thr Ser
385                 390                 395                 400

Met Cys Ile Gly Thr Gly Gln Gly Met Ala Gly Leu Phe Val Asn Glu
                405                 410                 415

Gln Leu

<210> SEQ ID NO 4
<211> LENGTH: 413
<212> TYPE: PRT
<213> ORGANISM: Penicillium chrysogenum

<400> SEQUENCE: 4

Met Ala Ser Pro Ile Pro Arg Gly Leu Arg Gln Val Leu Gln Lys Ser
1               5                   10                  15

Ser Asn Asp Ile Val Ile Leu Ser Ser Leu Arg Thr Pro Val Thr Arg
            20                  25                  30

Ala Lys Lys Gly Gly Phe Lys Asp Ala Tyr Pro Glu Glu Leu Leu Ala
        35                  40                  45

Ser Val Leu Gln Ala Thr Leu Lys Ala Asn Pro Asn Leu Asp Pro Ala
    50                  55                  60

Gln Ile Asp Asp Val Leu Ile Gly Ser Val Leu Gln Glu Leu Gly Gly
65                  70                  75                  80

Ala Lys Ala Gly Arg Met Gly Gln Ile His Ala Gly Phe Pro His Ser
                85                  90                  95

Val Pro Phe Asn Thr Ile Asn Arg Gln Cys Ser Ser Gly Leu Ala Ala
```

```
            100                 105                 110
Ile Thr Thr Ile Ala Asn Gly Ile Arg Ala Gly Ala Ile Asn Val Gly
        115                 120                 125

Val Gly Gly Gly Met Glu Ser Met Thr Arg Asn Tyr Gly Ser Arg Ala
        130                 135                 140

Ile Pro Thr Val Leu Trp Pro Glu Leu Lys Glu Ser Tyr Ser Gln Asp
145                 150                 155                 160

Ala Arg Asp Cys Ile Met Pro Met Gly Ile Thr Ser Glu Asn Val Ala
            165                 170                 175

Ser Arg Tyr Gly Val Ser Arg Ala Asp Gln Asp Ala Phe Ala Val Glu
        180                 185                 190

Ser His Ala Lys Ala Ser Ala Ala Gln Lys Ala Gly Arg Phe Asp Ser
        195                 200                 205

Glu Ile Val Ser Val Thr Thr Lys Thr Leu Asp Pro Glu Asn Pro Asp
        210                 215                 220

Ala Pro Ala Arg Asp Val Thr Val Ser Gln Asp Asp Gly Ile Arg His
225                 230                 235                 240

Gly Leu Ser Ile Glu Lys Val Gly Ala Leu Lys Pro Ala Phe Ser Pro
                245                 250                 255

Thr Gly Ala Ser Thr Ala Gly Asn Ser Ser Gln Val Ser Asp Gly Ala
            260                 265                 270

Ala Ala Thr Leu Leu Met Arg Arg Ser Thr Ala Glu Glu Leu Gly Leu
        275                 280                 285

Ser Gly Ser Ile Lys Ala Arg Trp Val Ala Ser Ala Val Ala Gly Cys
        290                 295                 300

Ala Pro Asp Glu Met Gly Val Gly Pro Ala Val Ala Ile Pro Lys Leu
305                 310                 315                 320

Leu Gln Thr Val Gly Val Glu Val Pro Glu Val Gly Val Trp Glu Ile
                325                 330                 335

Asn Glu Ala Phe Ala Ser Gln Ala Leu Tyr Ser Val Arg Lys Leu Gly
            340                 345                 350

Ile Asp Gln Ala Lys Val Asn Pro Asn Gly Gly Ala Ile Ala Ile Gly
        355                 360                 365

His Pro Leu Gly Ala Thr Gly Ala Arg Gln Leu Ala Thr Leu Leu Pro
        370                 375                 380

Glu Leu Glu Arg Ser Gly Gln Glu Ile Gly Val Ile Ser Met Cys Ile
385                 390                 395                 400

Gly Thr Gly Met Gly Met Ala Gly Met Phe Val Arg Glu
                405                 410

<210> SEQ ID NO 5
<211> LENGTH: 401
<212> TYPE: PRT
<213> ORGANISM: Acinetobacter sp.

<400> SEQUENCE: 5

Met Leu Asn Ala Tyr Ile Tyr Asp Gly Leu Arg Thr Pro Phe Gly Arg
1               5                   10                  15

His Ala Gly Glu Leu Ala Ser Ile Arg Pro Asp Asp Leu Ala Gly Leu
            20                  25                  30

Val Ile Gln Arg Leu Ile Glu Lys Thr Gly Val Ala Gly Ala Asp Ile
        35                  40                  45

Glu Asp Val Ile Phe Gly Asp Thr Asn Gln Ala Gly Glu Asp Ser Arg
    50                  55                  60
```

```
Asn Ile Ala Arg His Ala Leu Leu Ala Gly Leu Pro Val Thr Val
 65                  70                  75                  80

Pro Gly Gln Thr Val Asn Arg Leu Cys Ala Ser Gly Leu Ala Ala Ile
                 85                  90                  95

Ile Asp Ser Ala Arg Ala Ile Thr Cys Gly Glu Gly Asp Leu Tyr Ile
            100                 105                 110

Ala Gly Gly Val Glu Ser Met Ser Arg Ala Pro Phe Val Met Gly Lys
        115                 120                 125

Ala Glu Ser Ala Tyr Ser Arg Asp Ala Lys Ile Tyr Asp Thr Thr Ile
    130                 135                 140

Gly Thr Arg Phe Pro Asn Lys Lys Ile Val Ala Gln Tyr Gly Gly His
145                 150                 155                 160

Ser Met Pro Glu Thr Gly Asp Asn Val Ala Val Glu Tyr Gly Ile Ser
                165                 170                 175

Arg Glu Gln Ala Asp Leu Phe Ala Ala Gln Ser Gln Ala Lys Tyr Gln
            180                 185                 190

Lys Ala Leu Glu Glu Gly Phe Phe Ala Gly Glu Ile Thr Ala Val Glu
        195                 200                 205

Val Ser Gln Gly Lys Lys Leu Pro Pro Lys Gln Val Thr Glu Asp Glu
    210                 215                 220

His Pro Arg Pro Ser Ser Thr Leu Glu Ala Leu Ser Lys Leu Lys Pro
225                 230                 235                 240

Leu Phe Glu Gly Gly Val Val Thr Ala Gly Asn Ala Ser Gly Ile Asn
                245                 250                 255

Asp Gly Ala Ala Ala Leu Leu Ile Gly Ser Glu Val Ala Gly Gln Lys
            260                 265                 270

Tyr Gly Leu Thr Pro Met Ala Lys Ile Leu Ser Ala Ala Ala Gly
        275                 280                 285

Val Glu Pro Arg Ile Met Gly Ala Gly Pro Ile Glu Ala Ile Lys Lys
    290                 295                 300

Ala Val Ala Arg Ala Gly Leu Thr Leu Asp Asp Leu Asp Ile Ile Glu
305                 310                 315                 320

Ile Asn Glu Ala Phe Ala Ser Gln Val Leu Ser Cys Leu Lys Gly Leu
                325                 330                 335

Gly Ile Asp Phe Asn Asp Pro Arg Val Asn Pro Asn Gly Gly Ala Ile
            340                 345                 350

Ala Val Gly His Pro Leu Gly Ala Ser Gly Ala Arg Leu Ala Leu Thr
        355                 360                 365

Val Ala Arg Glu Leu Gln Arg Arg Asn Lys Lys Tyr Ala Val Val Ser
    370                 375                 380

Leu Cys Ile Gly Val Gly Gln Gly Leu Ala Met Val Ile Glu Asn Val
385                 390                 395                 400

Ser

<210> SEQ ID NO 6
<211> LENGTH: 393
<212> TYPE: PRT
<213> ORGANISM: Clostridium kluyveri

<400> SEQUENCE: 6

Met Arg Glu Val Val Ile Val Ser Ala Val Arg Thr Ala Ile Gly Ser
  1               5                  10                  15

Phe Gly Gly Thr Leu Lys Asp Val Ser Ala Val Asp Leu Gly Ala Ile
                 20                  25                  30
```

Val Ile Lys Glu Ala Val Lys Arg Ala Gly Ile Lys Pro Glu Gln Val
             35                  40                  45

Asp Glu Val Ile Phe Gly Asn Val Ile Gln Ala Gly Val Gly Gln Ser
 50                  55                  60

Leu Ala Arg Gln Ser Ala Val Tyr Ala Gly Leu Pro Val Glu Val Pro
 65                  70                  75                  80

Ala Phe Thr Val Asn Lys Leu Cys Gly Ser Gly Leu Arg Thr Val Ser
                 85                  90                  95

Leu Ala Ala Ser Leu Ile Ser Asn Gly Asp Ala Asp Thr Ile Val Val
             100                 105                 110

Gly Gly Ser Glu Asn Met Ser Ala Ser Pro Tyr Leu Ile Pro Lys Ala
             115                 120                 125

Arg Phe Gly Tyr Arg Met Gly Glu Ala Lys Ile Tyr Asp Ala Met Leu
130                 135                 140

His Asp Gly Leu Ile Asp Ser Phe Asn Asn Tyr His Met Gly Ile Thr
145                 150                 155                 160

Ala Glu Asn Ile Ala Glu Lys Trp Gly Ile Thr Arg Glu Asp Gln Asp
                165                 170                 175

Lys Phe Ala Leu Ala Ser Gln Gln Lys Ala Glu Ala Ile Lys Ala
             180                 185                 190

Gly Lys Phe Lys Asp Glu Ile Val Pro Val Thr Val Lys Met Lys Lys
             195                 200                 205

Lys Glu Val Val Phe Asp Thr Asp Glu Asp Pro Arg Phe Gly Thr Thr
210                 215                 220

Ile Glu Thr Leu Ala Lys Leu Lys Pro Ala Phe Lys Arg Asp Gly Thr
225                 230                 235                 240

Gly Thr Val Thr Ala Gly Asn Ser Ser Gly Ile Asn Asp Ser Ser Ala
                245                 250                 255

Ala Leu Ile Leu Met Ser Ala Asp Lys Ala Lys Glu Leu Gly Val Lys
             260                 265                 270

Pro Met Ala Lys Tyr Val Asp Phe Ala Ser Ala Gly Leu Asp Pro Ala
             275                 280                 285

Ile Met Gly Tyr Gly Pro Tyr Tyr Ala Thr Lys Lys Val Leu Ala Lys
290                 295                 300

Thr Asn Leu Thr Ile Lys Asp Phe Asp Leu Ile Glu Ala Asn Glu Ala
305                 310                 315                 320

Phe Ala Ala Gln Ser Ile Ala Val Ala Arg Asp Leu Glu Phe Asp Met
                325                 330                 335

Ser Lys Val Asn Val Asn Gly Gly Ala Ile Ala Leu Gly His Pro Val
             340                 345                 350

Gly Cys Ser Gly Ala Arg Ile Leu Val Thr Leu Leu His Glu Met Gln
             355                 360                 365

Lys Arg Asp Ala Lys Lys Gly Leu Ala Thr Leu Cys Ile Gly Gly Gly
             370                 375                 380

Gln Gly Thr Ala Val Val Val Glu Arg
385                 390

<210> SEQ ID NO 7
<211> LENGTH: 391
<212> TYPE: PRT
<213> ORGANISM: Clostridium kluyveri

<400> SEQUENCE: 7

Met Lys Asp Ala Val Ile Val Ser Ala Val Arg Thr Ala Ile Gly Ser
 1               5                  10                  15

Phe Gly Gly Thr Leu Lys Asp Ile Ser Ala Val Asp Leu Gly Ala Ile
            20                  25                  30

Val Ile Lys Glu Ala Val Lys Arg Ala Gly Ile Lys Pro Glu Gln Val
        35                  40                  45

Asp Glu Val Ile Phe Gly Asn Val Ile Gln Ala Gly Leu Gly Gln Ser
50                  55                  60

Pro Ala Arg Gln Ala Ala Val Lys Ala Gly Ile Pro Val Glu Val Pro
65                  70                  75                  80

Ala Phe Thr Leu Asn Lys Val Cys Gly Ser Gly Leu Arg Ser Val Ser
                85                  90                  95

Leu Ala Ala Gln Leu Ile Lys Ile Gly Asp Asp Ile Val Val
                100                 105                 110

Gly Gly Thr Glu Asn Met Ser Ala Ala Pro Tyr Leu Leu Pro Lys Ala
            115                 120                 125

Arg Trp Gly His Arg Met Gly Glu Gly Lys Leu Val Asp Ala Met Ile
130                 135                 140

Lys Asp Gly Leu Trp Glu Ala Phe Asn Asn Tyr His Met Gly Ile Thr
145                 150                 155                 160

Ala Glu Asn Ile Ala Glu Lys Trp Gly Ile Thr Arg Asp Met Gln Asp
                165                 170                 175

Glu Phe Ala Leu Ala Ser Gln Gln Lys Ala Glu Ala Ala Ile Lys Ala
            180                 185                 190

Gly Lys Phe Lys Asp Glu Ile Val Pro Val Thr Val Lys Gln Lys Lys
        195                 200                 205

Lys Glu Ile Ile Phe Asp Thr Asp Glu Phe Pro Arg Phe Gly Thr Thr
210                 215                 220

Ile Glu Ala Leu Ala Lys Leu Lys Pro Ser Phe Lys Lys Asp Gly Thr
225                 230                 235                 240

Val Thr Ala Gly Asn Ala Ser Gly Ile Asn Asp Ala Ala Ala Leu
                245                 250                 255

Val Val Met Ser Ala Asp Lys Ala Lys Glu Leu Gly Ile Lys Pro Leu
            260                 265                 270

Ala Lys Ile Val Ser Tyr Gly Ser Lys Gly Leu Asp Pro Thr Ile Met
        275                 280                 285

Gly Tyr Gly Pro Phe Tyr Ala Thr Lys Leu Ala Leu Glu Lys Ala Asn
290                 295                 300

Leu Ser Ile Ala Asp Leu Asp Leu Ile Glu Ala Asn Glu Ala Phe Ala
305                 310                 315                 320

Ser Gln Ser Leu Ala Val Ala Lys Asp Leu Glu Phe Asp Met Ser Lys
                325                 330                 335

Val Asn Val Asn Gly Gly Ala Ile Ala Leu Gly His Pro Val Gly Cys
            340                 345                 350

Ser Gly Ala Arg Ile Leu Val Thr Leu Leu Tyr Glu Met Gln Arg Arg
        355                 360                 365

Asp Ala Lys Lys Gly Leu Ala Thr Leu Cys Ile Gly Gly Gly Met Gly
370                 375                 380

Thr Ala Leu Ile Val Glu Arg
385                 390

<210> SEQ ID NO 8
<211> LENGTH: 391
<212> TYPE: PRT
<213> ORGANISM: Clostridium kluyveri

<400> SEQUENCE: 8

```
Met Arg Glu Val Val Ile Val Ser Ala Val Arg Thr Ala Ile Gly Ser
1               5                   10                  15

Phe Gly Gly Thr Leu Lys Asp Val Pro Ala Val Glu Leu Gly Ala Val
            20                  25                  30

Val Ile Lys Glu Ala Val Lys Arg Ala Asn Val Lys Pro Glu Gln Ile
        35                  40                  45

Asp Glu Val Ile Phe Gly Asn Val Ile Gln Ala Gly Leu Gly Gln Ser
    50                  55                  60

Pro Ala Arg Gln Ala Ala Val Lys Ala Gly Ile Pro Val Glu Val Pro
65                  70                  75                  80

Ala Phe Thr Leu Asn Lys Val Cys Gly Ser Gly Leu Arg Ser Val Ser
                85                  90                  95

Leu Ala Ala Gln Val Ile Lys Ala Gly Asp Ala Asp Ile Val Val Val
            100                 105                 110

Gly Gly Met Glu Asn Met Ser Ala Ala Pro Tyr Val Leu Pro Lys Ala
        115                 120                 125

Arg Trp Gly His Arg Met Gly Glu Gly Lys Ile Val Asp Ala Met Ile
130                 135                 140

Lys Asp Gly Leu Trp Glu Ala Phe Asn Asn Tyr His Met Gly Ile Thr
145                 150                 155                 160

Ala Glu Asn Ile Ala Glu Lys Trp Gly Leu Thr Arg Glu Glu Gln Asp
                165                 170                 175

Glu Phe Ser Ala Ala Ser Gln Gln Lys Ala Glu Ala Ala Gln Lys Ala
            180                 185                 190

Gly Lys Phe Lys Asp Glu Ile Val Pro Val Thr Val Lys Ile Lys Lys
        195                 200                 205

Lys Glu Val Val Phe Asp Thr Asp Glu Tyr Ile Lys Pro Gly Thr Thr
210                 215                 220

Val Glu Thr Leu Ala Lys Leu Arg Pro Ala Phe Lys Lys Asp Gly Thr
225                 230                 235                 240

Val Thr Ala Gly Asn Ala Ser Gly Ile Asn Asp Ala Ala Ala Ala Leu
                245                 250                 255

Val Val Met Ser Ala Asp Lys Ala Lys Glu Leu Gly Ile Lys Pro Leu
            260                 265                 270

Ala Lys Ile Val Ser Tyr Gly Ser Ala Gly Leu Asp Pro Thr Ile Met
        275                 280                 285

Gly Tyr Gly Pro Phe His Ala Thr Lys Ala Ala Leu Glu Lys Ala Asn
290                 295                 300

Leu Ser Val Ala Asp Leu Asp Leu Ile Glu Ala Asn Glu Ala Phe Ala
305                 310                 315                 320

Ser Gln Ser Leu Ala Val Ala Lys Asp Leu Glu Phe Asp Met Ser Lys
                325                 330                 335

Val Asn Val Asn Gly Gly Ala Ile Ala Leu Gly His Pro Val Gly Ala
            340                 345                 350

Ser Gly Ala Arg Ile Leu Val Thr Leu Leu His Glu Met Gln Arg Arg
        355                 360                 365

Asp Ala Lys Lys Gly Leu Ala Thr Leu Cys Ile Gly Gly Gly Met Gly
370                 375                 380

Thr Ala Leu Ile Val Glu Arg
385                 390
```

<210> SEQ ID NO 9

```
<211> LENGTH: 408
<212> TYPE: PRT
<213> ORGANISM: Corynebacterium glutamicum

<400> SEQUENCE: 9
```

| | | | | | | | | | | | | | | |
|---|---|---|---|---|---|---|---|---|---|---|---|---|---|---|
|Met|Asn|Pro|Gln|Asp|Ile|Val|Ile|Cys|Ser|Pro|Leu|Arg|Thr|Pro|Val|
|1| | | |5| | | | |10| | | | |15| |

Gly Ala Tyr Gly Gly Ser Phe Thr Gly Val Pro Val Glu Glu Leu Ala
            20                  25                  30

Thr Thr Val Ile Asn Ala Ile Glu Ala Thr Gly Ile Thr Gly Asp
        35                  40                  45

Asp Val Asp Asp Leu Ile Leu Gly Gln Ala Ser Pro Asn Gly Ala Ala
    50                  55                  60

Pro Ala Leu Gly Arg Val Val Ala Leu Asp Ser Lys Leu Gly Gln Asn
65                  70                  75                  80

Val Pro Gly Met Gln Leu Asp Arg Arg Cys Gly Ser Gly Leu Gln Ala
                85                  90                  95

Ile Val Thr Ala Ala Ala His Val Ala Ser Gly Ala Ala Asp Leu Ile
            100                 105                 110

Ile Ala Gly Gly Ala Glu Ser Met Ser Arg Val Glu Tyr Thr Val Ser
        115                 120                 125

Gly Asp Ile Arg Trp Gly Val Lys Gly Gly Asp Met Gln Leu Arg Asp
    130                 135                 140

Arg Leu Ala Glu Ala Arg Glu Thr Ala Gly Gly Arg Asn His Pro Ile
145                 150                 155                 160

Pro Gly Gly Met Ile Glu Thr Ala Glu Asn Leu Arg Arg Glu Tyr Gly
                165                 170                 175

Ile Ser Arg Glu Glu Gln Asp Lys Ile Ser Ala Ala Ser Gln Gln Arg
            180                 185                 190

Trp Gly Lys Ala Ala Asp Ala Gly Leu Phe Asp Asp Glu Ile Val Pro
        195                 200                 205

Val Thr Val Pro Ala Lys Lys Arg Gly Gln Glu Pro Thr Ile Val Ser
    210                 215                 220

Arg Asp Glu His Gly Arg Pro Gly Thr Thr Val Glu Lys Leu Ala Ala
225                 230                 235                 240

Leu Arg Pro Ile Met Gly Arg Gln Asp Ala Glu Ala Thr Val Thr Ala
                245                 250                 255

Gly Asn Ala Ser Gly Gln Asn Asp Gly Ala Ala Ala Val Ile Val Thr
            260                 265                 270

Thr Arg Ala Lys Ala Glu Glu Lys Gly Leu Arg Pro Val Met Arg Leu
        275                 280                 285

Ala Gly Trp Ser Val Ala Val Pro Pro Glu Thr Met Gly Ile Gly
    290                 295                 300

Pro Val Pro Ala Thr Lys Lys Val Leu Asp Arg Leu Gly Leu Thr Leu
305                 310                 315                 320

Glu Asp Ile Gly Ala Ile Glu Leu Asn Glu Ala Phe Ala Ala Gln Ala
                325                 330                 335

Leu Ser Val Leu Lys Glu Trp Asn Ile Ser Trp Glu Asp Glu Arg Val
            340                 345                 350

Asn Pro Leu Gly Ser Gly Ile Ser Met Gly His Pro Val Gly Ala Thr
        355                 360                 365

Gly Ala Arg Met Ala Val Thr Leu Ala His Arg Met Gln Arg Glu Asn
    370                 375                 380

Thr Gln Tyr Gly Leu Ala Thr Met Cys Ile Gly Gly Gly Gln Gly Leu

```
                385                 390                 395                 400

Ala Ala Val Phe Glu Lys Glu Asn
                405

<210> SEQ ID NO 10
<211> LENGTH: 401
<212> TYPE: PRT
<213> ORGANISM: Escherichia coli

<400> SEQUENCE: 10

Met Arg Glu Ala Phe Ile Cys Asp Gly Ile Arg Thr Pro Ile Gly Arg
1               5                   10                  15

Tyr Gly Gly Ala Leu Ser Ser Val Arg Ala Asp Leu Ala Ala Ile
                20                  25                  30

Pro Leu Arg Glu Leu Leu Val Arg Asn Pro Arg Leu Asp Ala Glu Cys
            35                  40                  45

Ile Asp Asp Val Ile Leu Gly Cys Ala Asn Gln Ala Gly Glu Asp Asn
    50                  55                  60

Arg Asn Val Ala Arg Met Ala Thr Leu Leu Ala Gly Leu Pro Gln Ser
65                  70                  75                  80

Val Ser Gly Thr Thr Ile Asn Arg Leu Cys Gly Ser Gly Leu Asp Ala
                85                  90                  95

Leu Gly Phe Ala Ala Arg Ala Ile Lys Ala Gly Asp Gly Asp Leu Leu
            100                 105                 110

Ile Ala Gly Gly Val Glu Ser Met Ser Arg Ala Pro Phe Val Met Gly
        115                 120                 125

Lys Ala Ser Ala Phe Ser Arg Gln Ala Glu Met Phe Asp Thr Thr
    130                 135                 140

Ile Gly Trp Arg Phe Val Asn Pro Leu Met Ala Gln Gln Phe Gly Thr
145                 150                 155                 160

Asp Ser Met Pro Glu Thr Ala Glu Asn Val Ala Glu Leu Leu Lys Ile
                165                 170                 175

Ser Arg Glu Asp Gln Asp Ser Phe Ala Leu Arg Ser Gln Gln Arg Thr
            180                 185                 190

Ala Lys Ala Gln Ser Ser Gly Ile Leu Ala Glu Glu Ile Val Pro Val
        195                 200                 205

Val Leu Lys Asn Lys Lys Gly Val Val Thr Glu Ile Gln His Asp Glu
    210                 215                 220

His Leu Arg Pro Glu Thr Thr Leu Glu Gln Leu Arg Gly Leu Lys Ala
225                 230                 235                 240

Pro Phe Arg Ala Asn Gly Val Ile Thr Ala Gly Asn Ala Ser Gly Val
                245                 250                 255

Asn Asp Gly Ala Ala Ala Leu Ile Ile Ala Ser Glu Gln Met Ala Ala
            260                 265                 270

Ala Gln Gly Leu Thr Pro Arg Ala Arg Ile Val Ala Met Ala Thr Ala
        275                 280                 285

Gly Val Glu Pro Arg Leu Met Gly Leu Gly Pro Val Pro Ala Thr Arg
    290                 295                 300

Arg Val Leu Glu Arg Ala Gly Leu Ser Ile His Asp Met Asp Val Ile
305                 310                 315                 320

Glu Leu Asn Glu Ala Phe Ala Ala Gln Ala Leu Gly Val Leu Arg Glu
                325                 330                 335

Leu Gly Leu Pro Asp Asp Ala Pro His Val Asn Pro Asn Gly Gly Ala
            340                 345                 350
```

```
Ile Ala Leu Gly His Pro Leu Gly Met Ser Gly Ala Arg Leu Ala Leu
            355                 360                 365

Ala Ala Ser His Glu Leu His Arg Arg Asn Gly Arg Tyr Ala Leu Cys
370                 375                 380

Thr Met Cys Ile Gly Val Gly Gln Gly Ile Ala Met Ile Leu Glu Arg
385                 390                 395                 400

Val

<210> SEQ ID NO 11
<211> LENGTH: 400
<212> TYPE: PRT
<213> ORGANISM: Pseudomonas putida

<400> SEQUENCE: 11

Met His Asp Val Phe Ile Cys Asp Ala Ile Arg Thr Pro Ile Gly Arg
1               5                   10                  15

Phe Gly Gly Ala Leu Ala Ser Val Arg Ala Asp Asp Leu Ala Ala Val
            20                  25                  30

Pro Leu Lys Ala Leu Ile Glu Arg Asn Pro Gly Val Gln Trp Asp Gln
        35                  40                  45

Val Asp Glu Val Phe Phe Gly Cys Ala Asn Gln Ala Gly Glu Asp Asn
50                  55                  60

Arg Asn Val Ala Arg Met Ala Leu Leu Leu Ala Gly Leu Pro Glu Ser
65                  70                  75                  80

Ile Pro Gly Val Thr Leu Asn Arg Leu Cys Ala Ser Gly Met Asp Ala
                85                  90                  95

Val Gly Thr Ala Phe Arg Ala Ile Ala Ser Gly Glu Met Glu Leu Val
            100                 105                 110

Ile Ala Gly Gly Val Glu Ser Met Ser Arg Ala Pro Phe Val Met Gly
        115                 120                 125

Lys Ala Glu Ser Ala Tyr Ser Arg Asn Met Lys Leu Glu Asp Thr Thr
130                 135                 140

Ile Gly Trp Arg Phe Ile Asn Pro Leu Met Lys Ser Gln Tyr Gly Val
145                 150                 155                 160

Asp Ser Met Pro Glu Thr Ala Asp Asn Val Ala Asp Asp Tyr Gln Val
                165                 170                 175

Ser Arg Ala Asp Gln Asp Ala Phe Ala Leu Arg Ser Gln Gln Lys Ala
            180                 185                 190

Ala Ala Ala Gln Ala Ala Gly Phe Phe Ala Glu Glu Ile Val Pro Val
        195                 200                 205

Arg Ile Ala His Lys Lys Gly Glu Ile Ile Val Glu Arg Asp Glu His
210                 215                 220

Leu Arg Pro Glu Thr Thr Leu Glu Ala Leu Thr Lys Leu Lys Pro Val
225                 230                 235                 240

Asn Gly Pro Asp Lys Thr Val Thr Ala Gly Asn Ala Ser Gly Val Asn
                245                 250                 255

Asp Gly Ala Ala Ala Met Ile Leu Ala Ser Ala Ala Val Lys Lys
            260                 265                 270

His Gly Leu Thr Pro Arg Ala Arg Val Leu Gly Met Ala Ser Gly Gly
        275                 280                 285

Val Ala Pro Arg Val Met Gly Ile Gly Pro Val Pro Ala Val Arg Lys
290                 295                 300

Leu Thr Glu Arg Leu Gly Ile Ala Val Ser Asp Phe Asp Val Ile Glu
305                 310                 315                 320
```

```
Leu Asn Glu Ala Phe Ala Ser Gln Gly Leu Ala Val Leu Arg Glu Leu
                325                 330                 335

Gly Val Ala Asp Asp Ala Pro Gln Val Asn Pro Asn Gly Gly Ala Ile
            340                 345                 350

Ala Leu Gly His Pro Leu Gly Met Ser Gly Ala Arg Leu Val Leu Thr
        355                 360                 365

Ala Leu His Gln Leu Glu Lys Ser Gly Gly Arg Lys Gly Leu Ala Thr
    370                 375                 380

Met Cys Val Gly Val Gly Gln Gly Leu Ala Leu Ala Ile Glu Arg Val
385                 390                 395                 400

<210> SEQ ID NO 12
<211> LENGTH: 394
<212> TYPE: PRT
<213> ORGANISM: Ralstonia eutropha

<400> SEQUENCE: 12

Met Thr Arg Glu Val Val Val Ser Gly Val Arg Thr Ala Ile Gly Thr
1               5                   10                  15

Thr Phe Gly Gly Ser Leu Lys Asp Val Ala Pro Ala Glu Leu Gly Ala
            20                  25                  30

Leu Val Val Arg Glu Ala Leu Ala Arg Ala Gln Val Ser Gly Asp Asp
        35                  40                  45

Val Gly His Val Val Phe Gly Asn Val Ile Gln Thr Glu Pro Arg Asp
    50                  55                  60

Met Tyr Leu Gly Arg Val Ala Ala Val Asn Gly Gly Val Thr Ile Asn
65                  70                  75                  80

Ala Pro Ala Leu Thr Val Asn Arg Leu Cys Gly Ser Gly Leu Gln Ala
                85                  90                  95

Ile Val Ser Ala Ala Gln Thr Ile Leu Leu Gly Asp Thr Asp Val Ala
            100                 105                 110

Ile Gly Gly Gly Ala Glu Ser Met Ser Arg Ala Pro Tyr Leu Ala Pro
        115                 120                 125

Ala Ala Arg Trp Gly Ala Arg Met Gly Asp Ala Gly Leu Val Asp Met
    130                 135                 140

Met Leu Gly Ala Leu His Asp Pro Phe His Arg Ile His Met Gly Val
145                 150                 155                 160

Thr Ala Glu Asn Val Ala Lys Glu Tyr Asp Ile Ser Arg Ala Gln Gln
                165                 170                 175

Asp Glu Ala Ala Leu Glu Ser His Arg Arg Ala Ser Ala Ala Ile Lys
            180                 185                 190

Ala Gly Tyr Phe Lys Asp Gln Ile Val Pro Val Val Ser Lys Gly Arg
        195                 200                 205

Lys Gly Asp Val Thr Phe Asp Thr Asp Glu His Val Arg His Asp Ala
    210                 215                 220

Thr Ile Asp Asp Met Thr Lys Leu Arg Pro Val Phe Val Lys Glu Asn
225                 230                 235                 240

Gly Thr Val Thr Ala Gly Asn Ala Ser Gly Leu Asn Asp Ala Ala Ala
                245                 250                 255

Ala Val Val Met Met Glu Arg Ala Glu Ala Glu Arg Arg Gly Leu Lys
            260                 265                 270

Pro Leu Ala Arg Leu Val Ser Tyr Gly His Ala Gly Val Asp Pro Lys
        275                 280                 285

Ala Met Gly Ile Gly Pro Val Pro Ala Thr Lys Ile Ala Leu Glu Arg
    290                 295                 300
```

```
Ala Gly Leu Gln Val Ser Asp Leu Asp Val Ile Glu Ala Asn Glu Ala
305                 310                 315                 320

Phe Ala Ala Gln Ala Cys Ala Val Thr Lys Ala Leu Gly Leu Asp Pro
                325                 330                 335

Ala Lys Val Asn Pro Asn Gly Ser Gly Ile Ser Leu Gly His Pro Ile
            340                 345                 350

Gly Ala Thr Gly Ala Leu Ile Thr Val Lys Ala Leu His Glu Leu Asn
        355                 360                 365

Arg Val Gln Gly Arg Tyr Ala Leu Val Thr Met Cys Ile Gly Gly Gly
    370                 375                 380

Gln Gly Ile Ala Ala Ile Phe Glu Arg Ile
385                 390

<210> SEQ ID NO 13
<211> LENGTH: 406
<212> TYPE: PRT
<213> ORGANISM: Rhodococcus sp.

<400> SEQUENCE: 13

Met Ala Glu Val Phe Leu Val Asp Gly Ala Arg Thr Pro Gln Gly Arg
1               5                   10                  15

Tyr Gly Gly Ala Leu Ala Gly Val Arg Pro Asp Asp Leu Ala Gly Leu
            20                  25                  30

Val Val Ala Glu Ala Ala Arg Arg Ala Gly Ile Pro Gly Asp Ala Val
        35                  40                  45

Asp Glu Val Ile Leu Gly Ala Ala Asn Gln Ala Gly Glu Asp Asn Arg
    50                  55                  60

Asp Val Ala Arg Met Ala Val Leu Leu Ala Gly Leu Pro Asp Ser Val
65                  70                  75                  80

Pro Gly Tyr Thr Val Asn Arg Leu Cys Ala Ser Gly Leu Thr Ala Val
            85                  90                  95

Ala Ser Ala Ala His Thr Ile Arg Ser Gly Glu Ala Asp Ile Val Ile
            100                 105                 110

Ala Gly Gly Val Glu Ser Met Thr Arg Ala Pro Trp Val Met Ala Lys
            115                 120                 125

Pro Gly Thr Pro Trp Ala Arg Pro Gly Glu Val Ala Asp Thr Ser Leu
        130                 135                 140

Gly Trp Arg Phe Thr Asn Pro Arg Phe Thr Ala Ala Asp Arg Asp Val
145                 150                 155                 160

Pro Ala Gly Ala Gly Pro Asp Val Arg Lys Val Thr Leu Ser Met Gly
            165                 170                 175

Glu Thr Ala Glu Glu Val Ala Ala Leu Glu Gly Val Thr Arg Ala Glu
                180                 185                 190

Ser Asp Ala Phe Ala Leu Arg Ser Gln Glu Arg Ala Ile Ala Ala Val
            195                 200                 205

Asp Ala Gly Arg Phe Glu Arg Glu Ile Val Pro Val Pro Val Arg Asp
        210                 215                 220

Gly Glu Leu Ala Ala Asp Glu Thr Pro Arg Arg Gly Thr Thr Leu Glu
225                 230                 235                 240

Lys Leu Gly Ser Leu Lys Pro Val Phe Arg Thr Gly Gly Ile Val Thr
            245                 250                 255

Ala Gly Ser Ser Ser Ser Leu Ser Asp Gly Ala Ala Ala Leu Val Val
            260                 265                 270

Ala Ser Glu Ala Ala Val Glu Lys Tyr Gly Leu Thr Val Arg Gly Arg
```

```
            275                 280                 285
Ile Val Thr Ser Ala Ser Ala Gly Ile Ala Pro Asn Val Met Gly Leu
            290                 295                 300

Gly Pro Val Pro Ala Thr Arg Lys Ala Leu Ala Arg Ala Asn Trp Ser
305                 310                 315                 320

Ile Ser Asp Leu Gly Ala Ala Glu Leu Asn Glu Ala Phe Ala Ala Gln
                325                 330                 335

Ser Leu Gly Val Ile Arg Gln Leu Lys Leu Asp Glu Ser Ile Val Asn
                340                 345                 350

Ala Asp Gly Gly Ala Ile Ala Leu Gly His Pro Leu Gly Cys Ser Gly
                355                 360                 365

Ala Arg Ile Leu Leu Thr Leu Leu Gly Arg Met Glu Arg Glu Gly Ala
                370                 375                 380

Arg Arg Gly Leu Ala Thr Leu Cys Val Gly Val Gly Gln Gly Val Ala
385                 390                 395                 400

Met Leu Ile Glu Ala Pro
            405

<210> SEQ ID NO 14
<211> LENGTH: 327
<212> TYPE: PRT
<213> ORGANISM: Penicillium chrysogenum

<400> SEQUENCE: 14

Met Ser Ala Pro Gly Ala Gly His Glu Phe Pro Ala Gln Glu Val Ser
1               5                   10                  15

Trp Gln Lys Arg Asp Val Leu Leu Phe Ala Asn Ser Ile Gly Val Lys
                20                  25                  30

Ala Asp Glu Leu His Phe Leu Tyr Glu Leu His Pro Asn Phe Ala Val
            35                  40                  45

Phe Pro Thr Tyr Ser Leu Ile Leu Arg Met Ser Lys Asn Thr Ser Asp
        50                  55                  60

Phe Arg Thr Ile Ala Leu Thr Pro Lys Pro Leu Ala Phe Lys Leu Thr
65                  70                  75                  80

Asp Gln Glu Val Thr Asp Phe Tyr Ala Arg Gln Lys Ala Val His Ile
                85                  90                  95

Pro Gly Val Pro Asp Leu Asp His Arg His Gly Val Asp Gly Gln Arg
            100                 105                 110

Lys Ile Thr Ile Leu Lys Pro Leu Pro Thr Thr Ser Ala Gly Arg Lys
        115                 120                 125

Phe Glu Leu Arg Asn Lys Val Ile Gly Val Tyr Asp Lys Gly Lys Pro
130                 135                 140

Gly Thr Val Ile Glu Thr Glu Gln Ser Ile Val Asp Lys Glu Ser Gly
145                 150                 155                 160

Glu Val Tyr Ser Lys Val Val Ser Ser Gly Phe Leu Val Gly Gln Gly
                165                 170                 175

Gly Trp Gly Gly Pro Lys Gly Pro Ser Thr Val Asn Tyr Ala Pro Pro
            180                 185                 190

Glu Gly Arg Ala Pro Asp Ala Thr His Val Val Gln Ser Asn Ser Glu
        195                 200                 205

Thr Ala His Leu Tyr Arg Leu Asn Gly Asp Tyr Asn Pro Leu His Ala
    210                 215                 220

Thr Pro Glu Pro Gly Gln Lys Met Gly Phe Gly Gly Ile Ile Ile His
225                 230                 235                 240
```

```
Gly Leu Phe Ser Trp Asn Ser Ala Ala His Gly Ile Leu Arg Glu Phe
                245                 250                 255

Gly Gly Ser Asn Pro Ala Asn Met Lys Glu Phe Gln Ala Arg Phe Ala
        260                 265                 270

Ser Pro Val Arg Pro Gly Asp Lys Leu Thr Thr Glu Ile Trp Arg Met
    275                 280                 285

Gly Asn Ile Gln Asp Gly Tyr Glu Glu Ile Arg Phe Val Thr Lys Asn
290                 295                 300

Asp Lys Gly Arg Val Val Leu Ser Asn Gly Arg Cys Leu Leu Lys Val
305                 310                 315                 320

Thr Gly Val Lys Ser Lys Leu
                325

<210> SEQ ID NO 15
<211> LENGTH: 901
<212> TYPE: PRT
<213> ORGANISM: Penicillium chrysogenum

<400> SEQUENCE: 15

Met Ser Glu Leu Arg Phe Asp Asn Gln Thr Val Val Thr Gly Ala
1               5                   10                  15

Gly Gly Gly Leu Gly Lys Ala Tyr Ala Leu Phe Ala Ser Arg Gly
                20                  25                  30

Ala Asn Val Val Asn Asp Leu Gly Ala Ser His Lys Gly Glu Gly
                35                  40                  45

Lys Ser Gly Lys Ala Ala Asp Val Val Glu Glu Ile Arg Ala Ala
        50                  55                  60

Gly Gly Lys Ala Val Ala Asn Tyr Asp Ser Val Glu Asn Gly Asp Ala
65                  70                  75                  80

Ile Ile Glu Thr Ala Ile Lys Ala Phe Gly Arg Ile Asp Ile Leu Leu
                85                  90                  95

Asn Asn Ala Gly Ile Leu Arg Asp Ile Ser Phe Lys Asn Met Lys Asp
                100                 105                 110

Ala Asp Trp Asp Leu Ile Asn Arg Val His Thr Tyr Gly Ala Tyr Lys
            115                 120                 125

Cys Ala Arg Ala Ala Trp Pro His Phe Arg Lys Gln Lys Phe Gly Arg
130                 135                 140

Val Ile Asn Thr Ala Ser Ala Ala Gly Leu Phe Gly Ser Phe Gly Gln
145                 150                 155                 160

Ala Asn Tyr Ser Ala Ala Lys Leu Gly Gln Val Gly Phe Thr Glu Thr
                165                 170                 175

Leu Ala Lys Glu Gly Ala Lys Tyr Asn Ile Ile Ala Asn Val Ile Ala
                180                 185                 190

Pro Ile Ala Ala Ser Arg Met Thr Ala Thr Val Met Pro Pro Asp Val
            195                 200                 205

Leu Glu Asn Leu Lys Pro Asp Trp Val Pro Leu Val Ala Ala Leu
                210                 215                 220

Val His Ser Ser Asn Thr Thr Glu Thr Gly Gly Ile Tyr Glu Val Gly
225                 230                 235                 240

Gly Gly His Val Ala Lys Leu Arg Trp Glu Arg Ala Lys Gly Ala Leu
                245                 250                 255

Leu Lys Thr Asp Asp Ser Leu Thr Pro Gly Ala Ile Ala Arg Lys Trp
            260                 265                 270

Asn Asp Val Asn Asp Phe Ser Gln Pro Glu Tyr Pro Thr Gly Pro Ala
                275                 280                 285
```

```
Asp Phe Met Ala Phe Leu Glu Asp Gly Leu Lys Thr Pro Ser Ala Gln
            290                 295                 300

Pro Gly Gln Glu Pro Asp Phe Lys Gly Arg Val Ala Leu Val Thr Gly
305                 310                 315                 320

Gly Gly Ala Gly Leu Gly Arg Ala Tyr Cys Leu Gln Phe Ala Lys Leu
                325                 330                 335

Gly Ala Ser Val Val Asn Asp Leu Val Asp Pro Glu Pro Val Val
                340                 345                 350

Gln Glu Ile Lys Lys Leu Gly Gly Lys Ala Val Gly Asn Lys Ala Ser
            355                 360                 365

Cys Glu Asp Gly Asp Ala Val Val Lys Ser Ala Ile Asp Ala Phe Gly
370                 375                 380

Arg Ile Asp Ile Leu Val Asn Asn Ala Gly Ile Leu Arg Asp Lys Ala
385                 390                 395                 400

Phe Thr Asn Met Asp Asp Asn Leu Trp Asn Ser Val Val Asn Val His
                405                 410                 415

Leu Arg Gly Thr Tyr Lys Val Thr Lys Ala Ala Trp Pro Tyr Phe Leu
            420                 425                 430

Lys Gln Lys Tyr Gly Arg Val Val Asn Thr Ala Ser Thr Ser Gly Ile
            435                 440                 445

Tyr Gly Asn Phe Gly Gln Ala Asn Tyr Ala Ala Ala Lys Leu Gly Ile
450                 455                 460

Leu Gly Leu Ser Arg Thr Leu Ala Leu Glu Gly Ala Lys Tyr Asn Ile
465                 470                 475                 480

Lys Val Asn Thr Ile Ala Pro Asn Ala Gly Thr Asn Met Thr Arg Thr
                485                 490                 495

Ile Met Pro Glu Glu Met Val Gln Ala Phe Lys Pro Asp Tyr Val Ala
            500                 505                 510

Pro Leu Val Val Leu Leu Cys Ser Asp Met Ala Pro Glu Pro Ser Thr
515                 520                 525

Lys Gly Leu Phe Glu Cys Gly Ser Gly Trp Phe Gly Arg Thr Arg Trp
530                 535                 540

Gln Arg Thr Gly Gly His Gly Phe Pro Val Asp Val Lys Leu Thr Pro
545                 550                 555                 560

Glu Glu Val Val Arg Asn Trp Lys Gln Ile Ile Asn Phe Asp Asp Gly
                565                 570                 575

Arg Ala Asp His Pro Glu Asp Gly Gln Ala Gly Ala Glu Lys Ile Met
                580                 585                 590

Ala Asn Met Ser Asn Arg Val His Gly Asp Thr Ser Thr Glu Asn Glu
            595                 600                 605

Thr Leu Lys Asn Ile Lys Lys Ala Lys Ala Leu Ser Ser Glu Gly Thr
610                 615                 620

Pro Phe Asn Tyr Glu Asp Arg Asp Val Ile Leu Tyr Asn Leu Ser Leu
625                 630                 635                 640

Gly Ala Lys Arg Thr Asp Leu Pro Leu Val Tyr Glu Asn Asn Asp Gln
                645                 650                 655

Phe Gln Ala Leu Pro Ser Tyr Gly Val Val Pro Trp Phe Asn Thr Ala
                660                 665                 670

Thr Pro Trp Asn Met Asp Asp Leu Val Lys Asp Phe Ser Pro Met Met
            675                 680                 685

Leu Leu His Gly Glu Gln Tyr Met Glu Val Arg Lys Phe Pro Ile Pro
690                 695                 700
```

Thr Thr Ala Asn Thr Leu Thr Tyr Pro Lys Leu Ile Asp Val Ile Asp
705                 710                 715                 720

Lys Gly Asn Ala Ala Ile Val Val Ala Gly Tyr Thr Thr Lys Asp Ala
            725                 730                 735

Lys Thr Gly Glu Asp Leu Phe Tyr Asn Glu Ser Ser Val Phe Ile Arg
                740                 745                 750

Gly Ser Gly Gly Phe Gly Gly Ser Pro Lys Pro Thr Ala Val Arg Pro
            755                 760                 765

Lys Ala Ala Thr Ala Ala Tyr Lys Ala Pro Gln Arg Gln Pro Asp Ala
        770                 775                 780

Val Val Glu Glu Lys Thr Ser Glu Asp Gln Ala Ala Leu Tyr Arg Leu
785                 790                 795                 800

Asn Gly Asp Arg Asn Pro Leu His Ile Asp Pro Glu Phe Ser Lys Val
                805                 810                 815

Gly Gly Phe Lys Thr Pro Ile Leu His Gly Leu Cys Ser Leu Gly Val
            820                 825                 830

Ser Ala Lys Ala Val Phe Ser Lys Tyr Gly Pro Tyr Lys Asn Leu Lys
        835                 840                 845

Val Arg Phe Ala Gly Val Val Leu Pro Gly Gln Thr Leu Lys Thr Glu
850                 855                 860

Met Trp Lys Glu Gly Asn Thr Val Leu Phe Gln Ala Thr Val Val Glu
865                 870                 875                 880

Thr Gly Lys Pro Ala Ile Thr Gly Ala Gly Ala Glu Leu Leu Glu Gly
                885                 890                 895

Ala Lys Ala Lys Leu
            900

<210> SEQ ID NO 16
<211> LENGTH: 319
<212> TYPE: PRT
<213> ORGANISM: Penicillium chrysogenum

<400> SEQUENCE: 16

Met Leu Asn Ser Thr Leu Arg Phe Val Ser Leu Arg Arg Gly Pro Thr
1               5                   10                  15

Val Ala Arg Asn Phe Cys Ser Thr Ser Ala Val Arg Ala Ala Glu Val
            20                  25                  30

Lys Ser Leu Gly Val Val Gly Ala Gly Gln Met Gly Leu Gly Ile Ala
        35                  40                  45

Leu Val Ala Ala Gln Lys Ala Asn Val Pro Val Thr Leu Val Asp Thr
    50                  55                  60

Ser Gln Ala Ser Leu Asp Lys Gly Leu Lys Phe Ala Asp Lys Leu Leu
65                  70                  75                  80

Glu Lys Asp Val Ala Lys Gln Arg Leu Thr Arg Glu Ala Ala Asp Glu
                85                  90                  95

Ala Arg Gly Leu Ile Ser Thr Ser Leu Thr Leu Asp Gly Leu Ser Ala
            100                 105                 110

Val Asp Phe Val Ile Glu Ala Val Pro Glu Ile Pro Asp Leu Lys Thr
        115                 120                 125

Lys Ile Phe Ala Ser Leu Ala Gln Ile Ala Pro Lys His Ala Ile Leu
    130                 135                 140

Ala Thr Asn Thr Ser Ser Ile Ser Ile Thr Lys Ile Ala Ala Ala Thr
145                 150                 155                 160

Ser Ala Asp Pro Thr Asp Leu Gln Ala Ser Ser Arg Val Ile Ser Thr
                165                 170                 175

```
His Phe Met Asn Pro Val Pro Ile Gln Lys Gly Val Glu Ile Ile Arg
            180                 185                 190

Gly Leu Gln Thr Ser Glu Glu Thr Met Asp Thr Ala Ile Ala Phe Val
        195                 200                 205

Gln Arg Met Gly Lys Val Ala Ser Val Ser Ala Asp Thr Pro Gly Phe
210                 215                 220

Leu Ala Asn Arg Ile Leu Met Pro Tyr Ile Asn Glu Ala Val Ile Cys
225                 230                 235                 240

Leu Glu Thr Gly Val Gly Gln Arg Glu Asp Ile Asp Asn Ile Met Lys
            245                 250                 255

Thr Gly Thr Asn Val Pro Met Gly Pro Leu Val Leu Ala Asp Phe Ile
            260                 265                 270

Gly Leu Asp Thr Cys Leu Ala Ile Met Asn Val Leu His Gln Asp Thr
        275                 280                 285

Gly Asp Ser Lys Tyr Arg Pro Ala Gly Leu Leu Arg Arg Met Val Asp
290                 295                 300

Ala Gly Trp Leu Gly Lys Lys Ser Gly Lys Gly Phe Tyr Asp Tyr
305                 310                 315

<210> SEQ ID NO 17
<211> LENGTH: 335
<212> TYPE: PRT
<213> ORGANISM: Penicillium chrysogenum

<400> SEQUENCE: 17

Met Ala Thr Glu Tyr Pro His Arg Ile Ala Leu Leu Gly Leu Gly Thr
1               5                   10                  15

Ile Gly Leu Ser Met Leu Ala Met His Leu Arg Arg Pro Asp Thr Ser
            20                  25                  30

Ile Thr Val Tyr Asp Pro Arg Pro Asn Tyr Glu Ser Gln Ile Arg Ser
        35                  40                  45

Thr Leu Pro Ser Leu Leu Asp Cys Pro Glu Ser Thr Thr Leu Ile Asp
    50                  55                  60

Asp Leu Leu Arg Thr Ser Arg Leu Lys Leu Ala Ser Thr Val Ala Glu
65                  70                  75                  80

Ala Ile Gln Asn Ala Asn Ile Ile Gln Glu Gln Ser Pro Glu Val Thr
                85                  90                  95

Ala Ser Lys Gln Ala Leu Trp Lys Glu Val Ala Gly Leu Thr Gly Pro
            100                 105                 110

Asp Val His Leu Trp Ser Ser Ser Gly Ile Ser Ala Ser Val Gln
        115                 120                 125

Ala Ser Gly Cys Glu Ala Ala Asp Arg Val Ala Glu Arg Leu Leu Val
    130                 135                 140

Ala His Pro Phe Asn Pro Pro His Leu Met Pro Leu Ile Glu Ile Val
145                 150                 155                 160

Pro Gly Pro Glu Thr Asn Pro Glu Arg Val Glu Phe Val Arg Lys Tyr
                165                 170                 175

Phe Gly Asp Val Pro Gly Pro Arg Ala Ser Gly Gly Asp Gln Ser Ala
            180                 185                 190

Ser Gln His Tyr Arg Pro Ile Thr Leu His Lys Glu Ile Pro Gly Phe
        195                 200                 205

Val Gly Asn Arg Leu Ala Phe Ala Leu Leu Arg Glu Ala Cys Tyr Leu
    210                 215                 220

Val Gly Glu Gly Val Val Ser Ala Lys Asp Leu Asp Ser Leu Val Thr
```

```
                    225                 230                 235                 240

Ala Ser Leu Gly Pro Arg Trp Ala Gly Ser Gly Val Phe Glu Ser Tyr
                245                 250                 255

His Ala Gly Gly Gly Glu Gly Gly Ile Gly Ala Phe Leu Gln Lys Leu
                260                 265                 270

Thr Pro Thr Ile Gln Asp Val Trp Gly Glu Leu Gly Gln Ile Asp Ile
                275                 280                 285

Gln Gly Glu Gln Thr Trp Lys Asp Val Val Lys Gln Thr Glu Asp
        290                 295                 300

Ala Tyr Gly Pro Tyr Thr Pro Glu Thr Arg Lys Lys Lys Glu Met
305                 310                 315                 320

Leu Arg Asp Val Val Glu Leu Gln Lys Lys Lys Trp Gly Glu Leu
                325                 330                 335

<210> SEQ ID NO 18
<211> LENGTH: 505
<212> TYPE: PRT
<213> ORGANISM: Acinetobacter sp.

<400> SEQUENCE: 18

Met Thr His Pro Ile Lys Lys Ile Ala Ile Ile Gly Val Gly Val Met
1               5                   10                  15

Gly Ser Gly Ile Ala Gln Ile Ala Ala Gln Ser Gly His Ile Thr Tyr
                20                  25                  30

Leu Tyr Asp Ala Lys Ala Gly Ala Ala Gln Ala Lys Gln Gln Leu
            35                  40                  45

Ala Ile Thr Phe Gln Lys Leu Leu Asp Lys Asn Lys Ile Thr Thr Glu
        50                  55                  60

Tyr Ala Asp Ala Ala Asn Ala Asn Leu Leu Ile Ala Asn Glu Leu His
65                  70                  75                  80

Asp Leu Lys Asp Cys Asp Leu Ile Val Glu Ala Ile Val Glu Arg Leu
                85                  90                  95

Asp Ile Lys Gln Ser Leu Met Ser Gln Leu Glu Ala Ile Val Pro Glu
            100                 105                 110

Thr Thr Ile Leu Ala Ser Asn Thr Ser Ser Leu Ser Ile Thr Ala Ile
        115                 120                 125

Ala Ser Asn Cys Lys His Pro Glu Arg Val Ala Gly Tyr His Phe Phe
130                 135                 140

Asn Pro Val Pro Leu Met Lys Val Val Glu Val Ile Gln Gly Leu Lys
145                 150                 155                 160

Thr Asp Pro Lys His Ile Glu Thr Leu Asn Gln Leu Ser Arg Val Leu
                165                 170                 175

Gly His Arg Pro Val Val Ala Lys Asp Thr Pro Gly Phe Ile Ile Asn
            180                 185                 190

His Ala Gly Arg Ala Tyr Gly Thr Glu Ala Leu Lys Ile Leu Asn Glu
        195                 200                 205

Asn Val Thr Asp Ile Ser Glu Ile Asp Arg Ile Leu Arg Asp Gly Val
    210                 215                 220

Gly Phe Arg Met Gly Pro Phe Glu Leu Met Asp Leu Thr Gly Leu Asp
225                 230                 235                 240

Val Ser His Pro Val Met Glu Ser Ile Tyr His Gln Tyr Tyr Glu Glu
                245                 250                 255

Ala Arg Tyr Arg Pro Asn Ser Leu Thr Lys Gln Met Leu Glu Ala Lys
            260                 265                 270
```

```
Gln Leu Gly Arg Lys Val Gly Gln Gly Phe Tyr Asp Tyr Arg Thr Gly
            275                 280                 285
Ser Lys Thr Gly Glu Thr Ser Ala Lys Val Ala Glu Arg Leu Thr Leu
        290                 295                 300
Tyr Pro Lys Val Trp Ile Ala Ala Asp Phe Glu Asp Lys Gln Leu
305                 310                 315                 320
Leu Ile Asn Tyr Leu Thr Thr His Asn Ile Gln Leu Asp Val Gly Ala
                325                 330                 335
Lys Pro Gln Ala Asp Ser Leu Cys Leu Ala Cys Tyr Gly Glu Asp
            340                 345                 350
Thr Thr His Ala Ala Leu Arg Leu Asn Val Asn Pro Ala His Ser Val
            355                 360                 365
Ala Ile Asp Met Leu Tyr Gly Ile Glu Lys His Arg Thr Leu Met Pro
370                 375                 380
Ser Leu Ile Thr Glu Val Thr Tyr Ser His Ala Ala His Ser Ile Phe
385                 390                 395                 400
Asn Leu Asp Gly Ala Met Val Ser Thr Ile Gly Glu Ser Ile Gly Phe
                405                 410                 415
Val Ala Gln Arg Ile Leu Ala Met Val Ile Asn Leu Gly Cys Asp Ile
            420                 425                 430
Ala Gln Gln Ala Ile Ala Ser Val Asp Asp Ile Asn Ala Ala Val Arg
        435                 440                 445
Leu Gly Leu Gly Tyr Pro Phe Gly Pro Ile Glu Trp Gly Asp Glu Ile
    450                 455                 460
Gly Ser Asn Lys Ile Leu Leu Ile Leu Asn Arg Ile Thr Ala Leu Thr
465                 470                 475                 480
Ser Asp Pro Arg Tyr Arg Pro Ser Pro Trp Leu Gln Arg Arg Val Ala
                485                 490                 495
Leu Asn Leu Pro Leu Thr Phe Thr Thr
            500                 505

<210> SEQ ID NO 19
<211> LENGTH: 282
<212> TYPE: PRT
<213> ORGANISM: Clostridium kluyveri

<400> SEQUENCE: 19

Met Ser Ile Lys Ser Val Ala Val Leu Gly Ser Gly Thr Met Ser Arg
1               5                   10                  15
Gly Ile Val Gln Ala Phe Ala Glu Ala Gly Ile Asp Val Ile Ile Arg
            20                  25                  30
Gly Arg Thr Glu Gly Ser Ile Gly Lys Gly Leu Ala Ala Val Lys Lys
        35                  40                  45
Ala Tyr Asp Lys Lys Val Ser Lys Gly Lys Ile Ser Gln Glu Asp Ala
    50                  55                  60
Asp Lys Ile Val Gly Arg Val Ser Thr Thr Glu Leu Glu Lys Leu
65                  70                  75                  80
Ala Asp Cys Asp Leu Ile Ile Glu Ala Ala Ser Glu Asp Met Asn Ile
                85                  90                  95
Lys Lys Asp Tyr Phe Gly Lys Leu Glu Glu Ile Cys Lys Pro Glu Thr
            100                 105                 110
Ile Phe Ala Thr Asn Thr Ser Ser Leu Ser Ile Thr Glu Val Ala Thr
        115                 120                 125
Ala Thr Lys Arg Pro Asp Lys Phe Ile Gly Met His Phe Phe Asn Pro
    130                 135                 140
```

Ala Asn Val Met Lys Leu Val Glu Ile Ile Arg Gly Met Asn Thr Ser
145                 150                 155                 160

Gln Glu Thr Phe Asp Ile Ile Lys Glu Ala Ser Ile Lys Ile Gly Lys
                165                 170                 175

Thr Pro Val Glu Val Ala Glu Ala Pro Gly Phe Val Val Asn Lys Ile
            180                 185                 190

Leu Val Pro Met Ile Asn Glu Ala Val Gly Ile Leu Ala Glu Gly Ile
            195                 200                 205

Ala Ser Ala Glu Asp Ile Asp Thr Ala Met Lys Leu Gly Ala Asn His
210                 215                 220

Pro Met Gly Pro Leu Ala Leu Gly Asp Leu Ile Gly Leu Asp Val Val
225                 230                 235                 240

Leu Ala Val Met Asp Val Leu Tyr Ser Glu Thr Gly Asp Ser Lys Tyr
            245                 250                 255

Arg Ala His Thr Leu Leu Arg Lys Tyr Val Arg Ala Gly Trp Leu Gly
                260                 265                 270

Arg Lys Ser Gly Lys Gly Phe Phe Ala Tyr
            275                 280

<210> SEQ ID NO 20
<211> LENGTH: 319
<212> TYPE: PRT
<213> ORGANISM: Clostridium kluyveri

<400> SEQUENCE: 20

Met Asp Ile Lys Asn Val Ala Val Leu Gly Thr Gly Thr Met Gly Asn
1               5                   10                  15

Gly Ile Val Gln Leu Cys Ala Glu Ser Gly Leu Asn Val Asn Met Phe
            20                  25                  30

Gly Arg Thr Asp Ala Ser Leu Glu Arg Gly Phe Thr Ser Ile Lys Thr
        35                  40                  45

Ser Leu Lys Asn Leu Glu Glu Lys Gly Lys Ile Lys Thr Asn Ile Ser
    50                  55                  60

Lys Glu Ile Leu Lys Arg Ile Lys Gly Val Lys Thr Ile Glu Glu Ala
65                  70                  75                  80

Val Glu Gly Val Asp Phe Val Ile Glu Cys Ile Ala Glu Asp Leu Glu
                85                  90                  95

Leu Lys Gln Glu Val Phe Ser Lys Leu Asp Glu Ile Cys Ala Pro Glu
            100                 105                 110

Val Ile Leu Ala Ser Asn Thr Ser Gly Leu Ser Pro Thr Asp Ile Ala
            115                 120                 125

Ile Asn Thr Lys His Pro Glu Arg Val Val Ile Ala His Phe Trp Asn
130                 135                 140

Pro Pro Gln Phe Ile Pro Leu Val Glu Val Val Pro Gly Lys His Thr
145                 150                 155                 160

Asp Ser Lys Thr Val Asp Ile Thr Met Asp Trp Ile Glu His Ile Gly
            165                 170                 175

Lys Lys Gly Val Lys Met Arg Lys Glu Cys Leu Gly Phe Ile Gly Asn
            180                 185                 190

Arg Leu Gln Leu Ala Leu Leu Arg Glu Ala Leu Tyr Ile Val Glu Gln
            195                 200                 205

Gly Phe Ala Thr Ala Glu Glu Val Asp Lys Ala Ile Glu Tyr Gly His
210                 215                 220

Gly Arg Arg Leu Pro Val Thr Gly Pro Ile Cys Ser Ala Asp Leu Gly

```
                225                 230                 235                 240
Gly Leu Asp Ile Phe Asn Asn Ile Ser Ser Tyr Leu Phe Lys Asp Leu
                245                 250                 255

Cys Asn Asp Thr Glu Pro Ser Lys Leu Leu Lys Ser Lys Val Asp Gly
                260                 265                 270

Gly Asn Leu Gly Ser Lys Thr Gly Lys Gly Phe Tyr Asn Trp Thr Pro
                275                 280                 285

Glu Phe Leu Gln Lys Lys Gln Asn Glu Arg Ile Gln Leu Leu Met Asp
                290                 295                 300

Phe Leu Glu Lys Asp Lys Asn Asp Lys Ser Ile Glu Arg Asn Ile
305                 310                 315
```

<210> SEQ ID NO 21
<211> LENGTH: 475
<212> TYPE: PRT
<213> ORGANISM: Escherichia coli

<400> SEQUENCE: 21

```
Met Met Ile Asn Val Gln Thr Val Ala Val Ile Gly Ser Gly Thr Met
1               5                   10                  15

Gly Ala Gly Ile Ala Glu Val Ala Ala Ser His Gly His Gln Val Leu
                20                  25                  30

Leu Tyr Asp Ile Ser Ala Glu Ala Leu Thr Arg Ala Ile Asp Gly Ile
                35                  40                  45

His Ala Arg Leu Asn Ser Arg Val Thr Arg Gly Lys Leu Thr Ala Glu
            50                  55                  60

Thr Cys Glu Arg Thr Leu Lys Arg Leu Ile Pro Val Thr Asp Ile His
65                  70                  75                  80

Ala Leu Ala Ala Ala Asp Leu Val Ile Glu Ala Ala Ser Glu Arg Leu
                85                  90                  95

Glu Val Lys Lys Ala Leu Phe Ala Gln Leu Ala Glu Val Cys Pro Pro
                100                 105                 110

Gln Thr Leu Leu Thr Thr Asn Thr Ser Ser Ile Ser Ile Thr Ala Ile
                115                 120                 125

Ala Ala Glu Ile Lys Asn Pro Glu Arg Val Ala Gly Leu His Phe Phe
            130                 135                 140

Asn Pro Ala Pro Val Met Lys Leu Val Glu Val Val Ser Gly Leu Ala
145                 150                 155                 160

Thr Ala Ala Glu Val Val Glu Gln Leu Cys Glu Leu Thr Leu Ser Trp
                165                 170                 175

Gly Lys Gln Pro Val Arg Cys His Ser Thr Pro Gly Phe Ile Val Asn
                180                 185                 190

Arg Val Ala Arg Pro Tyr Tyr Ser Glu Ala Trp Arg Ala Leu Glu Glu
                195                 200                 205

Gln Val Ala Ala Pro Glu Val Ile Asp Ala Ala Leu Arg Asp Gly Ala
            210                 215                 220

Gly Phe Pro Met Gly Pro Leu Glu Leu Thr Asp Leu Ile Gly Gln Asp
225                 230                 235                 240

Val Asn Phe Ala Val Thr Cys Ser Val Phe Asn Ala Phe Trp Gln Glu
                245                 250                 255

Arg Arg Phe Leu Pro Ser Leu Val Gln Gln Glu Leu Val Ile Gly Gly
                260                 265                 270

Arg Leu Gly Lys Lys Ser Gly Leu Gly Val Tyr Asp Trp Arg Ala Glu
                275                 280                 285
```

-continued

```
Arg Glu Ala Val Val Gly Leu Glu Ala Val Ser Asp Ser Phe Ser Pro
    290                 295                 300

Met Lys Val Glu Lys Lys Ser Asp Gly Val Thr Glu Ile Asp Asp Val
305                 310                 315                 320

Leu Leu Ile Glu Thr Gln Gly Glu Thr Ala Gln Ala Leu Ala Ile Arg
                325                 330                 335

Leu Ala Arg Pro Val Val Ile Asp Lys Met Ala Gly Lys Val Val
            340                 345                 350

Thr Ile Ala Ala Ala Val Asn Pro Asp Ser Ala Thr Arg Lys Ala
        355                 360                 365

Ile Tyr Tyr Leu Gln Gln Gly Lys Thr Val Leu Gln Ile Ala Asp
370                 375                 380

Tyr Pro Gly Met Leu Ile Trp Arg Thr Val Ala Met Ile Ile Asn Glu
385                 390                 395                 400

Ala Leu Asp Ala Leu Gln Lys Gly Val Ala Ser Glu Gln Asp Ile Asp
                405                 410                 415

Thr Ala Met Arg Leu Gly Val Asn Tyr Pro Tyr Gly Pro Leu Ala Trp
            420                 425                 430

Gly Ala Gln Leu Gly Trp Gln Arg Ile Leu Arg Leu Leu Glu Asn Leu
        435                 440                 445

Gln His His Tyr Gly Glu Glu Arg Tyr Arg Pro Cys Ser Leu Leu Arg
    450                 455                 460

Gln Arg Ala Leu Leu Glu Ser Gly Tyr Glu Ser
465                 470                 475

<210> SEQ ID NO 22
<211> LENGTH: 320
<212> TYPE: PRT
<213> ORGANISM: Euglena gracilis

<400> SEQUENCE: 22

Met Met Ser Arg Asn Val Phe Thr Cys Cys Arg Ala Ile Arg Thr Tyr
1               5                   10                  15

Ala Thr Ala Pro Gly Leu Ser Thr Val Gly Val Val Met Gly Ala
            20                  25                  30

Met Gly His Gly Ile Ala Gln Met Thr Ala Ala Gly Tyr Lys Val
        35                  40                  45

Val Ala Val Asp Ile Asp Ala Asn Met Leu Ser Lys Gly Ile Lys Ala
50                  55                  60

Val Glu Asp Ser Leu Ser Lys Val Ala Ala Lys Ala Val Lys Asp Gly
65                  70                  75                  80

Lys Ala Asp Lys Ala Thr Ala Glu Lys Asn Ala Ala Asp Val Arg Ser
                85                  90                  95

Arg Ile Thr Thr Ser Gly Asp Ile Gly Ala Leu Ser Ser Cys Asp Leu
            100                 105                 110

Val Ile Glu Ser Ile Ile Glu Asp Leu Asn Ile Lys Lys Lys Phe Phe
        115                 120                 125

Ala Asp Leu Gly Lys Val Ala Gly Ala Asn Ala Ile Leu Ala Ser Asn
    130                 135                 140

Thr Ser Ser Phe Pro Ile Thr Gln Leu Gly Glu Ala Ser Gly Arg Thr
145                 150                 155                 160

Ser Asn Phe Leu Gly Leu His Phe Phe Asn Pro Val Gln Met Met Lys
                165                 170                 175

Leu Val Glu Val Ile Lys Thr Lys Asp Thr Lys Glu Asp Val Tyr Lys
            180                 185                 190
```

Leu Gly Phe Ala Phe Ser Lys Ser Ile Gly Lys Glu Pro Val Ala Cys
            195                 200                 205

Gly Asp Thr Pro Gly Phe Ile Val Asn Arg Leu Leu Val Pro Phe Leu
210                 215                 220

Ala Gln Gly Leu Leu Met Leu Asp Arg Gly Val Ala Ser Val Gln Asp
225                 230                 235                 240

Ile Asp Val Ala Met Met Tyr Gly Ala Gly Met Pro Met Gly Pro Leu
            245                 250                 255

Thr Leu Ala Asp Tyr Val Gly Leu Asp Val Cys Met His Ile Leu Glu
            260                 265                 270

Gly Trp Thr Ser Gln Tyr Pro Asn Glu Pro Ala Phe Val Ile Pro Gln
            275                 280                 285

Pro Leu Lys Ala Lys Val Ala Ala Gly Lys Leu Gly Arg Lys Thr Gly
            290                 295                 300

Glu Gly Phe Trp Lys Trp Glu Gly Asp Lys Pro Val Ala Pro Ala Ala
305                 310                 315                 320

<210> SEQ ID NO 23
<211> LENGTH: 505
<212> TYPE: PRT
<213> ORGANISM: Pseudomonas putida

<400> SEQUENCE: 23

Met Ala Ala Leu Ala Ser Asn Val Gln Val Ala Val Ile Gly Ala Gly
1               5                   10                  15

Ala Met Gly Ala Gly Ile Ala Gln Val Ala Ala Gln Ala Gly His Pro
            20                  25                  30

Val Lys Leu Tyr Asp Asn Arg Pro Gly Ala Ala Ala Gln Ala Val Thr
        35                  40                  45

Gly Ile Asp Arg Gln Leu Ala Arg Leu Val Asp Lys Gly Lys Leu Leu
    50                  55                  60

Ala Ala Glu Arg Glu Thr Ile Asn Ala Arg Leu Cys Pro Val Asp Thr
65                  70                  75                  80

Leu Glu Ala Leu Ala Asp Ala Gly Leu Val Ile Glu Ala Ile Val Glu
                85                  90                  95

Asn Leu Gln Val Lys Gln Ala Leu Phe Ser Gln Leu Glu Thr Leu Cys
            100                 105                 110

Ala Ala Asp Cys Ile Leu Ala Ser Asn Thr Ser Ser Leu Ser Ile Thr
        115                 120                 125

Ser Leu Ala Ala Gly Leu Glu Arg Pro Gln His Val Val Gly Met His
    130                 135                 140

Phe Phe Asn Pro Ala Pro Leu Met Ala Leu Val Glu Val Val Ser Gly
145                 150                 155                 160

Leu Ala Thr Asp Pro Ala Val Ala Ala Cys Ile Tyr Ala Thr Ala Gln
                165                 170                 175

Ala Trp Gly Lys Gln Pro Val His Ala Arg Ser Thr Pro Gly Phe Ile
            180                 185                 190

Val Asn Arg Val Ala Arg Pro Phe Tyr Ala Glu Ser Leu Arg Leu Leu
        195                 200                 205

Gln Glu Gly Ala Ala Asp Cys Ala Ser Leu Asp Ala Leu Met Arg Asp
    210                 215                 220

Ser Gly Gly Phe Arg Met Gly Ala Phe Glu Leu Thr Asp Leu Ile Gly
225                 230                 235                 240

His Asp Val Asn Tyr Ala Val Thr Cys Ser Val Phe Asp Ala Phe Tyr

```
                    245                 250                 255
Gly Asp Phe Arg Phe Gln Pro Ser Leu Val Gln Lys Glu Leu Val Asp
                260                 265                 270

Ala Gly His Leu Gly Arg Lys Thr Gly Gln Gly Phe Tyr Arg Tyr Ala
            275                 280                 285

Glu Gly Val Glu Arg Pro Gln Pro Ala Glu Leu His Ser Ser Ala Cys
        290                 295                 300

Ala Glu Ala Cys Val Val Glu Gly Asn Leu Gly Val Met Gln Pro Leu
305                 310                 315                 320

Val Glu Arg Leu Arg Gln Ser Gly Ile Ala Val Thr Gln Arg Ala Gly
                325                 330                 335

Ser Gly Leu Ile Gln Val Gly Asp Ala Thr Leu Ala Leu Ser Asp Gly
            340                 345                 350

Arg Leu Ala Ser Gln Arg Ala Arg Glu Asp Gly Leu Arg Asn Leu Val
        355                 360                 365

Leu Leu Asp Leu Ala Leu Asp Tyr Ser Ser Ala Thr Arg Ile Ala Ile
370                 375                 380

Ser Trp Ser Ala Asp Thr Ser Asp Ser Ala Arg Asp Gln Ala Val Ala
385                 390                 395                 400

Leu Leu Gln Arg Ala Gly Leu Lys Val Thr Gly Val Ala Asp Leu Pro
                405                 410                 415

Gly Leu Val Val Leu Arg Thr Val Ala Met Leu Ala Asn Glu Ala Ala
            420                 425                 430

Asp Ala Val Leu Gln Gly Val Gly Ser Ala Ala Asp Ile Asp Leu Ala
        435                 440                 445

Met Arg Ala Gly Val Asn Tyr Pro Cys Gly Pro Leu Ala Trp Ala Ala
    450                 455                 460

Asn Ile Gly Ile Ala His Thr Leu Arg Val Leu Asp Asn Leu Gln Cys
465                 470                 475                 480

Ser Tyr Gly Glu Ser Arg Tyr Arg Pro Ser Leu Leu Leu Arg Arg Cys
                485                 490                 495

Glu Ala Lys Gly Gly Thr Leu His Asp
            500                 505

<210> SEQ ID NO 24
<211> LENGTH: 246
<212> TYPE: PRT
<213> ORGANISM: Cupriavidus necator

<400> SEQUENCE: 24

Met Thr Gln Arg Ile Ala Tyr Val Thr Gly Gly Met Gly Gly Ile Gly
1               5                   10                  15

Thr Ala Ile Cys Gln Arg Leu Ala Lys Asp Gly Phe Arg Val Val Ala
            20                  25                  30

Gly Cys Gly Pro Asn Ser Pro Arg Arg Glu Lys Trp Leu Glu Gln Gln
        35                  40                  45

Lys Ala Leu Gly Phe Asp Phe Ile Ala Ser Glu Gly Asn Val Ala Asp
    50                  55                  60

Trp Asp Ser Thr Lys Thr Ala Phe Asp Lys Val Lys Ser Glu Val Gly
65                  70                  75                  80

Glu Val Asp Val Leu Ile Asn Asn Ala Gly Ile Thr Arg Asp Val Val
                85                  90                  95

Phe Arg Lys Met Thr Arg Ala Asp Trp Asp Ala Val Ile Asp Thr Asn
            100                 105                 110
```

```
Leu Thr Ser Leu Phe Asn Val Thr Lys Gln Val Ile Asp Gly Met Ala
            115                 120                 125

Asp Arg Gly Trp Gly Arg Ile Val Asn Ile Ser Ser Val Asn Gly Gln
        130                 135                 140

Lys Gly Gln Phe Gly Gln Thr Asn Tyr Ser Thr Ala Lys Ala Gly Leu
145                 150                 155                 160

His Gly Phe Thr Met Ala Leu Ala Gln Glu Val Ala Thr Lys Gly Val
                165                 170                 175

Thr Val Asn Thr Val Ser Pro Gly Tyr Ile Ala Thr Asp Met Val Lys
            180                 185                 190

Ala Ile Arg Gln Asp Val Leu Asp Lys Ile Val Ala Thr Ile Pro Val
        195                 200                 205

Lys Arg Leu Gly Leu Pro Glu Glu Ile Ala Ser Ile Cys Ala Trp Leu
210                 215                 220

Ser Ser Glu Glu Ser Gly Phe Ser Thr Gly Ala Asp Phe Ser Leu Asn
225                 230                 235                 240

Gly Gly Leu His Met Gly
                245

<210> SEQ ID NO 25
<211> LENGTH: 284
<212> TYPE: PRT
<213> ORGANISM: Rhodococcus sp.

<400> SEQUENCE: 25

Met Thr Ser Thr Ala Pro Lys Asn Val Gly Val Gly Gly Gly Gly Arg
1               5                   10                  15

Met Gly Ala Gly Ile Ala Gln Val Phe Ala Thr Leu Gly Ser Thr Val
            20                  25                  30

Ile Ile Ala Glu Ser Gly Asp Arg Glu Ala Ala Val Lys Arg Val Ser
        35                  40                  45

Asp Gly Leu Asp Arg Ala His Glu Arg Gly Lys Leu Gly Asp Val Asp
    50                  55                  60

Pro Ala Thr Ile Leu Gly Arg Val Ser Thr Val Ala Ala Pro Asp Ala
65                  70                  75                  80

Leu Pro Pro Ala Leu Asp Leu Val Val Glu Ala Val Pro Glu Leu Val
                85                  90                  95

Asp Leu Lys Leu Ser Val Leu Ser Leu Val Glu Lys Thr Val Ser Pro
            100                 105                 110

Thr Thr Val Ile Ala Ser Asn Thr Ser Ser Ile Ser Ile Ala Glu Leu
        115                 120                 125

Gly Ser Ala Leu Gly Asp Pro Ala Arg Leu Ile Gly Met His Phe Phe
    130                 135                 140

Asn Pro Val Pro Ala Ser Ser Leu Val Glu Ile Val Arg Ala Pro Ala
145                 150                 155                 160

Thr Asp Ala Gly Val Val Glu Lys Val Arg Glu Trp Val Ala Gln Leu
                165                 170                 175

Gly Lys Thr Glu Val Leu Val Asn Asp Ser Pro Gly Phe Ala Thr Ser
            180                 185                 190

Arg Leu Gly Val Cys Leu Gly Leu Glu Ala Ile Arg Met Leu Glu Glu
        195                 200                 205

Gly Val Ala Asp Ala Glu Ser Ile Asp Arg Ala Met Glu Leu Gly Tyr
    210                 215                 220

Arg His Pro Met Gly Pro Leu Arg Ser Thr Asp Leu Val Gly Leu Asp
225                 230                 235                 240
```

```
Val Arg Leu Ala Ile Ala Glu His Leu Ala Lys Thr Leu Gly Asp Arg
            245                 250                 255

Phe Ala Pro Pro Ala Leu Leu Arg Glu Lys Val Ala Lys Gly Glu Leu
        260                 265                 270

Gly Arg Lys Thr Gly Gln Gly Phe Phe Thr Trp Ser
        275                 280

<210> SEQ ID NO 26
<211> LENGTH: 699
<212> TYPE: PRT
<213> ORGANISM: Rhodopseudomonas palustris

<400> SEQUENCE: 26

Met Ser Glu Val Val Thr Arg Ala Thr Gln Asp Gln Val Ala Ile Val
1               5                   10                  15

Thr Val Asp Ser Pro Pro Val Asn Ala Leu Ser Ala Ala Val Arg Arg
            20                  25                  30

Gly Ile Leu Glu Asn Val Asn Ala Ala Val Ala Asp Pro Ala Val Gln
        35                  40                  45

Ala Ile Val Leu Val Cys Ala Gly Arg Thr Phe Ile Ala Gly Ala Asp
50                  55                  60

Ile Thr Glu Phe Gly Lys Pro Pro Gln Pro Pro Ala Leu Asn Asp Val
65              70                  75                  80

Ile Ala Ala Leu Glu Asn Ser Pro Lys Pro Thr Ile Ala Ala Ile His
                85                  90                  95

Gly Thr Ala Leu Gly Gly Gly Leu Glu Val Ala Leu Gly Cys His Phe
            100                 105                 110

Arg Val Ala Val Lys Glu Ala Lys Leu Gly Leu Pro Glu Val Lys Leu
        115                 120                 125

Gly Leu Leu Pro Gly Ala Gly Gly Thr Gln Arg Leu Pro Arg Ala Val
130                 135                 140

Gly Pro Glu Leu Ala Val Gln Met Ile Val Gly Gly Ser Pro Ile Gly
145                 150                 155                 160

Ala Ala Glu Ala Leu Lys His Gly Leu Val Glu Glu Val Val Glu Asn
                165                 170                 175

Leu Val Ala Gly Ala Val Ala Phe Ala Lys Lys Val Leu Ala Glu Lys
            180                 185                 190

Arg Pro Leu Arg Arg Leu Arg Asp Asp Ser Lys Leu Ala Ala Ala
        195                 200                 205

Lys Ala Asp Arg Ser Ile Phe Thr Asn Ala Val Ala Ala Met Thr Lys
210                 215                 220

Lys Ala Arg Gly Leu Glu Ala Pro Phe Ala Cys Ala Asp Ala Ile Gly
225                 230                 235                 240

Ala Ala Ile Asp Leu Pro Phe Glu Glu Gly Leu Lys Lys Glu Arg Glu
                245                 250                 255

Gly Phe Met Lys Leu Val Val Ser Asp Gln Ser Lys Ala Gln Arg Tyr
            260                 265                 270

Ala Phe Phe Ala Glu Arg Glu Ala Ala Lys Val Asp Gly Val Pro Asp
        275                 280                 285

Gly Thr Lys Pro Arg Pro Val Ser Arg Val Ala Ile Ile Gly Ala Gly
290                 295                 300

Thr Met Gly Gly Gly Ile Ala Met Ser Phe Ala Asn Ala Gly Ile Pro
305                 310                 315                 320

Val Thr Leu Ile Glu Thr Gly Glu Glu Gln Leu Lys Arg Gly Leu Gly
```

325                 330                 335
Ile Met Gln Lys Asn Trp Glu Ala Thr Ala Ala Arg Gly Gly Leu Pro
                340                 345                 350
Pro Asp Ala Pro Ala Lys Arg Met Ala Leu Ile Thr Gly Leu Val Gly
            355                 360                 365
Leu Glu Asn Val Lys Asp Ala Asp Leu Ile Ile Glu Ala Val Phe Glu
        370                 375                 380
Thr Met Ala Val Lys Lys Glu Val Phe Thr Ala Val Asp Ala His Ala
385                 390                 395                 400
Lys Pro Gly Ala Val Leu Ala Ser Asn Thr Ser Tyr Leu Ser Ile Asp
                405                 410                 415
Glu Ile Ala Ala Thr Thr Lys Arg Pro Gln Asp Val Leu Gly Met His
            420                 425                 430
Phe Phe Ser Pro Ala Asn Val Met Lys Leu Cys Glu Ile Val Arg Gly
        435                 440                 445
Ala Lys Thr Ala Pro Asp Ala Leu Leu Thr Ala Val Ser Ile Ala Lys
    450                 455                 460
Lys Ile Ala Lys Val Pro Val Val Gly Val Cys Asp Gly Phe Val
465                 470                 475                 480
Gly Asn Arg Met Leu Ala Ala Arg Ser Lys Gln Ser Glu Lys Leu Leu
                485                 490                 495
Phe Glu Gly Ala Leu Pro Gln Gln Val Asp Ala Val Thr Lys Phe
            500                 505                 510
Gly Met Pro Met Gly Pro Phe Ala Met Gly Asp Leu Ala Gly Leu Asp
        515                 520                 525
Ile Gly Trp Arg Ser Arg Lys Asp Arg Gly Ile Lys Ser Glu Ile Ala
    530                 535                 540
Asp Ala Leu Cys Glu Ala Gly Arg Phe Gly Gln Lys Thr Gly Lys Gly
545                 550                 555                 560
Tyr Tyr Lys Tyr Glu Gln Gly Ser Arg Ala Pro Met Pro Asp Pro Glu
                565                 570                 575
Val Glu Thr Leu Ile Asn Asp Thr Leu Ala Lys Leu Gly Leu Lys Arg
            580                 585                 590
Arg Asp Ile Thr Asp Glu Glu Ile Leu Glu Arg Met Val Tyr Pro Met
        595                 600                 605
Ile Asn Glu Gly Ala Arg Ile Leu Glu Glu Lys Ile Ala Ala Arg Pro
    610                 615                 620
Ser Asp Ile Asp Val Val Trp Leu Tyr Gly Tyr Gly Trp Pro Ile Tyr
625                 630                 635                 640
Arg Gly Gly Pro Met His Tyr Ala Asp Ser Val Gly Leu Lys His Ile
                645                 650                 655
Ala Glu Arg Leu Ser Ala Tyr Ala Lys Ala Thr Asn Asp Pro Ser Leu
            660                 665                 670
Glu Pro Ala Pro Leu Leu Ala Arg Leu Ala Ala Glu Gly Lys Thr Phe
        675                 680                 685
Ala Ser Leu Thr Gln Pro Ser Lys Ala Ala Ala
    690                 695

<210> SEQ ID NO 27
<211> LENGTH: 278
<212> TYPE: PRT
<213> ORGANISM: Penicillium chrysogenum

<400> SEQUENCE: 27

```
Met Ser Leu Leu Thr Thr Tyr Thr Thr Gln Asn Thr Thr Lys Ile Ala
1               5                   10                  15

His Leu Thr Ile Ser His Ala Gln Lys Leu Asn Ser Leu Thr Thr Pro
            20                  25                  30

Leu Leu Thr Ser Leu Thr Gln Thr Leu Ser Lys Leu Ser Asn Thr Asn
        35                  40                  45

Leu His Ala Ile Thr Leu Thr Gly Ala Gly Gln Lys Ser Phe Ile Gly
    50                  55                  60

Gly Ala Asp Leu Asn Glu Leu Ser Thr Leu Arg Asn Ala Pro Thr Ala
65                  70                  75                  80

Arg Lys Phe Ile Thr Ser Val His Glu Thr Cys Thr Ala Ile Arg Thr
                85                  90                  95

Cys Pro Val Pro Val Ile Ala Arg Ile Asn Gly Phe Ala Leu Gly Ala
            100                 105                 110

Gly Leu Glu Ile Ala Ala Ala Cys Asp Leu Arg Val Ala Ala Lys Gly
        115                 120                 125

Ala Val Phe Gly Met Pro Glu Val Arg Leu Gly Ile Pro Ser Val Val
    130                 135                 140

Glu Ala Ala Leu Leu Pro Gly Leu Ile Gly Trp Gly Arg Thr Arg Gln
145                 150                 155                 160

Leu Leu Leu Leu Gly Gly Met Ile Ser Ala Ser Glu Ala Leu Arg Trp
                165                 170                 175

Gly Leu Val Glu Arg Val Val Glu Asp Glu Leu Asp Leu Ala Val
        180                 185                 190

Ala Glu Trp Thr Ser Glu Ile Gly Arg Asn Gly Pro Leu Ala Val Arg
    195                 200                 205

Arg Gln Lys Ala Leu Ile Ser Arg Trp Glu Glu Leu Ser Leu Ala Gly
210                 215                 220

Gly Ile Glu Ala Gly Ile Glu Ala Phe Gly Glu Cys Phe Asp Gly Asp
225                 230                 235                 240

Cys Gly Thr Glu Pro Gly Arg Met Ile Gly Glu Phe Phe Arg Glu Lys
                245                 250                 255

Glu Arg Ser Lys Ala Arg Ile Glu Ala Arg Asn Lys Val Val Ala Gly
            260                 265                 270

Ser Lys Gly Glu Glu Gly
        275

<210> SEQ ID NO 28
<211> LENGTH: 244
<212> TYPE: PRT
<213> ORGANISM: Penicillium chrysogenum

<400> SEQUENCE: 28

Met Thr Glu Ile Pro Thr Phe His Asn Leu Ser Leu Glu Arg His Gly
1               5                   10                  15

Asn Val Phe Val Leu Thr Met Gln Lys Pro Glu Asn Arg Leu Asn
            20                  25                  30

Ser Ser Tyr Cys Gln Glu Met Ile Arg Ala Tyr Arg Ser Val Glu Arg
        35                  40                  45

Ile Leu Gly Ser Asp Ser Glu Gly Ala Val Ile Thr Arg Gly Asn Asp
    50                  55                  60

Ala Lys Phe Trp Cys Thr Gly Leu Glu Leu Asp Glu Ser Asp Ser Asn
65                  70                  75                  80

Pro Phe Ala Asn Thr Asp Gly Phe Tyr Pro Leu Ile His Thr Ile Leu
                85                  90                  95
```

```
Asp Phe Pro Phe Pro Thr Val Ala Leu Leu Thr Gly His Thr Phe Gly
            100                 105                 110

Gly Ala Cys Pro Leu Ala Leu Ala His Asp Tyr Arg Ile Met Asn Ser
            115                 120                 125

Arg Arg Gly Phe Ile Ser Met Pro Pro Val Asn Leu Gly Leu His Phe
        130                 135                 140

Asp Gly Ile Gly Ser Leu Pro Arg Leu Lys Leu Arg Pro Gln Val Ala
145                 150                 155                 160

Arg Lys Met Leu Leu Glu Ala His Arg Trp Thr Gly Pro Glu Ala Leu
                165                 170                 175

Glu Asp Gly Ile Val Asp Ala Val Ala Glu Pro Glu Asp Met Leu Asn
            180                 185                 190

Val Ala Leu Glu Leu Gly Ala Lys Trp Ala Pro Lys Ala Lys Met Gly
        195                 200                 205

Val Tyr Ala Leu Leu Arg Gln Glu Leu Trp Gly Asp Ala Ile Lys Lys
    210                 215                 220

Phe Gln Arg Ile Ser Tyr Val His Ser Arg Val Thr Ser Ala Pro Ala
225                 230                 235                 240

Lys Val Lys Ile

<210> SEQ ID NO 29
<211> LENGTH: 300
<212> TYPE: PRT
<213> ORGANISM: Penicillium chrysogenum

<400> SEQUENCE: 29

Met Ala Pro Ser Asp Arg Leu Thr Gln Val Asn Glu His Leu Asn Tyr
1               5                   10                  15

Pro Ala Gly Leu Leu Ala Gly Gln Val Ala Ile Ile Thr Gly Ala Gly
            20                  25                  30

Gln Gly Ile Gly Ala Glu Ala Ala Arg Leu Phe Ala Asn Glu Gly Ala
        35                  40                  45

Lys Val Val Val Ala Asp Ile Asp Ser Lys Lys Ala Asn Ala Val Ala
    50                  55                  60

Asp Ala Ile Asn Ser Ala Lys Ala Gly Arg Ala Leu Ala Val Val Gly
65                  70                  75                  80

Asp Val Leu Asp Ser Asn Tyr Ile Thr Glu Leu Val Lys Lys Thr Ala
                85                  90                  95

Glu Phe Gly Asn Gly Lys Ile His Ile Ile Val Asn Asn Ala Gly Phe
            100                 105                 110

Thr Trp Asp Gly Val Ile His Lys Met Thr Asp Lys Gln Trp Glu Thr
        115                 120                 125

Met Leu Ala Val His Asn Thr Ala Pro Phe Gln Leu Val Arg Ala Ala
    130                 135                 140

Ala Pro Tyr Phe Arg Val Lys Asp Gln Glu Pro Arg Val Val Ile Asn
145                 150                 155                 160

Ile Ser Ser Thr Ser Gly Val His Gly Asn Ala Gly Gln Ala Asn Tyr
                165                 170                 175

Ala Val Ala Lys Ala Gly Val Val Gly Leu Thr Arg Thr Ile Ala Lys
            180                 185                 190

Glu Trp Gly Pro Ser Phe Gly Val Arg Ser Asn Thr Ile Ala Phe Gly
        195                 200                 205

Phe Val Thr Thr Arg Leu Thr Ala Ala Lys Glu Glu Gly Ala Phe Ile
    210                 215                 220
```

```
Thr Thr Pro Asp Gly Thr Lys Val Ala Leu Gly Ile Pro Gly Lys Gln
225                 230                 235                 240

Leu Ala Thr Lys Lys Gly Ser Ala Asp Gln Glu Lys Lys Ala Ala Pro
            245                 250                 255

Thr Tyr Pro Asp Ile Pro Leu Gly Arg Pro Ala Thr Pro Glu Glu Ala
        260                 265                 270

Ala Arg Ala Val Leu Gly Val Ala Ser Pro Trp Phe Ser Tyr Val Asn
        275                 280                 285

Gly Glu Thr Ile Arg Val Thr Gly Gly Arg Asn Met
        290                 295                 300

<210> SEQ ID NO 30
<211> LENGTH: 327
<212> TYPE: PRT
<213> ORGANISM: Penicillium chrysogenum

<400> SEQUENCE: 30

Met Ser Ala Pro Gly Ala Gly His Glu Phe Pro Ala Gln Glu Val Ser
1               5                   10                  15

Trp Gln Lys Arg Asp Val Leu Leu Phe Ala Asn Ser Ile Gly Val Lys
            20                  25                  30

Ala Asp Glu Leu His Phe Leu Tyr Glu Leu His Pro Asn Phe Ala Val
        35                  40                  45

Phe Pro Thr Tyr Ser Leu Ile Leu Arg Met Ser Lys Asn Thr Ser Asp
    50                  55                  60

Phe Arg Thr Ile Ala Leu Thr Pro Lys Pro Leu Ala Phe Lys Leu Thr
65                  70                  75                  80

Asp Gln Glu Val Thr Asp Phe Tyr Ala Arg Gln Lys Ala Val His Ile
                85                  90                  95

Pro Gly Val Pro Asp Leu Asp His Arg His Gly Val Asp Gly Gln Arg
            100                 105                 110

Lys Ile Thr Ile Leu Lys Pro Leu Pro Thr Thr Ser Ala Gly Arg Lys
        115                 120                 125

Phe Glu Leu Arg Asn Lys Val Ile Gly Val Tyr Asp Lys Gly Lys Pro
    130                 135                 140

Gly Thr Val Ile Glu Thr Glu Gln Ser Ile Val Asp Lys Glu Ser Gly
145                 150                 155                 160

Glu Val Tyr Ser Lys Val Val Ser Ser Gly Phe Leu Val Gly Gln Gly
                165                 170                 175

Gly Trp Gly Gly Pro Lys Gly Ser Thr Val Asn Tyr Ala Pro Pro
            180                 185                 190

Glu Gly Arg Ala Pro Asp Ala Thr His Val Val Gln Ser Asn Ser Glu
        195                 200                 205

Thr Ala His Leu Tyr Arg Leu Asn Gly Asp Tyr Asn Pro Leu His Ala
    210                 215                 220

Thr Pro Glu Pro Gly Gln Lys Met Gly Phe Gly Gly Ile Ile His
225                 230                 235                 240

Gly Leu Phe Ser Trp Asn Ser Ala Ala His Gly Ile Leu Arg Glu Phe
                245                 250                 255

Gly Gly Ser Asn Pro Ala Asn Met Lys Glu Phe Gln Ala Arg Phe Ala
            260                 265                 270

Ser Pro Val Arg Pro Gly Asp Lys Leu Thr Thr Glu Ile Trp Arg Met
        275                 280                 285

Gly Asn Ile Gln Asp Gly Tyr Glu Glu Ile Arg Phe Val Thr Lys Asn
```

```
              290                 295                 300
Asp Lys Gly Arg Val Val Leu Ser Asn Gly Arg Cys Leu Leu Lys Val
305                 310                 315                 320

Thr Gly Val Lys Ser Lys Leu
                325

<210> SEQ ID NO 31
<211> LENGTH: 901
<212> TYPE: PRT
<213> ORGANISM: Penicillium chrysogenum

<400> SEQUENCE: 31

Met Ser Glu Leu Arg Phe Asp Asn Gln Thr Val Val Thr Gly Ala
1               5                   10                  15

Gly Gly Gly Leu Gly Lys Ala Tyr Ala Leu Phe Phe Ala Ser Arg Gly
                20                  25                  30

Ala Asn Val Val Asn Asp Leu Gly Ala Ser His Lys Gly Glu Gly
                35                  40                  45

Lys Ser Gly Lys Ala Ala Asp Val Val Glu Glu Ile Arg Ala Ala
50                  55                  60

Gly Gly Lys Ala Val Ala Asn Tyr Asp Ser Val Glu Asn Gly Asp Ala
65                  70                  75                  80

Ile Ile Glu Thr Ala Ile Lys Ala Phe Gly Arg Ile Asp Ile Leu Leu
                85                  90                  95

Asn Asn Ala Gly Ile Leu Arg Asp Ile Ser Phe Lys Asn Met Lys Asp
                100                 105                 110

Ala Asp Trp Asp Leu Ile Asn Arg Val His Thr Tyr Gly Ala Tyr Lys
                115                 120                 125

Cys Ala Arg Ala Ala Trp Pro His Phe Arg Lys Gln Lys Phe Gly Arg
130                 135                 140

Val Ile Asn Thr Ala Ser Ala Ala Gly Leu Phe Gly Ser Phe Gly Gln
145                 150                 155                 160

Ala Asn Tyr Ser Ala Ala Lys Leu Gly Gln Val Gly Phe Thr Glu Thr
                165                 170                 175

Leu Ala Lys Glu Gly Ala Lys Tyr Asn Ile Ile Ala Asn Val Ile Ala
                180                 185                 190

Pro Ile Ala Ala Ser Arg Met Thr Ala Thr Val Met Pro Pro Asp Val
                195                 200                 205

Leu Glu Asn Leu Lys Pro Asp Trp Val Val Pro Leu Val Ala Ala Leu
                210                 215                 220

Val His Ser Ser Asn Thr Thr Glu Thr Gly Gly Ile Tyr Glu Val Gly
225                 230                 235                 240

Gly Gly His Val Ala Lys Leu Arg Trp Glu Arg Ala Lys Gly Ala Leu
                245                 250                 255

Leu Lys Thr Asp Asp Ser Leu Thr Pro Gly Ala Ile Ala Arg Lys Trp
                260                 265                 270

Asn Asp Val Asn Asp Phe Ser Gln Pro Glu Tyr Pro Thr Gly Pro Ala
                275                 280                 285

Asp Phe Met Ala Phe Leu Glu Asp Gly Leu Lys Thr Pro Ser Ala Gln
                290                 295                 300

Pro Gly Gln Glu Pro Asp Phe Lys Gly Arg Val Ala Leu Val Thr Gly
305                 310                 315                 320

Gly Gly Ala Gly Leu Gly Arg Ala Tyr Cys Leu Gln Phe Ala Lys Leu
                325                 330                 335
```

```
Gly Ala Ser Val Val Asn Asp Leu Val Asp Pro Glu Pro Val Val
            340                 345                 350
Gln Glu Ile Lys Lys Leu Gly Gly Lys Ala Val Gly Asn Lys Ala Ser
        355                 360                 365
Cys Glu Asp Gly Asp Ala Val Val Lys Ser Ala Ile Asp Ala Phe Gly
        370                 375                 380
Arg Ile Asp Ile Leu Val Asn Asn Ala Gly Ile Leu Arg Asp Lys Ala
385                 390                 395                 400
Phe Thr Asn Met Asp Asp Asn Leu Trp Asn Ser Val Val Asn Val His
                405                 410                 415
Leu Arg Gly Thr Tyr Lys Val Thr Lys Ala Ala Trp Pro Tyr Phe Leu
        420                 425                 430
Lys Gln Lys Tyr Gly Arg Val Val Asn Thr Ala Ser Thr Ser Gly Ile
        435                 440                 445
Tyr Gly Asn Phe Gly Gln Ala Asn Tyr Ala Ala Ala Lys Leu Gly Ile
        450                 455                 460
Leu Gly Leu Ser Arg Thr Leu Ala Leu Glu Gly Ala Lys Tyr Asn Ile
465                 470                 475                 480
Lys Val Asn Thr Ile Ala Pro Asn Ala Gly Thr Asn Met Thr Arg Thr
                485                 490                 495
Ile Met Pro Glu Glu Met Val Gln Ala Phe Lys Pro Asp Tyr Val Ala
                500                 505                 510
Pro Leu Val Val Leu Leu Cys Ser Asp Met Ala Pro Glu Pro Ser Thr
        515                 520                 525
Lys Gly Leu Phe Glu Cys Gly Ser Gly Trp Phe Gly Arg Thr Arg Trp
        530                 535                 540
Gln Arg Thr Gly Gly His Gly Phe Pro Val Asp Val Lys Leu Thr Pro
545                 550                 555                 560
Glu Glu Val Val Arg Asn Trp Lys Gln Ile Ile Asn Phe Asp Asp Gly
                565                 570                 575
Arg Ala Asp His Pro Glu Asp Gly Gln Ala Gly Ala Glu Lys Ile Met
                580                 585                 590
Ala Asn Met Ser Asn Arg Val His Gly Asp Thr Ser Thr Glu Asn Glu
                595                 600                 605
Thr Leu Lys Asn Ile Lys Lys Ala Lys Ala Leu Ser Ser Glu Gly Thr
        610                 615                 620
Pro Phe Asn Tyr Glu Asp Arg Asp Val Ile Leu Tyr Asn Leu Ser Leu
625                 630                 635                 640
Gly Ala Lys Arg Thr Asp Leu Pro Leu Val Tyr Glu Asn Asn Asp Gln
                645                 650                 655
Phe Gln Ala Leu Pro Ser Tyr Gly Val Val Pro Trp Phe Asn Thr Ala
                660                 665                 670
Thr Pro Trp Asn Met Asp Asp Leu Val Lys Asp Phe Ser Pro Met Met
        675                 680                 685
Leu Leu His Gly Glu Gln Tyr Met Glu Val Arg Lys Phe Pro Ile Pro
        690                 695                 700
Thr Thr Ala Asn Thr Leu Thr Tyr Pro Lys Leu Ile Asp Val Ile Asp
705                 710                 715                 720
Lys Gly Asn Ala Ala Ile Val Val Ala Gly Tyr Thr Thr Lys Asp Ala
                725                 730                 735
Lys Thr Gly Glu Asp Leu Phe Tyr Asn Glu Ser Ser Val Phe Ile Arg
        740                 745                 750
Gly Ser Gly Gly Phe Gly Gly Ser Pro Lys Pro Thr Ala Val Arg Pro
```

```
            755                 760                 765
Lys Ala Ala Thr Ala Ala Tyr Lys Ala Pro Gln Arg Gln Pro Asp Ala
    770                 775                 780

Val Val Glu Lys Thr Ser Glu Asp Gln Ala Ala Leu Tyr Arg Leu
785                 790                 795                 800

Asn Gly Asp Arg Asn Pro Leu His Ile Asp Pro Glu Phe Ser Lys Val
                805                 810                 815

Gly Gly Phe Lys Thr Pro Ile Leu His Gly Leu Cys Ser Leu Gly Val
            820                 825                 830

Ser Ala Lys Ala Val Phe Ser Lys Tyr Gly Pro Tyr Lys Asn Leu Lys
            835                 840                 845

Val Arg Phe Ala Gly Val Val Leu Pro Gly Gln Thr Leu Lys Thr Glu
            850                 855                 860

Met Trp Lys Glu Gly Asn Thr Val Leu Phe Gln Ala Thr Val Val Glu
865                 870                 875                 880

Thr Gly Lys Pro Ala Ile Thr Gly Ala Gly Ala Glu Leu Leu Glu Gly
                885                 890                 895

Ala Lys Ala Lys Leu
                900

<210> SEQ ID NO 32
<211> LENGTH: 293
<212> TYPE: PRT
<213> ORGANISM: Penicillium chrysogenum

<400> SEQUENCE: 32

Met Phe Ala Arg Gln Cys Thr Arg Leu Ala Thr Ser Arg Thr Ser Ala
1               5                   10                  15

Pro Leu Thr Ser Tyr Leu Ala Arg Val Arg Gly Tyr Ser Ser Ala Ala
                20                  25                  30

Gly Ser Tyr Glu His Ile Leu Thr Ser Thr Pro Lys Pro Gly Val Gly
            35                  40                  45

Leu Ile Thr Leu Asn Arg Pro Lys Ala Leu Asn Ala Leu Cys Ser Pro
    50                  55                  60

Leu Phe Lys Glu Leu Asn Glu Ala Leu Ser Asn Tyr Asp Asn Asp Lys
65                  70                  75                  80

Ser Ile Gly Ala Ile Ile Ile Thr Gly Ser Glu Lys Ala Phe Ala Ala
                85                  90                  95

Gly Ala Asp Ile Lys Glu Met Ala Pro Leu Ser Phe Ser Ala Ala Tyr
            100                 105                 110

Ser Asp Asn Phe Ile Ala Pro Trp Ser His Leu Ala Thr Ser Ile Arg
        115                 120                 125

Thr Pro Val Ile Ala Ala Val Ser Gly Tyr Ala Leu Gly Gly Gly Cys
    130                 135                 140

Glu Leu Ala Leu Met Cys Asp Ile Leu Tyr Cys Ser Glu Asn Ala Thr
145                 150                 155                 160

Phe Gly Gln Pro Glu Ile Lys Leu Gly Thr Ile Pro Gly Ala Gly Gly
                165                 170                 175

Ser Gln Arg Leu Thr Arg Ala Ile Gly Lys Ser Lys Ala Met Glu Leu
            180                 185                 190

Ile Leu Thr Gly Lys Asn Phe Ser Gly Lys Glu Ala Gly Glu Trp Gly
        195                 200                 205

Val Ala Ala Lys Val Val Pro Gly Gly Lys Glu Glu Leu Leu Glu Gln
    210                 215                 220
```

```
Ala Tyr Lys Thr Ala Glu Thr Ile Ala Ser Tyr Ser Arg Val Ala Val
225                 230                 235                 240

Val Ala Gly Lys Glu Val Val Asn Lys Ser Gln Glu Leu Ser Leu Lys
            245                 250                 255

Glu Gly Val Glu Tyr Glu Arg Arg Leu Phe His Ala Leu Phe Gly Ser
                260                 265                 270

Lys Asp Gln Lys Ile Gly Met Thr Ala Phe Glu Lys Lys Lys Pro
            275                 280                 285

Glu Trp Ser His Glu
            290
```

```
<210> SEQ ID NO 33
<211> LENGTH: 261
<212> TYPE: PRT
<213> ORGANISM: Acinetobacter sp.

<400> SEQUENCE: 33

Met Ile Pro Asp Gln Asp Asn Phe Val Glu Ile Asp Phe Ser Ile Glu
1               5                   10                  15

Gln Ile Ala Ile Val Lys Ile Asn Arg Pro Ala Ser Lys Asn Ala Leu
            20                  25                  30

Asn Thr Glu Val Arg Lys Gln Leu Ala Gln Ala Phe Thr Glu Leu Ser
        35                  40                  45

Phe Asn Asp Gln Ile Asn Ala Ile Val Leu Thr Gly Gly Glu Asp Val
    50                  55                  60

Phe Ala Ala Gly Ala Asp Leu Lys Glu Met Ala Thr Ala Ser Ser Thr
65                  70                  75                  80

Asp Met Leu Leu Arg His Thr Glu Arg Tyr Trp Asn Ala Ile Ala Gln
                85                  90                  95

Cys Pro Lys Pro Val Ile Ala Ala Val Asn Gly Tyr Ala Leu Gly Gly
            100                 105                 110

Gly Cys Glu Leu Ala Met His Thr Asp Ile Ile Ile Ala Gly Lys Ser
        115                 120                 125

Ala Thr Phe Gly Gln Pro Glu Ile Lys Val Gly Leu Met Pro Gly Ala
    130                 135                 140

Gly Gly Thr Gln Arg Leu Phe Arg Ala Val Gly Lys Phe His Ala Met
145                 150                 155                 160

Arg Met Ile Met Thr Gly Val Met Val Pro Ala Glu Glu Ala Tyr Leu
                165                 170                 175

Ile Gly Leu Val Ser Gln Val Thr Glu Asp Ser Gln Thr Ile Pro Thr
            180                 185                 190

Ala Ile Lys Met Ala Gln Ser Leu Ala Lys Met Pro Pro Ile Ala Leu
        195                 200                 205

Gln Gln Ile Lys Glu Val Ala Leu Met Ser Glu Asp Val Pro Leu Asn
    210                 215                 220

Ala Gly Leu Thr Leu Glu Arg Lys Ser Phe Gln Leu Leu Phe Ser Thr
225                 230                 235                 240

Glu Asp Lys Asn Glu Gly Ile Asn Ala Phe Ile Glu Lys Arg Lys Pro
                245                 250                 255

Ser Tyr His Gly Lys
            260
```

```
<210> SEQ ID NO 34
<211> LENGTH: 136
<212> TYPE: PRT
<213> ORGANISM: Aeromonas salmonicida
```

<400> SEQUENCE: 34

```
Met Asn Thr Leu Pro Leu Glu Ile Gly Gln Lys Ala Ser Leu Thr Lys
1               5                  10                  15
Arg Phe Gly Ala Ala Glu Val Glu Ala Phe Ala Gly Leu Ser Glu Asp
            20                  25                  30
Phe Asn Pro Leu His Leu Asp Ser Ala Phe Ala Thr Thr Pro Phe
        35                  40                  45
Glu Arg Pro Ile Val His Gly Met Leu Leu Ala Ser Leu Phe Ser Gly
    50                  55                  60
Leu Leu Gly Gln Gln Leu Pro Gly Lys Gly Thr Val Tyr Leu Gly Gln
65                  70                  75                  80
Ser Leu Ser Phe Lys Gln Pro Val Phe Val Gly Asp Glu Val Thr Ala
                85                  90                  95
Glu Val Glu Ile Ile Ala Met Arg Ser Asp Lys Pro Ile Ile Thr Leu
            100                 105                 110
Ala Thr Arg Ile Leu Ala Ala Gly Gly Ala Leu Ala Leu Ala Val Thr
        115                 120                 125
Gly Glu Ala Val Val Lys Val Gly
    130                 135
```

<210> SEQ ID NO 35
<211> LENGTH: 259
<212> TYPE: PRT
<213> ORGANISM: Clostridium kluyveri

<400> SEQUENCE: 35

```
Met Glu Phe Lys Asn Ile Ile Leu Glu Lys Asp Gly Asn Val Ala Ser
1               5                  10                  15
Ile Thr Leu Asn Arg Pro Lys Ala Leu Asn Ala Leu Asn Ala Ala Thr
            20                  25                  30
Leu Lys Glu Ile Asp Ala Ala Ile Asn Asp Ile Ala Glu Asp Asp Asn
        35                  40                  45
Val Tyr Ala Val Ile Ile Thr Gly Ser Gly Lys Ala Phe Val Ala Gly
    50                  55                  60
Ala Asp Ile Ala Glu Met Lys Asp Leu Thr Ala Val Glu Gly Arg Lys
65                  70                  75                  80
Phe Ser Val Leu Gly Asn Lys Ile Phe Arg Lys Leu Glu Asn Leu Glu
                85                  90                  95
Lys Pro Val Ile Ala Ala Ile Asn Gly Phe Ala Leu Gly Gly Gly Cys
            100                 105                 110
Glu Leu Ser Leu Ser Cys Asp Ile Arg Ile Ala Ser Ser Lys Ala Lys
        115                 120                 125
Phe Gly Gln Pro Glu Val Gly Leu Gly Ile Thr Pro Gly Phe Gly Gly
    130                 135                 140
Thr Gln Arg Leu Ala Arg Ala Ile Gly Val Gly Met Ala Lys Glu Leu
145                 150                 155                 160
Ile Tyr Thr Gly Lys Val Ile Asn Ala Glu Glu Ala Leu Arg Ile Gly
                165                 170                 175
Leu Val Asn Lys Val Val Glu Pro Asp Lys Leu Leu Glu Glu Ala Lys
            180                 185                 190
Ala Leu Val Asp Ala Ile Ile Val Asn Ala Pro Ile Ala Val Arg Met
        195                 200                 205
Cys Lys Ala Ala Ile Asn Gln Gly Leu Gln Cys Asp Ile Asp Thr Gly
    210                 215                 220
```

```
Val Ala Tyr Glu Ala Glu Val Phe Gly Glu Cys Phe Ala Thr Glu Asp
225                 230                 235                 240

Arg Val Glu Gly Met Thr Ala Phe Val Glu Lys Arg Asp Lys Ala Phe
                245                 250                 255

Lys Asn Lys

<210> SEQ ID NO 36
<211> LENGTH: 257
<212> TYPE: PRT
<213> ORGANISM: Clostridium kluyveri

<400> SEQUENCE: 36

Met Thr Tyr Lys Thr Leu Leu Glu Lys Gln Asn Gly Ile Thr Ile
1               5                   10                  15

Ile Lys Met Asn Thr Pro His Asn Leu Asn Ala Ile Ser Gln Gln Ser
                20                  25                  30

Val Glu Asp Leu Phe Ala Val Leu Gln Val Ile Lys Asn Asp Asp Asn
            35                  40                  45

Cys Arg Val Val Ile Leu Thr Gly Glu Gly Lys Gly Phe Ile Gly Gly
    50                  55                  60

Ala Asp Ile Lys His Met Ala Cys Leu Asp Ala Ile Glu Gly Gly Gln
65                  70                  75                  80

Phe Cys Phe Ala Val Ser Lys Cys Thr Leu Glu Met Glu Lys Met Gly
                85                  90                  95

Lys Val Phe Ile Ala Ala Val Asn Gly Phe Ala Leu Gly Ala Gly Leu
                100                 105                 110

Glu Val Ala Leu Gly Cys Asp Ile Arg Ile Phe Ser Lys His Ala Lys
            115                 120                 125

Ile Gly Phe Pro Glu Thr Gly Leu Gly Val Ile Pro Gly Ala Gly Gly
    130                 135                 140

Ala Gln Arg Leu Gln Arg Leu Val Gly Ile Gly Lys Ala Ser Glu Ile
145                 150                 155                 160

Ile Phe Thr Gly Asp Ile Ile Gly Ala Asp Asp Ala Leu Arg Phe Gly
                165                 170                 175

Ile Ala Asn Gln Val Thr Glu Pro Glu Ser Leu Met Asp Thr Ala Met
                180                 185                 190

Ser Met Ala Glu Lys Ile Leu Thr Lys Ser Pro Val Gly Thr Arg Leu
            195                 200                 205

Ala Lys Glu Ala Leu Gln Lys Gly Arg Asp Thr Asp Leu Glu Lys Ala
    210                 215                 220

Leu Glu Tyr Asp Lys Asn Leu Phe Gly Leu Cys Phe Ser Thr Glu Asp
225                 230                 235                 240

Lys Lys Glu Gly Met Ala Ala Phe Ile Glu Lys Arg Lys Pro Val Phe
                245                 250                 255

Lys

<210> SEQ ID NO 37
<211> LENGTH: 255
<212> TYPE: PRT
<213> ORGANISM: Escherichia coli

<400> SEQUENCE: 37

Met Ser Glu Leu Ile Val Ser Arg Gln Gln Arg Val Leu Leu Leu Thr
1               5                   10                  15

Leu Asn Arg Pro Ala Ala Arg Asn Ala Leu Asn Asn Ala Leu Leu Met
```

```
            20                  25                  30
Gln Leu Val Asn Glu Leu Glu Ala Ala Thr Asp Thr Ser Ile Ser
            35                  40                  45

Val Cys Val Ile Thr Gly Asn Ala Arg Phe Phe Ala Gly Ala Asp
 50                  55                  60

Leu Asn Glu Met Ala Glu Lys Asp Leu Ala Ala Thr Leu Asn Asp Thr
 65                  70                  75                  80

Arg Pro Gln Leu Trp Ala Arg Leu Gln Ala Phe Asn Lys Pro Leu Ile
                85                  90                  95

Ala Ala Val Asn Gly Tyr Ala Leu Gly Ala Gly Cys Glu Leu Ala Leu
                100                 105                 110

Leu Cys Asp Val Val Ala Gly Glu Asn Ala Arg Phe Gly Leu Pro
                115                 120                 125

Glu Ile Thr Leu Gly Ile Met Pro Gly Ala Gly Gly Thr Gln Arg Leu
                130                 135                 140

Ile Arg Ser Val Gly Lys Ser Leu Ala Ser Lys Met Val Leu Ser Gly
145                 150                 155                 160

Glu Ser Ile Thr Ala Gln Gln Ala Gln Ala Gly Leu Val Ser Asp
                165                 170                 175

Val Phe Pro Ser Asp Leu Thr Leu Glu Tyr Ala Leu Gln Leu Ala Ser
                180                 185                 190

Lys Met Ala Arg His Ser Pro Leu Ala Leu Gln Ala Ala Lys Gln Ala
                195                 200                 205

Leu Arg Gln Ser Gln Glu Val Ala Leu Gln Ala Gly Leu Ala Gln Glu
                210                 215                 220

Arg Gln Leu Phe Thr Leu Leu Ala Ala Thr Glu Asp Arg His Glu Gly
225                 230                 235                 240

Ile Ser Ala Phe Leu Gln Lys Arg Thr Pro Asp Phe Lys Gly Arg
                245                 250                 255

<210> SEQ ID NO 38
<211> LENGTH: 257
<212> TYPE: PRT
<213> ORGANISM: Pseudomonas putida

<400> SEQUENCE: 38

Met Pro Arg Tyr Leu Asp Val Gln Ala Pro Glu Asn Gly Val Gln Leu
 1               5                  10                  15

Ile Thr Leu Gln Arg Pro Glu Ala Leu Asn Ala Leu Cys Thr Glu Leu
                20                  25                  30

Leu Ala Glu Leu Ala Thr Ala Leu Asp Ala Ala Ala Arg Asp Asp Gln
                35                  40                  45

Ile Gly Val Val Val Leu Thr Gly Ser Arg Lys Ala Phe Ala Ala Gly
 50                  55                  60

Ala Asp Ile Arg Glu Met Ala Glu Arg Asp Leu Val Gly Ile Leu Asn
 65                  70                  75                  80

Asp Pro Arg Val Ala His Trp Gln Arg Ile Ala Ala Phe Ala Lys Pro
                85                  90                  95

Leu Ile Ala Ala Val Asn Gly Tyr Ala Leu Gly Gly Gly Cys Glu Leu
                100                 105                 110

Val Met Cys Ala Asp Ile Val Ile Ala Gly Ser Asp Ala Arg Phe Gly
                115                 120                 125

Gln Pro Glu Ile Asn Leu Gly Ile Ile Pro Gly Ala Gly Gly Thr Gln
                130                 135                 140
```

Arg Leu Leu Arg Ala Val Gly Lys Pro Leu Ala Met Gln Met Val Leu
145                 150                 155                 160

Thr Gly Glu Ala Ile Thr Ala Arg His Ala Gln Gln Ala Gly Leu Val
                165                 170                 175

Ser Glu Ile Thr Gln Pro Glu Phe Thr Val Glu Arg Ala Met Gln Ile
            180                 185                 190

Ala Arg Asn Ile Ala Ala Lys Ala Pro Leu Ala Val Arg Leu Ala Lys
        195                 200                 205

Glu Ala Leu Leu Lys Ala Gly Asp Thr Asp Leu Ala Ser Gly Leu Arg
210                 215                 220

Phe Glu Arg His Ala Phe Thr Leu Leu Ala Gly Thr Ala Asp Arg Asp
225                 230                 235                 240

Glu Gly Ile Gln Ala Phe Gln Glu Lys Arg Pro Ala Arg Phe Gln Gly
                245                 250                 255

Arg

<210> SEQ ID NO 39
<211> LENGTH: 263
<212> TYPE: PRT
<213> ORGANISM: Pseudomonas putida

<400> SEQUENCE: 39

Met Thr Phe Gln His Ile Leu Phe Ser Ile Glu Asp Gly Val Ala Phe
1               5                   10                  15

Leu Ser Leu Asn Arg Pro Glu Gln Leu Asn Ser Phe Asn Ala Ala Met
                20                  25                  30

His Leu Glu Val Arg Glu Ala Leu Lys Gln Val Arg Gln Ser Ser Asp
            35                  40                  45

Ala Arg Val Leu Leu Leu Thr Ala Glu Gly Arg Gly Phe Cys Ala Gly
        50                  55                  60

Gln Asp Leu Ser Asp Arg Asn Val Ala Pro Ala Glu Val Pro Asp
65                  70                  75                  80

Leu Gly Glu Ser Ile Asp Lys Phe Tyr Asn Pro Leu Val Arg Thr Leu
                85                  90                  95

Arg Asp Leu Pro Leu Pro Val Ile Cys Ala Val Asn Gly Val Ala Ala
            100                 105                 110

Gly Ala Gly Ala Asn Ile Pro Leu Ala Cys Asp Leu Val Leu Ala Gly
        115                 120                 125

Arg Ser Ala Ser Phe Ile Gln Ala Phe Cys Lys Ile Gly Leu Val Pro
130                 135                 140

Asp Ser Gly Gly Thr Trp Leu Leu Pro Arg Leu Val Gly Met Ala Arg
145                 150                 155                 160

Ala Lys Ala Leu Ala Met Leu Gly Glu Arg Leu Gly Ala Glu Gln Ala
                165                 170                 175

Gln Gln Trp Gly Leu Ile His Arg Val Val Asp Ala Ala Leu Arg
            180                 185                 190

Asp Glu Ala Leu Thr Leu Ala Arg Gln Leu Ala Ser Gln Pro Thr Tyr
        195                 200                 205

Gly Leu Ala Leu Ile Lys Arg Ser Leu Asn Ala Ser Phe Asp Asn Gly
210                 215                 220

Phe Asp Glu Gln Leu Glu Leu Glu Arg Asp Leu Gln Arg Leu Ala Gly
225                 230                 235                 240

Arg Ser Glu Asp Tyr Arg Glu Gly Val Ser Ala Phe Met Asn Lys Arg
                245                 250                 255

Thr Pro Ala Phe Lys Gly Arg
          260

<210> SEQ ID NO 40
<211> LENGTH: 699
<212> TYPE: PRT
<213> ORGANISM: Rhodopseudomonas palustris

<400> SEQUENCE: 40

Met Ser Glu Val Val Thr Arg Ala Thr Gln Asp Gln Val Ala Ile Val
1               5                   10                  15

Thr Val Asp Ser Pro Pro Val Asn Ala Leu Ser Ala Ala Val Arg Arg
            20                  25                  30

Gly Ile Leu Glu Asn Val Asn Ala Ala Val Ala Asp Pro Ala Val Gln
        35                  40                  45

Ala Ile Val Leu Val Cys Ala Gly Arg Thr Phe Ile Ala Gly Ala Asp
    50                  55                  60

Ile Thr Glu Phe Gly Lys Pro Gln Pro Pro Ala Leu Asn Asp Val
65                  70                  75                  80

Ile Ala Ala Leu Glu Asn Ser Pro Lys Pro Thr Ile Ala Ala Ile His
                85                  90                  95

Gly Thr Ala Leu Gly Gly Gly Leu Glu Val Ala Leu Gly Cys His Phe
            100                 105                 110

Arg Val Ala Val Lys Glu Ala Lys Leu Gly Leu Pro Glu Val Lys Leu
        115                 120                 125

Gly Leu Leu Pro Gly Ala Gly Gly Thr Gln Arg Leu Pro Arg Ala Val
    130                 135                 140

Gly Pro Glu Leu Ala Val Gln Met Ile Val Gly Gly Ser Pro Ile Gly
145                 150                 155                 160

Ala Ala Glu Ala Leu Lys His Gly Leu Val Glu Val Val Glu Asn
                165                 170                 175

Leu Val Ala Gly Ala Val Ala Phe Ala Lys Lys Val Leu Ala Glu Lys
            180                 185                 190

Arg Pro Leu Arg Arg Leu Arg Asp Asp Ser Lys Leu Ala Ala Ala
        195                 200                 205

Lys Ala Asp Arg Ser Ile Phe Thr Asn Ala Val Ala Ala Met Thr Lys
    210                 215                 220

Lys Ala Arg Gly Leu Glu Ala Pro Phe Ala Cys Ala Asp Ala Ile Gly
225                 230                 235                 240

Ala Ala Ile Asp Leu Pro Phe Glu Gly Leu Lys Lys Glu Arg Glu
                245                 250                 255

Gly Phe Met Lys Leu Val Val Ser Asp Gln Ser Lys Ala Gln Arg Tyr
            260                 265                 270

Ala Phe Phe Ala Glu Arg Glu Ala Lys Val Asp Gly Val Pro Asp
        275                 280                 285

Gly Thr Lys Pro Arg Pro Val Ser Arg Val Ala Ile Ile Gly Ala Gly
    290                 295                 300

Thr Met Gly Gly Gly Ile Ala Met Ser Phe Ala Asn Ala Gly Ile Pro
305                 310                 315                 320

Val Thr Leu Ile Glu Thr Gly Glu Glu Gln Leu Lys Arg Gly Leu Gly
                325                 330                 335

Ile Met Gln Lys Asn Trp Glu Ala Thr Ala Ala Arg Gly Gly Leu Pro
            340                 345                 350

Pro Asp Ala Pro Ala Lys Arg Met Ala Leu Ile Thr Gly Leu Val Gly
        355                 360                 365

```
Leu Glu Asn Val Lys Asp Ala Asp Leu Ile Ile Glu Ala Val Phe Glu
        370                 375                 380

Thr Met Ala Val Lys Lys Glu Val Phe Thr Ala Val Asp Ala His Ala
385                 390                 395                 400

Lys Pro Gly Ala Val Leu Ala Ser Asn Thr Ser Tyr Leu Ser Ile Asp
                405                 410                 415

Glu Ile Ala Ala Thr Thr Lys Arg Pro Gln Asp Val Leu Gly Met His
            420                 425                 430

Phe Phe Ser Pro Ala Asn Val Met Lys Leu Cys Glu Ile Val Arg Gly
        435                 440                 445

Ala Lys Thr Ala Pro Asp Ala Leu Leu Thr Ala Val Ser Ile Ala Lys
    450                 455                 460

Lys Ile Ala Lys Val Pro Val Val Gly Val Cys Asp Gly Phe Val
465                 470                 475                 480

Gly Asn Arg Met Leu Ala Ala Arg Ser Lys Gln Ser Glu Lys Leu Leu
                485                 490                 495

Phe Glu Gly Ala Leu Pro Gln Gln Val Asp Ala Val Val Thr Lys Phe
            500                 505                 510

Gly Met Pro Met Gly Pro Phe Ala Met Gly Asp Leu Ala Gly Leu Asp
        515                 520                 525

Ile Gly Trp Arg Ser Arg Lys Asp Arg Gly Ile Lys Ser Glu Ile Ala
    530                 535                 540

Asp Ala Leu Cys Glu Ala Gly Arg Phe Gly Gln Lys Thr Gly Lys Gly
545                 550                 555                 560

Tyr Tyr Lys Tyr Glu Gln Gly Ser Arg Ala Pro Met Pro Asp Pro Glu
                565                 570                 575

Val Glu Thr Leu Ile Asn Asp Thr Leu Ala Lys Leu Gly Leu Lys Arg
            580                 585                 590

Arg Asp Ile Thr Asp Glu Glu Ile Leu Glu Arg Met Val Tyr Pro Met
        595                 600                 605

Ile Asn Glu Gly Ala Arg Ile Leu Glu Glu Lys Ile Ala Ala Arg Pro
    610                 615                 620

Ser Asp Ile Asp Val Val Trp Leu Tyr Gly Tyr Gly Trp Pro Ile Tyr
625                 630                 635                 640

Arg Gly Gly Pro Met His Tyr Ala Asp Ser Val Gly Leu Lys His Ile
                645                 650                 655

Ala Glu Arg Leu Ser Ala Tyr Ala Lys Ala Thr Asn Asp Pro Ser Leu
            660                 665                 670

Glu Pro Ala Pro Leu Leu Ala Arg Leu Ala Glu Gly Lys Thr Phe
        675                 680                 685

Ala Ser Leu Thr Gln Pro Ser Lys Ala Ala Ala
    690                 695

<210> SEQ ID NO 41
<211> LENGTH: 242
<212> TYPE: PRT
<213> ORGANISM: Rhodococcus sp.

<400> SEQUENCE: 41

Met Asn Thr Leu Lys Ile Glu Asp Arg Asp Arg Met Val Val Thr
1               5                   10                  15

Leu His Arg Pro Ala Gln Arg Asn Ala Ile Asn Ala Glu Met Ile Gly
            20                  25                  30

Glu Leu His Gln Val Cys Ala Ser Leu Glu Ala Thr Pro Lys Pro Met
```

-continued

```
                35                  40                  45
Leu Leu Thr Gly Glu Gly Asp His Phe Ala Gly Gly Ala Asp Ile Ala
 50                  55                  60

Glu Leu Arg Glu Arg Gly Arg Asp Glu Ala Phe Ala Gly Ile Asn Arg
 65                  70                  75                  80

Asn Leu Phe Asp Arg Ile Ala Lys Leu Pro Met Pro Thr Val Ala Ala
                 85                  90                  95

Val Ser Gly Tyr Ala Leu Gly Gly Ala Glu Leu Ser Tyr Ala Cys
                100                 105                 110

Asp Ile Arg Ile Ala Thr Glu Thr Ala Val Phe Gly Asn Pro Glu Pro
                115                 120                 125

Gly Leu Gly Ile Met Ala Ala Gly Ala Ser Tyr Arg Leu Pro Glu
                130                 135                 140

Leu Val Gly Thr Ser Val Ala Lys Gln Val Leu Leu Gly Gly Arg Asn
145                 150                 155                 160

Leu Asp Ala Gln Asp Ala Leu Arg Ser Gly Leu Val Met Ser Val Val
                165                 170                 175

Ala Pro Gly Glu His Ile Asp Ala Ala His Lys Val Ile Asp Arg Ile
                180                 185                 190

Thr Arg Ser Ala Pro Leu Ala Leu Lys Leu Thr Lys Met Ile Val Asp
                195                 200                 205

Ala Pro Gly Ser His Pro Phe Ala Asp Asp Ile Ala Gln Ala Val Leu
                210                 215                 220

Phe Glu Ser Arg Asp Lys His Asp Arg Met Thr Ala Phe Leu Glu Lys
225                 230                 235                 240

Lys Lys
```

<210> SEQ ID NO 42
<211> LENGTH: 689
<212> TYPE: PRT
<213> ORGANISM: Penicillium chrysogenum

<400> SEQUENCE: 42

```
Met Pro Asp Phe Thr Asp Asn Leu Arg Pro Ser Gln Pro Asp Gly Pro
 1               5                  10                  15

Thr Thr Leu Ala Arg Glu Arg Gln Lys Ser Asn Ile Ala Thr Glu Glu
                 20                  25                  30

Leu Gly Gln His Leu Leu Gly Ser Asp Gly Phe Leu Val Arg Gln Ala
                 35                  40                  45

Arg Ile Leu Pro Ile Ile Gln Gln Glu Pro Leu Phe Ser Lys Asp Gln
 50                  55                  60

Gln Gln Asn Leu Ser Arg Pro Glu Arg Phe Lys Leu Gly Val Ala Arg
 65                  70                  75                  80

Ala Lys Leu Leu Arg Gln Met Lys Asp Thr His Lys Trp Ser His Leu
                 85                  90                  95

Glu Tyr Gln Met Ala Glu Tyr Leu Val Asp Asp Val Ser Pro Tyr Phe
                100                 105                 110

Leu His Met Glu Met Phe Ile Thr Thr Ile Arg Glu Gln Ala Ser Glu
                115                 120                 125

Glu Gln Gln Ala His Trp Leu Pro Leu Ile Glu Leu Trp Lys Ile Ile
                130                 135                 140

Gly Ala Tyr Ala Gln Thr Glu Leu Gly His Gly Ser Asn Val Arg Gly
145                 150                 155                 160

Leu Glu Leu Glu Ala Arg Trp Asp Asn Arg Thr Lys Glu Phe Val Leu
```

-continued

```
               165                 170                 175
His Ser Pro Thr Leu Thr Ala Ser Lys Trp Trp Asn Gly Ser Leu Gly
            180                 185                 190

Arg Leu Ala Asn His Ala Ile Val Val Ala Gln Leu Leu Pro Asp
            195                 200                 205

Pro Ser Ser Pro Asp Gln Tyr Val Ser His Gly Pro His Pro Phe Ile
210                 215                 220

Val Gln Val Arg Asp Met Lys Thr His Gln Pro Leu Asn Gly Ile Val
225                 230                 235                 240

Val Gly Asp Ile Gly Pro Lys Tyr Gly Tyr Ile Thr Met Asp Asn Ala
            245                 250                 255

Tyr Met Leu Phe Asp Gln Phe Arg Ile Pro His Ser Ala Met Leu Ser
            260                 265                 270

Arg Tyr Ser Lys Val Asp Leu Asn Thr Gly Ile Tyr Thr Lys Pro Glu
            275                 280                 285

Lys Pro Ala Leu Val Tyr Gly Ser Leu Thr Tyr Val Arg Ser Asn Met
            290                 295                 300

Val His Arg Ala Arg Leu Val Leu Ala Arg Ala Val Thr Val Ala Val
305                 310                 315                 320

Arg Tyr Ser Ser Val Arg Arg Gln Phe Gln Asp Arg Asp Gly Asp Lys
                325                 330                 335

Thr Gly Pro Glu Met Ser Val Leu Asp Tyr Pro Thr Val Gln Ile Arg
            340                 345                 350

Ile Leu Pro Leu Leu Ala Thr Thr Phe Ala Leu His Tyr Thr Gly Leu
            355                 360                 365

Ala Met Gln Thr Val Tyr Lys Asn Ala Arg Gln Asp Ile Glu Glu Gly
370                 375                 380

Asn Phe Asn Ser Leu Ala His Met His Ser Met Ser Ser Gly Leu Lys
385                 390                 395                 400

Ser Leu Cys Thr Ile Phe Ala Ala Asp Gly Ile Glu Thr Cys Arg Arg
                405                 410                 415

Ala Met Gly Gly His Gly Phe Gly Gly Gly Ser Gly Leu Ile Gln Val
                420                 425                 430

Asn Asn Asp Tyr Leu Ser Lys Pro Thr Val Glu Gly Asp Asn Trp Met
            435                 440                 445

Ile Thr Gln Gln Val Ala Ala Tyr Val Ile Lys Lys Met Thr Ala Ala
450                 455                 460

Val Gly Ser Pro Asp Thr Pro Gly Ile Asp Glu Thr Asp Ala Arg Phe
465                 470                 475                 480

Lys Glu Phe Ile Arg Asn Lys Arg Pro Glu Ser Glu Lys Arg Thr
                485                 490                 495

Tyr Asp Ile Leu Asn Ser Asp Leu Asp Ile Val Lys Ser Phe Glu Leu
                500                 505                 510

Arg Ala Thr Ala Met Ala Ser Ser Thr Lys Leu Ile Arg Val Ile Lys
                515                 520                 525

Lys Arg Asn Trp Asn Ser Leu Leu Ile Gln Leu His Lys Leu Ser Arg
            530                 535                 540

Ala Gln Ser Glu Ser Ile Ile Val Ala Thr Phe Phe Asp Ala Leu Ser
545                 550                 555                 560

Asn Asp Lys Thr Leu Ser Ala Pro Thr Lys Asn Val Leu Trp Asp Cys
            565                 570                 575

Tyr Arg Leu Phe Ala Leu Tyr Ser Met Glu Asn Glu Ser Phe Glu Phe
            580                 585                 590
```

```
Leu Arg Thr Asn Ala Val Ser Gln Thr Asp Leu Asp Ser Leu Ala Ser
        595                 600                 605

Arg Val Gln Asp Leu Met Ala Arg Ile Arg Pro His Ala Val Thr Leu
        610                 615                 620

Val Asp Ser Trp Met Ile Pro Asp Tyr Leu Leu Asp Ser Ala Leu Gly
625                 630                 635                 640

Arg Tyr Asp Gly Arg Val Tyr Glu Asp Leu Phe Asn Arg Ala His Arg
                645                 650                 655

Leu Asn Pro Leu Asn Arg Ile Thr Phe Asn Pro Asn Tyr Trp Glu Asp
        660                 665                 670

Glu Ile Val Lys Gly Ser Gly Asp Asn Gly Arg Gly Ile Leu Ser Lys
        675                 680                 685

Leu

<210> SEQ ID NO 43
<211> LENGTH: 425
<212> TYPE: PRT
<213> ORGANISM: Penicillium chrysogenum

<400> SEQUENCE: 43

Met Ser Val Ser Asn Val Pro Phe Ala Asp Pro Leu Trp Leu Asn Arg
1               5                   10                  15

Lys His Ser Pro Tyr Tyr Lys Asp Ser His Arg Lys Leu Gln Lys Glu
            20                  25                  30

Val Arg Gln Tyr Val Asp Glu His Ile Ser Pro Phe Cys Glu Glu Trp
        35                  40                  45

Glu Lys Gln Gly Phe Val Pro Pro Glu Ala Gln Lys Arg His Ala Glu
    50                  55                  60

Leu Gly Tyr Thr Ala Val Ala Ser Phe Pro Leu Ala Ala Asp Tyr Leu
65                  70                  75                  80

Asp Gly Gln Arg Leu Pro Gly Asp Ile Asn Pro Tyr Glu Trp Asp Gly
                85                  90                  95

Phe His Asp Ile Val Val Ile Asp Glu Leu Ala Arg Cys Gly Tyr Leu
            100                 105                 110

Gly Ile Val Trp Ala Leu Gly Cys Gly Asn Ser Ile Gly Gly Pro Pro
        115                 120                 125

Ile Ile Asn Phe Gly Asn Glu Glu Gln Lys Arg Arg Phe Leu Pro Asp
    130                 135                 140

Met Leu Lys Gly Lys Ile Arg Phe Cys Leu Gly Val Thr Glu Pro Asp
145                 150                 155                 160

Ala Gly Ser Asp Val Ala Gly Ile Thr Thr Val Ala Glu Arg Lys Gly
                165                 170                 175

Asp Ala Tyr Ile Val Asn Gly Ala Lys Lys Trp Ile Thr Asn Gly Ile
            180                 185                 190

Phe Ala Asp Phe Cys Thr Ala Val Arg Thr Gly Gly Ser Gly Thr
        195                 200                 205

His Gly Ile Ser Ala Leu Val Ile Pro Met Lys Ala Pro Gly Val Ile
    210                 215                 220

Cys Arg Lys Ile Glu Asn Ser Val His Ala Ser Gly Ser Thr Tyr
225                 230                 235                 240

Ile Glu Phe Asp Gln Val Glu Val Pro Val Asp Asn Leu Leu Gly Glu
                245                 250                 255

Glu Asn Lys Gly Phe Pro Val Ile Met Asn Asn Phe Asn His Glu Arg
            260                 265                 270
```

```
Leu Trp Leu Ala Cys Thr Ser Leu Arg Met Ala Arg Val Cys Ala Glu
            275                 280                 285

Asp Ala Tyr Gln His Ala Ile Thr Arg Glu Thr Phe Gly Lys Arg Leu
    290                 295                 300

Ile Glu Asn Gln Ile Ile Arg Ser Lys Phe Ser Ala Met Ala Arg Ser
305                 310                 315                 320

Leu Asp Ser Asn Tyr Ala Trp Met Glu Gln Leu Val Tyr Ile Ala Glu
                325                 330                 335

Ile Ala Lys Lys Glu Gly Thr Asp Ala Gly Thr Gly Gly Leu Phe Ala
                340                 345                 350

Asn Leu Lys Val Leu Ala Gly Gln Thr Leu Glu Lys Val Asn Arg Glu
                355                 360                 365

Ser Gln Gln Val Met Gly Gly Leu Gly Tyr Ser Lys Asn Gly Arg Gly
370                 375                 380

Ser Arg Ile Glu Gln Val Ser Arg Asp Val Arg Val Met Val Val Gly
385                 390                 395                 400

Gly Gly Ser Glu Glu Ile Leu Ser Glu Leu Ala Val Asn Gln Glu Ile
                405                 410                 415

Lys Ala Met Lys Lys Gln Ser Lys Leu
                420                 425

<210> SEQ ID NO 44
<211> LENGTH: 605
<212> TYPE: PRT
<213> ORGANISM: Penicillium chrysogenum

<400> SEQUENCE: 44

Met Ala Ala Gln Ser Arg Val Pro Ala Thr Ala Glu Ser Gly Thr Phe
1               5                   10                  15

Thr Gln Leu Gly Pro Leu Pro Asn Thr Tyr Thr Ser Asp Ile Ser Leu
                20                  25                  30

Gln Arg Met Leu Gly Trp Tyr Leu Pro Ala Gln Thr Leu Lys Leu Ile
            35                  40                  45

Glu Pro His Leu Ala Gln Leu Gly Glu Glu Ala Val Ser Pro Gln Val
    50                  55                  60

Phe Ala Trp Asn Ala Asp Ala Glu Thr Asn Leu Pro Tyr Val Lys Lys
65                  70                  75                  80

Tyr Asn Val Trp Gly Gln Arg Tyr Ala Tyr Asp Arg Leu Val Thr Thr
                85                  90                  95

Asp Gly Trp Lys Gln Leu Gly Lys Trp Gly Ala Lys His Gly Val Val
                100                 105                 110

Ser Leu Gly Tyr Asp His Thr Tyr Gly Val Tyr Arg Arg Thr Ala Gln
            115                 120                 125

Tyr Ala Ala Val Tyr Leu Tyr Ala Pro Ser Ser Ala Met Tyr Arg Cys
    130                 135                 140

Pro Met Ser Met Ser Asp Gly Ala Ala Leu Thr Ser Gly Gln Trp Met
145                 150                 155                 160

Thr Glu Arg Ala Gly Gly Ser Asp Val Gln Asn Thr Glu Thr Trp Ala
                165                 170                 175

Thr Tyr Ala Pro Leu Pro Gln Glu Ser Lys Thr Ser Asp Val Leu Ala
                180                 185                 190

Glu Gly Asp Tyr Leu Ile Ser Gly Phe Lys Phe Phe Ser Ser Ala Thr
            195                 200                 205

Asp Ala Asn Val Ala Phe Leu Leu Ala Lys Thr Asp Ser Gly Lys Leu
```

```
                210                 215                 220
Ser Thr Phe Ile Ala Pro Leu Arg Lys Thr Ser Ile Gly Ala Asp Gly
225                 230                 235                 240

Lys Pro Glu Glu Thr Ser Asn Gly Val Arg Ile His Arg Phe Lys Asn
                245                 250                 255

Lys Leu Gly Thr Lys Glu Leu Pro Thr Ala Glu Leu Glu Leu Lys Gly
            260                 265                 270

Met Arg Ala His Leu Val Gly Glu Leu Asp Gln Gly Ile Val Thr Ile
            275                 280                 285

Ala Pro Leu Leu Asn Thr Thr Arg Ile Gln Thr Leu Leu Gly Thr Leu
        290                 295                 300

Ser Thr Trp Arg Arg Ala Ile Ser Ile Thr Lys Asn Phe Ala Lys Ser
305                 310                 315                 320

Arg Thr Thr Val Gly Glu Pro Leu Trp Leu Ile Pro Met His Leu Arg
                325                 330                 335

Leu Leu Ala Asp Val Glu Val Lys His Arg Gly Ala Ile Asn Leu Ala
                340                 345                 350

Phe Phe Thr Ile Ala Val Met Gly Leu Ile Glu Asn Pro Ser Ser Pro
            355                 360                 365

Ala Arg His Ala His Met Pro Arg Asp Pro Thr Glu Ala Lys Val Val
        370                 375                 380

Phe Arg Val Leu Thr Ala Thr Ser Lys Gly Val Val Ser Lys Met Ser
385                 390                 395                 400

Met Val Gly Val Gln Glu Cys Gln Glu Ala Ile Gly Gly Val Gly Tyr
                405                 410                 415

Ile Asp Glu Pro Asp Glu Pro Glu Phe Asn Ile Ser Arg Leu Leu Arg
                420                 425                 430

Ser Ala Ala Val Tyr Pro Ile Trp Glu Gly Thr Thr Asn Val Leu Ala
            435                 440                 445

Ser Glu Leu Val Arg Phe Leu Met Lys Gly Asp Asn Leu Ser Ile Leu
        450                 455                 460

Ser Gly Trp Leu Gly His Val Val Ser Leu Ile Arg Thr Pro Ser Leu
465                 470                 475                 480

Ala Gly Ala Leu Lys Gln Ala Met Ala Ser Tyr Leu Ser Arg Val Thr
                485                 490                 495

Ser Thr Arg Pro Gln Ala Ala Leu Leu Ala Asp Ala Arg Arg Val Met
            500                 505                 510

Phe Thr Phe Ala Trp Ile Leu Ser Gly Ala Leu Leu Thr Leu Asp Ala
        515                 520                 525

Glu Arg Asp Glu Asp Glu Val Ala Met Glu Ile Ala Arg Arg Trp Val
    530                 535                 540

Leu Leu Gly Glu Gly Val Gly Glu Phe Val Tyr Arg Asp Ile Ala
545                 550                 555                 560

Lys Pro Tyr Gln Cys Phe Asn Leu Arg Ser Gly Arg Asp Glu His Thr
                565                 570                 575

Arg Leu Asp Cys Lys Ile Ala Trp Gly Val Glu Leu Pro Gly Lys Ile
                580                 585                 590

Val Phe Gly His Arg Ser Leu Ser Glu Ser Ser Lys Leu
            595                 600                 605

<210> SEQ ID NO 45
<211> LENGTH: 425
<212> TYPE: PRT
<213> ORGANISM: Penicillium chrysogenum
```

<400> SEQUENCE: 45

```
Met Met Asn Arg Ser Leu Leu Arg Ala Ala Arg Ser Ile Gln Ala
1               5                   10                  15

Gly Pro Thr Ser Val Ala Gly Arg Arg Tyr Ala Ser Ser Ala Val Phe
            20                  25                  30

Asn Trp Glu Asp Pro Leu Ala Ala Glu Leu Phe Thr Asp Glu Glu
        35                  40                  45

Leu Ala Ile Gln Asp Thr Ala Arg Gln Tyr Cys Gln Asp Lys Leu Ala
    50                  55                  60

Pro Arg Val Leu Glu Ala Tyr Arg Asn Glu Asp Tyr Asp Arg Arg Ile
65              70                  75                  80

Leu Glu Glu Met Gly Asp Leu Gly Leu Leu Gly Ala Ser Ile Glu Gly
                85                  90                  95

Tyr Gly Cys Ala Gly Val Ser Thr Val Ala Ser Gly Leu Ile Thr Lys
            100                 105                 110

Glu Val Glu Arg Val Asp Ser Gly Tyr Arg Ser Gly Met Ser Val Gln
            115                 120                 125

Ser Ser Leu Ala Met Thr Gly Ile Tyr Glu Phe Gly Thr Glu Glu Gln
130                 135                 140

Lys Gln Arg Phe Leu Pro Ser Leu Ala Lys Gly Thr Leu Ala Gly Cys
145                 150                 155                 160

Phe Gly Leu Thr Glu Pro Asn His Gly Ser Asp Pro Gly Ser Met Glu
                165                 170                 175

Thr Val Ala Arg Glu His Pro Thr Gln Lys Gly Met Tyr Leu Leu Ser
            180                 185                 190

Gly Ser Lys Thr Trp Ile Thr Asn Ser Pro Ile Ala Asp Val Ala Leu
            195                 200                 205

Val Trp Ala Lys Leu Glu Ser Thr Gly Lys Ile Arg Gly Phe Ile Val
210                 215                 220

Glu Arg Glu Arg Ala Thr Pro Gly Ser Tyr Glu Thr Pro Ala Ile Lys
225                 230                 235                 240

Asn Lys Ser Ala Leu Arg Ala Ser Ile Thr Gly Met Ile Gln Met Asp
                245                 250                 255

Asn Cys Pro Val Pro Ala Glu Asn Met Leu Pro Glu Val Glu Gly Leu
            260                 265                 270

Lys Gly Pro Phe Thr Cys Leu Asn Ser Ala Arg Leu Gly Ile Ala Phe
            275                 280                 285

Gly Ala Met Gly Ala Leu Glu Asp Cys Leu Ala Arg Ala Arg Glu Tyr
290                 295                 300

Ser Leu Glu Arg Lys Gln Phe Lys Gly Asn Pro Leu Ala Lys Tyr Gln
305                 310                 315                 320

Leu Ile Gln Met Lys Leu Ala Asn Ala Ala Thr Asp Ala Ala Tyr Gly
                325                 330                 335

Thr Leu Ala Ala Val Gln Val Ala Arg Leu Lys Asp Ala Gly Lys Ala
            340                 345                 350

Thr Pro Glu Met Ile Ser Met Ile Lys Arg Gln Asn Cys Asp Arg Ala
            355                 360                 365

Leu Ala Asn Ser Arg Ile Leu Gln Glu Val Phe Gly Gly Asn Ala Ala
            370                 375                 380

Ser Asp Glu Tyr His Ile Ala Arg His Val Ala Asn Leu Phe Val Val
385                 390                 395                 400

Gln Thr Tyr Glu Gly Gln Ser Asp Ile His Ala Leu Ile Leu Gly Arg
```

```
                    405                 410                 415
Ala Ile Thr Gly Lys Gln Ala Phe Val
                420                 425

<210> SEQ ID NO 46
<211> LENGTH: 633
<212> TYPE: PRT
<213> ORGANISM: Penicillium chrysogenum

<400> SEQUENCE: 46

Met Ser Ser Ser Gln Pro Ala Thr Ala Asp Ser Gly Tyr Ile Thr Asp
1               5                   10                  15

Pro Gly Pro Leu Glu Asn Thr Tyr Thr Ser Asp Pro Ser Leu Gln Arg
            20                  25                  30

Ala Leu Ala Trp Tyr Leu Pro Ser Ala Thr Leu Gln Ser Val Gln Pro
        35                  40                  45

His Leu Thr Gln Phe Gly Ala Glu Ala Ile Ser Glu Gln Val Arg Glu
    50                  55                  60

Trp Ser Ala Asp Ala Glu Arg Asn Val Pro Tyr Val Lys Ser His Asn
65                  70                  75                  80

Val Trp Gly Lys Arg Tyr Asp Tyr Asp Arg Leu Val Thr Thr Glu Gly
                85                  90                  95

Trp Lys Gln Leu Gly Lys Trp Gly Ala Arg Asn Arg Ile Val Ser Ala
            100                 105                 110

Gly Tyr Asp Lys Ser Leu Gly Val Asp Arg Arg Thr Val Gln Tyr Ala
        115                 120                 125

Leu Asn Tyr Leu Tyr Ser Pro Ser Ser Gly Leu Tyr Ser Cys Pro Ile
    130                 135                 140

Ser Met Thr Asp Gly Ala Ala Phe Ile Leu Ser Ser Arg Ile Asn Lys
145                 150                 155                 160

Leu Pro Ser Thr His Pro Phe His Thr Ala Phe Gln Gly Leu Ile Ser
                165                 170                 175

Glu Lys Asp Asp His Trp Thr Ser Gly Gln Trp Met Thr Glu Arg Ala
            180                 185                 190

Gly Gly Ser Asp Val Gln Asn Thr Glu Thr Trp Ala Thr Tyr Ser Pro
        195                 200                 205

Leu Ala Ser Ser Gly Ser Glu Pro Leu Gly Asp Gly Asp Tyr Leu
    210                 215                 220

Ile Ser Gly Phe Lys Phe Ser Ser Ala Thr Asp Ala Asn Leu Ala
225                 230                 235                 240

Leu Leu Leu Ala Lys Thr Pro Ser Gly Lys Leu Ser Thr Phe Leu Ala
                245                 250                 255

Pro Leu Arg Arg Thr Val Val Gly Gly Asp Gly Val Ser Arg Val Val
            260                 265                 270

Ser Asn Gly Val Arg Ile His Arg Leu Lys Asn Lys Leu Gly Thr Lys
        275                 280                 285

Glu Leu Pro Thr Ala Glu Leu Glu Lys Asp Met Arg Ala His Leu
    290                 295                 300

Ile Gly Glu Ile Asp Gln Gly Ile Val Thr Ile Ala Pro Leu Leu Asn
305                 310                 315                 320

Val Thr Arg Leu His Thr Phe Val Gly Ser Leu Ala Gly Trp Arg Arg
                325                 330                 335

Ala Ile Ser Ile Thr Lys Ser Phe Ala Lys Ala Arg Thr Thr Val Gly
            340                 345                 350
```

Glu Pro Leu Trp Leu Ile Pro Met His Leu Arg Leu Ala Asp Met
            355                 360                 365

Glu Val Lys His Arg Gly Ala Met Asn Leu Ala Trp Phe Thr Val Ala
370                 375                 380

Leu Phe Gly Val Val Glu Asp Arg Thr Pro Ser Ser Asn Lys Ile Ala
385                 390                 395                 400

His Leu Pro Gln Pro Gly Lys Glu Ala Glu Val Val Phe Arg Thr Leu
            405                 410                 415

Thr Ala Thr Ala Lys Ala Val Ile Ser Lys Met Ala Thr Ala Gly Ile
            420                 425                 430

Gln Glu Cys Gln Glu Ser Met Gly Gly Val Gly Tyr Met Asp Glu Ala
            435                 440                 445

Asp Glu Pro Glu Phe Asn Ile Ser Arg Ile Leu Arg Asn Asn Ala Val
            450                 455                 460

Asn Ser Ile Trp Glu Gly Thr Thr Asn Val Leu Ala Ser Glu Phe Val
465                 470                 475                 480

Arg Phe Leu Ile Lys Lys Asp Asn Leu Lys Ile Phe Gly Thr Trp Leu
                485                 490                 495

Asp Arg Thr Leu Ala Leu Ile Gln Ser Val Asp Leu Arg Asn Ala Leu
            500                 505                 510

Thr Ala Ala Trp Leu Ala Leu His Ala Arg Phe Met Thr Gln Asp Pro
            515                 520                 525

Ala Thr Thr Val Ala Asp Gly Arg Arg Phe Met Phe Thr Val Ala Trp
            530                 535                 540

Ile Leu Ser Gly Ala Leu Leu Ala Leu Asp Thr Glu Arg Asp Asn Asp
545                 550                 555                 560

Pro Val Thr Ala Glu Ile Ala Arg Arg Trp Ile Leu Ser Ala Glu Gly
                565                 570                 575

Gly Val Gly Glu Gln Val Phe His Asp Ile Val Thr Val Ser Gly Thr
            580                 585                 590

Ala Ser Ala Thr Ser Gly Gly Glu Glu His Leu Gln Trp Asp Cys Arg
            595                 600                 605

Ile Ala Trp Gly Val Asp Leu Pro Ala Asn Arg Ala Ser Gly His Arg
610                 615                 620

Ser Leu Gln Lys Ala Gly Ser Lys Leu
625                 630

<210> SEQ ID NO 47
<211> LENGTH: 695
<212> TYPE: PRT
<213> ORGANISM: Penicillium chrysogenum

<400> SEQUENCE: 47

Met Pro Ser Pro Pro Asp Trp Val Lys Ala Leu Lys Pro Ser Gly
1               5                   10                  15

Pro Gln Gly Ser Glu Leu Leu His Gln Glu Arg Ala Gln Ser Asn Val
                20                  25                  30

Asp Val Glu Arg Leu Ser Glu Leu Leu His Thr Lys Glu Thr Leu Glu
            35                  40                  45

Arg Arg Ala Ser Leu Leu Ala Leu Leu Gln Pro Glu Lys Val Phe Asp
        50                  55                  60

Lys Ser Gln Asn His Ser Leu Gly Arg Val Glu Arg Leu Gln Arg Ser
65                  70                  75                  80

Leu Ala Lys Ala Lys Arg Leu Gln Gln Leu Ala Glu Glu His Lys Trp
                85                  90                  95

-continued

Ser Met Gln Glu Leu His Ala Ala Asn Asp Leu Ile Gly Glu Pro Thr
                100                 105                 110

Pro Tyr Gly Leu His Ala Ser Met Phe Leu Val Thr Leu Arg Glu Gln
            115                 120                 125

Gly Thr Pro Glu Gln His Lys Leu Phe Leu Glu Arg Ala Glu Lys Tyr
130                 135                 140

Glu Ile Ile Gly Cys Tyr Ala Gln Thr Glu Leu Gly His Gly Ser Asn
145                 150                 155                 160

Val Arg Gly Leu Glu Thr Thr Ala Thr Trp Asn Ser Asn Asp Lys Thr
                165                 170                 175

Phe Thr Ile Asn Ser Pro Thr Leu Thr Ala Ser Lys Trp Trp Ile Gly
            180                 185                 190

Ser Leu Gly Arg Thr Ala Asn His Ala Val Val Met Ala Gln Leu Phe
        195                 200                 205

Ile Asp Gly Lys Asn Tyr Gly Pro His Pro Phe Val Val Gln Val Arg
    210                 215                 220

Asp Leu Glu Thr His Gln Pro Leu Asp Asn Val Tyr Val Gly Asp Ile
225                 230                 235                 240

Gly Pro Lys Phe Gly Tyr Asn Thr Met Asp Asn Gly Phe Leu Leu Phe
                245                 250                 255

Asn Asn Val Lys Ile Pro His Val Asn Met Leu Ala Arg Phe Cys Gln
            260                 265                 270

Val Asp Lys Glu Thr Asn Gln Tyr Ala Lys Pro Ala Met Pro Ser Leu
        275                 280                 285

Val Phe Gly Thr Met Thr Trp Val Arg Ala Asn Ile Val Leu Asp Ala
    290                 295                 300

Gly Gly Val Leu Ala Arg Gly Val Thr Ile Ala Thr Arg Tyr Cys Ala
305                 310                 315                 320

Val Arg Arg Gln Phe Gln Asp Arg Asp Ala Asp Pro His Ala Gly Glu
                325                 330                 335

Thr Gln Val Leu Asn Tyr Lys Met Val Gln Val Arg Leu Leu Pro Leu
            340                 345                 350

Leu Ala Ser Met Tyr Ala Leu His Phe Thr Gly Arg Gly Met Met Arg
        355                 360                 365

Leu Tyr Glu Glu Asn Gln Ser Arg Met Lys Ala Ala Ser Ser Pro Asp
    370                 375                 380

Gln Glu Ser Arg Gly Ala Gly Pro Glu Gln Leu Arg Ala Gly Ala Asn
385                 390                 395                 400

Leu Leu Ala Asp Leu His Ala Thr Ser Cys Gly Leu Lys Ala Leu Ala
                405                 410                 415

Ser Thr Thr Ala Gly Glu Gly Leu Glu Ile Cys Arg Arg Ala Cys Gly
            420                 425                 430

Gly His Gly Tyr Ser Ser Tyr Ser Gly Ile Gly Pro Ala Tyr Ala Asp
        435                 440                 445

Tyr Leu Pro Thr Leu Thr Trp Glu Gly Asp Asn Tyr Met Leu Thr Gln
    450                 455                 460

Gln Val Ala Arg Tyr Leu Leu Lys Ser Ala Arg Ala Val Leu Ala Gly
465                 470                 475                 480

Lys Pro Ala Arg Asn Asp Thr Ser Gln Ile Leu Gln Ala Tyr Leu Asp
                485                 490                 495

Arg Arg Asp Lys Gly Ala Ser Phe Asp Val Leu Asp Glu Asp Lys Asp
            500                 505                 510

-continued

```
Ile Val Ala Ala Phe Gly Trp Arg Thr Ala His Leu Thr Phe Glu Ala
            515                 520                 525

Leu Lys His Arg Asp Ala Glu Gln Arg Ser Trp Asn Ser Leu Leu Val
        530                 535                 540

Asp Phe Trp Arg Leu Ser Thr Ala His Ser Gln Tyr Leu Met Val Lys
545                 550                 555                 560

Asn Phe Tyr Glu Ala Val Ser Ser Pro Glu Leu Ser Gly Ala Leu Asp
                565                 570                 575

Pro Glu Thr Lys Gly Leu Met His Gln Leu Phe Arg Leu Phe Ser Leu
            580                 585                 590

His Thr Leu Glu Arg Glu Ala Ala Glu Phe Phe Ser Ser Gly Ala Val
        595                 600                 605

Thr Val Arg Gln Ile Thr Leu Thr Arg Thr Thr Ala Val Leu Lys Leu
    610                 615                 620

Leu Asp Asp Ile Arg Pro His Ala Val Arg Leu Val Asp Ala Trp Ala
625                 630                 635                 640

Ile Pro Asp Trp Gln Leu Asp Ser Ser Leu Gly Arg Tyr Asp Gly Lys
                645                 650                 655

Val Tyr Glu Asp Leu Phe Arg Arg Ala Ser Glu Glu Asn Pro Val Asn
            660                 665                 670

Glu Leu Val Phe Asp Pro Tyr Pro Trp Asn Ser Ala Leu Leu Lys Asn
        675                 680                 685

Glu Pro Ala Lys Ser Lys Leu
    690                 695

<210> SEQ ID NO 48
<211> LENGTH: 542
<212> TYPE: PRT
<213> ORGANISM: Penicillium chrysogenum

<400> SEQUENCE: 48

Met Ala Lys Thr Phe Ser Lys Glu Asp Val Ala Ser His Ser Lys Gly
1               5                   10                  15

Asp Ser Pro Trp Ile Ile Ile Asp Glu Asp Val Tyr Asp Val Ser Lys
            20                  25                  30

Phe Gln Glu Glu His Pro Val Leu Gln Arg Val Ala Gly Lys Asp Ala
        35                  40                  45

Ser Lys Gln Phe Trp Lys Tyr His Asn Glu Gly Ile Leu Lys Lys Tyr
    50                  55                  60

Lys Gly Gln Leu Gln Ile Gly Ser Leu Asp Thr Lys Lys Ala Ala Pro
65                  70                  75                  80

Ala Pro Pro Thr Pro Ala Pro Ala Pro Lys Lys Ala Ala Pro Glu Pro
                85                  90                  95

Lys Ser Thr Ala Ser Ser Ser Val Thr Pro Pro Ala Thr Gly Ala
            100                 105                 110

Pro Gln Asp Pro Tyr Gly Glu Leu Ile Pro Phe Ala Asp Pro Ser Trp
        115                 120                 125

Tyr Gln Gly Tyr Ala Ser Pro Tyr Phe Asn Glu Ser His Ala Ala Leu
    130                 135                 140

Arg Asp Glu Val Arg Gln Trp Val Glu Ser Ile Glu Pro Tyr Val
145                 150                 155                 160

Thr Glu Trp Asp Glu Ala Lys Glu Val Pro Ala His Ile Tyr Lys Gln
                165                 170                 175

Met Gly Glu Arg Gly Tyr Leu Ala Gly Leu Leu Gly Val His Phe Pro
            180                 185                 190
```

Glu Lys His Thr Pro His Arg Val Lys Ser Val Ser Pro Asp Arg Trp
            195                 200                 205

Asp Leu Phe His Glu Met Leu Leu Thr Asp Glu Leu Ser Arg Ala Gly
    210                 215                 220

Ser Gly Gly Leu Val Trp Ser Leu Ile Gly Tyr Gly Ile Gly Cys
225                 230                 235                 240

Pro Pro Leu Val Lys Phe Gly Lys Pro Leu Val Asp Arg Ile Leu
                245                 250                 255

Pro Gly Ile Leu Ala Gly Asp Lys Arg Ile Cys Leu Ala Ile Thr Glu
                260                 265                 270

Pro Asp Ala Gly Ser Asp Val Ala Asn Leu Gly Cys Glu Ala Lys Leu
            275                 280                 285

Thr Glu Asp Gly Lys His Tyr Ile Val Asn Gly Lys Lys Trp Ile
    290                 295                 300

Thr Asn Gly Ile Tyr Ser Asp Tyr Phe Thr Thr Ala Val Arg Thr Gly
305                 310                 315                 320

Lys Asp Gly Met Asn Gly Leu Ser Val Leu Leu Ile Glu Arg Glu Ala
                325                 330                 335

Gly Gly Val Ser Thr Arg Arg Met Asp Cys Gln Gly Val Trp Ser Ser
            340                 345                 350

Gly Thr Thr Tyr Val Thr Phe Glu Asp Val Lys Val Pro Val Glu Asn
    355                 360                 365

Leu Ile Gly Lys Glu Asn Gln Gly Phe Lys Val Ile Met Thr Asn Phe
370                 375                 380

Asn His Glu Arg Ile Gly Ile Val Ile Gln Cys Val Arg Phe Ser Arg
385                 390                 395                 400

Val Cys Tyr Glu Glu Ser Met Lys Tyr Ala His Lys Arg Lys Thr Phe
                405                 410                 415

Gly Lys Arg Leu Ile Asp His Pro Val Ile Arg Met Lys Leu Ala His
            420                 425                 430

Met Ala Arg Gln Ile Glu Ala Thr Tyr Asn Trp Leu Glu Asn Ile Ile
    435                 440                 445

Phe Gln Cys Gln Ser Met Glu Asp Thr Glu Ala Met Leu Lys Leu Gly
450                 455                 460

Gly Ala Ile Ala Gly Leu Lys Ala Gln Ser Thr Gln Cys Phe Glu Phe
465                 470                 475                 480

Cys Ala Arg Glu Ala Ser Gln Ile Phe Gly Gly Leu Ser Tyr Ser Arg
                485                 490                 495

Gly Gly Gln Gly Gly Lys Ile Glu Arg Leu Tyr Arg Asp Val Arg Ala
            500                 505                 510

Tyr Ala Ile Pro Gly Gly Ser Glu Glu Ile Met Leu Asp Leu Ser Met
    515                 520                 525

Arg Gln Ser Leu Arg Val His Gly Met Phe Gly Met Lys Leu
530                 535                 540

<210> SEQ ID NO 49
<211> LENGTH: 438
<212> TYPE: PRT
<213> ORGANISM: Penicillium chrysogenum

<400> SEQUENCE: 49

Met Ala Asp Thr Leu Arg Pro Ala Thr Ala Pro Tyr Ser Glu Pro Leu
1               5                   10                  15

Leu Pro Gln Leu Asp Val Arg Asn Pro Tyr Tyr Thr Asp Leu His His

```
                20                  25                  30
Asn Leu Arg Ala Thr Val Arg Glu Tyr Val Asp Thr Tyr Ile Ser Pro
            35                  40                  45
Tyr Ala Ala Glu Trp Glu Ala Gly Gln Val Pro Glu Ala Val Arg
        50                  55                  60
Arg Arg His Cys Lys Leu Gly Tyr Ser Ile Val His Pro Leu Thr Ser
 65                  70                  75                  80
Glu Glu Asp Ser Ala Gly Ile Ser Leu Pro Gly Asn Val Pro Arg Glu
                85                  90                  95
Lys Trp Asp Thr Trp Cys Ser Leu Ile Val Ser Asp Glu Leu Thr Arg
            100                 105                 110
Val Gly Tyr Val Gly Val Ile Trp Gly Leu Gly Gly Asn Gly Ile
        115                 120                 125
Gly Cys Pro Pro Val Ala Arg Phe Gly Asn Ala Glu Gln Arg Lys Lys
130                 135                 140
Trp Leu Pro Gly Val Ala Arg Gly Asp Ile Arg Phe Cys Leu Gly Ile
145                 150                 155                 160
Thr Glu Pro Asp Ala Gly Ser Asp Val Ala Asn Ile Gln Thr Thr Ala
            165                 170                 175
Gln Arg Asp Gly Asn His Tyr Val Val Asn Gly Ser Lys Lys Trp Ile
        180                 185                 190
Thr Asn Gly Ile Trp Ala Asp Tyr Cys Thr Ala Ala Val Arg Thr Gly
        195                 200                 205
Gly Pro Gly Arg Ser Gly Ile Ser Leu Leu Val Ile Pro Leu Ala Thr
        210                 215                 220
Ala Gly Val Thr Arg Arg Met His Asn Ser Gly Val Asn Ala Ser
225                 230                 235                 240
Gly Ser Thr Phe Ile Glu Phe Glu Asp Val Arg Val Pro Val Glu Asn
                245                 250                 255
Leu Val Gly Gln Glu Asn Lys Gly Phe Pro Leu Ile Met Ser Asn Phe
            260                 265                 270
Asn Pro Glu Arg Leu Ala Leu Ala Cys Ala Ser Leu Arg Leu Ala Arg
        275                 280                 285
Val Cys Ala Glu Asp Ala Tyr Asn Tyr Ala Ile Lys Arg Glu Thr Phe
        290                 295                 300
Gly Ser Ala Leu Ile Glu Lys Gln Ala Ile Gln Ser Lys Ile Phe Lys
305                 310                 315                 320
Phe Gly Leu Met Ile Glu Pro Ala Tyr Ala Phe Met Glu Gln Leu Val
            325                 330                 335
Asn Ile Leu Glu Leu Thr Lys Asp Arg Pro Ser Asp Val Asn Ile
        340                 345                 350
Gly Gly Met Thr Ala Leu Leu Lys Val Met Ser Thr Arg Ala Leu Glu
        355                 360                 365
Lys Ser Val Arg Glu Ala Gln Gln Ile Met Gly Gly Ala Gly Tyr Asn
        370                 375                 380
Lys Ala Gly Lys Gly Ala Arg Ile Glu Gln Ile Ser Arg Asp Ala Arg
385                 390                 395                 400
Val His Val Val Gly Gly Gly Ser Glu Glu Ile Met Ala Gly Leu Ala
                405                 410                 415
Leu Arg Glu Glu Thr Lys Ala Ile Arg Thr Arg Lys Ala Leu Glu
        420                 425                 430
Lys Arg Gln Ser Lys Val
        435
```

<210> SEQ ID NO 50
<211> LENGTH: 453
<212> TYPE: PRT
<213> ORGANISM: Penicillium chrysogenum

<400> SEQUENCE: 50

| | | | | | | | | | | | | | | | |
|---|---|---|---|---|---|---|---|---|---|---|---|---|---|---|---|
| Met | Asn | Phe | Asp | Leu | Pro | Ala | Asp | Leu | Lys | Thr | His | Leu | Glu | Ser | Ile |
| 1 | | | | 5 | | | | | 10 | | | | | 15 | |
| Asp | Ser | Phe | Ile | His | Ser | Thr | Ile | Leu | Pro | Leu | Gln | His | Ser | Asn | Asp |
| | | | 20 | | | | | 25 | | | | | 30 | | |
| Asn | Asn | Arg | Phe | Phe | Asp | His | Arg | Arg | Glu | Tyr | Glu | Arg | Thr | Asp | Trp |
| | | 35 | | | | | 40 | | | | | 45 | | | |
| Glu | Asn | Asn | Gly | Asn | Pro | Arg | Lys | Glu | Trp | Glu | Glu | Leu | Leu | Gly | Glu |
| 50 | | | | | 55 | | | | | 60 | | | | | |
| Ala | Arg | Thr | Leu | Ala | Asp | Ser | Ser | Gly | Leu | Tyr | Arg | Phe | Ala | Leu | Pro |
| 65 | | | | | 70 | | | | 75 | | | | | | 80 |
| Arg | Val | Tyr | Gly | Gly | Gln | Ser | His | Pro | Asp | Val | Asn | Leu | Trp | Met | Ser |
| | | | | 85 | | | | | 90 | | | | | 95 | |
| Ala | Ile | Arg | Tyr | His | Leu | Ser | Ser | Asn | Ala | Val | Tyr | Gly | Gly | Gly | Leu |
| | | | 100 | | | | | 105 | | | | | 110 | | |
| Gly | Leu | Ala | Asn | Asp | Leu | Gln | Asn | Glu | His | Cys | Ile | Val | Gly | Asn | Phe |
| | | 115 | | | | | 120 | | | | | 125 | | | |
| Pro | Asp | Val | Leu | Met | Leu | His | His | Phe | Gly | Asn | Glu | Gln | Gln | Arg | Asn |
| | 130 | | | | | 135 | | | | | 140 | | | | |
| Thr | Leu | Ile | Pro | Ala | Arg | Leu | Arg | Gly | Glu | Phe | Arg | Thr | Thr | Phe | Gly |
| 145 | | | | | 150 | | | | | 155 | | | | | 160 |
| Leu | Thr | Glu | Pro | Asp | His | Gly | Ser | Asp | Ala | Thr | Phe | Met | Ser | Thr | Thr |
| | | | | 165 | | | | | 170 | | | | | 175 | |
| Ala | Arg | Pro | Thr | Arg | Gly | Gly | Phe | Glu | Ile | Lys | Gly | Ala | Lys | Lys | Trp |
| | | | 180 | | | | | 185 | | | | | 190 | | |
| Gln | Thr | Gly | Ala | His | His | Cys | Thr | His | Phe | Leu | Ile | Phe | Ala | Arg | Thr |
| | | 195 | | | | | 200 | | | | | 205 | | | |
| Ser | Gly | Lys | Ala | Gly | Ser | Ala | Gln | Gly | Ile | Thr | Ala | Phe | Leu | Val | Pro |
| 210 | | | | | 215 | | | | | 220 | | | | | |
| Arg | Asp | Thr | Arg | Gly | Val | Arg | Ile | Val | Ser | Tyr | Glu | Trp | Thr | Leu | Asn |
| 225 | | | | | 230 | | | | | 235 | | | | | 240 |
| Met | Pro | Thr | Asp | His | Ala | Thr | Val | Glu | Leu | Asn | Ser | Val | Trp | Val | Pro |
| | | | | 245 | | | | | 250 | | | | | 255 | |
| Glu | Ser | Ala | Val | Leu | Gly | Ser | Ile | Asp | Gln | Gly | Leu | Ala | Ile | Ala | Gln |
| | | | 260 | | | | | 265 | | | | | 270 | | |
| Thr | Phe | Val | His | Glu | Asn | Arg | Ile | Arg | Gln | Ala | Ala | Ser | Ser | Cys | Gly |
| | | 275 | | | | | 280 | | | | | 285 | | | |
| Ala | Ala | Arg | Tyr | Cys | Leu | Asp | Arg | Ser | Ile | Asp | Arg | Ala | Arg | Ala | Arg |
| | 290 | | | | | 295 | | | | | 300 | | | | |
| Lys | Ile | Trp | Gly | Glu | Gly | Lys | Ser | Leu | Ala | Asp | Asn | Gln | Ala | Ile | Gln |
| 305 | | | | | 310 | | | | | 315 | | | | | 320 |
| Phe | Pro | Val | Val | Glu | Leu | Met | Thr | Gln | Val | Glu | Met | Leu | Arg | Leu | Phe |
| | | | | 325 | | | | | 330 | | | | | 335 | |
| Ile | Leu | Lys | Thr | Ser | Trp | Glu | Met | Asp | Arg | Ile | Val | Ala | Glu | Cys | Gln |
| | | | 340 | | | | | 345 | | | | | 350 | | |
| Ser | Ser | Lys | Ala | Gln | Arg | Ala | Pro | Trp | Val | Glu | Ile | Glu | Gly | Arg | Leu |
| | | 355 | | | | | 360 | | | | | 365 | | | |
| Ser | Asp | Gln | Val | Ala | Met | Cys | Asn | Phe | Trp | Ala | Asn | Arg | Leu | Cys | Cys |

-continued

```
            370                 375                 380
Gln Ala Ala Asp Arg Ala Ile Gln Ile His Gly Gly Asp Gly Tyr Ser
385                 390                 395                 400

Arg His Tyr Pro Phe Glu His Ile Tyr Arg His Phe Arg Arg Tyr Arg
                405                 410                 415

Ile Thr Glu Gly Ala Glu Ile Gln Met Arg Lys Ile Gly Ala Tyr
                420                 425                 430

Ile Phe Gly Phe Ala Gly Pro Lys Lys Arg Glu Met Lys His Glu His
            435                 440                 445

Ser Lys Ala Arg Ile
        450

<210> SEQ ID NO 51
<211> LENGTH: 441
<212> TYPE: PRT
<213> ORGANISM: Penicillium chrysogenum

<400> SEQUENCE: 51

Met Ala Tyr Asn Ser Pro Asn Pro Ile Pro Phe Ser Glu Pro Pro Tyr
1               5                   10                  15

Ile Arg Gly Leu Pro Ser Pro Tyr Ile Thr Pro Ala His Arg Arg Phe
            20                  25                  30

Gln Gln Ala Cys Arg Lys Phe Ala Thr Glu Asn Leu Ile Gln His Ala
        35                  40                  45

Leu Glu Trp Glu Arg Glu Gly Thr Val Pro Glu His Val Phe His Thr
    50                  55                  60

Phe Cys Lys His Asn Met Leu Leu Pro Asn Met Pro Ala Pro Leu Pro
65                  70                  75                  80

Val Asp Trp Leu Lys Arg Leu Gly Ile Asn Asp Ile Leu Gly Val Lys
                85                  90                  95

Val Glu Asp Trp Asp Tyr Ile Tyr Thr Gly Ile Tyr Cys Asp Glu Met
            100                 105                 110

Ala Arg Ser Gly Leu Ser Gly Pro Ser Gly Ser Leu Asn Ala Gly Phe
        115                 120                 125

Ala Phe Gly Ile Ala Pro Ile Tyr Lys Phe Gly Ser Thr Glu Leu Gln
    130                 135                 140

Glu Arg Phe Leu Pro Glu Leu Leu Thr Gly Lys Lys Arg Gly Cys Ile
145                 150                 155                 160

Ala Ile Thr Glu Pro Glu Ala Gly Ser Asp Val Ala Asn Ile Thr Thr
                165                 170                 175

Thr Ala Val Lys Ser Ala Asp Gly Gln His Tyr Ile Leu Asn Gly Ser
            180                 185                 190

Lys Lys Trp Ile Thr Asn Gly Ile Trp Ser Asp Tyr Ala Thr Met Ala
        195                 200                 205

Val Arg Thr Gly Gly Pro Gly Ala Ala Gly Leu Ser Val Leu Val Val
    210                 215                 220

Pro Leu Lys Gly His Pro Gly Val Ser Met Arg Arg Leu Lys Val Ser
225                 230                 235                 240

Gly Gln Ile Thr Gly Gly Thr Thr Tyr Ile Glu Leu Asp Asp Val Lys
                245                 250                 255

Val Pro Val Ser Asn Ile Ile Gly Lys Glu Gly Asp Gly Met Arg Ile
            260                 265                 270

Ile Met Thr Asn Phe Asn His Glu Arg Leu Val Ile Ala Val Gly Val
        275                 280                 285
```

```
Thr Arg Gln Ala Arg Val Ala Leu Ser Ala Ala Phe Ser Tyr Cys Leu
    290                 295                 300

Lys Arg Glu Ala Phe Gly Lys Thr Leu Met Asp Gln Pro Val Val Arg
305                 310                 315                 320

His Arg Leu Ala Lys Ala Gly Ala Glu Leu Glu Ser Met Trp Ala Trp
                325                 330                 335

Val Glu Gln Ile Leu Tyr Gln Leu Val His Leu Ser Lys Glu Glu Gly
            340                 345                 350

Asp Arg Gln Leu Gly Gly Leu Thr Ala Leu Ala Lys Ala Lys Ser Ala
        355                 360                 365

Met Val Leu Asn Glu Cys Ala Gln Thr Ala Val Leu Leu Phe Gly Gly
370                 375                 380

Asn Gly Phe Thr Lys Thr Gly Gln Gly Glu Leu Val Glu Ala Ile Leu
385                 390                 395                 400

Arg Asp Val Pro Gly Ala Arg Ile Pro Gly Ser Glu Asp Val Leu
                405                 410                 415

Leu Asp Leu Ser Val Arg Gln Leu Val Lys Leu Tyr Gln Ala Glu Glu
            420                 425                 430

Lys Lys Leu Ser Lys Asn Ala Lys Ile
        435                 440

<210> SEQ ID NO 52
<211> LENGTH: 439
<212> TYPE: PRT
<213> ORGANISM: Penicillium chrysogenum

<400> SEQUENCE: 52

Met Tyr Arg Ser Gln Ile Gln Arg Ala Leu Arg Ser Gln Trp Pro Ala
1               5                   10                  15

Leu Arg Gln Leu Gln Cys Arg Thr Gly Leu Ser Pro Arg Ala Arg Ala
            20                  25                  30

Ala Phe Ser Thr Ser Gly Arg Arg Asp Ile Met Gly Met Thr Gly Phe
        35                  40                  45

Thr Asp Glu Gln Leu Thr Val Arg Glu Ala Ile Ser His Ile Cys Ser
50                  55                  60

Arg Phe Pro Asn Thr Tyr Trp Gln Glu Arg Asp Gln Glu Lys Asp
65                  70                  75                  80

Pro Lys Glu Phe His Ala Ala Leu Ala Lys Asp Gly Trp Leu Gly Ile
                85                  90                  95

Ala Leu Pro Glu Ser Leu Gly Gly Ala Gly Leu Gly Ile Ser Glu Ala
            100                 105                 110

Thr Met Met Met Gln Thr Ile Thr Gln Ser Gly Ala Gly Met Ala Gly
        115                 120                 125

Ala Gln Ala Ile His Ala Asn Val Tyr Ala Thr Gln Pro Leu Ala Lys
130                 135                 140

Phe Gly Thr Lys Glu Gln Leu Glu Thr Ile Pro Asn Ile Ile Asn
145                 150                 155                 160

Gly Thr Trp Arg Thr Cys Phe Gly Val Thr Glu Pro Asn Thr Gly Leu
                165                 170                 175

Glu Thr Leu Lys Leu Thr Thr Leu Ala Ser Lys Thr Asp Asp Gly Tyr
            180                 185                 190

Ser Val Thr Gly Gln Lys Ile Trp Ile Thr Cys Ala Gln Val Ala Ser
        195                 200                 205

Lys Met Ile Leu Leu Ala Arg Thr Thr Pro Leu Glu Glu Val Lys Lys
210                 215                 220
```

```
Ser Ser Glu Gly Leu Ser Leu Phe Cys Ile Asp Ile Asp Arg Glu Asn
225                 230                 235                 240

Pro Gly Leu Asp Leu Arg Lys Ile Lys Lys Met Gly Gly Arg Ala Val
            245                 250                 255

Asp Ala Asn Glu Val Phe Phe Asp His Tyr Lys Ile Pro Ala Asn Thr
            260                 265                 270

Leu Ile Gly Glu Glu Asn Gln Gly Phe Lys Ile Ile Leu His Gly Met
            275                 280                 285

Asn Ala Glu Arg Cys Leu Leu Ala Gly Glu Ala Leu Gly Leu Gly Tyr
            290                 295                 300

Ala Ala Leu Glu Lys Ala Ser Gln Tyr Ala Lys Asp Arg Val Val Phe
305                 310                 315                 320

Gly Arg Pro Ile Gly Gln Asn Gln Gly Val Ala His Pro Leu Ala Asp
                325                 330                 335

Ala Phe Met Lys Leu Glu Ala Ala Lys Leu Ala Thr Tyr His Ala Ala
                340                 345                 350

Arg Leu Tyr Asp Thr Asn Asp Gly Ser Val Pro Phe His Glu Ile Gly
                355                 360                 365

Val Ala Cys Asn Ser Ala Lys Tyr Leu Ala Ala Glu Ala Ala Phe Thr
370                 375                 380

Ala Cys Glu Arg Ala Val Leu Ala His Gly Gly Met Gly Tyr Ala Val
385                 390                 395                 400

Glu Tyr Asp Val Glu Arg Tyr Met Arg Glu Cys Phe Val Pro Arg Ile
                405                 410                 415

Ala Pro Val Ser Arg Glu Met Ile Leu Asn Tyr Val Ser Glu Lys Val
                420                 425                 430

Leu Asp Leu Pro Arg Ser Tyr
            435

<210> SEQ ID NO 53
<211> LENGTH: 446
<212> TYPE: PRT
<213> ORGANISM: Penicillium chrysogenum

<400> SEQUENCE: 53

Met Ser Ala Ser Ser Arg Ile Pro Pro Ile Ala Gln Pro Phe Val Ser
1               5                   10                  15

Glu His Ala Lys Arg Thr Leu Asp Leu Val Glu Glu Phe Val Glu Lys
                20                  25                  30

Asp Cys Ile Pro Ala Asp Thr Val Phe Ser Ala Gln Leu Gly Glu Gly
            35                  40                  45

Glu Lys Arg Trp Thr Thr Thr Pro Thr Val Leu Glu Gly Leu Lys Glu
50                  55                  60

Lys Ala Lys Lys Leu Gly Leu Trp Asn Met Phe Leu Pro Lys Asn His
65                  70                  75                  80

Phe Thr Gln Gly Ala Gly Phe Ser Asn Leu Glu Tyr Gly Leu Met Ala
                85                  90                  95

Glu Leu Leu Gly Lys Ser Lys Val Ala Ser Glu Ala Thr Asn Asn Ala
                100                 105                 110

Ala Pro Asp Thr Gly Asn Met Glu Val Phe Ala Lys Tyr Gly Asn Asp
            115                 120                 125

Ala Gln Lys Lys Gln Trp Leu Ala Pro Leu Leu Glu Gly Lys Ile Arg
130                 135                 140

Ser Ala Phe Leu Met Thr Glu Pro Asp Val Ala Ser Ser Asp Ala Thr
```

```
            145                 150                 155                 160
Asn Ile Glu Leu Asn Ile Arg Arg Glu Gly Asn Glu Tyr Val Leu Asn
                165                 170                 175
Gly Ser Lys Trp Trp Ser Ser Gly Ala Gly Asp Pro Arg Cys Ala Ile
                180                 185                 190
Tyr Leu Val Met Gly Lys Thr Asp Pro Thr Asn Pro Asp Thr Tyr Lys
                195                 200                 205
Gln Gln Ser Val Ile Leu Val Pro Ala Gly Leu Pro Gly Ile Thr Val
            210                 215                 220
His Arg Met Leu Thr Val Tyr Gly Tyr Asp Asp Ala Pro His Gly His
225                 230                 235                 240
Gly His Ile Thr Phe Lys Asp Val Arg Val Pro Ala Ser Asn Met Val
                245                 250                 255
Leu Gly Glu Gly Arg Gly Phe Glu Ile Ile Gln Gly Arg Leu Gly Pro
                260                 265                 270
Gly Arg Ile His His Ala Met Arg Ala Ile Gly Ala Ala Glu Arg Ala
            275                 280                 285
Leu Glu Trp Leu Ile Ala Arg Val Asn Asp Glu Arg Lys Met Thr Phe
        290                 295                 300
Gly Lys Pro Leu Val Ala His Gly Val Ile Leu Glu Trp Ile Ala Lys
305                 310                 315                 320
Ser Arg Ile Glu Val Asp Ala Ala Arg Leu Ile Val Leu Asn Ala Ala
                325                 330                 335
Ile Lys Ile Asp Gln Gly Asp Ala Lys Ser Ala Leu Lys Glu Ile Ala
            340                 345                 350
Gln Ala Lys Val Leu Val Pro Gln Thr Ala Leu Thr Ile Ile Asp Arg
        355                 360                 365
Ala Val Gln Ala Tyr Gly Ala Gly Val Cys Gln Asp Thr Pro Leu
        370                 375                 380
Ala Tyr Leu Trp Ala Gly Ile Arg Thr Leu Arg Ile Ala Asp Gly Pro
385                 390                 395                 400
Asp Glu Val His Leu Gln Gln Leu Gly Lys Arg Glu Asn Lys Ala Arg
                405                 410                 415
Lys Asp Ala Val Thr Ala Lys Leu Asn Trp Gln Arg Glu Glu Ala Asp
                420                 425                 430
Arg Leu Leu Ala Ala Ser Gly Phe Lys Pro Lys Ser His Leu
            435                 440                 445

<210> SEQ ID NO 54
<211> LENGTH: 513
<212> TYPE: PRT
<213> ORGANISM: Penicillium chrysogenum

<400> SEQUENCE: 54

Met Pro Ser Glu Thr Leu Thr Arg Ala Glu Val Ala Lys His Asn Thr
1               5                   10                  15
Glu Asp Ser Leu Trp Cys Ile Ile Asp His Gln Val Tyr Asp Leu Thr
                20                  25                  30
Asp Phe Val Asp Ala His Pro Gly Gly Val Val Leu Ala Gln Val
            35                  40                  45
Ala Gly Lys Asp Ala Thr Ser Asp Phe Tyr Asn Leu His Arg Gln Glu
        50                  55                  60
Val Leu Glu Lys Tyr Arg Asp Gln Leu Cys Ile Gly Val Val Glu Gly
65                  70                  75                  80
```

```
Glu Lys Pro Glu Val Ile Arg Pro Phe Pro Gly Ala Leu Ser Pro Val
                85                  90                  95
Pro Tyr Ala Glu Pro Leu Trp Leu Arg Pro Gln Phe Lys Ser Pro Tyr
            100                 105                 110
Tyr Lys Glu Thr His Arg Asn Leu Gln Lys Ala Ile Arg Glu Phe Thr
        115                 120                 125
Asp Lys Tyr Val Thr Pro Glu Ala Gln Glu Lys Glu Gln Asp Gly Ser
130                 135                 140
Tyr Ile Ser Gln Glu Leu Ile Asn Arg Met Ala Glu Thr Asn Ile Leu
145                 150                 155                 160
Ala Met Arg Leu Gly Pro Gly Lys His Leu His Gly Arg Thr Leu Leu
                165                 170                 175
Gly Gly Val Val Asp Gly Lys Glu Phe Asp Tyr Leu His Asp Met Ile
            180                 185                 190
Ile Val Gln Glu Met Val Arg Ala Asn Ala Arg Gly Phe Gln Asp Gly
        195                 200                 205
Asn Met Ala Gly Met Ala Ile Ser Leu Thr Ala Val Gln Gln Trp Leu
210                 215                 220
His Asp Pro Val Leu Lys Glu Arg Leu Asn Asp Glu Val Leu Ser Gly
225                 230                 235                 240
Arg Lys Lys Met Cys Leu Ala Ile Thr Glu Ala Phe Ala Gly Ser Asp
                245                 250                 255
Val Ala Gly Leu Lys Thr Thr Ala Glu Lys Thr Pro Asp Gly Lys His
            260                 265                 270
Tyr Ile Val Asn Gly Thr Lys Lys Trp Ile Thr Asn Gly Met Phe Ala
        275                 280                 285
Asp Tyr Phe Val Thr Gly Cys Arg Thr Glu Lys Gly Phe Ser Val Leu
290                 295                 300
Leu Ile Pro Arg Gly Glu Gly Val Glu Thr Lys Gln Ile Lys Thr Ser
305                 310                 315                 320
Tyr Ser Thr Ala Ala Thr Ala Phe Val Glu Phe Asp Asn Val Lys
                325                 330                 335
Val Pro Val Gln Asn Leu Leu Gly Glu Glu His Lys Gly Phe Ile Val
            340                 345                 350
Ile Met Ser Asn Phe Asn His Glu Arg Phe Met Met Val Ala Ala Val
        355                 360                 365
Val Arg Met Ser Met Met Val Glu Glu Thr Met Lys Trp Ser Asn
370                 375                 380
Gln Arg Ile Val Phe Gly Lys Lys Leu Ile Glu Gln Pro Val Ile Arg
385                 390                 395                 400
Gln Lys Ile Ala Arg Met Ile Ser Leu Ala Glu Ser Asn Gln Ala Trp
                405                 410                 415
Leu Glu Ser Ile Ala Tyr Gln Met Cys Asn Met Thr Tyr Ala Gln Gln
            420                 425                 430
Ala Lys Leu Leu Gly Gly Pro Ile Gly Leu Leu Lys Ser His Cys Thr
        435                 440                 445
Gln Ala Ala Gly Glu Ile Ala Ser Leu Ala Thr Asn Ile Phe Gly Gly
450                 455                 460
Arg Gly Leu Thr Gln Ser Gly Met Gly Lys Val Ile Glu Met Phe His
465                 470                 475                 480
Arg Thr Tyr Lys Phe Asp Ala Ile Leu Gly Gly Thr Glu Glu Ile Leu
                485                 490                 495
Ala Asp Leu Gly Val Arg Gln Ala Met Lys Asn Phe Pro Lys Ser Met
```

Leu

<210> SEQ ID NO 55
<211> LENGTH: 436
<212> TYPE: PRT
<213> ORGANISM: Penicillium chrysogenum

<400> SEQUENCE: 55

Met Ala Ser Ile Ile Arg Ala Leu Arg Pro Leu Ser Arg Asn Pro Ser
1               5                   10                  15

Val Arg Leu Ala Gly Lys Arg Leu Ala Ala Gly Arg Pro Val Gln Ser
            20                  25                  30

Ala Tyr Ala Phe Ser Thr Thr Pro Arg Arg Glu Val Asp Leu Ser
        35                  40                  45

Glu Leu Thr Pro Thr Pro Ile Thr Leu Leu Ser Glu Thr Glu Ser Leu
50                  55                  60

Met Ala Asp Ser Val Ser Lys Phe Ala Val Glu Gln Ile Gly Pro Lys
65                  70                  75                  80

Val Arg Glu Met Asp Glu Ala Glu Thr Met Asp Ala Lys Val Val Glu
            85                  90                  95

Gln Leu Phe Glu Gln Gly Leu Met Gly Ile Glu Val Pro Glu Glu Phe
        100                 105                 110

Gly Gly Ala Gly Met Asn Phe Thr Ala Ala Ile Val Ala Ile Glu Glu
        115                 120                 125

Leu Ala Arg Val Asp Pro Ser Val Ser Val Leu Val Asp Val His Asn
130                 135                 140

Thr Leu Val Asn Thr Ala Ile Met Lys Tyr Gly Asp Ala Lys Ala Gln
145                 150                 155                 160

Arg Thr Trp Leu Pro Lys Leu Thr Thr Gly Thr Val Gly Ser Phe Cys
            165                 170                 175

Leu Ser Glu Pro Ala Ser Gly Ser Asp Ala Phe Ala Leu Gln Thr Lys
        180                 185                 190

Ala Glu Lys Thr Ala Asp Gly Tyr Lys Leu Asn Gly Ser Lys Met Trp
        195                 200                 205

Ile Thr Asn Ser Met Glu Ala Gly Val Phe Ile Val Phe Ala Asn Ile
210                 215                 220

Asp Pro Ser Lys Gly Tyr Lys Gly Ile Thr Ala Phe Ile Val Glu Lys
225                 230                 235                 240

Asp Thr Pro Gly Phe Ser Ile Ala Lys Lys Glu Lys Lys Leu Gly Ile
            245                 250                 255

Arg Ala Ser Ser Thr Cys Val Leu Asn Phe Asp Asp Cys Val Ile Pro
        260                 265                 270

Lys Ser Asn Leu Leu Gly Glu Glu Gly Gln Gly Tyr Lys Tyr Ala Ile
        275                 280                 285

Ser Val Leu Asn Glu Gly Arg Ile Gly Ile Ala Ala Gln Met Thr Gly
        290                 295                 300

Leu Ala Leu Gly Ala Trp Glu Asn Ala Ala Arg Tyr Val Trp Asn Asp
305                 310                 315                 320

Arg Arg Gln Phe Gly Glu Leu Ile Gly Asn Phe Gln Gly Met Gln His
            325                 330                 335

Gln Ile Ala Gln Ala Tyr Thr Glu Ile Ala Ala Arg Ala Leu Val
        340                 345                 350

Tyr Asn Ala Ala Arg Lys Lys Glu Ala Gly Gln Asp Phe Val Gln Asp

```
                355                 360                 365
Ala Ala Met Ala Lys Leu Tyr Ala Ser Gln Val Ala Gly Arg Val Ser
        370                 375                 380

Ser Ser Ala Val Glu Trp Met Gly Gly Met Gly Phe Val Arg Glu Gly
385                 390                 395                 400

Ile Ala Glu Lys Met Phe Arg Asp Ser Lys Ile Gly Ala Ile Tyr Glu
                405                 410                 415

Gly Thr Ser Asn Ile Gln Leu Gln Thr Ile Ala Lys Leu Leu Gln Lys
                420                 425                 430

Gln Tyr Thr Asn
        435

<210> SEQ ID NO 56
<211> LENGTH: 429
<212> TYPE: PRT
<213> ORGANISM: Penicillium chrysogenum

<400> SEQUENCE: 56

Met Ala Ser Leu Thr Leu Pro Ser Leu Leu Arg Thr Ser Thr Arg Ala
1               5                   10                  15

Val Arg Leu Asn Arg Thr Pro Ala Leu Thr Pro Cys Phe Arg Ser Ile
                20                  25                  30

Ser Thr Lys His Pro Lys Gly Phe Ile Pro Pro Ser Glu Asp Asp Leu
            35                  40                  45

Leu Glu Leu Arg Glu Arg Val Gln Asp Phe Thr Arg Arg Glu Ile Pro
        50                  55                  60

Ala Asp Val Ala Ala Arg Thr Asp Glu Gln Asn Glu Phe Pro Ala Glu
65                  70                  75                  80

Met Trp Arg Lys Met Gly Asp Ala Gly Phe Leu Gly Val Thr Ala Asn
                85                  90                  95

Glu Glu Tyr Gly Gly Leu Gly Met Gly Tyr Gln Ala His Cys Val Val
                100                 105                 110

Met Glu Glu Ile Ser Arg Ala Ser Gly Ser Ile Gly Leu Ser Tyr Ala
            115                 120                 125

Ala His Ser Gln Leu Cys Val Asn Gln Leu Ser Leu Asn Gly Ser Thr
        130                 135                 140

Glu Gln Lys Glu Arg Ile Leu Pro Gly Leu Leu Ser Gly Glu Lys Val
145                 150                 155                 160

Gly Ala Leu Ala Met Ser Glu His Ser Ala Gly Ser Asp Val Val Ser
                165                 170                 175

Met Lys Thr Thr Ala Lys Glu Val Asp Gly Trp Leu Leu Asn Gly
                180                 185                 190

Thr Lys Met Trp Ile Thr Asn Gly Pro Asp Ala Asp Tyr Ile Val Val
                195                 200                 205

Tyr Ala Lys Thr Glu Pro Glu Leu Gly Ser Lys Gly Ile Thr Ala Phe
        210                 215                 220

Leu Val Glu Lys Asp Phe Lys Gly Phe Ser Cys Ala Arg Lys Leu Asp
225                 230                 235                 240

Lys Leu Gly Met Arg Gly Ser Asn Thr Gly Glu Leu Ile Phe Glu Asp
                245                 250                 255

Val Phe Val Pro Arg Glu Asn Leu Leu Gly Glu Val Asn Arg Gly Val
                260                 265                 270

Arg Val Leu Met Glu Gly Leu Asp Leu Glu Arg Leu Val Leu Ser Ala
            275                 280                 285
```

Gly Pro Leu Gly Ile Met Gln Ala Ala Leu Asp Leu Val Leu Pro Tyr
290                 295                 300

Thr His Val Arg Lys Gln Phe Gly Ala Pro Ile Ala His Asn Gln Leu
305                 310                 315                 320

Val Gln Gly Lys Leu Ala Asp Met Tyr Thr Lys Leu Ala Ala Ser Arg
            325                 330                 335

Ala Tyr Thr Tyr Ala Thr Ala Arg Gln Val Asp Asn Ala Ala Val Glu
        340                 345                 350

Pro Gly Glu Leu Thr Val Arg Thr Gln Asp Cys Ala Gly Ala Ile Leu
    355                 360                 365

Tyr Ala Ala Glu Arg Ala Thr Glu Cys Thr Leu Asp Ala Ile Gln Leu
370                 375                 380

Met Gly Gly Ser Gly Tyr Ile Asn Glu Ile Pro Ala Gly Arg Leu Leu
385                 390                 395                 400

Arg Asp Ala Lys Leu Tyr Glu Ile Gly Ala Gly Thr Ser Glu Ile Arg
            405                 410                 415

Arg Met Val Ile Gly Arg Ala Phe Asn Lys Glu Tyr Ala
            420                 425

<210> SEQ ID NO 57
<211> LENGTH: 405
<212> TYPE: PRT
<213> ORGANISM: Penicillium Chrysogenum

<400> SEQUENCE: 57

Met Phe Ser Arg Ser Val Leu Gln Thr Ala Thr Arg Ser Val Arg Pro
1               5                   10                  15

Ala Ser Ala Arg Ala Val Pro Gln Leu Gly Lys Ala Pro Phe Gly Arg
            20                  25                  30

Arg Tyr Val Ser Val Tyr Gly Tyr Thr Gln Ala Lys Ala Leu Ile Tyr
        35                  40                  45

Ser Lys Tyr Gly Glu Pro Lys Asp Val Leu Arg Leu His Lys His Ser
    50                  55                  60

Ile Ser Ala Pro His Ala Thr Gln Val Asn Leu Arg Leu Leu Thr Ala
65                  70                  75                  80

Pro Met Asn Pro Ala Asp Val Asn Gln Ile Gln Gly Val Tyr Pro Ser
                85                  90                  95

Lys Pro Pro Phe Gln Thr Glu Leu Gly Asn Val Glu Pro Ala Ala Val
            100                 105                 110

Gly Gly Asn Glu Gly Ala Phe Glu Val Leu Ser Thr Gly Ala Gly Val
        115                 120                 125

Lys Asn Leu Ser Lys Gly Asp Trp Val Ile Met Lys Arg Thr Gly Leu
    130                 135                 140

Gly Thr Trp Arg Thr His Ala Gln Leu Asp Ser Gln Leu Ile Lys
145                 150                 155                 160

Val Glu Asn Lys Glu Gly Leu Thr Pro Leu Gln Val Gly Thr Val Ser
                165                 170                 175

Val Asn Pro Val Thr Ala Tyr Arg Met Leu Arg Asp Phe Cys Glu Trp
            180                 185                 190

Asp Trp Met Arg Ala Gly Glu Glu Trp Val Ile Gln Asn Gly Ala Asn
        195                 200                 205

Ser Gly Val Gly Arg Ala Ala Ile Gln Leu Gly Arg Glu Trp Gly Ile
    210                 215                 220

Lys Thr Leu Asn Val Ile Arg Gln Arg Lys Thr Pro Glu Glu Thr Glu
225                 230                 235                 240

-continued

```
Ala Leu Lys Gln Glu Leu Arg Asp Leu Gly Ala Thr Val Val Ile Thr
            245                 250                 255

Glu Glu Glu Met Leu Asn Gly Asn Phe Arg Asp Met Val His Glu Phe
        260                 265                 270

Thr Arg Lys Gly Arg Glu Pro Ile Arg Leu Ala Leu Asn Cys Val Gly
    275                 280                 285

Gly Lys Asn Ala Thr Ala Leu Ala Lys Thr Leu Ala Pro Asp Ser His
290                 295                 300

Met Val Thr Tyr Gly Ala Met Ser Lys Gln Pro Val Ala Leu Pro Ser
305                 310                 315                 320

Gly Leu Leu Ile Phe Lys Asn Leu Ala Phe Asp Gly Phe Trp Val Ser
                325                 330                 335

Lys Trp Gly Asp Lys Asn Pro Gln Leu Lys Glu Ser Thr Ile Lys Asp
            340                 345                 350

Val Leu Gln Leu Thr Arg Ser Gly Lys Phe Lys Asp Ile Pro Val Asp
        355                 360                 365

Glu Val Lys Trp Asn Trp Glu Thr Glu Gly Pro Glu Leu Ala Glu Ser
    370                 375                 380

Val Gln Gly Thr Leu Gly Gly Tyr Arg Ser Gly Lys Gly Val Phe Thr
385                 390                 395                 400

Phe Ser Gly Gly Asp
                405

<210> SEQ ID NO 58
<211> LENGTH: 373
<212> TYPE: PRT
<213> ORGANISM: Bos taurus

<400> SEQUENCE: 58

Met Trp Val Cys Gly Ala Leu Cys Arg Thr Arg Ala Pro Ala Gln Leu
1               5                   10                  15

Gly Gln Arg Leu Leu Pro Glu Ser Arg Arg Arg Pro Ala Ser Ala
            20                  25                  30

Ser Phe Ser Ala Ser Ala Glu Pro Ser Arg Val Arg Ala Leu Val Tyr
        35                  40                  45

Gly His His Gly Asp Pro Ala Lys Val Val Glu Leu Lys Asn Leu Glu
    50                  55                  60

Leu Ala Ala Val Gly Gly Ser His Val His Val Lys Met Leu Ala Ala
65                  70                  75                  80

Pro Ile Asn Pro Ser Asp Ile Asn Met Ile Gln Gly Asn Tyr Gly Leu
                85                  90                  95

Leu Pro Gln Leu Pro Ala Val Gly Gly Asn Glu Gly Val Gly Gln Val
            100                 105                 110

Val Ala Val Gly Ser Gly Val Thr Gly Val Lys Pro Gly Asp Trp Val
        115                 120                 125

Ile Pro Ala Asn Pro Gly Leu Gly Thr Trp Arg Thr Glu Ala Val Phe
    130                 135                 140

Gly Glu Glu Glu Leu Ile Thr Val Pro Ser Asp Ile Pro Leu Gln Ser
145                 150                 155                 160

Ala Ala Thr Leu Gly Val Asn Pro Cys Thr Ala Tyr Arg Met Leu Val
                165                 170                 175

Asp Phe Glu Arg Leu Arg Pro Arg Asp Ser Ile Ile Gln Asn Ala Ser
            180                 185                 190

Asn Ser Gly Val Gly Gln Ala Val Ile Gln Ile Ala Ala Ala Arg Gly
```

```
                195                 200                 205
Leu Arg Thr Ile Asn Val Leu Arg Asp Thr Pro Asp Leu Gln Lys Leu
210                 215                 220
Thr Asp Thr Leu Lys Asn Leu Gly Ala Asn His Val Val Thr Glu Glu
225                 230                 235                 240
Glu Leu Arg Lys Pro Glu Met Lys Ser Phe Phe Lys Asp Val Pro Gln
                245                 250                 255
Pro Arg Leu Ala Leu Asn Cys Val Gly Gly Lys Ser Ser Thr Glu Leu
            260                 265                 270
Leu Arg His Leu Ala Pro Gly Gly Thr Met Val Thr Tyr Gly Gly Met
        275                 280                 285
Ala Lys Gln Pro Val Ile Ala Ser Val Ser Gln Leu Ile Phe Lys Asp
290                 295                 300
Leu Lys Leu Arg Gly Phe Trp Leu Ser Gln Trp Lys Lys Asp His Ser
305                 310                 315                 320
Pro Asp Gln Phe Lys Glu Leu Ile Leu Thr Leu Cys Asp Leu Ile Arg
                325                 330                 335
Arg Gly Gln Leu Thr Ala Pro Ala Cys Ser Glu Val Pro Leu Gln Asp
            340                 345                 350
Tyr Leu Cys Ala Leu Glu Ala Ser Thr Gln Pro Phe Val Ser Ser Lys
        355                 360                 365
Gln Ile Leu Thr Met
    370

<210> SEQ ID NO 59
<211> LENGTH: 302
<212> TYPE: PRT
<213> ORGANISM: Cavia sp.

<400> SEQUENCE: 59

Met Gly Ser Trp Thr Lys Cys Gln Ser Cys Leu Ala Pro Gly Leu Leu
1               5                   10                  15
Gln Asn Arg Ala Ala Ile Val Thr Gly Gly Thr Gly Ile Gly Lys
            20                  25                  30
Ala Ile Ala Lys Glu Leu Leu His Leu Gly Cys Asn Val Val Ile Ala
        35                  40                  45
Ser Arg Lys Phe Asp Arg Leu Arg Ala Ala Glu Glu Leu Lys Ala
    50                  55                  60
Thr Leu Pro Pro Ser Asn Lys Ala Glu Val Thr Pro Ile Gln Cys Asn
65                  70                  75                  80
Ile Arg Lys Glu Glu Val Asn Asn Leu Met Lys Ser Thr Leu Ala
                85                  90                  95
Leu Tyr Gly Lys Ile Asp Phe Leu Val Asn Asn Gly Gly Gln Phe
            100                 105                 110
Trp Ser Ser Pro Glu His Ile Ser Ser Lys Gly Trp His Ala Val Ile
        115                 120                 125
Glu Thr Asn Leu Thr Gly Thr Phe Tyr Met Cys Lys Ala Ala Tyr Asn
    130                 135                 140
Ser Trp Met Lys Glu His Gly Gly Ala Ile Val Asn Ile Ile Leu
145                 150                 155                 160
Leu Asn Gly Gln Pro Phe Val Ala His Ser Gly Ala Ala Arg Gly Gly
                165                 170                 175
Val Tyr Asn Leu Thr Lys Ser Leu Ala Leu Gly Trp Ala Arg Ser Gly
            180                 185                 190
```

```
Ile Arg Ile Asn Cys Val Ala Pro Gly Thr Val Tyr Ser Gln Thr Ala
            195                 200                 205

Met Asp Asn Tyr Gly Asp Met Gly Lys Thr Leu Phe Ala Asp Ala Phe
210                 215                 220

Gln Lys Ile Pro Ala Lys Arg Leu Gly Val Pro Glu Glu Val Ser Ser
225                 230                 235                 240

Leu Val Cys Phe Leu Leu Ser Pro Ala Ala Ser Phe Ile Thr Gly Gln
            245                 250                 255

Leu Val Asn Val Asp Gly Gly Gln Ser Leu Tyr Cys Gln Asn His Asp
            260                 265                 270

Ile Pro Asp His Asp Asn Trp Pro Glu Gly Val Gly Asp Leu Ser Thr
            275                 280                 285

Val Lys Lys Met Lys Glu Ser Phe Lys Gln Lys Ala Lys Leu
290                 295                 300

<210> SEQ ID NO 60
<211> LENGTH: 386
<212> TYPE: PRT
<213> ORGANISM: Candida tropicalis

<400> SEQUENCE: 60

Met Tyr Ser Val Leu Lys Gln Ser Ile Arg Pro Arg Leu Leu Ala Thr
1               5                   10                  15

His Asn Gln Phe Arg Thr Met Ile Thr Ala Gln Ala Val Leu Tyr Thr
            20                  25                  30

Gln His Gly Glu Pro Lys Asp Val Leu Phe Thr Gln Ser Phe Glu Ile
        35                  40                  45

Asp Asp Asp Asn Leu Ala Pro Asn Glu Val Ile Val Lys Thr Leu Gly
50                  55                  60

Ser Pro Val Asn Pro Ser Asp Ile Asn Gln Ile Gln Gly Val Tyr Pro
65                  70                  75                  80

Ser Lys Pro Ala Lys Thr Thr Gly Phe Gly Thr Thr Glu Pro Ala Ala
                85                  90                  95

Pro Cys Gly Asn Glu Gly Leu Phe Glu Val Ile Lys Val Gly Ser Asn
            100                 105                 110

Val Ser Ser Leu Glu Ala Gly Asp Trp Val Ile Pro Ser His Val Asn
        115                 120                 125

Phe Gly Thr Trp Arg Thr His Ala Leu Gly Asn Asp Asp Asp Phe Ile
130                 135                 140

Lys Leu Pro Asn Pro Ala Gln Ser Lys Ala Asn Gly Lys Pro Asn Gly
145                 150                 155                 160

Leu Thr Ile Asn Gln Gly Ala Thr Ile Ser Val Asn Pro Leu Thr Ala
                165                 170                 175

Tyr Leu Met Leu Thr His Tyr Val Lys Leu Thr Pro Gly Lys Asp Trp
            180                 185                 190

Phe Ile Gln Asn Gly Gly Thr Ser Ala Val Gly Lys Tyr Ala Ser Gln
        195                 200                 205

Ile Gly Lys Leu Leu Asn Phe Asn Ser Ile Ser Val Ile Arg Asp Arg
210                 215                 220

Pro Asn Leu Asp Glu Val Val Ala Ser Leu Lys Glu Leu Gly Ala Thr
225                 230                 235                 240

Gln Val Ile Thr Glu Asp Gln Asn Asn Ser Arg Glu Phe Gly Pro Thr
                245                 250                 255

Ile Lys Glu Trp Ile Lys Gln Ser Gly Gly Glu Ala Lys Leu Ala Leu
            260                 265                 270
```

```
Asn Cys Val Gly Gly Lys Ser Ser Thr Gly Ile Ala Arg Lys Leu Asn
            275                 280                 285

Asn Asn Gly Leu Met Leu Thr Tyr Gly Gly Met Ser Phe Gln Pro Val
    290                 295                 300

Thr Ile Pro Thr Ser Leu Tyr Ile Phe Lys Asn Phe Thr Ser Ala Gly
305                 310                 315                 320

Phe Trp Val Thr Glu Leu Leu Lys Asn Asn Lys Glu Leu Lys Thr Ser
                325                 330                 335

Thr Leu Asn Gln Ile Ile Ala Trp Tyr Glu Glu Gly Lys Leu Thr Asp
            340                 345                 350

Ala Lys Ser Ile Glu Thr Leu Tyr Asp Gly Thr Lys Pro Leu His Glu
            355                 360                 365

Leu Tyr Gln Asp Gly Val Ala Asn Ser Lys Asp Gly Lys Gln Leu Ile
    370                 375                 380

Thr Tyr
385

<210> SEQ ID NO 61
<211> LENGTH: 379
<212> TYPE: PRT
<213> ORGANISM: Clostridium kluyveri

<400> SEQUENCE: 61

Met Asp Phe Thr Leu Thr Asn Glu Gln Lys Phe Val Glu Gln Met Val
1               5                   10                  15

Ser Glu Phe Thr Glu Asn Glu Val Lys Pro Ile Ala Ala Glu Ile Asp
                20                  25                  30

Glu Thr Glu Arg Phe Pro Leu Glu Thr Val Glu Lys Phe Ala Lys Tyr
            35                  40                  45

Gly Met Met Gly Met Pro Phe Pro Val Glu Tyr Gly Gly Ser Gly Thr
    50                  55                  60

Asp Tyr Leu Ser Tyr Ile Ile Ala Val Glu Gly Leu Ala Lys Ser Cys
65                  70                  75                  80

Thr Ser Ser Ser Thr Ile Leu Ser Ala His Thr Ser Leu Cys Ala Ala
                85                  90                  95

Pro Ile Tyr Asp Trp Gly Thr Glu Glu Gln Lys Gln Lys Tyr Leu Val
            100                 105                 110

Pro Leu Ala Lys Gly Glu Lys Leu Gly Ala Phe Gly Leu Thr Glu Pro
        115                 120                 125

Asn Ala Gly Thr Asp Ala Ala Gly Gln Gln Thr Thr Ala Val Leu Glu
    130                 135                 140

Gly Asp His Tyr Val Leu Asn Gly Gln Lys Ile Phe Ile Thr Asn Gly
145                 150                 155                 160

Ala Tyr Ala Asp Thr Phe Val Ile Phe Ala Met Thr Asp Arg Ser Lys
                165                 170                 175

Gly Thr Arg Gly Ile Thr Ala Phe Ile Val Lys Asp Phe Pro Gly
            180                 185                 190

Phe Ser Ile Gly Lys Ser Glu Asp Lys Leu Gly Ile Arg Ala Ser Ser
        195                 200                 205

Thr Thr Glu Leu Ile Phe Glu Asn Cys Ile Val Pro Lys Glu Asn Met
    210                 215                 220

Leu Gly Lys Glu Gly Lys Gly Phe Thr Val Ala Met His Thr Leu Asp
225                 230                 235                 240

Gly Gly Arg Ile Gly Ile Ala Ala Gln Ala Leu Gly Leu Ala Glu Gly
```

```
                     245                 250                 255
Ala Leu Ala Glu Ala Leu Asn Tyr Met Lys Glu Arg Lys Gln Phe Gly
                260                 265                 270

Lys Ala Leu Tyr Lys Phe Gln Gly Leu Ala Trp Met Val Ala Glu Leu
            275                 280                 285

Asp Thr Lys Ile Glu Ala Val Lys Gln Leu Val Tyr Lys Ala Ala Val
        290                 295                 300

Asn Lys Gln Met Gly Leu Pro Tyr Ser Val Glu Ala Arg Ala Lys
305                 310                 315                 320

Leu Ala Ala Ala Thr Val Ala Met Glu Thr Thr Lys Val Val Gln
                325                 330                 335

Ile Phe Gly Gly Tyr Gly Phe Thr Lys Asp Tyr Pro Val Glu Arg Met
                340                 345                 350

Met Arg Asp Ala Lys Ile Thr Glu Ile Tyr Glu Gly Thr Ser Gln Val
            355                 360                 365

Gln Lys Met Val Ile Ser Ala Asn Leu Phe Lys
        370                 375

<210> SEQ ID NO 62
<211> LENGTH: 562
<212> TYPE: PRT
<213> ORGANISM: Clostridium kluyveri

<400> SEQUENCE: 62

Met Asn Phe Glu Leu Thr Lys Glu Gln Gln Met Ile Arg Asp Asn Val
1               5                   10                  15

Arg Lys Phe Ala Glu Ala Lys Ile Glu Pro Ile Ala Phe Gln Leu Asp
                20                  25                  30

Glu Lys Asn Ile Phe Pro Glu Glu Ile Val Asn Glu Met Gly Asp Leu
            35                  40                  45

Ser Ile Met Gly Leu Pro Tyr Pro Lys Glu Tyr Gly Gly Ala Gly Lys
        50                  55                  60

Asp Val Leu Ser Tyr Ala Ile Ala Val Glu Glu Leu Ser Arg Val Asp
65                  70                  75                  80

Ala Gly Val Gly Val Ile Leu Ser Ala His Thr Ser Leu Gly Thr Trp
                85                  90                  95

Pro Ile Met Glu Phe Gly Thr Lys Glu Gln Lys Glu Lys Tyr Leu Val
            100                 105                 110

Pro Leu Ala Ser Gly Lys Lys Ile Ala Ala Phe Gly Leu Thr Glu Pro
        115                 120                 125

Asn Ala Gly Ser Asp Ala Gly Lys Thr Glu Thr Thr Ala Val Leu Glu
    130                 135                 140

Gly Asp His Tyr Val Ile Asn Gly Ser Lys Val Phe Ile Thr Asn Ala
145                 150                 155                 160

Asp Tyr Ala Asp Thr Tyr Val Ile Phe Ala Val Thr Thr Pro Gly Leu
                165                 170                 175

Gly Thr Lys Gly Ile Ser Ala Phe Ile Ile Glu Lys Gly Met Asp Gly
            180                 185                 190

Phe Thr Phe Gly Thr His Tyr Asn Lys Met Gly Ile Arg Ser Ser Ala
        195                 200                 205

Thr Ala Glu Leu Leu Phe Lys Asn Leu Lys Val Pro Lys Tyr Asn Leu
    210                 215                 220

Leu Gly Lys Glu Asn Glu Gly Phe Lys Ile Ala Met Gln Thr Leu Glu
225                 230                 235                 240
```

Gly Gly Arg Ile Gly Ile Ala Ala Gln Ala Leu Gly Ile Ala Gln Gly
                245                 250                 255

Ala Tyr Glu Lys Ala Leu Ser Tyr Ser Lys Glu Arg Val Gln Phe Gly
            260                 265                 270

Lys Pro Ile Ser Arg Gln Gln Ser Ile Ala Phe Lys Leu Ala Asp Met
            275                 280                 285

Ala Thr Lys Ile Arg Ala Ala Arg Phe Met Val Tyr Ser Ala Ala Val
        290                 295                 300

Leu Lys Gln Glu His Lys Asn Tyr Gly Met Glu Ser Ala Met Ala Lys
305                 310                 315                 320

Leu Tyr Ala Ser Asp Ile Cys Leu Glu Val Val Asn Asp Ala Val Gln
                325                 330                 335

Ile Tyr Gly Gly Ser Gly Phe Ile Lys Gly Phe Pro Val Glu Arg Met
            340                 345                 350

Tyr Arg Asp Ala Lys Ile Cys Thr Ile Tyr Glu Gly Thr Asn Glu Ile
            355                 360                 365

Gln Arg Leu Ile Ile Ser Asn Asp Ile Leu Gly Lys Pro Lys Lys Glu
        370                 375                 380

Pro Ile Glu Glu Asn Lys Glu Asn Lys Val Asn Lys Ala Lys Pro Ile
385                 390                 395                 400

Thr Gly Asn Arg Arg Val Ile Ile Lys Glu Gly Ser Pro Lys Glu
                405                 410                 415

Lys Val Asp Ala Phe Leu Asn Tyr Ile Lys Ser Glu Asn Ile Asp Ile
            420                 425                 430

Asn Lys Ser Glu Ala Ser Lys Gly Ser Ile Ala Asp Ala Asp Lys Val
        435                 440                 445

Cys Ser Ile Gly Leu Gly Leu Lys Asp Lys Lys Asp Leu Pro Leu Ile
    450                 455                 460

Gln Ser Leu Ala Asp Thr Val Gly Ala Glu Leu Gly Cys Ser Arg Pro
465                 470                 475                 480

Val Ala Glu Glu Arg Glu Trp Leu Pro Leu Asp Arg Tyr Val Gly Ile
                485                 490                 495

Ser Gly Gln Lys Phe Gly Gly Thr Phe Tyr Leu Ala Ile Gly Ile Ser
            500                 505                 510

Gly Gln Val Gln His Leu Lys Gly Ile Glu Asn Ala Gly Ile Ile Thr
        515                 520                 525

Ala Ile Asn Ile Asp Glu Asp Ala Pro Ile Phe Lys Ser Ser Asp Tyr
    530                 535                 540

Gly Ile Val Gly Asp Leu Tyr Glu Ile Val Pro Leu Leu Ile Glu Ala
545                 550                 555                 560

Leu Lys

<210> SEQ ID NO 63
<211> LENGTH: 539
<212> TYPE: PRT
<213> ORGANISM: Euglena gracilis

<400> SEQUENCE: 63

Met Ser Cys Pro Ala Ser Pro Ser Ala Ala Val Val Ser Ala Gly Ala
1               5                   10                  15

Leu Cys Leu Cys Val Ala Thr Val Leu Leu Ala Thr Gly Ser Asn Pro
            20                  25                  30

Thr Ala Leu Ser Thr Ala Ser Thr Arg Ser Pro Thr Ser Leu Val Arg
        35                  40                  45

```
Gly Val Asp Arg Gly Leu Met Arg Pro Thr Thr Ala Ala Leu Thr
    50                  55                  60

Thr Met Arg Glu Val Pro Gln Met Ala Glu Gly Phe Ser Gly Glu Ala
 65                  70                  75                  80

Thr Ser Ala Trp Ala Ala Gly Pro Gln Trp Ala Ala Pro Leu Val
                 85                  90                  95

Ala Ala Ala Ser Ser Ala Leu Ala Leu Trp Trp Trp Ala Ala Arg Arg
                100                 105                 110

Ser Val Arg Arg Pro Leu Ala Ala Leu Ala Glu Leu Pro Thr Ala Val
            115                 120                 125

Thr His Leu Ala Pro Pro Met Ala Met Phe Thr Thr Thr Ala Lys Val
        130                 135                 140

Ile Gln Pro Lys Ile Arg Gly Phe Ile Cys Thr Thr Thr His Pro Ile
145                 150                 155                 160

Gly Cys Glu Lys Arg Val Gln Glu Glu Ile Ala Tyr Ala Arg Ala His
                165                 170                 175

Pro Pro Thr Ser Pro Gly Pro Lys Arg Val Leu Val Ile Gly Cys Ser
                180                 185                 190

Thr Gly Tyr Gly Leu Ser Thr Arg Ile Thr Ala Phe Gly Tyr Gln
                195                 200                 205

Ala Ala Thr Leu Gly Val Phe Leu Ala Gly Pro Pro Thr Lys Gly Arg
        210                 215                 220

Pro Ala Ala Ala Gly Trp Tyr Asn Thr Val Ala Phe Glu Lys Ala Ala
225                 230                 235                 240

Leu Glu Ala Gly Leu Tyr Ala Arg Ser Leu Asn Gly Asp Ala Phe Asp
                245                 250                 255

Ser Thr Thr Lys Ala Arg Thr Val Glu Ala Ile Lys Arg Asp Leu Gly
                260                 265                 270

Thr Val Asp Leu Val Val Tyr Ser Ile Ala Ala Pro Lys Arg Thr Asp
            275                 280                 285

Pro Ala Thr Gly Val Leu His Lys Ala Cys Leu Lys Pro Ile Gly Ala
        290                 295                 300

Thr Tyr Thr Asn Arg Thr Val Asn Thr Asp Lys Ala Glu Val Thr Asp
305                 310                 315                 320

Val Ser Ile Glu Pro Ala Ser Pro Glu Glu Ile Ala Asp Thr Val Lys
                325                 330                 335

Val Met Gly Gly Glu Asp Trp Glu Leu Trp Ile Gln Ala Leu Ser Glu
                340                 345                 350

Ala Gly Val Leu Ala Glu Gly Ala Lys Thr Val Ala Tyr Ser Tyr Ile
            355                 360                 365

Gly Pro Glu Met Thr Trp Pro Val Tyr Trp Ser Gly Thr Ile Gly Glu
        370                 375                 380

Ala Lys Lys Asp Val Glu Lys Ala Ala Lys Arg Ile Thr Gln Gln Tyr
385                 390                 395                 400

Gly Cys Pro Ala Tyr Pro Val Ala Lys Ala Leu Val Thr Gln Ala
                405                 410                 415

Ser Ser Ala Ile Pro Val Val Pro Leu Tyr Ile Cys Leu Leu Tyr Arg
                420                 425                 430

Val Met Lys Glu Lys Gly Thr His Glu Gly Cys Ile Glu Gln Met Val
            435                 440                 445

Arg Leu Leu Thr Thr Lys Leu Tyr Pro Glu Asn Gly Ala Pro Ile Val
        450                 455                 460

Asp Glu Ala Gly Arg Val Arg Val Asp Asp Trp Glu Met Ala Glu Asp
```

```
                465                 470                 475                 480
Val Gln Gln Ala Val Lys Asp Leu Trp Ser Gln Val Ser Thr Ala Asn
                    485                 490                 495

Leu Lys Asp Ile Ser Asp Phe Ala Gly Tyr Gln Thr Glu Phe Leu Arg
                500                 505                 510

Leu Phe Gly Phe Gly Ile Asp Gly Val Asp Tyr Asp Gln Pro Val Asp
                515                 520                 525

Val Glu Ala Asp Leu Pro Ser Ala Ala Gln Gln
                530                 535

<210> SEQ ID NO 64
<211> LENGTH: 303
<212> TYPE: PRT
<213> ORGANISM: Homo sapiens

<400> SEQUENCE: 64

Met Ala Ser Trp Ala Lys Gly Arg Ser Tyr Leu Ala Pro Gly Leu Leu
1               5                   10                  15

Gln Gly Gln Val Ala Ile Val Thr Gly Ala Thr Gly Ile Gly Lys
            20                  25                  30

Ala Ile Val Lys Glu Leu Leu Glu Leu Gly Ser Asn Val Val Ile Ala
            35                  40                  45

Ser Arg Lys Leu Glu Arg Leu Lys Ser Ala Ala Asp Glu Leu Gln Ala
        50                  55                  60

Asn Leu Pro Pro Thr Lys Gln Ala Arg Val Ile Pro Ile Gln Cys Asn
65              70                  75                  80

Ile Arg Asn Glu Glu Glu Val Asn Asn Leu Val Lys Ser Thr Leu Asp
                85                  90                  95

Thr Phe Gly Lys Ile Asn Phe Leu Val Asn Asn Gly Gly Gln Phe
                100                 105                 110

Leu Ser Pro Ala Glu His Ile Ser Ser Lys Gly Trp His Ala Val Leu
            115                 120                 125

Glu Thr Asn Leu Thr Gly Thr Phe Tyr Met Cys Lys Ala Val Tyr Ser
        130                 135                 140

Ser Trp Met Lys Glu His Gly Gly Ser Ile Val Asn Ile Ile Val Pro
145             150                 155                 160

Thr Lys Ala Gly Phe Pro Leu Ala Val His Ser Gly Ala Ala Arg Ala
                165                 170                 175

Gly Val Tyr Asn Leu Thr Lys Ser Leu Ala Leu Glu Trp Ala Cys Ser
                180                 185                 190

Gly Ile Arg Ile Asn Cys Val Ala Pro Gly Val Ile Tyr Ser Gln Thr
            195                 200                 205

Ala Val Glu Asn Tyr Gly Ser Trp Gly Gln Ser Phe Phe Glu Gly Ser
        210                 215                 220

Phe Gln Lys Ile Pro Ala Lys Arg Ile Gly Val Pro Glu Glu Val Ser
225             230                 235                 240

Ser Val Val Cys Phe Leu Leu Ser Pro Ala Ala Ser Phe Ile Thr Gly
                245                 250                 255

Gln Ser Val Asp Val Asp Gly Gly Arg Ser Leu Tyr Thr His Ser Tyr
                260                 265                 270

Glu Val Pro Asp His Asp Asn Trp Pro Lys Gly Ala Gly Asp Leu Ser
            275                 280                 285

Val Val Lys Lys Met Lys Glu Thr Phe Lys Glu Lys Ala Lys Leu
        290                 295                 300
```

<210> SEQ ID NO 65
<211> LENGTH: 303
<212> TYPE: PRT
<213> ORGANISM: Mus musculus

<400> SEQUENCE: 65

Met Gly Ser Trp Lys Thr Gly Gln Ser Tyr Leu Ala Ala Gly Leu Leu
1               5                   10                  15

Lys Asn Gln Val Ala Val Val Thr Gly Gly Thr Gly Ile Gly Lys
            20                  25                  30

Ala Val Ser Arg Glu Leu Leu His Leu Gly Cys Asn Val Val Ile Ala
        35                  40                  45

Ser Arg Lys Leu Asp Arg Leu Thr Ala Ala Val Asp Glu Leu Arg Ala
    50                  55                  60

Ser Leu Pro Pro Ser Ser Ala Glu Val Ser Ala Ile Gln Cys Asn
65                  70                  75                  80

Ile Arg Lys Glu Glu Val Ser Asn Leu Val Lys Ser Thr Leu Ala
            85                  90                  95

Lys Tyr Gly Lys Ile Asn Phe Leu Val Asn Asn Gly Gly Gln Phe
            100                 105                 110

Met Ala Pro Val Glu Asp Ile Thr Ala Lys Gly Trp His Ala Val Ile
        115                 120                 125

Glu Thr Asn Leu Thr Gly Thr Phe Tyr Met Cys Lys Glu Val Tyr Asn
    130                 135                 140

Ser Trp Met Arg Glu His Gly Gly Ser Ile Val Asn Ile Ile Val Leu
145                 150                 155                 160

Leu Asn Asn Gly Phe Pro Thr Ala Ala His Thr Gly Ala Ala Arg Glu
            165                 170                 175

Gly Val Tyr Asn Leu Thr Lys Ser Met Ala Leu Ala Trp Ala Ser Ser
            180                 185                 190

Gly Val Arg Ile Asn Cys Val Ala Pro Gly Thr Ile Tyr Ser Gln Thr
        195                 200                 205

Ala Val Asp Asn Tyr Gly Glu Met Gly Gln Thr Leu Phe Glu Met Ala
    210                 215                 220

Phe Asp Ser Ile Pro Val Ser Ala Leu Gly Val Pro Glu Glu Ile Ser
225                 230                 235                 240

Leu Leu Ala Arg Phe Leu Leu Ser Pro Ala Ala Ser Tyr Ile Thr Gly
            245                 250                 255

Gln Leu Ile Asn Val Asp Gly Gly Gln Ala Leu His Thr His Ala Phe
            260                 265                 270

Ser Ile Pro Asp His Asp Asn Trp Pro Val Gly Ala Gly Asp Leu Ser
        275                 280                 285

Ile Val Lys Arg Ile Lys Glu Ser Phe Lys Lys Lys Ala Lys Leu
    290                 295                 300

<210> SEQ ID NO 66
<211> LENGTH: 373
<212> TYPE: PRT
<213> ORGANISM: Rattus norvegicus

<400> SEQUENCE: 66

Met Leu Val Ser Arg Arg Leu Thr Gly Ala Arg Ala Arg Ala Pro Leu
1               5                   10                  15

Leu Ala Ser Leu Leu Glu Ala Trp Cys Arg Gln Gly Arg Thr Thr Ser
            20                  25                  30

Ser Tyr Ser Ala Phe Ser Glu Pro Ser His Val Arg Ala Leu Val Tyr
            35                  40                  45

Gly Asn His Gly Asp Pro Ala Lys Val Ile Gln Leu Lys Asn Leu Glu
 50                  55                  60

Leu Thr Ala Val Glu Gly Ser Asp Val His Val Lys Met Leu Ala Ala
 65                  70                  75                  80

Pro Ile Asn Pro Ser Asp Ile Asn Met Ile Gln Gly Asn Tyr Gly Leu
                 85                  90                  95

Leu Pro Lys Leu Pro Ala Val Gly Gly Asn Glu Val Gly Gln Val
                100                 105                 110

Ile Ala Val Gly Ser Ser Val Ser Gly Leu Lys Pro Gly Asp Trp Val
            115                 120                 125

Ile Pro Ala Asn Ala Gly Leu Gly Thr Trp Arg Thr Glu Ala Val Phe
            130                 135                 140

Ser Glu Glu Ala Leu Ile Gly Val Pro Lys Asp Ile Pro Leu Gln Ser
145                 150                 155                 160

Ala Ala Thr Leu Gly Val Asn Pro Cys Thr Ala Tyr Arg Met Leu Val
                165                 170                 175

Asp Phe Glu Gln Leu Gln Pro Gly Asp Ser Val Ile Gln Asn Ala Ser
                180                 185                 190

Asn Ser Gly Val Gly Gln Ala Val Ile Gln Ile Ala Ser Ala Leu Gly
            195                 200                 205

Leu Lys Thr Ile Asn Val Ile Arg Asp Arg Pro Asp Ile Lys Lys Leu
            210                 215                 220

Thr Asp Arg Leu Lys Asp Leu Gly Ala Asp Tyr Val Leu Thr Glu Glu
225                 230                 235                 240

Glu Leu Arg Met Pro Glu Thr Lys Asn Ile Phe Lys Asp Leu Pro Leu
                245                 250                 255

Pro Arg Leu Ala Leu Asn Cys Val Gly Gly Lys Ser Ser Thr Glu Leu
                260                 265                 270

Leu Arg His Leu Ala Pro Gly Gly Thr Met Val Thr Tyr Gly Gly Met
            275                 280                 285

Ala Lys Gln Pro Val Thr Ala Ser Val Ser Met Leu Ile Phe Lys Asp
290                 295                 300

Leu Lys Leu Arg Gly Phe Trp Leu Ser Gln Trp Lys Lys Asn His Ser
305                 310                 315                 320

Pro Asp Glu Phe Lys Glu Leu Ile Leu Ile Leu Cys Asn Leu Ile Arg
                325                 330                 335

Gln Gly Gln Leu Thr Ala Pro Ala Trp Ser Gly Ile Pro Leu Gln Asp
            340                 345                 350

Tyr Gln Gln Ala Leu Glu Ala Ser Met Lys Pro Phe Val Ser Leu Lys
            355                 360                 365

Gln Ile Leu Thr Met
370

<210> SEQ ID NO 67
<211> LENGTH: 380
<212> TYPE: PRT
<213> ORGANISM: Saccharomyces cerevisiae

<400> SEQUENCE: 67

Met Leu Pro Thr Phe Lys Arg Tyr Met Ser Ser Ser Ala His Gln Ile
1               5                   10                  15

Pro Lys His Phe Lys Ser Leu Ile Tyr Ser Thr His Glu Val Glu Asp
            20                  25                  30

Cys Thr Lys Val Leu Ser Val Lys Asn Tyr Thr Pro Lys Gln Asp Leu
            35                  40                  45

Ser Gln Ser Ile Val Leu Lys Thr Leu Ala Phe Pro Ile Asn Pro Ser
 50                  55                  60

Asp Ile Asn Gln Leu Gln Gly Val Tyr Pro Ser Arg Pro Glu Lys Thr
 65                  70                  75                  80

Tyr Asp Tyr Ser Thr Asp Glu Pro Ala Ala Ile Ala Gly Asn Glu Gly
                 85                  90                  95

Val Phe Glu Val Val Ser Leu Pro Ser Gly Ser Ser Lys Gly Asp Leu
                100                 105                 110

Lys Leu Gly Asp Arg Val Ile Pro Leu Gln Ala Asn Gln Gly Thr Trp
            115                 120                 125

Ser Asn Tyr Arg Val Phe Ser Ser Ser Asp Leu Ile Lys Val Asn
130                 135                 140

Asp Leu Asp Leu Phe Ser Ala Ala Thr Val Ser Val Asn Gly Cys Thr
145                 150                 155                 160

Gly Phe Gln Leu Val Ser Asp Tyr Ile Asp Trp Asn Ser Asn Gly Asn
                165                 170                 175

Glu Trp Ile Ile Gln Asn Ala Gly Thr Ser Ser Val Ser Lys Ile Val
            180                 185                 190

Thr Gln Val Ala Lys Ala Lys Gly Ile Lys Thr Leu Ser Val Ile Arg
            195                 200                 205

Asp Arg Asp Asn Phe Asp Glu Val Ala Lys Val Leu Glu Asp Lys Tyr
210                 215                 220

Gly Ala Thr Lys Val Ile Ser Glu Ser Gln Asn Asn Asp Lys Thr Phe
225                 230                 235                 240

Ala Lys Glu Val Leu Ser Lys Ile Leu Gly Glu Asn Ala Arg Val Arg
                245                 250                 255

Leu Ala Leu Asn Ser Val Gly Gly Lys Ser Ser Ala Ser Ile Ala Arg
            260                 265                 270

Lys Leu Glu Asn Asn Ala Leu Met Leu Thr Tyr Gly Gly Met Ser Lys
            275                 280                 285

Gln Pro Val Thr Leu Pro Thr Ser Leu His Ile Phe Lys Gly Leu Thr
            290                 295                 300

Ser Lys Gly Tyr Trp Val Thr Glu Lys Asn Lys Lys Asn Pro Gln Ser
305                 310                 315                 320

Lys Ile Asp Thr Ile Ser Asp Phe Ile Lys Met Tyr Asn Tyr Gly His
                325                 330                 335

Ile Ile Ser Pro Arg Asp Glu Ile Glu Thr Leu Thr Trp Asn Thr Asn
            340                 345                 350

Thr Thr Thr Asp Glu Gln Leu Leu Glu Leu Val Lys Lys Gly Ile Thr
            355                 360                 365

Gly Lys Gly Lys Lys Met Val Val Leu Glu Trp
            370                 375                 380

<210> SEQ ID NO 68
<211> LENGTH: 365
<212> TYPE: PRT
<213> ORGANISM: Penicillium Chrysogenum

<400> SEQUENCE: 68

Met Ser Lys Arg Val Thr Ile Phe Asp Pro Pro Glu Gln Asp His Ser
 1               5                  10                  15

Lys Ala Leu Ile Glu Asn Val Leu Asp Leu Thr Pro Val Val Asp Leu

```
                20                  25                  30
Gly Pro Asp Val Phe Thr Asn Thr Arg Pro Leu Trp His Pro Pro Gly
             35                  40                  45
Ala Arg Gly Ile Tyr Gly Ala Ala Ile Ala Gln Ser Leu Ser Ala
 50                  55                  60
Ala Met Arg Thr Val Pro Ala Asp Tyr Ala Val His Ser Met His Cys
 65                  70                  75                  80
Tyr Phe Val Leu Ala Gly Asp Ser Glu Ile Pro Ile Leu Tyr His Val
                 85                  90                  95
Glu Arg Val Arg Asp Gly Arg Ser Phe Val Thr Arg Thr Val Gln Ala
                100                 105                 110
Arg Gln Arg Gly Arg Pro Ile Phe Thr Thr Thr Leu Ser Phe Ser Arg
             115                 120                 125
Val Gly Ser Gly Gly Glu Lys Thr Leu His His Ala Val Ser Lys Pro
             130                 135                 140
Asp Val Pro Leu Pro Glu Glu Ala Glu Pro Gly Ser Leu Lys Ala Leu
145                 150                 155                 160
Ser Asn Ala Gly Gly Gly Pro Phe Glu Ser Arg Lys Ala Gly Ile Leu
                165                 170                 175
Asn Arg Thr Ser Pro Asn Pro Glu Asp Lys Lys Val Arg Arg Tyr Ile
             180                 185                 190
Arg Ala Arg Gly Ala Ile Ser Glu Glu Gly Tyr Gln Ala His Leu
             195                 200                 205
Ser Ala Leu Ala Tyr Ile Thr Asp Ser Tyr Phe Ile Gly Thr Val Ser
             210                 215                 220
Ile Val His Asp Val Pro Arg Phe Ser Ser Pro Ala Glu Leu Glu Lys
225                 230                 235                 240
Leu Leu Asn Ala Leu Lys Asn Pro Ser Asp Leu Asp Asp Glu Asp Ile
                245                 250                 255
Thr Arg Ala Leu Arg Glu Leu Lys Glu Glu Ala Ala Glu Leu Arg
             260                 265                 270
Arg Arg Leu Glu Gly Ala Leu Asn Arg Ala Thr Gly Pro Lys Glu Val
             275                 280                 285
Asp His Lys Glu Val Gly Met Met Val Ser Leu Asp His Ser Ile Tyr
             290                 295                 300
Phe His Asn Pro Arg Ala Phe Arg Ala Asp Glu Trp Met Leu Ser Glu
305                 310                 315                 320
Ile Glu Ser Pro Trp Ala Gly Glu Gly Arg Gly Leu Ala Ile Gln Lys
                325                 330                 335
Leu Trp Ser Lys Asp Gly Val Leu Ile Ala Thr Cys Thr Gln Glu Val
             340                 345                 350
Cys Ile Cys Phe Tyr Ser Leu Tyr Ser Gly Gly Gln Cys
             355                 360                 365

<210> SEQ ID NO 69
<211> LENGTH: 525
<212> TYPE: PRT
<213> ORGANISM: Penicillium Chrysogenum

<400> SEQUENCE: 69

Met Ser Ala Ser Ala Leu Leu Lys Ser Arg Val Arg Arg Pro Ser Tyr
 1               5                  10                  15
Leu Lys Lys Leu Ala Lys Pro Glu Asp Leu Leu His His Phe Pro Asn
             20                  25                  30
```

```
Gly Thr Tyr Ile Gly Trp Ser Gly Phe Thr Val Gly Tyr Pro Lys
             35                  40                  45

Met Thr Pro Ile Ala Leu Ala Asp His Val Glu Lys Asn Asn Leu Gln
 50                  55                  60

Gly Gln Leu Lys Tyr Asn Leu Phe Val Gly Ala Ser Ser Gly Ala Glu
 65                  70                  75                  80

Thr Glu Asn Arg Trp Ala Arg Leu Asn Met Ile Glu Arg Arg Ser Pro
                 85                  90                  95

His Gln Val Gly Lys Glu Ile Ala Lys Gly Ile Asn Asn Gly Gln Ile
                100                 105                 110

Lys Phe Phe Asp Lys His Leu Ser Met Phe Pro Ser Asp Leu Val Tyr
            115                 120                 125

Gly Tyr Tyr Thr Leu Asn Lys Ser Lys Pro Thr Ile Asp Val Ala Val
        130                 135                 140

Ile Glu Ala Ser Ala Ile Thr Glu Asn Gly Gly Ile Ile Pro Gly Ala
145                 150                 155                 160

Ser Val Gly Ala Ser Pro Glu Leu Ile Gln Met Ala Asp Lys Val Ile
                165                 170                 175

Ile Glu Val Asn Thr Ser Met Pro Ser Phe Glu Gly Leu His Asp Ile
            180                 185                 190

Thr Cys Ser Asp Leu Pro Pro Gly Arg Lys Pro Tyr Leu Ile Met Ala
        195                 200                 205

Pro Glu Asp Arg Ile Gly Thr Ser Tyr Ile Pro Ile Asp Pro Glu Lys
    210                 215                 220

Val Val Ala Ile Val Glu Ser Asn Tyr Pro Asp Gln Thr Leu Pro Asn
225                 230                 235                 240

Ala Pro Glu Asp Glu Gly Ser Gln Ala Ile Ala Ser Asn Leu Ile Glu
                245                 250                 255

Phe Leu Lys His Glu Val Asn His Gly Arg Leu Pro Pro Asn Leu Leu
            260                 265                 270

Pro Ile Gln Ser Gly Ile Gly Asn Ile Ala Asn Ala Val Val Gly Gly
        275                 280                 285

Leu Ser Lys Gly Gly Ala Asp Phe Lys Asn Leu Lys Val Trp Thr Glu
    290                 295                 300

Val Leu Gln Asp Ser Phe Leu Asp Leu Phe Asp Ser Gly Asn Leu Asp
305                 310                 315                 320

Phe Ala Thr Ala Thr Ser Ile Arg Phe Ser Pro Asp Gly Phe Lys Arg
                325                 330                 335

Phe Tyr Asp Asn Trp Glu Gln Tyr Ala Gly Lys Leu Leu Leu Arg Ser
            340                 345                 350

Gln Gln Val Ser Asn Ser Pro Glu Ile Ile Arg Arg Leu Gly Cys Ile
        355                 360                 365

Gly Met Asn Thr Pro Val Glu Val Asp Ile Tyr Ala His Ala Asn Ser
    370                 375                 380

Thr Cys Val Met Gly Ser Arg Met Leu Asn Gly Leu Gly Gly Ser Ala
385                 390                 395                 400

Asp Phe Leu Arg Asn Ser Lys Tyr Ser Ile Met His Thr Pro Ser Ala
                405                 410                 415

Arg Pro Thr Lys Thr Asp Pro Thr Gly Val Ser Cys Ile Val Pro Phe
            420                 425                 430

Ala Thr His Ile Asp Gln Thr Glu His Asp Leu Asp Val Val Val Thr
        435                 440                 445

Glu Gln Gly Leu Ala Asp Val Arg Gly Leu Ser Pro Arg Glu Arg Ala
```

```
                450                 455                 460
Arg Val Ile Ile Lys Asn Cys Ser His Pro Asp Tyr Thr Pro Ile Leu
465                 470                 475                 480

Thr Asp Tyr Leu Asp Arg Ala Glu Phe Glu Cys Leu Arg Lys Gly Met
                    485                 490                 495

Gly His Glu Pro His Met Leu Phe Gln Ala Phe Asn Met His Lys Asn
                500                 505                 510

Leu Gln Glu Lys Gly Thr Met Lys Ile Asp Ser Trp Glu
            515                 520                 525

<210> SEQ ID NO 70
<211> LENGTH: 253
<212> TYPE: PRT
<213> ORGANISM: Penicillium Chrysogenum

<400> SEQUENCE: 70

Met Asp Lys Tyr Thr Ile Pro Leu Glu Lys Ala Val Glu Leu Thr Pro
1               5                   10                  15

Ile Pro Ser Glu Pro Asp Thr Phe Thr Asn Ala Gln Pro Leu Trp Ser
                20                  25                  30

Phe Ala Gly Gly Tyr Gly Val Tyr Gly Gly Ser Thr Val Ala His Cys
            35                  40                  45

Leu Val Ala Ala Gln Lys Thr Val Pro Cys Asp Tyr Val Ala His Ser
50                  55                  60

Leu His Cys Gly Phe Val Ser Pro Gly Asn Pro Lys Arg Pro Ile Glu
65                  70                  75                  80

Tyr Arg Val Glu Arg Thr Arg Asp Gly Lys Ser Phe Ile Thr Arg Thr
                85                  90                  95

Val His Ala Thr Gln Lys Ala Gly Val Ile Ser Glu Ala Ile Val Asn
            100                 105                 110

Phe Val Arg Val Gly Thr Tyr Ser Asn Asn Ala Ser His Asp Leu Val
        115                 120                 125

Asn Thr Gln Ile Arg Tyr Trp Val Arg Ala Lys Asp Pro Ile Gln Gln
130                 135                 140

Arg Ser Pro Gln Ala Gln Leu Ala Ala Leu Ala Tyr Met Ser Asp Ala
145                 150                 155                 160

Tyr Leu Ile Gly Ala Ala Val Gln Val His Asp Val Ala Gly Gln Ala
                165                 170                 175

Phe Gly Thr Lys Met Ala Met Ala Ala Ser Leu Asn His Thr Ile Tyr
            180                 185                 190

Phe His Asn Pro Glu Ala Val Arg Ala Asp Glu Trp Met Cys Ser Glu
        195                 200                 205

Arg Glu Ser Pro Trp Ala Gly Asn Asp Arg Ala Leu Val Val Gln Arg
210                 215                 220

Val Trp Ser Pro Glu Gly Ile Leu Val Ala Thr Cys Val Gln Glu Gly
225                 230                 235                 240

Val Leu Arg Val Gln Val Pro Ser Glu Lys Val Lys Leu
                245                 250

<210> SEQ ID NO 71
<211> LENGTH: 462
<212> TYPE: PRT
<213> ORGANISM: Penicillium Chrysogenum

<400> SEQUENCE: 71

Met Phe Gly Leu Ser Arg Arg Ser Ala Leu Ala Arg Ser Lys Ser Leu
```

-continued

```
1               5                   10                  15
Ala Ala Leu Pro Ala Arg Ala Ala Val Ala Ala Gln Pro Ser Cys Ile
                20                  25                  30
Asn Thr Gln Gly Phe His Ser Thr Pro Ser Gln Ala Ala Ser Arg Pro
                35                  40                  45
Thr Trp Met Pro Met Arg Val Lys Thr Pro Trp Ile Glu Ala Leu Thr
            50                  55                  60
Gln Ile Arg Glu Ala Gln Lys Ala Gly Pro Gln Glu Asn Ala Gly Gln
65                  70                  75                  80
Ser Val Lys Arg Asp Leu Ser Pro Lys Lys Met Ser Asp Ser Tyr Tyr
                85                  90                  95
Ser Ala Ile Leu Pro Leu Ala Gln Asp Lys Trp Leu Leu Asp Ser Tyr
                100                 105                 110
Leu Asn Ala Ser Gly His Ile Arg Leu Gly Ser Leu Leu Met Asp Leu
                115                 120                 125
Asp Ala Leu Ala Gly Ile Val Ala Tyr Arg His Thr Gly Asp Gly Val
                130                 135                 140
Ser Thr Val Thr Ala Ala Cys Asp Arg Ile Thr Ile Glu Asn Pro Leu
145                 150                 155                 160
Met Glu Ile Cys Asp Leu Glu Leu Ser Gly Gln Cys Thr Tyr Ala Thr
                165                 170                 175
Gly Arg Ser Ser Met Glu Ile Ser Leu Gln Val Thr Lys Ala Arg Pro
                180                 185                 190
Glu Gly Gln Glu Ala Lys Pro Glu Asp Ile Leu Ile Thr Cys Ala Phe
                195                 200                 205
Thr Met Val Ser Leu Asp Pro Ala Thr Lys Ala Pro Val Pro Val Ala
                210                 215                 220
Pro Leu Ile Val Glu Thr Glu Glu Lys Arg Leu Phe Gln Lys Gly
225                 230                 235                 240
Glu Ala Asn Tyr Gln Ala Lys Lys Ala Leu Arg Thr Arg Ser Leu Leu
                245                 250                 255
Gln Lys Ser Pro Asp Asp Glu Glu Ser Asn Leu Ile His Ser Met Trp
                260                 265                 270
Thr Lys Glu Met Ser Tyr Leu Asn Pro Gln Asn Pro Ala Thr Arg Pro
                275                 280                 285
Ala Asn Gln Val Phe Met Ser Asp Thr Val Leu Lys Ser Ala Met Ile
                290                 295                 300
Met Gln Pro Gln Asp Arg Asn Arg His Asn Phe Met Ile Phe Gly Gly
305                 310                 315                 320
Phe Leu Leu Lys Gln Thr Phe Glu Leu Ala Phe Cys Cys Ala Ala Ser
                325                 330                 335
Phe Ala His Ala Arg Pro Asn Phe Val Ala Leu Asp Pro Ser Thr Phe
                340                 345                 350
Glu Asn Pro Val Pro Val Gly Ser Val Leu Tyr Leu Arg Ala Thr Val
                355                 360                 365
Ser Tyr Thr Glu Pro Glu Glu Arg Glu Gly Asp Ser Thr Lys Tyr Thr
                370                 375                 380
Lys Val Gln Val Arg Val Asp Ser Lys Val Arg Asp Val Glu His Gly
385                 390                 395                 400
Thr Lys Lys Ser Thr Gly Met Phe Asn Tyr Thr Phe Leu Val Glu Lys
                405                 410                 415
Asp Val Gln Val Met Pro Lys Gly Tyr Gly Glu Phe Met Leu Trp Ala
                420                 425                 430
```

```
Asp Ala Arg Arg Arg Ala Gln Asn Ala Ala Ile Asp Pro Ala His
        435                 440                 445

Lys Met Ser Ala Leu Arg Ser Ile Lys Asp Ser Val Thr Glu
    450                 455                 460

<210> SEQ ID NO 72
<211> LENGTH: 357
<212> TYPE: PRT
<213> ORGANISM: Penicillium Chrysogenum

<400> SEQUENCE: 72

Met Ser Pro Gln Arg Gly Ala Pro Asp Asn Asp Asp Leu Thr Ser Pro
1               5                   10                  15

His Ser Phe Val Glu Leu Met Ser Leu Gln Arg Leu Glu Asp Ala Leu
            20                  25                  30

Ile Thr Tyr Pro Asp Ser Ala Lys Pro Glu Lys Ile Glu Arg Phe Arg
        35                  40                  45

Ser Leu Ala Thr Pro Tyr Asn Pro Gly Gln Gly Thr Arg Ser Phe Gly
    50                  55                  60

Gly His Val Tyr Ala Gln Ser Ala Tyr Ala Ala Ser Lys Thr Val Gly
65                  70                  75                  80

Pro Gly Leu Val Ile His Asp Met Thr Gly Thr Phe Ile Leu Gly Gly
                85                  90                  95

Leu Leu Asp Thr Pro Tyr Val Tyr Thr Val Arg His Ile Arg Asp Gly
            100                 105                 110

Tyr Met Tyr Ser Thr Arg Ala Val Asp Ala Arg Gln Ala Gly Arg Ile
        115                 120                 125

Cys Phe Ser Cys Ile Cys Ser Phe Lys Arg Asp Glu Lys Gln Arg Leu
    130                 135                 140

Phe Gln His Gln Pro Ala Ser Ala Gln Ala Arg Phe Asp Ser Ile Leu
145                 150                 155                 160

Ser Ala Lys Arg Pro Glu Asp Gln Glu Pro Ser Pro Ser Val Asp Ala
                165                 170                 175

Glu Trp Trp Ile Glu Ala Val Arg Gln Gly Asn Ile Ser Glu Ser Glu
            180                 185                 190

Phe Pro Gly Leu Asp Val Arg Lys Thr Asp Met Lys Asp Tyr Asn Cys
        195                 200                 205

Ala Glu Asp Val Lys Gln His Pro Glu Arg Tyr Arg Gln Leu Thr Gln
    210                 215                 220

Tyr Arg Leu Lys Gly Ser Pro Glu Glu Asp Pro Ala Ala Ser Leu Ala
225                 230                 235                 240

Gln Ile Arg Glu Arg Glu Glu Asn Gly Glu Tyr Asp Asn Leu Tyr Ala
                245                 250                 255

Cys Ala His Met Tyr Ser Ser Asp Lys Asn Ser Leu Leu Leu Ile Pro
            260                 265                 270

Arg Ala Leu Gly Ile Lys Asn Trp Thr Glu Met Ala Ser Leu Thr Leu
        275                 280                 285

Thr Val Ile Val His Gln His Gly Glu Ala Leu Arg Met Val Asn Trp
    290                 295                 300

Asp Ser Ile Gly Asp Asp Val Gly Val Asp Lys Leu Pro Met Lys
305                 310                 315                 320

Trp Phe Val Gln Glu Gly Trp Thr Pro Arg Ala Thr Glu Asn Arg Gly
                325                 330                 335

Thr His Glu Ser His Leu Trp Ser Pro Asp Gly Thr Leu Leu Ala Thr
```

340             345             350

Ser Leu Gln Asp Asn
            355

<210> SEQ ID NO 73
<211> LENGTH: 320
<212> TYPE: PRT
<213> ORGANISM: Mus musculus

<400> SEQUENCE: 73

Met Ser Ala Pro Glu Gly Leu Gly Asp Ala His Gly Asp Ala Asp Arg
1               5                   10                  15

Gly Asp Leu Ser Gly Asp Leu Arg Ser Val Leu Val Thr Ser Val Leu
            20                  25                  30

Asn Leu Glu Pro Leu Asp Glu Asp Leu Tyr Arg Gly Arg His Tyr Trp
        35                  40                  45

Val Pro Thr Ser Gln Arg Leu Phe Gly Gly Gln Ile Met Gly Gln Ala
    50                  55                  60

Leu Val Ala Ala Ala Lys Ser Val Ser Glu Asp Val His Val His Ser
65                  70                  75                  80

Leu His Cys Tyr Phe Val Arg Ala Gly Asp Pro Lys Val Pro Val Leu
                85                  90                  95

Tyr His Val Glu Arg Ile Arg Thr Gly Ala Ser Phe Ser Val Arg Ala
            100                 105                 110

Val Lys Ala Val Gln His Gly Lys Ala Ile Phe Ile Cys Gln Ala Ser
        115                 120                 125

Phe Gln Gln Met Gln Pro Ser Pro Leu Gln His Gln Phe Ser Met Pro
130                 135                 140

Ser Val Pro Pro Glu Asp Leu Leu Asp His Glu Ala Leu Ile Asp
145                 150                 155                 160

Gln Tyr Leu Arg Asp Pro Asn Leu His Lys Lys Tyr Arg Val Gly Leu
                165                 170                 175

Asn Arg Val Ala Ala Gln Glu Val Pro Ile Glu Ile Lys Val Val Asn
            180                 185                 190

Pro Pro Thr Leu Thr Gln Leu Gln Ala Leu Glu Pro Lys Gln Met Phe
        195                 200                 205

Trp Val Arg Ala Arg Gly Tyr Ile Gly Glu Gly Asp Ile Lys Met His
    210                 215                 220

Cys Cys Val Ala Ala Tyr Ile Ser Asp Tyr Ala Phe Leu Gly Thr Ala
225                 230                 235                 240

Leu Leu Pro His Gln Ser Lys Tyr Lys Val Asn Phe Met Ala Ser Leu
                245                 250                 255

Asp His Ser Met Trp Phe His Ala Pro Phe Arg Ala Asp His Trp Met
            260                 265                 270

Leu Tyr Glu Cys Glu Ser Pro Trp Ala Gly Gly Phe Arg Gly Leu Val
        275                 280                 285

His Gly Arg Leu Trp Arg Arg Asp Gly Val Leu Ala Val Thr Cys Ala
    290                 295                 300

Gln Glu Gly Val Ile Arg Leu Lys Pro Gln Val Ser Glu Ser Lys Leu
305                 310                 315                 320

<210> SEQ ID NO 74
<211> LENGTH: 472
<212> TYPE: PRT
<213> ORGANISM: Clostridium kluyveri

<400> SEQUENCE: 74

```
Met Ser Asn Glu Val Ser Ile Lys Glu Leu Ile Glu Lys Ala Lys Ala
1               5                   10                  15

Ala Gln Lys Lys Leu Glu Ala Tyr Ser Gln Glu Gln Val Asp Val Leu
            20                  25                  30

Val Lys Ala Leu Gly Lys Val Tyr Asp Asn Ala Glu Met Phe Ala
        35                  40                  45

Lys Glu Ala Val Glu Glu Thr Glu Met Gly Val Tyr Glu Asp Lys Val
    50                  55                  60

Ala Lys Cys His Leu Lys Ser Gly Ala Ile Trp Asn His Ile Lys Asp
65                  70                  75                  80

Lys Lys Thr Val Gly Ile Ile Lys Glu Glu Pro Glu Arg Ala Leu Val
                85                  90                  95

Tyr Val Ala Lys Pro Lys Gly Val Val Ala Ala Thr Thr Pro Ile Thr
            100                 105                 110

Asn Pro Val Val Thr Pro Met Cys Asn Ala Met Ala Ala Ile Lys Gly
        115                 120                 125

Arg Asn Thr Ile Ile Val Ala Pro His Pro Lys Ala Lys Lys Val Ser
130                 135                 140

Ala His Thr Val Glu Leu Met Asn Ala Glu Leu Lys Lys Leu Gly Ala
145                 150                 155                 160

Pro Glu Asn Ile Ile Gln Ile Val Glu Ala Pro Ser Arg Glu Ala Ala
                165                 170                 175

Lys Glu Leu Met Glu Ser Ala Asp Val Val Ile Ala Thr Gly Gly Ala
            180                 185                 190

Gly Arg Val Lys Ala Ala Tyr Ser Ser Gly Arg Pro Ala Tyr Gly Val
        195                 200                 205

Gly Pro Gly Asn Ser Gln Val Ile Val Asp Lys Gly Tyr Asp Tyr Asn
    210                 215                 220

Lys Ala Ala Gln Asp Ile Ile Thr Gly Arg Lys Tyr Asp Asn Gly Ile
225                 230                 235                 240

Ile Cys Ser Ser Glu Gln Ser Val Ile Ala Pro Ala Glu Asp Tyr Asp
                245                 250                 255

Lys Val Ile Ala Ala Phe Val Glu Asn Gly Ala Phe Tyr Val Glu Asp
            260                 265                 270

Glu Glu Thr Val Glu Lys Phe Arg Ser Thr Leu Phe Lys Asp Gly Lys
        275                 280                 285

Ile Asn Ser Lys Ile Ile Gly Lys Ser Val Gln Ile Ile Ala Asp Leu
    290                 295                 300

Ala Gly Val Lys Val Pro Glu Gly Thr Lys Val Ile Val Leu Lys Gly
305                 310                 315                 320

Lys Gly Ala Gly Glu Lys Asp Val Leu Cys Lys Glu Lys Met Cys Pro
                325                 330                 335

Val Leu Val Ala Leu Lys Tyr Asp Thr Phe Glu Glu Ala Val Glu Ile
            340                 345                 350

Ala Met Ala Asn Tyr Met Tyr Glu Gly Ala Gly His Thr Ala Gly Ile
        355                 360                 365

His Ser Asp Asn Asp Glu Asn Ile Arg Tyr Ala Arg Thr Val Leu Pro
    370                 375                 380

Ile Ser Arg Leu Val Val Asn Gln Pro Ala Thr Thr Ala Gly Gly Thr
385                 390                 395                 400

Val Leu Pro Ile Ser Arg Leu Val Val Asn Gln Pro Ala Thr Thr Ala
                405                 410                 415
```

```
Gly Gly Ser Phe Asn Asn Gly Phe Asn Pro Thr Thr Thr Leu Gly Cys
            420                 425                 430

Gly Ser Trp Gly Arg Asn Ser Ile Ser Glu Asn Leu Thr Tyr Glu His
        435                 440                 445

Leu Ile Asn Val Ser Arg Ile Gly Tyr Phe Asn Lys Glu Ala Lys Val
450                 455                 460

Pro Ser Tyr Glu Glu Ile Trp Gly
465                 470

<210> SEQ ID NO 75
<211> LENGTH: 451
<212> TYPE: PRT
<213> ORGANISM: Porphyromonas gingivalis

<400> SEQUENCE: 75

Met Glu Ile Lys Glu Met Val Ser Leu Ala Arg Lys Ala Gln Lys Glu
1               5                   10                  15

Tyr Gln Ala Thr His Asn Gln Glu Ala Val Asp Asn Ile Cys Arg Ala
            20                  25                  30

Ala Ala Lys Val Ile Tyr Glu Asn Ala Ala Ile Leu Ala Arg Glu Ala
        35                  40                  45

Val Asp Glu Thr Gly Met Gly Val Tyr Glu His Lys Val Ala Lys Asn
50                  55                  60

Gln Gly Lys Ser Lys Gly Val Trp Tyr Asn Leu His Asn Lys Lys Ser
65                  70                  75                  80

Ile Gly Ile Leu Asn Ile Asp Glu Arg Thr Gly Met Ile Glu Ile Ala
            85                  90                  95

Lys Pro Ile Gly Val Val Gly Ala Val Thr Pro Thr Thr Asn Pro Ile
        100                 105                 110

Val Thr Pro Met Ser Asn Ile Ile Phe Ala Leu Lys Thr Cys Asn Ala
    115                 120                 125

Ile Ile Ile Ala Pro His Pro Arg Ser Lys Lys Cys Ser Ala His Ala
130                 135                 140

Val Arg Leu Ile Lys Glu Ala Ile Ala Pro Phe Asn Val Pro Glu Gly
145                 150                 155                 160

Met Val Gln Ile Ile Glu Glu Pro Ser Ile Glu Lys Thr Gln Glu Leu
            165                 170                 175

Met Gly Ala Val Asp Val Val Ala Thr Gly Gly Met Gly Met Val
        180                 185                 190

Lys Ser Ala Tyr Ser Ser Gly Lys Pro Ser Phe Gly Val Gly Ala Gly
    195                 200                 205

Asn Val Gln Val Ile Val Asp Ser Asn Ile Asp Phe Glu Ala Ala Ala
210                 215                 220

Glu Lys Ile Ile Thr Gly Arg Ala Phe Asp Asn Gly Ile Ile Cys Ser
225                 230                 235                 240

Gly Glu Gln Ser Ile Ile Tyr Asn Glu Ala Asp Lys Glu Ala Val Phe
            245                 250                 255

Thr Ala Phe Arg Asn His Gly Ala Tyr Phe Cys Asp Glu Ala Glu Gly
        260                 265                 270

Asp Arg Ala Arg Ala Ala Ile Phe Glu Asn Gly Ala Ile Ala Lys Asp
    275                 280                 285

Val Val Gly Gln Ser Val Ala Phe Ile Ala Lys Lys Ala Asn Ile Asn
290                 295                 300

Ile Pro Glu Gly Thr Arg Ile Leu Val Val Glu Ala Arg Gly Val Gly
```

```
                305                 310                 315                 320
Ala Glu Asp Val Ile Cys Lys Glu Lys Met Cys Pro Val Met Cys Ala
                    325                 330                 335

Leu Ser Tyr Lys His Phe Glu Glu Gly Val Glu Ile Ala Arg Thr Asn
                    340                 345                 350

Leu Ala Asn Glu Gly Asn Gly His Thr Cys Ala Ile His Ser Asn Asn
                    355                 360                 365

Gln Ala His Ile Ile Leu Ala Gly Ser Glu Leu Thr Val Ser Arg Ile
                    370                 375                 380

Val Val Asn Ala Pro Ser Ala Thr Thr Ala Gly Gly His Ile Gln Asn
385                 390                 395                 400

Gly Leu Ala Val Thr Asn Thr Leu Gly Cys Gly Ser Trp Gly Asn Asn
                    405                 410                 415

Ser Ile Ser Glu Asn Phe Thr Tyr Lys His Leu Leu Asn Ile Ser Arg
                    420                 425                 430

Ile Ala Pro Leu Asn Ser Ser Ile His Ile Pro Asp Asp Lys Glu Ile
                    435                 440                 445

Trp Glu Leu
    450

<210> SEQ ID NO 76
<211> LENGTH: 876
<212> TYPE: PRT
<213> ORGANISM: Clostridium kluyveri

<400> SEQUENCE: 76

Met Lys Val Thr Asn Val Glu Glu Leu Met Lys Lys Leu Gln Lys Val
1               5                   10                  15

Arg Gln Ala Gln Glu Lys Phe Ser Thr Tyr Thr Gln Glu Gln Val Asp
                20                  25                  30

Glu Ile Phe Lys Gln Ala Ala Met Ala Ala Asn Ser Ala Arg Ile Lys
            35                  40                  45

Leu Ala Lys Met Ala Val Glu Glu Thr Gly Met Gly Ile Val Glu Asp
    50                  55                  60

Lys Val Ile Lys Asn His Phe Val Ser Glu Tyr Val Tyr Asn Lys Tyr
65                  70                  75                  80

Lys Asp Glu Gln Thr Cys Gly Val Leu Glu Arg Asp Glu Gly Phe Gly
                85                  90                  95

Met Val Arg Ile Ala Glu Pro Val Gly Val Ile Ala Ala Val Val Pro
                100                 105                 110

Thr Thr Asn Pro Thr Ser Thr Ala Ile Phe Lys Ala Leu Ile Ala Leu
            115                 120                 125

Lys Thr Arg Asn Gly Ile Val Phe Ser Pro His Pro Arg Ala Lys Arg
    130                 135                 140

Ser Thr Val Ala Ala Lys Ile Val Leu Asp Ala Ala Val Glu Ala
145                 150                 155                 160

Gly Ala Pro Val Glu Ile Ile Gly Trp Ile Asp Glu Pro Ser Ile Glu
                165                 170                 175

Leu Ser Gln Leu Val Met Lys Glu Ala Asp Leu Ile Leu Ala Thr Gly
                180                 185                 190

Gly Pro Gly Met Val Arg Ala Ala Tyr Ser Ser Gly Lys Pro Ala Ile
            195                 200                 205

Gly Val Gly Pro Gly Asn Thr Pro Val Ile Ile Asp Asp Ser Ala Asn
    210                 215                 220
```

-continued

```
Ile Lys Met Ala Val Asn Ser Ile Leu Leu Ser Lys Ser Phe Asp His
225                 230                 235                 240

Gly Val Ile Cys Ala Ser Glu Gln Ser Val Met Val Leu Asp Arg Ile
            245                 250                 255

Tyr Glu Glu Val Lys Thr Glu Phe Ser Glu Arg Gly Gly Tyr Ile Leu
        260                 265                 270

Lys Asn Asp Glu Ile Asp Lys Val Arg Glu Thr Ile Leu Val Asn Gly
    275                 280                 285

Ser Ile Ser Pro Asp Ile Val Gly Gln Ser Ala Arg Lys Ile Ala Glu
290                 295                 300

Met Ala Gly Val Lys Val Pro Glu Arg Thr Lys Ile Leu Ile Gly Glu
305                 310                 315                 320

Val Glu Ser Val Glu Leu Glu Pro Phe Ser Arg Glu Lys Leu Ser
            325                 330                 335

Pro Val Leu Ala Met Tyr Arg Val Lys Asn Phe Asn Asp Gly Leu Lys
            340                 345                 350

Lys Ala Ala Arg Leu Val Glu Leu Gly Gly Ile Gly His Thr Ser Val
        355                 360                 365

Leu Tyr Val Asn Thr Met Thr Gln Lys Glu Lys Val Glu Lys Phe Ser
370                 375                 380

Glu Ala Met Lys Thr Gly Arg Thr Leu Ile Asn Met Pro Ser Ala Gln
385                 390                 395                 400

Gly Ala Ile Gly Asp Leu Tyr Asn Phe Lys Leu Ala Pro Ser Leu Thr
                405                 410                 415

Leu Gly Cys Gly Ser Trp Gly Gly Asn Ser Ile Ser Glu Asn Val Gly
            420                 425                 430

Pro Lys His Leu Leu Asn Ile Lys Ser Ile Ala Glu Arg Arg Glu Asn
        435                 440                 445

Met Leu Trp Phe Arg Val Pro Glu Lys Ile Tyr Phe Lys Tyr Gly Ala
    450                 455                 460

Leu Gly Thr Ala Leu Lys Glu Leu Lys Thr Met His Lys Lys Val
465                 470                 475                 480

Phe Ile Val Thr Asp Lys Val Leu Tyr Gln Leu Gly Tyr Thr Asp Ser
                485                 490                 495

Ile Thr Lys Ile Leu Gly Glu Met Gly Val Gly Tyr Lys Ile Phe Thr
            500                 505                 510

Asp Val Glu Pro Asp Pro Thr Leu Ala Thr Ala Lys Lys Gly Ser Ala
        515                 520                 525

Glu Met Leu Gln Tyr Asn Pro Asp Thr Ile Ile Ser Val Gly Gly Gly
    530                 535                 540

Ser Ala Met Asp Ala Ala Lys Ile Met Trp Val Met Tyr Glu His Pro
545                 550                 555                 560

Glu Ile Lys Phe Glu Asp Leu Ala Met Arg Phe Met Asp Ile Arg Lys
                565                 570                 575

Arg Val Tyr Thr Phe Pro Lys Met Gly Glu Lys Ser Met Met Ile Ser
            580                 585                 590

Val Ala Thr Ser Ala Gly Thr Gly Ser Glu Val Thr Pro Phe Thr Val
        595                 600                 605

Ile Thr Asp Glu Lys Thr Gly Ala Lys Tyr Pro Leu Ala Asp Tyr Glu
    610                 615                 620

Leu Thr Pro Asp Ile Ala Ile Ile Asp Ala Glu Leu Met Met Asn Met
625                 630                 635                 640

Pro Lys Gly Leu Thr Ala Ala Ser Gly Ile Asp Ala Met Thr His Ala
```

```
                            645                 650                 655
Leu Glu Ser Tyr Val Ser Val Met Ala Ser Glu Tyr Thr Asn Gly Leu
                660                 665                 670

Ala Leu Glu Ala Ile Arg Leu Ile Phe Lys Tyr Leu Pro Leu Ala Tyr
                675                 680                 685

Ala Glu Gly Thr Thr Asn Val Lys Ala Arg Glu Lys Met Ala His Ala
                690                 695                 700

Ser Thr Met Ala Gly Met Ala Phe Ala Asn Ala Phe Leu Gly Val Cys
705                 710                 715                 720

His Ser Met Ala His Lys Leu Gly Ala His His Ile Pro His Gly
                    725                 730                 735

Ile Ala Asn Ala Leu Met Ile Asp Glu Val Ile Lys Phe Asn Ala Val
                740                 745                 750

Asn Asp Pro Arg Lys Gln Ala Ile Phe Pro Gln Tyr Lys Tyr Pro Asn
                755                 760                 765

Ala Lys Trp Arg Tyr Ala Arg Ile Ala Asp Tyr Leu Glu Leu Gly Gly
                770                 775                 780

Asn Ser Glu Asp Glu Lys Val Gly Leu Leu Ile Lys Ala Ile Asp Glu
785                 790                 795                 800

Leu Lys Glu Lys Ile Asn Ile Pro Lys Thr Ile Arg Glu Ala Gly Val
                805                 810                 815

Ala Glu Lys Lys Phe Tyr Ala Thr Leu Asp Asp Met Ser Glu Gln Ala
                820                 825                 830

Phe Asp Asp Gln Cys Thr Gly Ala Asn Pro Arg Tyr Pro Leu Ile Ser
                835                 840                 845

Glu Ile Lys Gln Met Tyr Ile Asn Ala Phe Asp Lys Val Ser Pro Val
                850                 855                 860

Val Asp Glu Glu Lys Leu Lys Val Ser Leu Leu
865                 870                 875

<210> SEQ ID NO 77
<211> LENGTH: 491
<212> TYPE: PRT
<213> ORGANISM: Clostridium kluyveri

<400> SEQUENCE: 77

Met Glu Ile Met Asp Lys Asp Leu Gln Ser Ile Gln Glu Val Arg Thr
1               5                   10                  15

Leu Ile Ala Lys Ala Lys Lys Ala Gln Ala Glu Phe Lys Asn Phe Ser
                20                  25                  30

Gln Glu Ala Val Asn Lys Val Ile Glu Lys Ile Ala Lys Ala Thr Glu
                35                  40                  45

Val Glu Ala Val Lys Leu Ala Lys Leu Ala Tyr Glu Asp Thr Gly Tyr
                50                  55                  60

Gly Lys Trp Glu Asp Lys Val Ile Lys Asn Lys Phe Ser Ser Ile Val
65                  70                  75                  80

Val Tyr Asn Tyr Ile Lys Asp Leu Lys Thr Val Gly Ile Leu Lys Glu
                85                  90                  95

Asp Lys Glu Lys Lys Leu Ile Asp Ile Ala Val Pro Leu Gly Val Ile
                100                 105                 110

Ala Gly Leu Ile Pro Ser Thr Asn Pro Thr Ser Thr Ala Ile Phe Lys
                115                 120                 125

Val Leu Ile Ala Leu Lys Ala Gly Asn Ala Ile Val Phe Ser Pro His
                130                 135                 140
```

```
Pro Thr Ala Val Arg Ser Ile Thr Glu Thr Val Lys Ile Met Gln Lys
145                 150                 155                 160

Ala Ala Val Glu Ala Gly Ala Pro Asp Gly Leu Ile Gln Cys Met Ser
                165                 170                 175

Ile Leu Thr Val Glu Gly Thr Ala Glu Leu Met Lys Asn Lys Asp Thr
            180                 185                 190

Ala Leu Ile Leu Ala Thr Gly Gly Glu Gly Met Val Arg Ala Ala Tyr
        195                 200                 205

Ser Ser Gly Thr Pro Ala Ile Gly Val Gly Pro Gly Asn Gly Pro Cys
    210                 215                 220

Phe Ile Glu Arg Thr Ala Asp Ile Pro Thr Ala Val Arg Lys Val Ile
225                 230                 235                 240

Gly Ser Asp Thr Phe Asp Asn Gly Val Ile Cys Ala Ser Glu Gln Ser
                245                 250                 255

Ile Ile Ala Glu Thr Val Lys Lys Ala Glu Ile Ile Glu Glu Phe Lys
            260                 265                 270

Arg Gln Lys Gly Tyr Phe Leu Asn Ala Glu Ser Glu Lys Val Gly
        275                 280                 285

Lys Ile Leu Leu Arg Ala Asn Gly Thr Pro Asn Pro Ala Ile Val Gly
290                 295                 300

Lys Asp Val Gln Ala Leu Ala Lys Leu Ala Gly Ile Ser Ile Pro Ser
305                 310                 315                 320

Asp Ala Val Ile Leu Leu Ser Glu Gln Thr Asp Val Ser Pro Lys Asn
                325                 330                 335

Pro Tyr Ala Lys Glu Lys Leu Ala Pro Val Leu Ala Phe Tyr Thr Val
            340                 345                 350

Glu Asp Trp His Glu Ala Cys Glu Lys Ser Leu Ala Leu Leu His Asn
        355                 360                 365

Gln Gly Ser Gly His Thr Leu Ile Ile His Ser Gln Asn Glu Glu Ile
    370                 375                 380

Ile Arg Glu Phe Ala Leu Lys Lys Pro Val Ser Arg Ile Leu Val Asn
385                 390                 395                 400

Ser Pro Gly Ser Leu Gly Gly Ile Gly Gly Ala Thr Asn Leu Val Pro
                405                 410                 415

Ser Leu Thr Leu Gly Cys Gly Ala Val Gly Gly Ser Ala Thr Ser Asp
            420                 425                 430

Asn Val Gly Pro Glu Asn Leu Phe Asn Ile Arg Lys Val Ala Tyr Gly
        435                 440                 445

Thr Thr Thr Val Glu Glu Ile Arg Glu Ala Phe Gly Val Gly Ala Ala
    450                 455                 460

Ser Ser Ser Ala Pro Ala Glu Pro Glu Asp Asn Glu Asp Val Gln Ala
465                 470                 475                 480

Ile Val Lys Ala Ile Met Ala Lys Leu Asn Leu
                485                 490

<210> SEQ ID NO 78
<211> LENGTH: 491
<212> TYPE: PRT
<213> ORGANISM: Clostridium kluyveri

<400> SEQUENCE: 78

Met Glu Ile Met Asp Lys Asp Leu Gln Ser Ile Gln Glu Val Arg Thr
1               5                   10                  15

Leu Ile Ala Lys Ala Lys Lys Ala Gln Ala Glu Phe Lys Asn Phe Ser
            20                  25                  30
```

Gln Glu Ala Val Asn Lys Val Ile Glu Lys Ile Ala Lys Ala Thr Glu
    35                  40                  45

Val Glu Ala Val Lys Leu Ala Lys Leu Ala Tyr Glu Asp Thr Gly Tyr
50                  55                  60

Gly Lys Trp Glu Asp Lys Val Ile Lys Asn Lys Phe Ser Ser Ile Val
65                  70                  75                  80

Val Tyr Asn Tyr Ile Lys Asp Leu Lys Thr Val Gly Ile Leu Lys Glu
                85                  90                  95

Asp Lys Glu Lys Lys Leu Ile Asp Ile Ala Val Pro Leu Gly Val Ile
                100                 105                 110

Ala Gly Leu Ile Pro Ser Thr Asn Pro Thr Ser Thr Ala Ile Phe Lys
            115                 120                 125

Val Leu Ile Ala Leu Lys Ala Gly Asn Ala Ile Val Phe Ser Pro His
    130                 135                 140

Pro Thr Ala Val Arg Ser Ile Thr Glu Thr Val Lys Ile Met Gln Lys
145                 150                 155                 160

Ala Ala Val Glu Ala Gly Ala Pro Asp Gly Leu Ile Gln Cys Met Ser
                165                 170                 175

Ile Leu Thr Val Glu Gly Thr Ala Glu Leu Met Lys Asn Lys Asp Thr
                180                 185                 190

Ala Leu Ile Leu Ala Thr Gly Gly Glu Gly Met Val Arg Ala Ala Tyr
            195                 200                 205

Ser Ser Gly Thr Pro Ala Ile Gly Val Gly Pro Gly Asn Gly Pro Cys
    210                 215                 220

Phe Ile Glu Arg Thr Ala Asp Ile Pro Thr Ala Val Arg Lys Val Ile
225                 230                 235                 240

Gly Ser Asp Thr Phe Asp Asn Gly Val Ile Cys Ala Ser Glu Gln Ser
                245                 250                 255

Ile Ile Ala Glu Thr Val Lys Lys Ala Glu Ile Ile Glu Glu Phe Lys
                260                 265                 270

Arg Gln Lys Gly Tyr Phe Leu Asn Ala Glu Glu Ser Glu Lys Val Gly
            275                 280                 285

Lys Ile Leu Leu Arg Ala Asn Gly Thr Pro Asn Pro Ala Ile Val Gly
    290                 295                 300

Lys Asp Val Gln Ala Leu Ala Lys Leu Ala Gly Ile Ser Ile Pro Ser
305                 310                 315                 320

Asp Ala Val Ile Leu Leu Ser Glu Gln Thr Asp Val Ser Pro Lys Asn
                325                 330                 335

Pro Tyr Ala Lys Glu Lys Leu Ala Pro Val Leu Ala Phe Tyr Thr Val
            340                 345                 350

Glu Asp Trp His Glu Ala Cys Glu Lys Ser Leu Ala Leu Leu His Asn
    355                 360                 365

Gln Gly Ser Gly His Thr Leu Ile Ile His Ser Gln Asn Glu Glu Ile
370                 375                 380

Ile Arg Glu Phe Ala Leu Lys Lys Pro Val Ser Arg Ile Leu Val Asn
385                 390                 395                 400

Ser Pro Gly Ser Leu Gly Gly Ile Gly Gly Ala Thr Asn Leu Val Pro
                405                 410                 415

Ser Leu Thr Leu Gly Cys Gly Ala Val Gly Gly Ser Ala Thr Ser Asp
            420                 425                 430

Asn Val Gly Pro Glu Asn Leu Phe Asn Ile Arg Lys Val Ala Tyr Gly
    435                 440                 445

```
Thr Thr Thr Val Glu Glu Ile Arg Glu Ala Phe Gly Val Gly Ala Ala
450                 455                 460
Ser Ser Ser Ala Pro Ala Glu Pro Glu Asp Asn Glu Asp Val Gln Ala
465                 470                 475                 480
Ile Val Lys Ala Ile Met Ala Lys Leu Asn Leu
                485                 490
```

<210> SEQ ID NO 79
<211> LENGTH: 469
<212> TYPE: PRT
<213> ORGANISM: Propionibacterium freudenreichi

<400> SEQUENCE: 79

```
Met Thr Ile Ser Pro Glu Leu Ile Gln Gln Val Val Arg Glu Thr Val
1               5                   10                  15
Arg Glu Val Ile Ser Arg Gln Asp Ser Gly Thr Asp Ala Pro Ser Gly
                20                  25                  30
Thr Asp Gly Ile Phe Thr Asp Met Asn Ser Ala Val Asp Ala Ala Asp
            35                  40                  45
Val Ala Trp Arg Gln Tyr Met Asp Cys Ser Leu Arg Asp Arg Asn Arg
50                  55                  60
Phe Ile Gln Ala Ile Arg Asp Val Ala Ser Glu Pro Asp Asn Leu Glu
65                  70                  75                  80
Tyr Met Ala Thr Ala Thr Val Glu Glu Thr Gly Met Gly Asn Val Pro
                85                  90                  95
His Lys Ile Leu Lys Asn Arg Tyr Ala Ala Leu Tyr Thr Pro Gly Thr
            100                 105                 110
Glu Asp Ile Ile Thr Glu Ala Trp Ser Gly Asp Asp Gly Leu Thr Thr
            115                 120                 125
Val Glu Phe Ser Pro Phe Gly Val Ile Gly Ala Ile Thr Pro Thr Thr
130                 135                 140
Asn Pro Thr Glu Thr Val Ile Asn Asn Thr Ile Gly Met Leu Ala Ala
145                 150                 155                 160
Gly Asn Ala Val Val Phe Ser Pro His Pro Arg Ala Lys Lys Ile Thr
                165                 170                 175
Leu Trp Leu Val Arg Lys Ile Asn Arg Ala Leu Ala Ala Gly Ala
            180                 185                 190
Pro Ala Asn Leu Val Val Thr Val Glu Glu Pro Ser Ile Asp Asn Thr
            195                 200                 205
Asn Ala Met Met Ser His Glu Lys Val Arg Met Leu Val Ala Thr Gly
210                 215                 220
Gly Pro Gly Ile Val Lys Ala Val Leu Ser Ser Gly Lys Lys Ala Ile
225                 230                 235                 240
Gly Ala Gly Ala Gly Asn Pro Pro Ala Val Val Asp Asp Thr Ala Asp
                245                 250                 255
Ile Ala Lys Ala Ala Arg Asp Ile Val Asp Gly Ala Ser Phe Asp Asn
            260                 265                 270
Asn Leu Pro Cys Thr Ala Glu Lys Glu Val Leu Ala Val Asp Ser Ile
            275                 280                 285
Ala Asp Leu Leu Lys Phe Glu Met Leu Lys His Gly Cys Phe Glu Leu
290                 295                 300
Lys Asp Arg Ala Val Met Asp Lys Leu Ala Ala Leu Val Thr Lys Gly
305                 310                 315                 320
Gln His Ala Asn Ala Ala Tyr Val Gly Lys Pro Ala Ala Gln Leu Ala
                325                 330                 335
```

Ser Glu Val Gly Leu Ser Ala Pro Lys Asp Thr Arg Leu Leu Ile Cys
            340                 345                 350

Glu Val Pro Phe Asp His Pro Phe Val Gln Val Glu Leu Met Met Pro
        355                 360                 365

Ile Leu Pro Ile Val Arg Met Pro Asp Val Thr Ala Ile Asp Lys
370                 375                 380

Ala Val Glu Val Glu His Gly Asn Arg His Thr Ala Val Met His Ser
385                 390                 395                 400

Ser Asn Val Asn Ala Leu Thr Lys Met Gly Lys Leu Ile Gln Thr Thr
            405                 410                 415

Ile Phe Val Lys Asn Gly Pro Ser Tyr Asn Gly Ile Gly Ile Asp Gly
            420                 425                 430

Glu Gly Phe Pro Thr Phe Thr Ile Ala Gly Pro Thr Gly Glu Gly Leu
        435                 440                 445

Thr Ser Ala Arg Cys Phe Ala Arg Lys Arg Cys Val Leu Lys Ser
    450                 455                 460

Gly Leu Asn Ile Arg
465

<210> SEQ ID NO 80
<211> LENGTH: 858
<212> TYPE: PRT
<213> ORGANISM: Clostridium acetobutylicum

<400> SEQUENCE: 80

Met Lys Val Thr Asn Gln Lys Glu Leu Lys Gln Lys Leu Asn Glu Leu
1               5                   10                  15

Arg Glu Ala Gln Lys Lys Phe Ala Thr Tyr Thr Gln Glu Gln Val Asp
            20                  25                  30

Lys Ile Phe Lys Gln Cys Ala Ile Ala Ala Lys Glu Arg Ile Asn
        35                  40                  45

Leu Ala Lys Leu Ala Val Glu Glu Thr Gly Ile Gly Leu Val Glu Asp
    50                  55                  60

Lys Ile Ile Lys Asn His Phe Ala Ala Glu Tyr Ile Tyr Asn Lys Tyr
65                  70                  75                  80

Lys Asn Glu Lys Thr Cys Gly Ile Ile Asp His Asp Asp Ser Leu Gly
            85                  90                  95

Ile Thr Lys Val Ala Glu Pro Ile Gly Ile Val Ala Ala Ile Val Pro
        100                 105                 110

Thr Thr Asn Pro Thr Ser Thr Ala Ile Phe Lys Ser Leu Ile Ser Leu
    115                 120                 125

Lys Thr Arg Asn Ala Ile Phe Phe Ser Pro His Pro Arg Ala Lys Lys
130                 135                 140

Ser Thr Ile Ala Ala Lys Leu Ile Leu Asp Ala Ala Val Lys Ala
145                 150                 155                 160

Gly Ala Pro Lys Asn Ile Ile Gly Trp Ile Asp Glu Pro Ser Ile Glu
            165                 170                 175

Leu Ser Gln Asp Leu Met Ser Glu Ala Asp Ile Ile Leu Ala Thr Gly
        180                 185                 190

Gly Pro Ser Met Val Lys Ala Ala Tyr Ser Ser Gly Lys Pro Ala Ile
    195                 200                 205

Gly Val Gly Ala Gly Asn Thr Pro Ala Ile Ile Asp Glu Ser Ala Asp
210                 215                 220

Ile Asp Met Ala Val Ser Ser Ile Ile Leu Ser Lys Thr Tyr Asp Asn

-continued

```
            225                 230                 235                 240
        Gly Val Ile Cys Ala Ser Glu Gln Ser Ile Leu Val Met Asn Ser Ile
                            245                 250                 255
        Tyr Glu Lys Val Lys Glu Glu Phe Val Lys Arg Gly Ser Tyr Ile Leu
                            260                 265                 270
        Asn Gln Asn Glu Ile Ala Lys Ile Lys Glu Thr Met Phe Lys Asn Gly
                            275                 280                 285
        Ala Ile Asn Ala Asp Ile Val Gly Lys Ser Ala Tyr Ile Ile Ala Lys
                            290                 295                 300
        Met Ala Gly Ile Glu Val Pro Gln Thr Thr Lys Ile Leu Ile Gly Glu
        305                 310                 315                 320
        Val Gln Ser Val Glu Lys Ser Glu Leu Phe Ser His Glu Lys Leu Ser
                            325                 330                 335
        Pro Val Leu Ala Met Tyr Lys Val Lys Asp Phe Asp Glu Ala Leu Lys
                            340                 345                 350
        Lys Ala Gln Arg Leu Ile Glu Leu Gly Gly Ser Gly His Thr Ser Ser
                            355                 360                 365
        Leu Tyr Ile Asp Ser Gln Asn Asn Lys Asp Lys Val Lys Glu Phe Gly
                            370                 375                 380
        Leu Ala Met Lys Thr Ser Arg Thr Phe Ile Asn Met Pro Ser Ser Gln
        385                 390                 395                 400
        Gly Ala Ser Gly Asp Leu Tyr Asn Phe Ala Ile Ala Pro Ser Phe Thr
                            405                 410                 415
        Leu Gly Cys Gly Thr Trp Gly Gly Asn Ser Val Ser Gln Asn Val Glu
                            420                 425                 430
        Pro Lys His Leu Leu Asn Ile Lys Ser Val Ala Glu Arg Arg Glu Asn
                            435                 440                 445
        Met Leu Trp Phe Lys Val Pro Gln Lys Ile Tyr Phe Lys Tyr Gly Cys
        450                 455                 460
        Leu Arg Phe Ala Leu Lys Glu Leu Lys Asp Met Asn Lys Lys Arg Ala
        465                 470                 475                 480
        Phe Ile Val Thr Asp Lys Asp Leu Phe Lys Leu Gly Tyr Val Asn Lys
                            485                 490                 495
        Ile Thr Lys Val Leu Asp Glu Ile Asp Ile Lys Tyr Ser Ile Phe Thr
                            500                 505                 510
        Asp Ile Lys Ser Asp Pro Thr Ile Asp Ser Val Lys Lys Gly Ala Lys
                            515                 520                 525
        Glu Met Leu Asn Phe Glu Pro Asp Thr Ile Ile Ser Ile Gly Gly Gly
        530                 535                 540
        Ser Pro Met Asp Ala Ala Lys Val Met His Leu Leu Tyr Glu Tyr Pro
        545                 550                 555                 560
        Glu Ala Glu Ile Glu Asn Leu Ala Ile Asn Phe Met Asp Ile Arg Lys
                            565                 570                 575
        Arg Ile Cys Asn Phe Pro Lys Leu Gly Thr Lys Ala Ile Ser Val Ala
                            580                 585                 590
        Ile Pro Thr Thr Ala Gly Thr Gly Ser Glu Ala Thr Pro Phe Ala Val
                            595                 600                 605
        Ile Thr Asn Asp Glu Thr Gly Met Lys Tyr Pro Leu Thr Ser Tyr Glu
                            610                 615                 620
        Leu Thr Pro Asn Met Ala Ile Ile Asp Thr Glu Leu Met Leu Asn Met
        625                 630                 635                 640
        Pro Arg Lys Leu Thr Ala Ala Thr Gly Ile Asp Ala Leu Val His Ala
                            645                 650                 655
```

Ile Glu Ala Tyr Val Ser Val Met Ala Thr Asp Tyr Thr Asp Glu Leu
              660                 665                 670

Ala Leu Arg Ala Ile Lys Met Ile Phe Lys Tyr Leu Pro Arg Ala Tyr
          675                 680                 685

Lys Asn Gly Thr Asn Asp Ile Glu Ala Arg Glu Lys Met Ala His Ala
      690                 695                 700

Ser Asn Ile Ala Gly Met Ala Phe Ala Asn Ala Phe Leu Gly Val Cys
705                 710                 715                 720

His Ser Met Ala His Lys Leu Gly Ala Met His His Val Pro His Gly
              725                 730                 735

Ile Ala Cys Ala Val Leu Ile Glu Glu Val Ile Lys Tyr Asn Ala Thr
          740                 745                 750

Asp Cys Pro Thr Lys Gln Thr Ala Phe Pro Gln Tyr Lys Ser Pro Asn
      755                 760                 765

Ala Lys Arg Lys Tyr Ala Glu Ile Ala Glu Tyr Leu Asn Leu Lys Gly
      770                 775                 780

Thr Ser Asp Thr Glu Lys Val Thr Ala Leu Ile Glu Ala Ile Ser Lys
785                 790                 795                 800

Leu Lys Ile Asp Leu Ser Ile Pro Gln Asn Ile Ser Ala Ala Gly Ile
              805                 810                 815

Asn Lys Lys Asp Phe Tyr Asn Thr Leu Asp Lys Met Ser Glu Leu Ala
          820                 825                 830

Phe Asp Asp Gln Cys Thr Thr Ala Asn Pro Arg Tyr Pro Leu Ile Ser
      835                 840                 845

Glu Leu Lys Asp Ile Tyr Ile Lys Ser Phe
      850                 855

<210> SEQ ID NO 81
<211> LENGTH: 862
<212> TYPE: PRT
<213> ORGANISM: Clostridium acetobutylicum

<400> SEQUENCE: 81

Met Lys Val Thr Thr Val Lys Glu Leu Asp Glu Lys Leu Lys Val Ile
1               5                   10                  15

Lys Glu Ala Gln Lys Lys Phe Ser Cys Tyr Ser Gln Glu Met Val Asp
            20                  25                  30

Glu Ile Phe Arg Asn Ala Ala Met Ala Ala Ile Asp Ala Arg Ile Glu
        35                  40                  45

Leu Ala Lys Ala Ala Val Leu Glu Thr Gly Met Gly Leu Val Glu Asp
    50                  55                  60

Lys Val Ile Lys Asn His Phe Ala Gly Glu Tyr Ile Tyr Asn Lys Tyr
65              70                  75                  80

Lys Asp Glu Lys Thr Cys Gly Ile Ile Glu Arg Asn Glu Pro Tyr Gly
            85                  90                  95

Ile Thr Lys Ile Ala Glu Pro Ile Gly Val Val Ala Ala Ile Ile Pro
        100                 105                 110

Val Thr Asn Pro Thr Ser Thr Thr Ile Phe Lys Ser Leu Ile Ser Leu
    115                 120                 125

Lys Thr Arg Asn Gly Ile Phe Phe Ser Pro His Pro Arg Ala Lys Lys
130                 135                 140

Ser Thr Ile Leu Ala Ala Lys Thr Ile Leu Asp Ala Ala Val Lys Ser
145                 150                 155                 160

Gly Ala Pro Glu Asn Ile Ile Gly Trp Ile Asp Glu Pro Ser Ile Glu

```
            165                 170                 175
Leu Thr Gln Tyr Leu Met Gln Lys Ala Asp Ile Thr Leu Ala Thr Gly
            180                 185                 190
Gly Pro Ser Leu Val Lys Ser Ala Tyr Ser Ser Gly Lys Pro Ala Ile
            195                 200                 205
Gly Val Gly Pro Gly Asn Thr Pro Val Ile Ile Asp Glu Ser Ala His
            210                 215                 220
Ile Lys Met Ala Val Ser Ser Ile Ile Leu Ser Lys Thr Tyr Asp Asn
225                 230                 235                 240
Gly Val Ile Cys Ala Ser Glu Gln Ser Val Ile Val Leu Lys Ser Ile
            245                 250                 255
Tyr Asn Lys Val Lys Asp Glu Phe Gln Glu Arg Gly Ala Tyr Ile Ile
            260                 265                 270
Lys Lys Asn Glu Leu Asp Lys Val Arg Glu Val Ile Phe Lys Asp Gly
            275                 280                 285
Ser Val Asn Pro Lys Ile Val Gly Gln Ser Ala Tyr Thr Ile Ala Ala
            290                 295                 300
Met Ala Gly Ile Lys Val Pro Lys Thr Thr Arg Ile Leu Ile Gly Glu
305                 310                 315                 320
Val Thr Ser Leu Gly Glu Glu Glu Pro Phe Ala His Glu Lys Leu Ser
            325                 330                 335
Pro Val Leu Ala Met Tyr Glu Ala Asp Asn Phe Asp Asp Ala Leu Lys
            340                 345                 350
Lys Ala Val Thr Leu Ile Asn Leu Gly Gly Leu Gly His Thr Ser Gly
            355                 360                 365
Ile Tyr Ala Asp Glu Ile Lys Ala Arg Asp Lys Ile Asp Arg Phe Ser
            370                 375                 380
Ser Ala Met Lys Thr Val Arg Thr Phe Val Asn Ile Pro Thr Ser Gln
385                 390                 395                 400
Gly Ala Ser Gly Asp Leu Tyr Asn Phe Arg Ile Pro Pro Ser Phe Thr
            405                 410                 415
Leu Gly Cys Gly Phe Trp Gly Gly Asn Ser Val Ser Glu Asn Val Gly
            420                 425                 430
Pro Lys His Leu Leu Asn Ile Lys Thr Val Ala Glu Arg Arg Glu Asn
            435                 440                 445
Met Leu Trp Phe Arg Val Pro His Lys Val Tyr Phe Lys Phe Gly Cys
            450                 455                 460
Leu Gln Phe Ala Leu Lys Asp Leu Lys Asp Leu Lys Lys Lys Arg Ala
465                 470                 475                 480
Phe Ile Val Thr Asp Ser Asp Pro Tyr Asn Leu Asn Tyr Val Asp Ser
            485                 490                 495
Ile Ile Lys Ile Leu Glu His Leu Asp Ile Asp Phe Lys Val Phe Asn
            500                 505                 510
Lys Val Gly Arg Glu Ala Asp Leu Lys Thr Ile Lys Lys Ala Thr Glu
            515                 520                 525
Glu Met Ser Ser Phe Met Pro Asp Thr Ile Ile Ala Leu Gly Gly Thr
            530                 535                 540
Pro Glu Met Ser Ser Ala Lys Leu Met Trp Val Leu Tyr Glu His Pro
545                 550                 555                 560
Glu Val Lys Phe Glu Asp Leu Ala Ile Lys Phe Met Asp Ile Arg Lys
            565                 570                 575
Arg Ile Tyr Thr Phe Pro Lys Leu Gly Lys Lys Ala Met Leu Val Ala
            580                 585                 590
```

Ile Thr Thr Ser Ala Gly Ser Gly Ser Glu Val Thr Pro Phe Ala Leu
        595                 600                 605

Val Thr Asp Asn Asn Thr Gly Asn Lys Tyr Met Leu Ala Asp Tyr Glu
610                 615                 620

Met Thr Pro Asn Met Ala Ile Val Asp Ala Glu Leu Met Met Lys Met
625                 630                 635                 640

Pro Lys Gly Leu Thr Ala Tyr Ser Gly Ile Asp Ala Leu Val Asn Ser
            645                 650                 655

Ile Glu Ala Tyr Thr Ser Val Tyr Ala Ser Glu Tyr Thr Asn Gly Leu
        660                 665                 670

Ala Leu Glu Ala Ile Arg Leu Ile Phe Lys Tyr Leu Pro Glu Ala Tyr
        675                 680                 685

Lys Asn Gly Arg Thr Asn Glu Lys Ala Arg Glu Lys Met Ala His Ala
        690                 695                 700

Ser Thr Met Ala Gly Met Ala Ser Ala Asn Ala Phe Leu Gly Leu Cys
705                 710                 715                 720

His Ser Met Ala Ile Lys Leu Ser Ser Glu His Asn Ile Pro Ser Gly
            725                 730                 735

Ile Ala Asn Ala Leu Leu Ile Glu Glu Val Ile Lys Phe Asn Ala Val
        740                 745                 750

Asp Asn Pro Val Lys Gln Ala Pro Cys Pro Gln Tyr Lys Tyr Pro Asn
        755                 760                 765

Thr Ile Phe Arg Tyr Ala Arg Ile Ala Asp Tyr Ile Lys Leu Gly Gly
        770                 775                 780

Asn Thr Asp Glu Glu Lys Val Asp Leu Leu Ile Asn Lys Ile His Glu
785                 790                 795                 800

Leu Lys Lys Ala Leu Asn Ile Pro Thr Ser Ile Lys Asp Ala Gly Val
            805                 810                 815

Leu Glu Glu Asn Phe Tyr Ser Ser Leu Asp Arg Ile Ser Glu Leu Ala
        820                 825                 830

Leu Asp Asp Gln Cys Thr Gly Ala Asn Pro Arg Phe Pro Leu Thr Ser
        835                 840                 845

Glu Ile Lys Glu Met Tyr Ile Asn Cys Phe Lys Lys Gln Pro
        850                 855                 860

<210> SEQ ID NO 82
<211> LENGTH: 453
<212> TYPE: PRT
<213> ORGANISM: Vibrio fluvialis

<400> SEQUENCE: 82

Met Asn Lys Pro Gln Ser Trp Glu Ala Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Thr His Gly Glu Gly Pro Tyr Ile Val Asp Val Asn Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Phe Gly Arg Met Ser Asp Gln Thr Val Met Leu
                85                  90                  95

Ser Glu Lys Leu Val Glu Val Ser Pro Phe Asp Ser Gly Arg Val Phe

```
            100                 105                 110
Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
        130                 135                 140

Thr Arg Trp Asn Ala Tyr His Gly Val Thr Ala Val Ser Ala Ser Met
145                 150                 155                 160

Thr Gly Lys Pro Tyr Asn Ser Val Phe Gly Leu Pro Leu Pro Gly Phe
                    165                 170                 175

Val His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Arg Glu Gly Ala Asp Thr Ile Ala Gly Phe Phe Ala Glu Pro
        210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                    245                 250                 255

Glu Val Ile Cys Gly Phe Gly Arg Thr Gly Asn Thr Trp Gly Cys Val
            260                 265                 270

Thr Tyr Asp Phe Thr Pro Asp Ala Ile Ile Ser Ser Lys Asn Leu Thr
        275                 280                 285

Ala Gly Phe Phe Pro Met Gly Ala Val Ile Leu Gly Pro Glu Leu Ser
        290                 295                 300

Lys Arg Leu Glu Thr Ala Ile Glu Ala Ile Glu Glu Phe Pro His Gly
305                 310                 315                 320

Phe Thr Ala Ser Gly His Pro Val Gly Cys Ala Ile Ala Leu Lys Ala
                    325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ala Val
        370                 375                 380

Lys Asp Lys Ala Ser Lys Thr Pro Phe Asp Gly Asn Leu Ser Val Ser
385                 390                 395                 400

Glu Arg Ile Ala Asn Thr Cys Thr Asp Leu Gly Leu Ile Cys Arg Pro
                    405                 410                 415

Leu Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
        450

<210> SEQ ID NO 83
<211> LENGTH: 449
<212> TYPE: PRT
<213> ORGANISM: Bacillus weihenstephanensis

<400> SEQUENCE: 83

Met Gln Ala Thr Glu Gln Thr Gln Ser Leu Lys Lys Thr Asp Glu Lys
1               5                   10                  15
```

Tyr Leu Trp His Ala Met Arg Gly Ala Ala Pro Ser Pro Thr Asn Leu
               20                  25                  30

Ile Ile Thr Lys Ala Glu Gly Ala Trp Val Thr Asp Ile Asp Gly Asn
           35                  40                  45

Arg Tyr Leu Asp Gly Met Ser Gly Leu Trp Cys Val Asn Val Gly Tyr
       50                  55                  60

Gly Arg Lys Glu Leu Ala Arg Ala Ala Phe Glu Gln Leu Glu Glu Met
65                  70                  75                  80

Pro Tyr Phe Pro Leu Thr Gln Ser His Val Pro Ala Ile Lys Leu Ala
               85                  90                  95

Glu Lys Leu Asn Glu Trp Leu Asp Asp Glu Tyr Val Ile Phe Phe Ser
           100                 105                 110

Asn Ser Gly Ser Glu Ala Asn Glu Thr Ala Phe Lys Ile Ala Arg Gln
       115                 120                 125

Tyr His Gln Gln Lys Gly Asp His Gly Arg Tyr Lys Phe Ile Ser Arg
   130                 135                 140

Tyr Arg Ala Tyr His Gly Asn Ser Met Gly Ala Leu Ala Ala Thr Gly
145                 150                 155                 160

Gln Ala Gln Arg Lys Tyr Lys Tyr Glu Pro Leu Gly Gln Gly Phe Leu
               165                 170                 175

His Val Ala Pro Pro Asp Thr Tyr Arg Asn Pro Glu Asp Val His Thr
           180                 185                 190

Leu Ala Ser Ala Glu Glu Ile Asp Arg Val Met Thr Trp Glu Leu Ser
       195                 200                 205

Gln Thr Val Ala Gly Val Ile Met Glu Pro Ile Ile Thr Gly Gly Gly
   210                 215                 220

Ile Leu Met Pro Pro Asp Gly Tyr Met Gly Lys Val Lys Glu Ile Cys
225                 230                 235                 240

Glu Lys His Gly Ala Leu Leu Ile Cys Asp Glu Val Ile Cys Gly Phe
               245                 250                 255

Gly Arg Thr Gly Lys Pro Phe Gly Phe Met Asn Tyr Gly Val Lys Pro
           260                 265                 270

Asp Ile Ile Thr Met Ala Lys Gly Ile Thr Ser Ala Tyr Leu Pro Leu
       275                 280                 285

Ser Ala Thr Ala Val Arg Arg Glu Val Tyr Glu Ala Phe Val Gly Ser
   290                 295                 300

Asp Asp Tyr Asp Arg Phe Arg His Val Asn Thr Phe Gly Gly Asn Pro
305                 310                 315                 320

Ala Ala Cys Ala Leu Ala Leu Lys Asn Leu Glu Ile Met Glu Asn Glu
               325                 330                 335

Lys Leu Ile Glu Arg Ser Lys Glu Leu Gly Glu Arg Leu Leu Tyr Glu
           340                 345                 350

Leu Glu Asp Val Lys Glu His Pro Asn Val Gly Asp Val Arg Gly Lys
       355                 360                 365

Gly Leu Leu Leu Gly Ile Glu Leu Val Glu Asp Lys Gln Thr Lys Glu
   370                 375                 380

Pro Ala Ser Ile Glu Lys Met Asn Lys Val Ile Asn Ala Cys Lys Glu
385                 390                 395                 400

Lys Gly Leu Ile Ile Gly Lys Asn Gly Asp Thr Val Ala Gly Tyr Asn
               405                 410                 415

Asn Ile Leu Gln Leu Ala Pro Pro Leu Ser Ile Thr Glu Glu Asp Phe
           420                 425                 430

Thr Phe Ile Val Lys Thr Met Lys Glu Cys Leu Ser Arg Ile Asn Gly

Gln

<210> SEQ ID NO 84
<211> LENGTH: 456
<212> TYPE: PRT
<213> ORGANISM: Pseudomonas aeruginosa

<400> SEQUENCE: 84

```
Met Asn Ser Gln Ile Thr Asn Ala Lys Thr Arg Glu Trp Gln Ala Leu
1               5                   10                  15

Ser Arg Asp His His Leu Pro Pro Phe Thr Asp Tyr Lys Gln Leu Asn
            20                  25                  30

Glu Lys Gly Ala Arg Ile Ile Thr Lys Ala Glu Gly Val Tyr Ile Trp
        35                  40                  45

Asp Ser Glu Gly Asn Lys Ile Leu Asp Ala Met Ala Gly Leu Trp Cys
    50                  55                  60

Val Asn Val Gly Tyr Gly Arg Glu Glu Leu Val Gln Ala Ala Thr Arg
65                  70                  75                  80

Gln Met Arg Glu Leu Pro Phe Tyr Asn Leu Phe Phe Gln Thr Ala His
                85                  90                  95

Pro Pro Val Val Glu Leu Ala Lys Ala Ile Ala Asp Val Ala Pro Glu
            100                 105                 110

Gly Met Asn His Val Phe Phe Thr Gly Ser Gly Ser Glu Ala Asn Asp
        115                 120                 125

Thr Val Leu Arg Met Val Arg His Tyr Trp Ala Thr Lys Gly Gln Pro
130                 135                 140

Gln Lys Lys Val Val Ile Gly Arg Trp Asn Gly Tyr His Gly Ser Thr
145                 150                 155                 160

Val Ala Gly Val Ser Leu Gly Gly Met Lys Ala Leu His Glu Gln Gly
                165                 170                 175

Asp Phe Pro Ile Pro Gly Ile Val His Ile Ala Gln Pro Tyr Trp Tyr
            180                 185                 190

Gly Glu Gly Gly Asp Met Ser Pro Asp Glu Phe Gly Val Trp Ala Ala
        195                 200                 205

Glu Gln Leu Glu Lys Lys Ile Leu Glu Val Gly Glu Glu Asn Val Ala
    210                 215                 220

Ala Phe Ile Ala Glu Pro Ile Gln Gly Ala Gly Gly Val Ile Val Pro
225                 230                 235                 240

Pro Asp Thr Tyr Trp Pro Lys Ile Arg Glu Ile Leu Ala Lys Tyr Asp
                245                 250                 255

Ile Leu Phe Ile Ala Asp Glu Val Ile Cys Gly Phe Gly Arg Thr Gly
            260                 265                 270

Glu Trp Phe Gly Ser Gln Tyr Tyr Gly Asn Ala Pro Asp Leu Met Pro
        275                 280                 285

Ile Ala Lys Gly Leu Thr Ser Gly Tyr Ile Pro Met Gly Gly Val Val
    290                 295                 300

Val Arg Asp Glu Ile Val Glu Val Leu Asn Gln Gly Gly Glu Phe Tyr
305                 310                 315                 320

His Gly Phe Thr Tyr Ser Gly His Pro Val Ala Ala Val Ala Leu
                325                 330                 335

Glu Asn Ile Arg Ile Leu Arg Glu Glu Lys Ile Ile Glu Lys Val Lys
            340                 345                 350

Ala Glu Thr Ala Pro Tyr Leu Gln Lys Arg Trp Gln Glu Leu Ala Asp
```

His Pro Leu Val Gly Glu Ala Arg Gly Val Gly Met Val Ala Ala Leu
355                 360                 365

Glu Leu Val Lys Asn Lys Thr Arg Glu Arg Phe Thr Asp Lys Gly
370                 375                 380

Val Gly Met Leu Cys Arg Glu His Cys Phe Arg Asn Gly Leu Ile Met
385                 390                 395                 400

Arg Ala Val Gly Asp Thr Met Ile Ile Ser Pro Pro Leu Val Ile Asp
        405                 410                 415

Pro Ser Gln Ile Asp Glu Leu Ile Thr Leu Ala Arg Lys Cys Leu Asp
420                 425                 430

Gln Thr Ala Ala Ala Val Leu Ala
435                 440                 445

450                 455

<210> SEQ ID NO 85
<211> LENGTH: 538
<212> TYPE: PRT
<213> ORGANISM: Penicillium Chrysogenum

<400> SEQUENCE: 85

Met Thr Ala Leu Arg Ile Ser Thr Thr Leu Ser Arg Lys Ala Leu Thr
1               5                   10                  15

Ala Cys Arg Pro Arg Leu Phe Leu Gly Val Arg Thr Ser Val Arg Pro
                20                  25                  30

Trp Gln Pro Phe Ser Thr Ser Thr Ser Thr Arg Tyr Ser Ile Thr Thr
            35                  40                  45

Pro Leu Lys Ser Leu Ala Pro Lys Val Glu Arg Ser Gly Ser Lys Leu
        50                  55                  60

Tyr Lys Asp Ala Asp Ala Ala Val Ala Asp Ile Lys Ser Gly Ser Thr
65                  70                  75                  80

Ile Leu Ser Ser Gly Phe Gly Leu Cys Gly Val Ala Glu Thr Leu Ile
                85                  90                  95

Asn Ala Met His Arg Arg Gly Ala Asp Gln Leu His Ser Leu Thr Ala
                100                 105                 110

Val Ser Asn Asn Ala Gly Ala Ala Gly Lys Gly Gly Leu Ser Thr Leu
            115                 120                 125

Ser Gln Asn Gly Gln Ile Asn Arg Leu Ile Leu Ser Tyr Leu Gly Asn
        130                 135                 140

Asn Lys Ala Leu Glu Lys Lys Tyr Leu Thr Gly His Ile Ala Ile Glu
145                 150                 155                 160

Leu Cys Pro Gln Gly Thr Leu Ala Glu Arg Leu Arg Ala Gly Gly Ala
                165                 170                 175

Gly Ile Pro Ala Phe Phe Thr Pro Thr Gly Glu Gly Lys Ile Pro Val
            180                 185                 190

Arg Met Asp Glu Ser Gly Lys Val Leu Glu Ser Gly Lys Pro Arg Glu
        195                 200                 205

Thr Arg Glu Phe Asn Gly Lys Thr Tyr Leu Met Glu Glu Ala Leu Thr
210                 215                 220

Gly Asp Val Ala Ile Leu Arg Ala Trp Lys Ala Asp Glu Ala Gly Asn
225                 230                 235                 240

Cys Val Phe Arg Tyr Thr Thr Lys Ala Phe Gly Pro Ile Met Ala Lys
                245                 250                 255

Ala Ala Thr Leu Thr Ile Val Glu Ala Glu Asn Ile Val Pro Ile Gly
            260                 265                 270

```
Ser Ile Asp Pro Asn Asp Val Asp Leu Pro Gly Ile Phe Val Asp Arg
            275                 280                 285

Ile Val Pro Ala Thr Asp Lys His Ile Glu Ile Arg Lys Leu Arg
        290                 295                 300

Ser Gly Glu Thr Thr Val Ala Gly Ser Gly Lys Asp Glu Ala Arg Ile
305                 310                 315                 320

Gln Arg Glu Leu Ile Gly Arg Ala Ala Lys Glu Leu Lys Pro Gly
                325                 330                 335

Phe Tyr Val Asn Leu Gly Val Gly Ile Pro Thr Leu Ala Pro Ser Phe
                340                 345                 350

Leu Pro Lys Asp Val Lys Val Trp Ile Gln Ser Glu Asn Gly Ile Leu
            355                 360                 365

Gly Met Gly Asp Tyr Pro Thr Glu Gln Glu Leu Asp Pro Asp Ile Ile
    370                 375                 380

Asn Ala Gly Lys Glu Thr Val Thr Leu Val Pro Gly Ala Ala Thr Phe
385                 390                 395                 400

Asp Ser Ser Glu Ser Phe Gly Met Ile Arg Gly Gly His Val Asp Val
                405                 410                 415

Ser Ile Leu Gly Ala Leu Gln Val Ser Ala Asn Gly Asp Leu Ala Asn
                420                 425                 430

Tyr Met Ile Pro Gly Lys Val Phe Lys Gly Met Gly Gly Ala Met Asp
            435                 440                 445

Leu Ile Ser Asn Pro Glu Lys Thr Lys Ile Val Val Ala Thr Ser His
    450                 455                 460

Val Ala Lys Asp Gly Ser Pro Lys Ile Val Gln Lys Cys Ser Leu Pro
465                 470                 475                 480

Leu Thr Gly Ala Asn Val Val Ser Thr Ile Ile Thr Asp Leu Cys Val
                485                 490                 495

Phe Gln Val Asp Arg Ala Thr Gly Glu Leu Thr Leu Thr Glu Leu Ala
            500                 505                 510

Pro Gly Val Glu Val Glu Val Gln Ser Lys Thr Asp Ala Lys Phe
        515                 520                 525

Thr Ile Ala Asp Thr Leu Glu Ile Met Glu
    530                 535

<210> SEQ ID NO 86
<211> LENGTH: 1362
<212> TYPE: DNA
<213> ORGANISM: Vibrio fluvialis
<220> FEATURE:
<221> NAME/KEY: CDS
<222> LOCATION: (1)..(1362)

<400> SEQUENCE: 86 atg aac aaa ccg caa agc tgg gaa gcc cgg gcc gag acc tat tcg ctc      48
Met Asn Lys Pro Gln Ser Trp Glu Ala Arg Ala Glu Thr Tyr Ser Leu
1               5                   10                  15 tat ggt ttc acc gac atg cct tcg ctg cat cag cgc ggc acg gtc gtc      96
Tyr Gly Phe Thr Asp Met Pro Ser Leu His Gln Arg Gly Thr Val Val
                20                  25                  30 gtg acc cat ggc gag gga ccc tat atc gtc gat gtg aat ggc cgg cgt     144
Val Thr His Gly Glu Gly Pro Tyr Ile Val Asp Val Asn Gly Arg Arg
            35                  40                  45 tat ctg gac gcc aac tcg ggc ctg tgg aac atg gtc gcg ggc ttt gac     192
Tyr Leu Asp Ala Asn Ser Gly Leu Trp Asn Met Val Ala Gly Phe Asp
        50                  55                  60 cac aag ggg ctg atc gac gcc gcc aag gcc caa tac gag cgt ttt ccc     240
```

|  |  |
|---|---|
| His Lys Gly Leu Ile Asp Ala Ala Lys Ala Gln Tyr Glu Arg Phe Pro<br>65                         70                    75                    80 |  |
| ggt tat cac gcc ttt ttc ggc cgc atg tcc gat cag acg gta atg ctg<br>Gly Tyr His Ala Phe Phe Gly Arg Met Ser Asp Gln Thr Val Met Leu<br>                      85                    90                    95 | 288 |
| tcg gaa aag ctg gtc gag gtg tcg ccc ttt gat tcg ggc cgg gtg ttc<br>Ser Glu Lys Leu Val Glu Val Ser Pro Phe Asp Ser Gly Arg Val Phe<br>100                         105                    110 | 336 |
| tat aca aac tcg ggg tcc gag gcg aat gac acc atg gtc aag atg cta<br>Tyr Thr Asn Ser Gly Ser Glu Ala Asn Asp Thr Met Val Lys Met Leu<br>              115                    120                    125 | 384 |
| tgg ttc ctg cat gca gcc gag ggc aaa ccg caa aag cgc aag atc ctg<br>Trp Phe Leu His Ala Ala Glu Gly Lys Pro Gln Lys Arg Lys Ile Leu<br>130                         135                    140 | 432 |
| acc cgc tgg aac gcc tat cac ggc gtg acc gcc gtt tcg gcc agc atg<br>Thr Arg Trp Asn Ala Tyr His Gly Val Thr Ala Val Ser Ala Ser Met<br>145                       150                    155                    160 | 480 |
| acc ggc aag ccc tat aat tcg gtc ttt ggc ctg ccg ctg ccg ggc ttt<br>Thr Gly Lys Pro Tyr Asn Ser Val Phe Gly Leu Pro Leu Pro Gly Phe<br>                       165                    170                    175 | 528 |
| gtg cat ctg acc tgc ccg cat tac tgg cgc tat ggc gaa gag ggc gaa<br>Val His Leu Thr Cys Pro His Tyr Trp Arg Tyr Gly Glu Glu Gly Glu<br>180                       185                    190 | 576 |
| acc gaa gag cag ttc gtc gcc cgc ctc gcc cgc gag ctg gag gaa acg<br>Thr Glu Glu Gln Phe Val Ala Arg Leu Ala Arg Glu Leu Glu Glu Thr<br>195                       200                    205 | 624 |
| atc cag cgc gag ggc gcc gac acc atc gcc ggt ttc ttt gcc gaa ccg<br>Ile Gln Arg Glu Gly Ala Asp Thr Ile Ala Gly Phe Phe Ala Glu Pro<br>210                       215                    220 | 672 |
| gtg atg ggc gcg ggc ggc gtg att ccc ccg gcc aag ggc tat ttc cag<br>Val Met Gly Ala Gly Gly Val Ile Pro Pro Ala Lys Gly Tyr Phe Gln<br>225                       230                    235                    240 | 720 |
| gcg atc ctg cca atc ctg cgc aaa tat gac atc ccg gtc atc tcg gac<br>Ala Ile Leu Pro Ile Leu Arg Lys Tyr Asp Ile Pro Val Ile Ser Asp<br>                       245                    250                    255 | 768 |
| gag gtg atc tgc ggt ttc gga cgc acc ggt aac acc tgg ggc tgc gtg<br>Glu Val Ile Cys Gly Phe Gly Arg Thr Gly Asn Thr Trp Gly Cys Val<br>              260                    265                    270 | 816 |
| acc tat gac ttt aca ccc gat gca atc atc tcg tcc aag aat ctt aca<br>Thr Tyr Asp Phe Thr Pro Asp Ala Ile Ile Ser Ser Lys Asn Leu Thr<br>275                       280                    285 | 864 |
| gcg ggc ttt ttc ccc atg ggg gcg gtg atc ctt ggc ccg gaa ctt tcc<br>Ala Gly Phe Phe Pro Met Gly Ala Val Ile Leu Gly Pro Glu Leu Ser<br>290                       295                    300 | 912 |
| aaa cgg ctg gaa acc gca atc gag gcg atc gag gaa ttc ccc cat ggc<br>Lys Arg Leu Glu Thr Ala Ile Glu Ala Ile Glu Glu Phe Pro His Gly<br>305                       310                    315                    320 | 960 |
| ttt acc gcc tcg ggc cat ccg gtc ggc tgt gct att gcg ctg aaa gca<br>Phe Thr Ala Ser Gly His Pro Val Gly Cys Ala Ile Ala Leu Lys Ala<br>                       325                    330                    335 | 1008 |
| atc gac gtg gtg atg aat gaa ggg ctg gct gag aac gtc cgc cgc ctt<br>Ile Asp Val Val Met Asn Glu Gly Leu Ala Glu Asn Val Arg Arg Leu<br>              340                    345                    350 | 1056 |
| gcc ccc cgt ttc gag gaa agg ctg aaa cat atc gcc gag cgc ccg aac<br>Ala Pro Arg Phe Glu Glu Arg Leu Lys His Ile Ala Glu Arg Pro Asn<br>                       355                    360                    365 | 1104 |
| atc ggt gaa tat cgc ggc atc ggc ttc atg tgg gcg ctg gag gct gtc<br>Ile Gly Glu Tyr Arg Gly Ile Gly Phe Met Trp Ala Leu Glu Ala Val<br>370                       375                    380 | 1152 |

```
aag gac aag gca agc aag acg ccg ttc gac ggc aac ctg tcg gtc agc      1200
Lys Asp Lys Ala Ser Lys Thr Pro Phe Asp Gly Asn Leu Ser Val Ser
385                 390                 395                 400 gag cgt atc gcc aat acc tgc acc gat ctg ggg ctg att tgc cgg ccg      1248
Glu Arg Ile Ala Asn Thr Cys Thr Asp Leu Gly Leu Ile Cys Arg Pro
            405                 410                 415 ctt ggt cag tcc gtc gtc ctt tgt ccg ccc ttt atc ctg acc gag gcg      1296
Leu Gly Gln Ser Val Val Leu Cys Pro Pro Phe Ile Leu Thr Glu Ala
        420                 425                 430 cag atg gat gag atg ttc gat aaa ctc gaa aaa gcc ctt gat aag gtc      1344
Gln Met Asp Glu Met Phe Asp Lys Leu Glu Lys Ala Leu Asp Lys Val
    435                 440                 445 ttt gcc gag gtt gcc tga                                              1362
Phe Ala Glu Val Ala
    450

<210> SEQ ID NO 87
<211> LENGTH: 453
<212> TYPE: PRT
<213> ORGANISM: Vibrio fluvialis

<400> SEQUENCE: 87

Met Asn Lys Pro Gln Ser Trp Glu Ala Arg Ala Glu Thr Tyr Ser Leu
1               5                   10                  15

Tyr Gly Phe Thr Asp Met Pro Ser Leu His Gln Arg Gly Thr Val Val
            20                  25                  30

Val Thr His Gly Glu Gly Pro Tyr Ile Val Asp Val Asn Gly Arg Arg
        35                  40                  45

Tyr Leu Asp Ala Asn Ser Gly Leu Trp Asn Met Val Ala Gly Phe Asp
    50                  55                  60

His Lys Gly Leu Ile Asp Ala Ala Lys Ala Gln Tyr Glu Arg Phe Pro
65                  70                  75                  80

Gly Tyr His Ala Phe Phe Gly Arg Met Ser Asp Gln Thr Val Met Leu
                85                  90                  95

Ser Glu Lys Leu Val Glu Val Ser Pro Phe Asp Ser Gly Arg Val Phe
            100                 105                 110

Tyr Thr Asn Ser Gly Ser Glu Ala Asn Asp Thr Met Val Lys Met Leu
        115                 120                 125

Trp Phe Leu His Ala Ala Glu Gly Lys Pro Gln Lys Arg Lys Ile Leu
    130                 135                 140

Thr Arg Trp Asn Ala Tyr His Gly Val Thr Ala Val Ser Ala Ser Met
145                 150                 155                 160

Thr Gly Lys Pro Tyr Asn Ser Val Phe Gly Leu Pro Leu Pro Gly Phe
                165                 170                 175

Val His Leu Thr Cys Pro His Tyr Trp Arg Tyr Gly Glu Glu Gly Glu
            180                 185                 190

Thr Glu Glu Gln Phe Val Ala Arg Leu Ala Arg Glu Leu Glu Glu Thr
        195                 200                 205

Ile Gln Arg Glu Gly Ala Asp Thr Ile Ala Gly Phe Phe Ala Glu Pro
    210                 215                 220

Val Met Gly Ala Gly Gly Val Ile Pro Pro Ala Lys Gly Tyr Phe Gln
225                 230                 235                 240

Ala Ile Leu Pro Ile Leu Arg Lys Tyr Asp Ile Pro Val Ile Ser Asp
                245                 250                 255

Glu Val Ile Cys Gly Phe Gly Arg Thr Gly Asn Thr Trp Gly Cys Val
            260                 265                 270
```

```
Thr Tyr Asp Phe Thr Pro Asp Ala Ile Ile Ser Ser Lys Asn Leu Thr
            275                 280                 285

Ala Gly Phe Phe Pro Met Gly Ala Val Ile Leu Gly Pro Glu Leu Ser
    290                 295                 300

Lys Arg Leu Glu Thr Ala Ile Glu Ala Ile Glu Glu Phe Pro His Gly
305                 310                 315                 320

Phe Thr Ala Ser Gly His Pro Val Gly Cys Ala Ile Ala Leu Lys Ala
                325                 330                 335

Ile Asp Val Val Met Asn Glu Gly Leu Ala Glu Asn Val Arg Arg Leu
            340                 345                 350

Ala Pro Arg Phe Glu Glu Arg Leu Lys His Ile Ala Glu Arg Pro Asn
        355                 360                 365

Ile Gly Glu Tyr Arg Gly Ile Gly Phe Met Trp Ala Leu Glu Ala Val
370                 375                 380

Lys Asp Lys Ala Ser Lys Thr Pro Phe Asp Gly Asn Leu Ser Val Ser
385                 390                 395                 400

Glu Arg Ile Ala Asn Thr Cys Thr Asp Leu Gly Leu Ile Cys Arg Pro
                405                 410                 415

Leu Gly Gln Ser Val Val Leu Cys Pro Pro Phe Ile Leu Thr Glu Ala
            420                 425                 430

Gln Met Asp Glu Met Phe Asp Lys Leu Glu Lys Ala Leu Asp Lys Val
        435                 440                 445

Phe Ala Glu Val Ala
    450

<210> SEQ ID NO 88
<211> LENGTH: 1362
<212> TYPE: DNA
<213> ORGANISM: Artificial
<220> FEATURE:
<223> OTHER INFORMATION: Vibrio fluvialis JS17 omega-aminotransferase
      codon optimised gene

<400> SEQUENCE: 88
atgaataaac cacagtcttg ggaagctcgt gctgaaacct atagcctgta cggctttacc      60
gatatgccgt ctctgcacca gcgtggtact gtagtggtaa cgcacggtga gggcccgtac     120
atcgtggacg ttaatggccg ccgttacctg gatgcaaaca gcggcctgtg aacatggtt     180 gcgggcttcg accacaaagg cctgatcgat gccgcaaaag cgcagtacga acgcttcccg     240
ggttatcacg cgttctttgg ccgtatgagc gaccagactg tgatgctgag cgaaaaactg     300
gttgaagtgt ccccgttcga tagcggtcgt gtcttttaca ctaactctgg cagcgaggct     360
aacgatacca tggttaagat gctgtggttc ctgcacgcag cggaaggcaa acctcagaaa     420
cgtaaaattc tgacccgttg gaacgcttat acggtgtga ctgctgtttc cgcatctatg      480
accggtaaac cgtataacag cgtgttcggt ctgccgctgc ctggcttcgt gcatctgacc     540
tgcccgcact actggcgtta tggtgaggaa ggcgaaactg aggaacagtt cgtggcgcgt     600
ctggctcgtg aactggaaga aaccattcaa gcgaaggtg cagatactat cgcgggcttc      660
tttgcggagc tgttatggg tgccggcggt gtgattccgc cggcgaaggg ctatttccag      720
gcaatcctgc cgatcctgcg caagtacgac attccggtta tttctgacga agtgatctgc     780
ggcttcggcc gcaccggtaa cacctggggc tgcgtgacgt atgacttcac tccggacgca     840
atcattagct ctaaaaacct gactgcgggt tccttcccta tgggcgccgt aatcctgggc     900
ccagaactgt ctaagcgcct ggaaaccgcc atcgaggcaa tcgaagagtt cccgcacggt     960
```

```
ttcactgcta gcggccatcc ggtaggctgc gcaatcgcgc tgaaggcgat cgatgttgtc    1020
atgaacgagg gcctggcgga aaacgtgcgc cgcctggcgc cgcgttttga agaacgtctg    1080
aaacacattg ctgagcgccc gaacattggc gaatatcgcg gcatcggttt catgtgggcc    1140
ctggaagcag ttaaagataa agctagcaag accccgttcg acggcaacct gtccgtgagc    1200
gaacgtatcg ctaataccty tacggacctg ggtctgatct gccgtccgct gggtcagtcc    1260
gtagttctgt gcccaccatt tatcctgacc gaagcgcaga tggatgaaat gttcgataaa    1320
ctggagaaag ctctggataa agtgttcgct gaagtcgcgt aa    1362
```

<210> SEQ ID NO 89
<211> LENGTH: 1350
<212> TYPE: DNA
<213> ORGANISM: Bacillus weihenstephanensis
<220> FEATURE:
<221> NAME/KEY: CDS
<222> LOCATION: (1)..(1350)

<400> SEQUENCE: 89

```
gtg caa gcg acg gag caa aca caa agt ttg aaa aaa aca gat gaa aag      48
Val Gln Ala Thr Glu Gln Thr Gln Ser Leu Lys Lys Thr Asp Glu Lys
1               5                  10                  15 tac ctt tgg cat gcg atg aga gga gca gcc cct agt cca acg aat tta     96
Tyr Leu Trp His Ala Met Arg Gly Ala Ala Pro Ser Pro Thr Asn Leu
                20                  25                  30 att atc aca aaa gca gaa ggg gca tgg gtg acg gat att gat gga aac    144
Ile Ile Thr Lys Ala Glu Gly Ala Trp Val Thr Asp Ile Asp Gly Asn
            35                  40                  45 cgt tat tta gac ggt atg tcc ggt ctt tgg tgc gtg aat gtt ggg tat    192
Arg Tyr Leu Asp Gly Met Ser Gly Leu Trp Cys Val Asn Val Gly Tyr
        50                  55                  60 ggt cga aaa gaa ctt gca aga gcg gcg ttt gaa cag ctt gaa gaa atg    240
Gly Arg Lys Glu Leu Ala Arg Ala Ala Phe Glu Gln Leu Glu Glu Met
65                  70                  75                  80 ccg tat ttc cct ctg act caa agt cat gtt cct gct att aaa tta gca    288
Pro Tyr Phe Pro Leu Thr Gln Ser His Val Pro Ala Ile Lys Leu Ala
                85                  90                  95 gaa aaa ttg aat gaa tgg ctt gat gat gaa tac gtc att ttc ttt tct    336
Glu Lys Leu Asn Glu Trp Leu Asp Asp Glu Tyr Val Ile Phe Phe Ser
                100                 105                 110 aac agt gga tcg gaa gcg aat gaa aca gca ttt aaa att gct cgt caa    384
Asn Ser Gly Ser Glu Ala Asn Glu Thr Ala Phe Lys Ile Ala Arg Gln
            115                 120                 125 tat cat caa caa aaa ggt gat cat gga cgc tat aag ttt att tcc cgc    432
Tyr His Gln Gln Lys Gly Asp His Gly Arg Tyr Lys Phe Ile Ser Arg
        130                 135                 140 tac cgc gct tat cac ggt aac tca atg gga gct ctt gca gca aca ggt    480
Tyr Arg Ala Tyr His Gly Asn Ser Met Gly Ala Leu Ala Ala Thr Gly
145                 150                 155                 160 caa gca cag cga aag tat aaa tat gaa cca ctc ggg caa gga ttc ctg    528
Gln Ala Gln Arg Lys Tyr Lys Tyr Glu Pro Leu Gly Gln Gly Phe Leu
                165                 170                 175 cat gta gca ccg cct gat acg tat cga aat cca gag gat gtt cat aca    576
His Val Ala Pro Pro Asp Thr Tyr Arg Asn Pro Glu Asp Val His Thr
                180                 185                 190 ctg gca agt gct gag gaa atc gat cgt gtc atg aca tgg gag tta agc    624
Leu Ala Ser Ala Glu Glu Ile Asp Arg Val Met Thr Trp Glu Leu Ser
            195                 200                 205 caa aca gta gcc ggt gtg att atg gag cca atc att act ggg ggc gga    672
Gln Thr Val Ala Gly Val Ile Met Glu Pro Ile Ile Thr Gly Gly Gly
```

```
                210                 215                 220
att tta atg cct cct gat gga tat atg gga aaa gta aaa gaa att tgc      720
Ile Leu Met Pro Pro Asp Gly Tyr Met Gly Lys Val Lys Glu Ile Cys
225                 230                 235                 240 gag aag cac ggt gcg ttg ctc att tgt gat gaa gtt ata tgt gga ttt      768
Glu Lys His Gly Ala Leu Leu Ile Cys Asp Glu Val Ile Cys Gly Phe
                245                 250                 255 ggc cgg aca ggg aag cca ttt gga ttt atg aat tat ggc gtc aaa cca      816
Gly Arg Thr Gly Lys Pro Phe Gly Phe Met Asn Tyr Gly Val Lys Pro
            260                 265                 270 gat atc att aca atg gca aaa ggt att aca agt gcg tat ctt cct ttg      864
Asp Ile Ile Thr Met Ala Lys Gly Ile Thr Ser Ala Tyr Leu Pro Leu
        275                 280                 285 tca gca aca gca gtt aga cga gag gtt tat gag gca ttc gta ggt agt      912
Ser Ala Thr Ala Val Arg Arg Glu Val Tyr Glu Ala Phe Val Gly Ser
    290                 295                 300 gat gat tat gat cgc ttc cgc cat gta aat acg ttc gga ggg aat cct      960
Asp Asp Tyr Asp Arg Phe Arg His Val Asn Thr Phe Gly Gly Asn Pro
305                 310                 315                 320 gct gct tgc gct tta gct ttg aag aat tta gaa att atg gag aat gag     1008
Ala Ala Cys Ala Leu Ala Leu Lys Asn Leu Glu Ile Met Glu Asn Glu
                325                 330                 335 aaa ctc att gaa cgt tcc aaa gaa ttg ggt gaa cga ctg tta tat gag     1056
Lys Leu Ile Glu Arg Ser Lys Glu Leu Gly Glu Arg Leu Leu Tyr Glu
            340                 345                 350 cta gag gat gta aaa gag cat cca aac gta ggg gat gtt cgc gga aag     1104
Leu Glu Asp Val Lys Glu His Pro Asn Val Gly Asp Val Arg Gly Lys
        355                 360                 365 ggc ctt ctt tta ggc att gaa cta gtg gaa gat aag caa aca aaa gaa     1152
Gly Leu Leu Leu Gly Ile Glu Leu Val Glu Asp Lys Gln Thr Lys Glu
    370                 375                 380 ccg gct tcc att gaa aag atg aac aaa gtc atc aat gct tgt aaa gaa     1200
Pro Ala Ser Ile Glu Lys Met Asn Lys Val Ile Asn Ala Cys Lys Glu
385                 390                 395                 400 aaa ggt cta att att ggt aaa aat ggt gac act gtc gca ggt tac aat     1248
Lys Gly Leu Ile Ile Gly Lys Asn Gly Asp Thr Val Ala Gly Tyr Asn
                405                 410                 415 aat att ttg cag ctt gca cct cca tta agc atc aca gag gaa gac ttt     1296
Asn Ile Leu Gln Leu Ala Pro Pro Leu Ser Ile Thr Glu Glu Asp Phe
            420                 425                 430 act ttt atc gtt aaa aca atg aaa gaa tgt tta tcc cgc att aac ggg     1344
Thr Phe Ile Val Lys Thr Met Lys Glu Cys Leu Ser Arg Ile Asn Gly
        435                 440                 445 cag taa                                                              1350
Gln

<210> SEQ ID NO 90
<211> LENGTH: 449
<212> TYPE: PRT
<213> ORGANISM: Bacillus weihenstephanensis

<400> SEQUENCE: 90

Val Gln Ala Thr Glu Gln Thr Gln Ser Leu Lys Lys Thr Asp Glu Lys
1               5                   10                  15

Tyr Leu Trp His Ala Met Arg Gly Ala Ala Pro Ser Pro Thr Asn Leu
                20                  25                  30

Ile Ile Thr Lys Ala Glu Gly Ala Trp Val Thr Asp Ile Asp Gly Asn
            35                  40                  45

Arg Tyr Leu Asp Gly Met Ser Gly Leu Trp Cys Val Asn Val Gly Tyr
```

```
        50                  55                  60
Gly Arg Lys Glu Leu Ala Arg Ala Ala Phe Glu Gln Leu Glu Met
 65                  70                  75                  80

Pro Tyr Phe Pro Leu Thr Gln Ser His Val Pro Ala Ile Lys Leu Ala
                 85                  90                  95

Glu Lys Leu Asn Glu Trp Leu Asp Asp Glu Tyr Val Ile Phe Phe Ser
                100                 105                 110

Asn Ser Gly Ser Glu Ala Asn Glu Thr Ala Phe Lys Ile Ala Arg Gln
                115                 120                 125

Tyr His Gln Gln Lys Gly Asp His Gly Arg Tyr Lys Phe Ile Ser Arg
                130                 135                 140

Tyr Arg Ala Tyr His Gly Asn Ser Met Gly Ala Leu Ala Ala Thr Gly
145                 150                 155                 160

Gln Ala Gln Arg Lys Tyr Lys Tyr Glu Pro Leu Gly Gln Gly Phe Leu
                165                 170                 175

His Val Ala Pro Pro Asp Thr Tyr Arg Asn Pro Glu Asp Val His Thr
                180                 185                 190

Leu Ala Ser Ala Glu Glu Ile Asp Arg Val Met Thr Trp Glu Leu Ser
                195                 200                 205

Gln Thr Val Ala Gly Val Ile Met Glu Pro Ile Ile Thr Gly Gly Gly
                210                 215                 220

Ile Leu Met Pro Pro Asp Gly Tyr Met Gly Lys Val Lys Glu Ile Cys
225                 230                 235                 240

Glu Lys His Gly Ala Leu Leu Ile Cys Asp Glu Val Ile Cys Gly Phe
                245                 250                 255

Gly Arg Thr Gly Lys Pro Phe Gly Phe Met Asn Tyr Gly Val Lys Pro
                260                 265                 270

Asp Ile Ile Thr Met Ala Lys Gly Ile Thr Ser Ala Tyr Leu Pro Leu
                275                 280                 285

Ser Ala Thr Ala Val Arg Arg Glu Val Tyr Glu Ala Phe Val Gly Ser
                290                 295                 300

Asp Asp Tyr Asp Arg Phe Arg His Val Asn Thr Phe Gly Gly Asn Pro
305                 310                 315                 320

Ala Ala Cys Ala Leu Ala Leu Lys Asn Leu Glu Ile Met Glu Asn Glu
                325                 330                 335

Lys Leu Ile Glu Arg Ser Lys Glu Leu Gly Glu Arg Leu Leu Tyr Glu
                340                 345                 350

Leu Glu Asp Val Lys Glu His Pro Asn Val Gly Asp Val Arg Gly Lys
                355                 360                 365

Gly Leu Leu Leu Gly Ile Glu Leu Val Glu Asp Lys Gln Thr Lys Glu
                370                 375                 380

Pro Ala Ser Ile Glu Lys Met Asn Lys Val Ile Asn Ala Cys Lys Glu
385                 390                 395                 400

Lys Gly Leu Ile Ile Gly Lys Asn Gly Asp Thr Val Ala Gly Tyr Asn
                405                 410                 415

Asn Ile Leu Gln Leu Ala Pro Pro Leu Ser Ile Thr Glu Glu Asp Phe
                420                 425                 430

Thr Phe Ile Val Lys Thr Met Lys Glu Cys Leu Ser Arg Ile Asn Gly
                435                 440                 445

Gln

<210> SEQ ID NO 91
<211> LENGTH: 1350
```

<212> TYPE: DNA
<213> ORGANISM: Artificial
<220> FEATURE:
<223> OTHER INFORMATION: B. weihenstephanensis KBAB4 aminotransferase
      codon-optimised gene

<400> SEQUENCE: 91

```
atgcaggcta ccgaacaaac ccaatctctg aaaaagactg acgaaaaata tctgtggcac      60
gcgatgcgcg gtgcagctcc gtctccgacc aacctgatta ttaccaaagc tgaaggcgcg     120
tgggtgaccg acattgacgg taaccgttat ctggatggca tgagcggcct gtggtgtgtt     180
aatgtcggtt atggccgtaa ggagctggcg cgcgcggcat ttgaacaact ggaagaaatg     240
ccgtacttcc cgctgactca agccatgtg  ccggctatca aactggcgga aaaactgaac     300
gaatggctgg acgacgaata cgtgattttc ttctctaatt ctggctccga agcaaacgaa     360
accgcattca aaatcgcccg tcaatatcac cagcagaaag tgaccacgg  ccgctataaa     420
ttcatcagcc gttatcgtgc ataccatggt aattctatgg gtgcgctggc tgctaccggt     480
caggctcagc gcaaatacaa gtacgaaccg ctgggtcagg gttttctgca cgttgcacca     540
ccggatacct accgtaaccc ggaagacgtc cacaccctgg cttctgccga gaaatcgat      600
cgtgttatga cctgggagct gtcccagact gttgcgggtg ttatcatgga acctattatt     660
accggtggtg gcattctgat gccgccggac ggttatatgg gtaaagtcaa ggaaatctgc     720
gaaaaacacg gcgcgctgct gatctgcgat gaagttatct gtggcttcgg tcgcaccggc     780
aaaccatttg gcttcatgaa ttatggcgta aaacctgaca ttattaccat ggctaaaggc     840
attacttccg cttatctgcc gctgagcgcg accgcagttc gccgcgaagt ttatgaagcg     900
tttgttggtt ctgatgatta cgaccgtttc cgtcatgtaa acacgtttgg cggtaaccca     960
gcggcatgtg cgctggcgct gaaaaacctg gaaatcatgg aaaacgaaaa gctgatcgaa    1020
cgtagcaaag aactgggtga acgtctgctg tacgaactgg aagatgtcaa agaacacccg    1080
aacgtgggcg atgttcgcgg taaaggcctg ctgctgggta ttgaactggt tgaagacaaa    1140
cagaccaagg aaccggcttc cattgaaaag atgaacaaag tgattaacgc gtgcaaagag    1200
aaaggcctga tcattggtaa gaacggtgat ccgtggcag  gttataacaa cattctgcag    1260
ctggcgccgc ctctgagcat cactgaagaa gatttcacct tcatcgtcaa aactatgaag    1320
gagtgcctga ccgcatcaa  tggtcagtaa                                     1350
```

<210> SEQ ID NO 92
<211> LENGTH: 255
<212> TYPE: PRT
<213> ORGANISM: Saccharomyces cerevisiae

<400> SEQUENCE: 92

```
Met Ala Glu Leu Arg Val Leu Val Ala Val Lys Arg Val Ile Asp Tyr
1               5                   10                  15

Ala Val Lys Ile Arg Val Lys Pro Asp Arg Thr Gly Val Val Thr Asp
            20                  25                  30

Gly Val Lys His Ser Met Asn Pro Phe Cys Glu Ile Ala Val Glu Glu
        35                  40                  45

Ala Val Arg Leu Lys Glu Lys Lys Leu Val Lys Glu Val Ile Ala Val
    50                  55                  60

Ser Cys Gly Pro Ala Gln Cys Gln Glu Thr Ile Arg Thr Ala Leu Ala
65                  70                  75                  80

Met Gly Ala Asp Arg Gly Ile His Val Glu Val Pro Pro Ala Glu Ala
                85                  90                  95
```

Glu Arg Leu Gly Pro Leu Gln Val Ala Arg Val Leu Ala Lys Leu Ala
            100                 105                 110

Glu Lys Glu Lys Val Asp Leu Val Leu Gly Lys Gln Ala Ile Asp
        115                 120                 125

Asp Asp Cys Asn Gln Thr Gly Gln Met Thr Ala Gly Phe Leu Asp Trp
130                 135                 140

Pro Gln Gly Thr Phe Ala Ser Gln Val Thr Leu Glu Gly Asp Lys Leu
145                 150                 155                 160

Lys Val Glu Arg Glu Ile Asp Gly Gly Leu Glu Thr Leu Arg Leu Lys
                165                 170                 175

Leu Pro Ala Val Val Thr Ala Asp Leu Arg Leu Asn Glu Pro Arg Tyr
            180                 185                 190

Ala Thr Leu Pro Asn Ile Met Lys Ala Lys Lys Lys Ile Glu Val
            195                 200                 205

Ile Lys Pro Gly Asp Leu Gly Val Asp Leu Thr Ser Lys Leu Ser Val
210                 215                 220

Ile Ser Val Glu Asp Pro Pro Gln Arg Thr Ala Gly Val Lys Val Glu
225                 230                 235                 240

Thr Thr Glu Asp Leu Val Ala Lys Leu Lys Glu Ile Gly Arg Ile
            245                 250                 255

<210> SEQ ID NO 93
<211> LENGTH: 860
<212> TYPE: DNA
<213> ORGANISM: artificial
<220> FEATURE:
<223> OTHER INFORMATION: Microscilla marina

<400> SEQUENCE: 93
ggtaccggat ccctaacagg aggaattaac catggtccag aaagacctgt tcaaagacaa      60
agttgttctg gtaactggcg gtcgttctgg tatcggttac gcaatttctc agatgatgct     120
ggaactgggt gcgaaagttg ttatcgcttc tcgcaaagag gatctgctga acaggctgc     180 tgaagaactg tctcagtacg gtgaatgctc ctacctggct tgcgacatcc gtaatctga     240 ccagcgtact gcgctgatgg agaagatcaa agctgacaac ggtcgtctgg atatcctggt     300
taacaacgct ggcggtcagt ccccggcacc ggcagaaacc atctctgaaa cggctggga     360 cgctgttatc aacaacaacc tgaacggtac tttccacatg tcctctctga tggcgcgtca     420
cttcttcatc ccgcagaaag aaggttgcat catcaacatc atcgctaaca tctaccgcgg     480
tttcccgtct atggttcaca ccggtgcagc acgtgctggc gttgaaaacc tgaccaaaac     540
tctggcggtt gagtggggcg actacaacat ccgcgttaac gcgattgctc cgggtactat     600
cgaatcttcc ggtctggata cttacccgaa gccggtacag acatcctgg gtgaagcgcg     660 tgctgcagta ccactgaaac gcttcggtac tgttactgaa atcgctaaca ccacttgctt     720
cctggcttct ccgctggctt cttacatctc cggtgtttct ctgtacgttg acggtgcaca     780
gcacctgaac ggtggtgacc cgatgaagct gactcgcctg atgcgtgcat tcaccaagtc     840
tcgtgagctc taataagctt                                                 860

<210> SEQ ID NO 94
<211> LENGTH: 273
<212> TYPE: PRT
<213> ORGANISM: Microscilla marina

<400> SEQUENCE: 94

-continued

Met Val Gln Lys Asp Leu Phe Lys Asp Lys Val Val Leu Val Thr Gly
1 5 10 15

Gly Arg Ser Gly Ile Gly Tyr Ala Ile Ser Gln Met Met Leu Glu Leu
20 25 30

Gly Ala Lys Val Val Ile Ala Ser Arg Lys Glu Asp Leu Leu Lys Gln
35 40 45

Ala Ala Glu Glu Leu Ser Gln Tyr Gly Glu Cys Ser Tyr Leu Ala Cys
50 55 60

Asp Ile Arg Glu Ser Asp Gln Arg Thr Ala Leu Met Glu Lys Ile Lys
65 70 75 80

Ala Asp Asn Gly Arg Leu Asp Ile Leu Val Asn Asn Ala Gly Gly Gln
85 90 95

Phe Pro Ala Pro Ala Glu Thr Ile Ser Glu Asn Gly Trp Asp Ala Val
100 105 110

Ile Asn Asn Asn Leu Asn Gly Thr Phe His Met Ser Ser Leu Met Ala
115 120 125

Arg His Phe Phe Ile Pro Gln Lys Glu Gly Cys Ile Ile Asn Ile Ile
130 135 140

Ala Asn Ile Tyr Arg Gly Phe Pro Ser Met Val His Thr Gly Ala Ala
145 150 155 160

Arg Ala Gly Val Glu Asn Leu Thr Lys Thr Leu Ala Val Glu Trp Gly
165 170 175

Asp Tyr Asn Ile Arg Val Asn Ala Ile Ala Pro Gly Thr Ile Glu Ser
180 185 190

Ser Gly Leu Asp Thr Tyr Pro Lys Pro Val Gln Asp Ile Leu Gly Glu
195 200 205

Ala Arg Ala Ala Val Pro Leu Lys Arg Phe Gly Thr Val Thr Glu Ile
210 215 220

Ala Asn Thr Thr Cys Phe Leu Ala Ser Pro Leu Ala Ser Tyr Ile Ser
225 230 235 240

Gly Val Ser Leu Tyr Val Asp Gly Ala Gln His Leu Asn Gly Gly Asp
245 250 255

Pro Met Lys Leu Thr Arg Leu Met Arg Ala Phe Thr Lys Ser Arg Glu
260 265 270

Thr

<210> SEQ ID NO 95
<211> LENGTH: 1241
<212> TYPE: DNA
<213> ORGANISM: Artificial
<220> FEATURE:
<223> OTHER INFORMATION: Clostridium beijerinckii

<400> SEQUENCE: 95
ggtaccggat ccctaacagg aggaattaat catgatcttc aagccggaac tgatcaaagg 60
tatcgctaaa acttctcacc cgtacggttg ccgtaaagaa gttctgaacc agatcgaata 120
ctgcaaaaac gctaagcagt tccacggtcc gaagaaagtt ctgatcatcg gtgcttcttc 180
cggtttcggt ctggcaactc gcatttctct ggcgttcggt ggtgcgaaag cagacaccat 240
cggtgtttct ttcgaaaccg gtatcactga ccgccgtact ggtactgcag gctggtacaa 300
caacatcttc ttcaaagagt tcgcagaaaa agaaggtctg attgctaaaa acttcatcgg 360
tgacgcattc tctgacgaag ttaaagaaaa cgttatcaaa tacatcaaaa acgagttcgg 420
taagatcgat ctgctgatct actctctggc ttctccgcgc cgtaaagatc cgaaaaccgg 480

```
taacatctac gactccactc tgaaaaccac ttctggcgag ttccagggcc caaccatcga    540
catggaaact gacgaactgg ttactaccaa agttaactcc gcaactgaca agaaatcga     600 agcgaccaag aaagtaatgg gtggtgaaga ttggtctgaa tggtgcaaac tgctgctgga    660
aaacgactgc ctgtctgaca agctatcac tatctcttac tcttacatcg gtgcttctcg    720
cacttacaaa atctaccgtg aaggtactat cggtgaagcg aagcgtcacc tggaaaacac    780
tgcgattcag atcgacaaag aatggcagaa gaagatcaac ggtaaagcat tcgtttctgt    840
taacaaagca atcgttacca aggcttctgc ttacatcccg tctttctctc tgtacgctgc    900
tgttctgtac aaagtaatga agaaaaaaaa tctgcacgaa aactgcatca tgcagatgca    960
gcgtatgttc gctgacaaaa tctacgctga aaatctgctg gagttcgacg actccggtcg   1020
tctgcgtatg gacgactggg aactgcgtga agatgtacag tctgaagtta acgaactgtg   1080
ggaaaaaatc actccggata acttcaagat cctgtctgac tacgacggtt acaagaaaga   1140
gttcatgcag ctgaacggct tcgaaatcga cggtgttaac tactctgaag atatcgacat   1200
cgaagcgctg aagcgcctgg aaccggagct ctaataagct t                      1241
```

<210> SEQ ID NO 96
<211> LENGTH: 400
<212> TYPE: PRT
<213> ORGANISM: Clostridium beijerinckii

<400> SEQUENCE: 96

```
Met Ile Phe Lys Pro Glu Leu Ile Lys Gly Ile Ala Lys Thr Ser His
1               5                   10                  15

Pro Tyr Gly Cys Arg Lys Glu Val Leu Asn Gln Ile Glu Tyr Cys Lys
            20                  25                  30

Asn Ala Lys Gln Phe His Gly Pro Lys Lys Val Leu Ile Ile Gly Ala
        35                  40                  45

Ser Ser Gly Phe Gly Leu Ala Thr Arg Ile Ser Leu Ala Phe Gly Gly
    50                  55                  60

Ala Lys Ala Asp Thr Ile Gly Val Ser Phe Glu Thr Gly Ile Thr Asp
65                  70                  75                  80

Arg Arg Thr Gly Thr Ala Gly Trp Tyr Asn Asn Ile Phe Phe Lys Glu
                85                  90                  95

Phe Ala Glu Lys Glu Gly Leu Ile Ala Lys Asn Phe Ile Gly Asp Ala
            100                 105                 110

Phe Ser Asp Glu Val Lys Glu Asn Val Ile Lys Tyr Ile Lys Asn Glu
        115                 120                 125

Phe Gly Lys Ile Asp Leu Leu Ile Tyr Ser Leu Ala Ser Pro Arg Arg
    130                 135                 140

Lys Asp Pro Lys Thr Gly Asn Ile Tyr Asp Ser Thr Leu Lys Thr Thr
145                 150                 155                 160

Ser Gly Glu Phe Gln Gly Pro Thr Ile Asp Met Glu Thr Asp Glu Leu
                165                 170                 175

Val Thr Thr Lys Val Asn Ser Ala Thr Asp Lys Glu Ile Glu Ala Thr
            180                 185                 190

Lys Lys Val Met Gly Gly Glu Asp Trp Ser Glu Trp Cys Lys Leu Leu
        195                 200                 205

Leu Glu Asn Asp Cys Leu Ser Asp Lys Ala Ile Thr Ile Ser Tyr Ser
    210                 215                 220

Tyr Ile Gly Ala Ser Arg Thr Tyr Lys Ile Tyr Arg Glu Gly Thr Ile
225                 230                 235                 240
```

Gly Glu Ala Lys Arg His Leu Glu Asn Thr Ala Ile Gln Ile Asp Lys
             245                 250                 255

Glu Trp Gln Lys Lys Ile Asn Gly Lys Ala Phe Val Ser Val Asn Lys
        260                 265                 270

Ala Ile Val Thr Lys Ala Ser Ala Tyr Ile Pro Ser Phe Ser Leu Tyr
    275                 280                 285

Ala Ala Val Leu Tyr Lys Val Met Lys Glu Lys Asn Leu His Glu Asn
290                 295                 300

Cys Ile Met Gln Met Gln Arg Met Phe Ala Asp Lys Ile Tyr Ala Glu
305                 310                 315                 320

Asn Leu Leu Glu Phe Asp Asp Ser Gly Arg Leu Arg Met Asp Asp Trp
                325                 330                 335

Glu Leu Arg Glu Asp Val Gln Ser Glu Val Asn Glu Leu Trp Glu Lys
            340                 345                 350

Ile Thr Pro Asp Asn Phe Lys Ile Leu Ser Asp Tyr Asp Gly Tyr Lys
        355                 360                 365

Lys Glu Phe Met Gln Leu Asn Gly Phe Glu Ile Asp Gly Val Asn Tyr
    370                 375                 380

Ser Glu Asp Ile Asp Ile Glu Ala Leu Lys Arg Leu Glu Pro Glu Thr
385                 390                 395                 400

<210> SEQ ID NO 97
<211> LENGTH: 1238
<212> TYPE: DNA
<213> ORGANISM: Artificial
<220> FEATURE:
<223> OTHER INFORMATION: Aeromonas hydrophila subsp. hydrophila

<400> SEQUENCE: 97
ggtaccggat ccctaacagg aggaattaat catgatcatc aagccgaaag ttcgtggctt      60
catctgcacc actactcacc cggttggttg cgaagctaac gttcgtcgtc agatcgctta    120
caccaaagcg aaaggtacta tcgaaaacgg tccgaagaaa gttctggtta tcggtgcttc    180
taccggttac ggtctggctt ctcgcattgc tgctgcattc ggttctggtg cggcaactct    240
gggcgtattc ttcgaaaaag cgggttctga aaccaaaact gcaactgctg ctggtacaa    300 ctccgcagca ttcgacaaag cagctaaaga agcgggtctg tacgctaaat ctatcaacgg    360
tgacgcattc tctaacgaat gccgcgctaa agttatcgaa ctgatcaagc aggacctggg    420
tcagatcgac ctggttgttt actctctggc ttctccggta cgtaagctgc cggataccgg    480
tgaagttgtt cgttctgcac tgaaaccgat cggtgaagtt acaccacta ctgctatcga    540 caccaacaaa gaccagatca tcactgcaac cgttgagccg gctaacgaag aagaaatcca    600
gaacaccatc accgtaatgg gtggtcagga ctgggaactg tggatggctg cgctgcgcga    660
tgctggcgta ctggcagacg gtgcgaagtc tgttgcttac tcttacatcg gtactgaccl    720 gacctggcca atctactggc acggtactct gggtcgtgcg aaagaagatt ggaccgcgc    780 tgcagctgct atccgcggtg acctggcagg caaaggtggt actgcgcacg ttgctgtact    840
gaaatctgtt gttactcagg cttcttctgc gattccggta atgccgctgt acatctctat    900
ggcattcaag attatgaaag agaaaggtat ccacgaaggt tgcatggaac aggttgaccg    960
tatgatgcgt actcgtctgt acgctgcaga catggcgctg gatgaccagg cgcgtatccg   1020
tatggacgac tgggaactgc gtgaagatgt tcagcagact tgccgcgacc tgtggccgtc   1080
tatcacttct gaaacctgt gcgaactgac tgactacacc ggttacaagc aggagttcct   1140
gcgtctgttc ggtttcggtc tggaagaagt tgactacgac gctgacgtta acccggacgt   1200
taagttcgac gttgttgaac tagagctcta ataagctt      1238

<210> SEQ ID NO 98
<211> LENGTH: 399
<212> TYPE: PRT
<213> ORGANISM: Aeromonas hydrophila subsp. hydrophila

<400> SEQUENCE: 98

| Met | Ile | Ile | Lys | Pro | Lys | Val | Arg | Gly | Phe | Ile | Cys | Thr | Thr | Thr | His |
|---|---|---|---|---|---|---|---|---|---|---|---|---|---|---|---|
| 1 | | | | 5 | | | | | 10 | | | | | 15 | |

Pro Val Gly Cys Glu Ala Asn Val Arg Arg Gln Ile Ala Tyr Thr Lys
                20                  25                  30

Ala Lys Gly Thr Ile Glu Asn Gly Pro Lys Lys Val Leu Val Ile Gly
            35                  40                  45

Ala Ser Thr Gly Tyr Gly Leu Ala Ser Arg Ile Ala Ala Phe Gly
        50                  55                  60

Ser Gly Ala Ala Thr Leu Gly Val Phe Phe Glu Lys Ala Gly Ser Glu
65                  70                  75                  80

Thr Lys Thr Ala Thr Ala Gly Trp Tyr Asn Ser Ala Ala Phe Asp Lys
                85                  90                  95

Ala Ala Lys Glu Ala Gly Leu Tyr Ala Lys Ser Ile Asn Gly Asp Ala
            100                 105                 110

Phe Ser Asn Glu Cys Arg Ala Lys Val Ile Glu Leu Ile Lys Gln Asp
        115                 120                 125

Leu Gly Gln Ile Asp Leu Val Val Tyr Ser Leu Ala Ser Pro Val Arg
130                 135                 140

Lys Leu Pro Asp Thr Gly Glu Val Val Arg Ser Ala Leu Lys Pro Ile
145                 150                 155                 160

Gly Glu Val Tyr Thr Thr Thr Ala Ile Asp Thr Asn Lys Asp Gln Ile
                165                 170                 175

Ile Thr Ala Thr Val Glu Pro Ala Asn Glu Glu Ile Gln Asn Thr
            180                 185                 190

Ile Thr Val Met Gly Gly Gln Asp Trp Glu Leu Trp Met Ala Ala Leu
        195                 200                 205

Arg Asp Ala Gly Val Leu Ala Asp Gly Ala Lys Ser Val Ala Tyr Ser
    210                 215                 220

Tyr Ile Gly Thr Asp Leu Thr Trp Pro Ile Tyr Trp His Gly Thr Leu
225                 230                 235                 240

Gly Arg Ala Lys Glu Asp Leu Asp Arg Ala Ala Ala Ile Arg Gly
                245                 250                 255

Asp Leu Ala Gly Lys Gly Gly Thr Ala His Val Ala Val Leu Lys Ser
            260                 265                 270

Val Val Thr Gln Ala Ser Ser Ala Ile Pro Val Met Pro Leu Tyr Ile
        275                 280                 285

Ser Met Ala Phe Lys Ile Met Lys Glu Lys Gly Ile His Glu Gly Cys
    290                 295                 300

Met Glu Gln Val Asp Arg Met Met Arg Thr Arg Leu Tyr Ala Ala Asp
305                 310                 315                 320

Met Ala Leu Asp Asp Gln Ala Arg Ile Arg Met Asp Asp Trp Glu Leu
                325                 330                 335

Arg Glu Asp Val Gln Gln Thr Cys Arg Asp Leu Trp Pro Ser Ile Thr
            340                 345                 350

Ser Glu Asn Leu Cys Glu Leu Thr Asp Tyr Thr Gly Tyr Lys Gln Glu
        355                 360                 365

Phe Leu Arg Leu Phe Gly Phe Gly Leu Glu Glu Val Asp Tyr Asp Ala
    370                 375                 380

Asp Val Asn Pro Asp Val Lys Phe Asp Val Val Glu Leu Glu Thr
385                 390                 395

<210> SEQ ID NO 99
<211> LENGTH: 1142
<212> TYPE: DNA
<213> ORGANISM: Artificial
<220> FEATURE:
<223> OTHER INFORMATION: Yarrowia lipolytica

<400> SEQUENCE: 99
ggtaccggat ccctaacagg aggaattaac catggccggc ttcggtactc cgtctttcgg      60
tctgcgcttc aactccgttg gtcgtgcatt cgtattctct cagactggcg aaccgaaaga     120
cgttattcag gtactggaat acccaatcga aaaaccgctg gaaaaccagg ttctgctgaa     180
atctctgggc ttcactatca acccggctga catcaaccag ctggaaggtg tttacccgtc     240
tgtaccgccg aaatctgtac agatcaacaa cgaagatgct gctatcggtg gtaacgaagg     300
tctgttccag gttctggacc cgggtgctaa atctggtctg aagaaaggcg actgggtact     360
gccgcgtaaa acttgcttcg gcacctggcg ttctcacgcg ctggttgaag ctgataccgt     420
tgttaagatc gacaacaccg acctgaccaa agttcaggca actaccgttt ctgttaaccc     480
gtctactgct tacgaaatgc tgaaagacct gaaagaaggt gactggttca tccagaacgg     540
tggtaactcc ggtgttggtc gtgctgcgat tcagatcggt cacatccgcg gtctgaaatc     600
tatctccgtt gttcgtgacc gtccggatct ggaagttctg aagaaagaac tgactgacct     660
gggtgcaact cacgttatca ctgaagaaga agcgtctgac aaactgttct ccaagcagat     720
caaatcctgg actggcggta aaatcaagct ggcactgaac tgcatcggtg gtaaatctgc     780
aacttccatc atgcgtcagc tgggtgctgg cggttctatc gttacttacg gtggtatgtc     840
caagaagccg ctgactttcc gactggtcc gttcatcttc aaagacatca ctgcgaaagg     900
ttactggctg actcgctggg ctgacaagca cccggaagaa aaagcgaaaa ctatcgaaaa     960
catcttcaaa ttctaccgcg agaagaaatt cgttgctccg ccagttaaca tctccactct    1020
ggacttctct aaaggtaacg acgttgttct gtctgagttc ctggatgcac tgggtaaagc    1080
acagaaaggt ggtggtaaga agcagctggt acagtgggtt gaatacgagc tctaataagc    1140
tt                                                                    1142

<210> SEQ ID NO 100
<211> LENGTH: 367
<212> TYPE: PRT
<213> ORGANISM: Yarrowia lipolytica

<400> SEQUENCE: 100

Met Ala Gly Phe Gly Thr Pro Ser Phe Gly Leu Arg Phe Asn Ser Val
1               5                   10                  15

Gly Arg Ala Phe Val Phe Ser Gln Thr Gly Glu Pro Lys Asp Val Ile
            20                  25                  30

Gln Val Leu Glu Tyr Pro Ile Glu Lys Pro Leu Glu Asn Gln Val Leu
        35                  40                  45

Leu Lys Ser Leu Gly Phe Thr Ile Asn Pro Ala Asp Ile Asn Gln Leu
    50                  55                  60

Glu Gly Val Tyr Pro Ser Val Pro Pro Lys Ser Val Gln Ile Asn Asn
65                  70                  75                  80

Glu Asp Ala Ala Ile Gly Gly Asn Glu Gly Leu Phe Gln Val Leu Asp
                85                  90                  95

Pro Gly Ala Lys Ser Gly Leu Lys Lys Gly Asp Trp Val Leu Pro Arg
            100                 105                 110

Lys Thr Cys Phe Gly Thr Trp Arg Ser His Ala Leu Val Glu Ala Asp
        115                 120                 125

Thr Val Val Lys Ile Asp Asn Thr Asp Leu Thr Lys Val Gln Ala Thr
    130                 135                 140

Thr Val Ser Val Asn Pro Ser Thr Ala Tyr Glu Met Leu Lys Asp Leu
145                 150                 155                 160

Lys Glu Gly Asp Trp Phe Ile Gln Asn Gly Asn Ser Gly Val Gly
                165                 170                 175

Arg Ala Ala Ile Gln Ile Gly His Ile Arg Gly Leu Lys Ser Ile Ser
            180                 185                 190

Val Val Arg Asp Arg Pro Asp Leu Glu Val Leu Lys Lys Glu Leu Thr
        195                 200                 205

Asp Leu Gly Ala Thr His Val Ile Thr Glu Glu Ala Ser Asp Lys
    210                 215                 220

Leu Phe Ser Lys Gln Ile Lys Ser Trp Thr Gly Gly Lys Ile Lys Leu
225                 230                 235                 240

Ala Leu Asn Cys Ile Gly Gly Lys Ser Ala Thr Ser Ile Met Arg Gln
                245                 250                 255

Leu Gly Ala Gly Gly Ser Ile Val Thr Tyr Gly Gly Met Ser Lys Lys
            260                 265                 270

Pro Leu Thr Phe Pro Thr Gly Pro Phe Ile Phe Lys Asp Ile Thr Ala
        275                 280                 285

Lys Gly Tyr Trp Leu Thr Arg Trp Ala Asp Lys His Pro Glu Glu Lys
    290                 295                 300

Ala Lys Thr Ile Glu Asn Ile Phe Lys Phe Tyr Arg Glu Lys Lys Phe
305                 310                 315                 320

Val Ala Pro Pro Val Asn Ile Ser Thr Leu Asp Phe Ser Lys Gly Asn
                325                 330                 335

Asp Val Val Leu Ser Glu Phe Leu Asp Ala Leu Gly Lys Ala Gln Lys
            340                 345                 350

Gly Gly Gly Lys Lys Gln Leu Val Gln Trp Val Glu Tyr Glu Thr
        355                 360                 365

<210> SEQ ID NO 101
<211> LENGTH: 1856
<212> TYPE: DNA
<213> ORGANISM: Artificial
<220> FEATURE:
<223> OTHER INFORMATION: Clostridium kluyveri

<400> SEQUENCE: 101
ggtaccggat ccctaacagg aggaattaac catggacctg gcagaataca aaggcgtatg     60
ggtattcgct gaacagcgtg acggtgaact gcagaaagtt gcgctgcagc tggttggtaa    120
aggtcgtgaa ctggctgaca ctctgggtgt tgaactgact gcggtactgc tgggttctga    180
agttgatgac ctggcgaaag aactggttgc ttacggcgca gacaacgtac tgtacgcaga    240
ctctccgctg ctgaagcact acaccactga cggttacacc aaagttatcg acgaactgat    300
caaagagcgt aagccggaaa tcctgctgat cggtgcgact ttcatcggtc gtgacctggg    360
tccgcgcgtt gctggtcgcg tattcaccgg tctgactgca gactgcaccg gtctggatat    420

```
cgacgaagcg accaagaacc tgatgatgac tcgtccggca ttcggtggta acctgatggc    480
aactatcgct tgcgaaaaaa ctcgtccgca gatgtccacc gttcgtccgg gcgtattcaa    540
cgcactgccg cgcgacgctt cccgtactgg taagatcgaa aaaatcgctg ctaacgttgc    600
taaagacgac atccgtatcg aagttctgga agttgttaag tctgctggcg acaccatcga    660
catctctgaa gcagacgtta tcgtttctgg tggtcgcggt ctgggtggtc cggacggctt    720
caaagttctg aaagaactgg ctgatctgct gggtggtact atcggtggtt ctcgcgctac    780
catcgacgct ggctggatcg acaagtctta ccaggttggt cagactggta aaaccgttcg    840
tccgggtctg tacatcgctt gcggtatctc cggtcagatt cagcacctgg caggcatgca    900
ggattccggc ttcatcgttg ctatcaacaa agacgaaaac gcaccgatga tgcaagttgc    960
tgatctggcg attgttggtg acctgtacaa agttgttcca gagttcgttg aacaggttaa   1020
agcgctgaac ttgtaataac tagtctaaca ggaggaatta atcatgaaga tcgttgtttg   1080
cctgaaacag gttccggata ccactgaagt taagatcgac ccgaaaaccg gtactctgat   1140
ccgtgaaggc gtaccgtcta tcatcaaccc ggatgacaaa aacgcgctgg aagaatccat   1200
tgctctgaaa gagaaagttg gcggcaccgt aactgttgtt tctatgggtc cgccacaggc   1260
tgttgatgcg ctgcgtgaag cgctggcaat gggtgctgac gaagcaatcc tggtatctga   1320
ccgcgctttc gctggtgctg acactcaggc aacttcttac gcactggcag gcgcactgaa   1380
aaacctggaa tacgacctga ttttcgctgg tcgtcaggct atcgacggtg acactgcaca   1440
ggttggtccg cagatcgctg aaaaactggg tatcccgcag atcacttacg ttgaaaaagt   1500
tgacgttgac ggtgacactc tgaccgtaca gcgtgcatgg aagatggtt acgaagttgc   1560 gaaaatcaaa actccgtgca tgctgactgc tatcaaagag ctgaaccagc cgcgctacat   1620
gaacatgaag aacatcttcg aagtattcaa gaaagaagtt aaaatctggt ctgctgacga   1680
cctggacgtt gacaaaaaca gctgggtct gaacggttcc tgcaccaaag ttaagcgttc   1740
tcacaccaaa gaagcgaaag gtgctggcga aatcgttaac aagccgatca agaagcggt   1800 tgcttactcc atctccaagc tgcgtgaaaa acacgttatc gagctctaat aagctt       1856
```

<210> SEQ ID NO 102
<211> LENGTH: 334
<212> TYPE: PRT
<213> ORGANISM: Clostridium kluyveri

<400> SEQUENCE: 102

```
Met Asp Leu Ala Glu Tyr Lys Gly Val Trp Val Phe Ala Glu Gln Arg
1               5                   10                  15

Asp Gly Glu Leu Gln Lys Val Ala Leu Gln Leu Val Gly Lys Gly Arg
            20                  25                  30

Glu Leu Ala Asp Thr Leu Gly Val Glu Leu Thr Ala Val Leu Leu Gly
        35                  40                  45

Ser Glu Val Asp Leu Ala Lys Glu Leu Val Ala Tyr Gly Ala Asp
    50                  55                  60

Asn Val Leu Tyr Ala Asp Ser Pro Leu Leu Lys His Tyr Thr Thr Asp
65                  70                  75                  80

Gly Tyr Thr Lys Val Ile Asp Glu Leu Ile Lys Glu Arg Lys Pro Glu
                85                  90                  95

Ile Leu Leu Ile Gly Ala Thr Phe Ile Gly Arg Asp Leu Gly Pro Arg
            100                 105                 110

Val Ala Gly Arg Val Phe Thr Gly Leu Thr Ala Asp Cys Thr Gly Leu
        115                 120                 125
```

```
Asp Ile Asp Glu Ala Thr Lys Asn Leu Met Met Thr Arg Pro Ala Phe
            130                 135                 140

Gly Gly Asn Leu Met Ala Thr Ile Ala Cys Glu Lys Thr Arg Pro Gln
145                 150                 155                 160

Met Ser Thr Val Arg Pro Gly Val Phe Asn Ala Leu Pro Arg Asp Ala
                165                 170                 175

Ser Arg Thr Gly Lys Ile Glu Lys Ile Ala Ala Asn Val Ala Lys Asp
                180                 185                 190

Asp Ile Arg Ile Glu Val Leu Glu Val Val Lys Ser Ala Gly Asp Thr
            195                 200                 205

Ile Asp Ile Ser Glu Ala Asp Val Ile Val Ser Gly Gly Arg Gly Leu
210                 215                 220

Gly Gly Pro Asp Gly Phe Lys Val Leu Lys Glu Leu Ala Asp Leu Leu
225                 230                 235                 240

Gly Gly Thr Ile Gly Gly Ser Arg Ala Thr Ile Asp Ala Gly Trp Ile
                245                 250                 255

Asp Lys Ser Tyr Gln Val Gly Gln Thr Gly Lys Thr Val Arg Pro Gly
                260                 265                 270

Leu Tyr Ile Ala Cys Gly Ile Ser Gly Gln Ile Gln His Leu Ala Gly
                275                 280                 285

Met Gln Asp Ser Gly Phe Ile Val Ala Ile Asn Lys Asp Glu Asn Ala
290                 295                 300

Pro Met Met Gln Val Ala Asp Leu Ala Ile Val Gly Asp Leu Tyr Lys
305                 310                 315                 320

Val Val Pro Glu Phe Val Glu Gln Val Lys Ala Leu Asn Leu
                325                 330

<210> SEQ ID NO 103
<211> LENGTH: 259
<212> TYPE: PRT
<213> ORGANISM: Clostridium kluyveri

<400> SEQUENCE: 103

Met Lys Ile Val Val Cys Leu Lys Gln Val Pro Asp Thr Thr Glu Val
1               5                   10                  15

Lys Ile Asp Pro Lys Thr Gly Thr Leu Ile Arg Glu Gly Val Pro Ser
                20                  25                  30

Ile Ile Asn Pro Asp Asp Lys Asn Ala Leu Glu Glu Ser Ile Ala Leu
            35                  40                  45

Lys Glu Lys Val Gly Gly Thr Val Thr Val Val Ser Met Gly Pro Pro
50                  55                  60

Gln Ala Val Asp Ala Leu Arg Glu Ala Leu Ala Met Gly Ala Asp Glu
65                  70                  75                  80

Ala Ile Leu Val Ser Asp Arg Ala Phe Ala Gly Ala Asp Thr Gln Ala
                85                  90                  95

Thr Ser Tyr Ala Leu Ala Gly Ala Leu Lys Asn Leu Glu Tyr Asp Leu
                100                 105                 110

Ile Phe Ala Gly Arg Gln Ala Ile Asp Gly Asp Thr Ala Gln Val Gly
            115                 120                 125

Pro Gln Ile Ala Glu Lys Leu Gly Ile Pro Gln Ile Thr Tyr Val Glu
            130                 135                 140

Lys Val Asp Val Asp Gly Asp Thr Leu Thr Val Gln Arg Ala Trp Glu
145                 150                 155                 160

Asp Gly Tyr Glu Val Ala Lys Ile Lys Thr Pro Cys Met Leu Thr Ala
```

```
                    165                 170                 175
Ile Lys Glu Leu Asn Gln Pro Arg Tyr Met Asn Met Lys Asn Ile Phe
                180                 185                 190

Glu Val Phe Lys Lys Glu Val Lys Ile Trp Ser Ala Asp Asp Leu Asp
            195                 200                 205

Val Asp Lys Asn Lys Leu Gly Leu Asn Gly Ser Cys Thr Lys Val Lys
        210                 215                 220

Arg Ser His Thr Lys Glu Ala Lys Gly Ala Gly Glu Ile Val Asn Lys
225                 230                 235                 240

Pro Ile Lys Glu Ala Val Ala Tyr Ser Ile Ser Lys Leu Arg Glu Lys
                245                 250                 255

His Val Ile

<210> SEQ ID NO 104
<211> LENGTH: 1196
<212> TYPE: DNA
<213> ORGANISM: Artificial
<220> FEATURE:
<223> OTHER INFORMATION: Megasphaera elsdenii

<400> SEQUENCE: 104
ggtaccggat ccctaacagg aggaattaac catggacttc aacctgactg atatccagca      60
ggacttcctg aaactggcac acgacttcgg tgaaaaaaaa ctggcaccaa ccgtaactga     120
acgtgaccac aaaggtatct acgacaaaga gctgatcgac gaactgctgt ctctgggtat     180
cactggcgct tacttcgaag agaaatacgg tggttctggt gacgacggtg gtgacgttct     240
gtcttacatc ctggctgttg aagaactggc gaaatacgac gctggcgttg ctatcactct     300
gtctgcaacc gtttctctgt gcgcaaaccc gatctggcag ttcggtactg aagcgcagaa     360
agagaagttc ctggttccgc tggttgaagg tactaaactg ggtgcattcg gtctgactga     420
accgaacgct ggtactgacg cttctggtca gcagactatc gctaccaaaa acgacgacgg     480
tacttacact ctgaacggtt ctaaaatctt catcactaac ggtggtgcag ctgacatcta     540
catcgttttc gcaatgactg acaagtctaa aggtaaccac ggtatcactg cattcatcct     600
ggaagatggt actccgggct tcacttacgg taagaaagaa gataaaatgg gtatccacac     660
ttctcagact atggaactgg tattccagga cgttaaagtt ccggcagaaa acatgctggg     720
tgaagaaggt aaaggcttca aaatcgcgat gatgactctg gacggtggtc gtatcggtgt     780
tgctgctcag gcgctgggta tcgctgaagc ggcactggct gacgcggtag aatactccaa     840
gcagcgtgta cagttcggta agccgctgtg caaattccag tctatctcct tcaaactggc     900
tgatatgaag atgcagatcg aagcagctcg caacctggtt tacaaagcgg catgtaagaa     960
gcaggaaggt aagccgttca ccgttgatgc tgctatcgct aaacgcgttg cttctgacgt    1020
tgcgatgcgc gtaactactg aagctgttca gattttcggt ggttacggtt actctgaaga    1080
ataccoggtt gcgcgtcaca tgcgtgacgc taaaatcact cagatttacg aaggtactaa    1140
cgaagttcag ctgatggtta ctggcggtgc gctgctgcgt gagctctaat aagctt        1196

<210> SEQ ID NO 105
<211> LENGTH: 385
<212> TYPE: PRT
<213> ORGANISM: Megasphaera elsdenii

<400> SEQUENCE: 105

Met Asp Phe Asn Leu Thr Asp Ile Gln Gln Asp Phe Leu Lys Leu Ala
1               5                   10                  15
```

His Asp Phe Gly Glu Lys Lys Leu Ala Pro Thr Val Thr Glu Arg Asp
            20                  25                  30

His Lys Gly Ile Tyr Asp Lys Glu Leu Ile Asp Glu Leu Leu Ser Leu
        35                  40                  45

Gly Ile Thr Gly Ala Tyr Phe Glu Glu Lys Tyr Gly Gly Ser Gly Asp
    50                  55                  60

Asp Gly Gly Asp Val Leu Ser Tyr Ile Leu Ala Val Glu Glu Leu Ala
65                  70                  75                  80

Lys Tyr Asp Ala Gly Val Ala Ile Thr Leu Ser Ala Thr Val Ser Leu
                85                  90                  95

Cys Ala Asn Pro Ile Trp Gln Phe Gly Thr Glu Ala Gln Lys Glu Lys
            100                 105                 110

Phe Leu Val Pro Leu Val Glu Gly Thr Lys Leu Gly Ala Phe Gly Leu
        115                 120                 125

Thr Glu Pro Asn Ala Gly Thr Asp Ala Ser Gly Gln Gln Thr Ile Ala
130                 135                 140

Thr Lys Asn Asp Asp Gly Thr Tyr Thr Leu Asn Gly Ser Lys Ile Phe
145                 150                 155                 160

Ile Thr Asn Gly Gly Ala Ala Asp Ile Tyr Ile Val Phe Ala Met Thr
                165                 170                 175

Asp Lys Ser Lys Gly Asn His Gly Ile Thr Ala Phe Ile Leu Glu Asp
            180                 185                 190

Gly Thr Pro Gly Phe Thr Tyr Gly Lys Lys Glu Asp Lys Met Gly Ile
        195                 200                 205

His Thr Ser Gln Thr Met Glu Leu Val Phe Gln Asp Val Lys Val Pro
210                 215                 220

Ala Glu Asn Met Leu Gly Glu Glu Gly Lys Gly Phe Lys Ile Ala Met
225                 230                 235                 240

Met Thr Leu Asp Gly Gly Arg Ile Gly Val Ala Ala Gln Ala Leu Gly
                245                 250                 255

Ile Ala Glu Ala Ala Leu Ala Asp Ala Val Glu Tyr Ser Lys Gln Arg
            260                 265                 270

Val Gln Phe Gly Lys Pro Leu Cys Lys Phe Gln Ser Ile Ser Phe Lys
        275                 280                 285

Leu Ala Asp Met Lys Met Gln Ile Glu Ala Ala Arg Asn Leu Val Tyr
290                 295                 300

Lys Ala Ala Cys Lys Lys Gln Glu Gly Lys Pro Phe Thr Val Asp Ala
305                 310                 315                 320

Ala Ile Ala Lys Arg Val Ala Ser Asp Val Ala Met Arg Val Thr Thr
                325                 330                 335

Glu Ala Val Gln Ile Phe Gly Gly Tyr Gly Tyr Ser Glu Glu Tyr Pro
            340                 345                 350

Val Ala Arg His Met Arg Asp Ala Lys Ile Thr Gln Ile Tyr Glu Gly
        355                 360                 365

Thr Asn Glu Val Gln Leu Met Val Thr Gly Gly Ala Leu Leu Arg Glu
370                 375                 380

Thr
385

<210> SEQ ID NO 106
<211> LENGTH: 1421
<212> TYPE: DNA
<213> ORGANISM: Artificial
<220> FEATURE:

<223> OTHER INFORMATION: Acinetobacter sp.

<400> SEQUENCE: 106

```
ggtaccttttt ttgggctaac aggaggaatt aaccatgatc aacaagatca tcaacgatat    60
cgaaccgatt ctgaaatcta cccagacgg ttctaccatc atgacttctg gcttcggtac    120
taccggtcag ccggaagcgc tgctggaagc gctgatcgac ttcgcaccga aagagctgac    180
tatcatcaac aacaacgctt cttccggtcc gaacggtctg actcagctgt tcactgctgg    240
tctggttaag aaactgatct gctcctaccc gaaatctatc tcttccaccg ttttcccgga    300
cctgtaccgc gctggtaaga tcgaactgga actggttccg cagggtaacc tggcttgccg    360
tatccaggca gctggcgcgg tctgggtgc agtattcact ccgactggtt acggtactaa    420
gatcgctgaa ggtaaagaaa ctcgtatcat caacggtaaa aactacgttc tggaataccc    480
gctggaagct gactacgcat tcatctacgc tgacaaagct gaccgctggg gtaacctgac    540
ttaccgtaaa gcggcacgta acttcggtcc gatcatggcg aaagcagcta aaaccactat    600
tgctcaggtt aaccagactg ttgaactggg cgatctggac ccggaatgca tcatcactcc    660
gggtatcttc gtacagcacg ttgttcgtct gggtgacatc aaataatttt ttgggctaac    720
aggaggaatt aaccatgact attcagaagc gttctcgcga agatatcgct atcatgatcg    780
ctaaagacat cccggacggt tcttacgtta acctgggtat cggtctgccg actcacgttg    840
ctaaatatct gccgaaagac aaagaaatct tcctgcactc tgaaaacggt gttctggcat    900
tcggtccgcc gccagcagaa ggtgaagaag atcaggacct ggttaacgct ggtaaagagc    960
tggtaactct gctgtctggt ggttgcttca tgcaccacgg tgactccttc gacatcatgc   1020
gtggtggtca cctggatatc tgcgttatcg gtgcattcca ggttgcgctg aacggtgacc   1080
tggctaactg gcacaccggt aaagacgacg acgttccggc agtaggtggt gcaatggacc   1140
tggctgttgg tgcgaagcgt atcttcgttt acatggaaca caccaccaag aaaggtgaac   1200
cgaaaatcgt taagcacctg acttacccga tcaccggtga acagtgcgta gaccgtatct   1260
acactgacct gtgcaccatc gaactgaaag acggtcaggc ttacgttatc gaaatggttg   1320
acggtctgga tttcgacact ctgcaggcgc tgactgaatg cccgctgatc gaccactgca   1380
cctactcttc tctgattcag ctcagataag gatccgagct c                       1421
```

<210> SEQ ID NO 107
<211> LENGTH: 223
<212> TYPE: PRT
<213> ORGANISM: Acinetobacter sp.

<400> SEQUENCE: 107

```
Met Ile Asn Lys Ile Ile Asn Asp Ile Glu Pro Ile Leu Lys Ser Ile
1               5                   10                  15

Pro Asp Gly Ser Thr Ile Met Thr Ser Gly Phe Gly Thr Thr Gly Gln
                20                  25                  30

Pro Glu Ala Leu Leu Glu Ala Leu Ile Asp Phe Ala Pro Lys Glu Leu
            35                  40                  45

Thr Ile Ile Asn Asn Asn Ala Ser Ser Gly Pro Asn Gly Leu Thr Gln
        50                  55                  60

Leu Phe Thr Ala Gly Leu Val Lys Lys Leu Ile Cys Ser Tyr Pro Lys
65                  70                  75                  80

Ser Ile Ser Ser Thr Val Phe Pro Asp Leu Tyr Arg Ala Gly Lys Ile
                85                  90                  95

Glu Leu Glu Leu Val Pro Gln Gly Asn Leu Ala Cys Arg Ile Gln Ala
```

```
                  100                 105                 110
Ala Gly Ala Gly Leu Gly Ala Val Phe Thr Pro Thr Gly Tyr Gly Thr
            115                 120                 125

Lys Ile Ala Glu Gly Lys Glu Thr Arg Ile Ile Asn Gly Lys Asn Tyr
130                 135                 140

Val Leu Glu Tyr Pro Leu Glu Ala Asp Tyr Ala Phe Ile Tyr Ala Asp
145                 150                 155                 160

Lys Ala Asp Arg Trp Gly Asn Leu Thr Tyr Arg Lys Ala Ala Arg Asn
                165                 170                 175

Phe Gly Pro Ile Met Ala Lys Ala Ala Lys Thr Thr Ile Ala Gln Val
            180                 185                 190

Asn Gln Thr Val Glu Leu Gly Asp Leu Asp Pro Glu Cys Ile Ile Thr
        195                 200                 205

Pro Gly Ile Phe Val Gln His Val Val Arg Leu Gly Asp Ile Lys
    210                 215                 220

<210> SEQ ID NO 108
<211> LENGTH: 1190
<212> TYPE: DNA
<213> ORGANISM: Artificial
<220> FEATURE:
<223> OTHER INFORMATION: Deinococcus radiodurans

<400> SEQUENCE: 108
ggtaccggat ccctaacagg aggaattaac catggacttc aatctgccgg acgatctgcg      60
tgaagttcag gcaactatcc gtgacttcat gctgactcgc gttgaagatc gcgctcagga     120
aatcgaacac accaactccg taccgccgga actgatcaaa gaagcggcag acctgggtct     180
gttcggtctg tctatcccgg aagaatacg tggtgttggt ctgtcctctc tgggtcgttg     240
cgcagtttac gaagcgatgg gtcagggtca catgggcttc ggtggtatga tctccgcaca     300
cgcttctatc ggtacttctg gtctggttaa actgggtaac gaagagcaga agcagcgttt     360
cctgccgcgt atggcggcag cgaatgcat cgctggcttc gctatcactg aaccaagctc     420
cggttctgac gctggtaaca tccgtactaa agctgttaag aaaggcgacg tttacgttct     480
gaacggtact aagcactaca tctccaacgc tccgatcgct ggtctgctga ccgttatcgc     540
tatcactgac ccggcacagg gttcccgtgg tatgtccgca ttcctggttg aaccgcagtc     600
tactccgggc gtatctatcg gtaaaatcga cgaaaaaatg ggtcagaaag gtgcgctgtc     660
tgcagaagtt atcttcgaag atgctgaaat cccggctgct aaccttctcg gtccggaaaa     720
ccgcggttac cgtgaagcgc tgggtattct gactaacggt cgcgttggta tcgctgcacg     780
ttctactggc gcgatgcagc gtctgctgga cctgtctgtt gcacacgctc agactcgcga     840
gcagttcggt aagccgatcg ctgagttcca ggcggtacag ttcatgctgg cagaaatgga     900
agttgcgatt cagacttctc gcgtactgtg gcagaaagtt gcatggatgg ttgaccaggg     960
tcaggacgtt aagcgtatgg cgtctgttgc taaataccac gcaactgaaa tgctgtctca    1020
ggttgctgac aaagcggtac aggttgctgg cggtatgggt tacgttaaag acgctccgtt    1080
cgaacgtttc taccgcgacc agcgtctgct gcgtatctac gaaggtactt ctgaaatcca    1140
gaaagttatc atcgctgctg aactgctgcg tcgcgagctc taataagctt                1190

<210> SEQ ID NO 109
<211> LENGTH: 383
<212> TYPE: PRT
<213> ORGANISM: Deinococcus radiodurans
```

<400> SEQUENCE: 109

```
Met Asp Phe Asn Leu Pro Asp Leu Arg Glu Val Gln Ala Thr Ile
1               5                   10                  15

Arg Asp Phe Met Leu Thr Arg Val Glu Asp Arg Ala Gln Glu Ile Glu
            20                  25                  30

His Thr Asn Ser Val Pro Pro Glu Leu Ile Lys Glu Ala Ala Asp Leu
        35                  40                  45

Gly Leu Phe Gly Leu Ser Ile Pro Glu Glu Tyr Gly Gly Val Gly Leu
    50                  55                  60

Ser Ser Leu Gly Arg Cys Ala Val Tyr Glu Ala Met Gly Gln Gly His
65                  70                  75                  80

Met Gly Phe Gly Gly Met Ile Ser Ala His Ala Ser Ile Gly Thr Ser
                85                  90                  95

Gly Leu Val Lys Leu Gly Asn Glu Glu Lys Gln Arg Phe Leu Pro
            100                 105                 110

Arg Met Ala Ala Gly Glu Cys Ile Ala Gly Phe Ala Ile Thr Glu Pro
            115                 120                 125

Ser Ser Gly Ser Asp Ala Gly Asn Ile Arg Thr Lys Ala Val Lys Lys
        130                 135                 140

Gly Asp Val Tyr Val Leu Asn Gly Thr Lys His Tyr Ile Ser Asn Ala
145                 150                 155                 160

Pro Ile Ala Gly Leu Leu Thr Val Ile Ala Ile Thr Asp Pro Ala Gln
                165                 170                 175

Gly Ser Arg Gly Met Ser Ala Phe Leu Val Glu Pro Gln Ser Thr Pro
            180                 185                 190

Gly Val Ser Ile Gly Lys Ile Asp Glu Lys Met Gly Gln Lys Gly Ala
        195                 200                 205

Leu Ser Ala Glu Val Ile Phe Glu Asp Ala Glu Ile Pro Ala Ala Asn
    210                 215                 220

Leu Leu Gly Pro Glu Asn Arg Gly Tyr Arg Glu Ala Leu Gly Ile Leu
225                 230                 235                 240

Thr Asn Gly Arg Val Gly Ile Ala Ala Arg Ser Thr Gly Ala Met Gln
                245                 250                 255

Arg Leu Leu Asp Leu Ser Val Ala His Ala Gln Thr Arg Glu Gln Phe
            260                 265                 270

Gly Lys Pro Ile Ala Glu Phe Gln Ala Val Gln Phe Met Leu Ala Glu
        275                 280                 285

Met Glu Val Ala Ile Gln Thr Ser Arg Val Leu Trp Gln Lys Val Ala
    290                 295                 300

Trp Met Val Asp Gln Gly Gln Asp Val Lys Arg Met Ala Ser Val Ala
305                 310                 315                 320

Lys Tyr His Ala Thr Glu Met Leu Ser Gln Val Ala Asp Lys Ala Val
                325                 330                 335

Gln Val Ala Gly Gly Met Gly Tyr Val Lys Asp Ala Pro Phe Glu Arg
            340                 345                 350

Phe Tyr Arg Asp Gln Arg Leu Leu Arg Ile Tyr Glu Gly Thr Ser Glu
        355                 360                 365

Ile Gln Lys Val Ile Ile Ala Ala Glu Leu Leu Arg Arg Glu Thr
    370                 375                 380
```

<210> SEQ ID NO 110
<211> LENGTH: 1202
<212> TYPE: DNA
<213> ORGANISM: Artificial

```
<220> FEATURE:
<223> OTHER INFORMATION: Arabidopsis thaliana

<400> SEQUENCE: 110
ggtaccggat ccctaacagg aggaattaac catggcctct tctctgctgt tcgacgacac    60
tcagctgcag ttcaaagaat ccgtttccaa gttcgctcag acaacatcg ctccgcacgc    120
tgaacgtatc gacaaaacta actccttccc gaaagacgtt aacctgtgga actgatggg    180
cgagttcaat ctgcacggta tcactgcgcc agaagaatac ggtggtctgg gtctgggtta    240
cctgtaccac tgcatcgcga tggaagaaat ctctcgcgct tctggttctg ttgctctgtc    300
ttacggcgca cactctaacc tgtgcatcaa ccagctggta cgtaacggta ctgctgcaca    360
gaaagagaag tatctgccga aactgatctc cggtgaacac gttggtgcac tggcgatgtc    420
tgaaccgaac gctggttctg acgttgttgg tatgaagtgc aaagcagaaa agttgacgg    480
tggttacatt ctgaacggta caagatgtg gtgcaccaac ggtccgtctg ctgaaactct    540
ggttgtttac gctaaaactg acaccaaagc gggttctaaa ggtatcactg cattcatcat    600
cgaaaaggt atgaccggtt ctccactgc tcagaagctg acaagctgg gtatgcgcgg     660
ttctgacact tgcgaactgg tattcgaaaa ctgcttcgta ccggaagaaa acatcctgga    720
taaagaaggt aaaggcgttt acgttctgat gtccggtctg gatctggaac gtctggtact    780
ggcagctggt ccgctgggta tcatgcaggc ttgcctggat aacgtactgc cgtacatccg    840
tcagcgtgaa cagttcggtc gtccggttgg cgagttccag ttcatccagg gtaaagttgc    900
tgacatgtac actgcgctgc agtcctcccg ttcttacgtt tactccgttg ctcgcgactg    960
cgacaacggt aaagttgatc cgaaagactg cgcaggcact atcctgtgcg cagctgaacg   1020
tgcaactcag gttgcgctgc aggcgattca gtgcctgggt ggtaacggtt acatcaacga   1080
atacgcaact ggtcgtctgc tgcgcgacgc gaagctgtac gaaatcggtg ctggtacttc   1140
tgaaatccgc cgtatcgtta tcggtcgtga actgttcaaa gaagaagagc tctaataagc   1200
tt                                                                  1202

<210> SEQ ID NO 111
<211> LENGTH: 387
<212> TYPE: PRT
<213> ORGANISM: Arabidopsis thaliana

<400> SEQUENCE: 111

Met Ala Ser Ser Leu Leu Phe Asp Asp Thr Gln Leu Gln Phe Lys Glu
1               5                   10                  15

Ser Val Ser Lys Phe Ala Gln Asp Asn Ile Ala Pro His Ala Glu Arg
            20                  25                  30

Ile Asp Lys Thr Asn Ser Phe Pro Lys Asp Val Asn Leu Trp Lys Leu
        35                  40                  45

Met Gly Glu Phe Asn Leu His Gly Ile Thr Ala Pro Glu Glu Tyr Gly
    50                  55                  60

Gly Leu Gly Leu Gly Tyr Leu Tyr His Cys Ile Ala Met Glu Glu Ile
65                  70                  75                  80

Ser Arg Ala Ser Gly Ser Val Ala Leu Ser Tyr Gly Ala His Ser Asn
                85                  90                  95

Leu Cys Ile Asn Gln Leu Val Arg Asn Gly Thr Ala Ala Gln Lys Glu
            100                 105                 110

Lys Tyr Leu Pro Lys Leu Ile Ser Gly Glu His Val Gly Ala Leu Ala
        115                 120                 125
```

Met Ser Glu Pro Asn Ala Gly Ser Asp Val Val Gly Met Lys Cys Lys
            130                 135                 140
Ala Glu Lys Val Asp Gly Gly Tyr Ile Leu Asn Gly Asn Lys Met Trp
145                 150                 155                 160
Cys Thr Asn Gly Pro Ser Ala Glu Thr Leu Val Val Tyr Ala Lys Thr
                165                 170                 175
Asp Thr Lys Ala Gly Ser Lys Gly Ile Thr Ala Phe Ile Ile Glu Lys
            180                 185                 190
Gly Met Thr Gly Phe Ser Thr Ala Gln Lys Leu Asp Lys Leu Gly Met
        195                 200                 205
Arg Gly Ser Asp Thr Cys Glu Leu Val Phe Glu Asn Cys Phe Val Pro
    210                 215                 220
Glu Glu Asn Ile Leu Asp Lys Glu Gly Lys Gly Val Tyr Val Leu Met
225                 230                 235                 240
Ser Gly Leu Asp Leu Glu Arg Leu Val Leu Ala Ala Gly Pro Leu Gly
                245                 250                 255
Ile Met Gln Ala Cys Leu Asp Asn Val Leu Pro Tyr Ile Arg Gln Arg
            260                 265                 270
Glu Gln Phe Gly Arg Pro Val Gly Glu Phe Gln Phe Ile Gln Gly Lys
        275                 280                 285
Val Ala Asp Met Tyr Thr Ala Leu Gln Ser Ser Arg Ser Tyr Val Tyr
    290                 295                 300
Ser Val Ala Arg Asp Cys Asp Asn Gly Lys Val Asp Pro Lys Asp Cys
305                 310                 315                 320
Ala Gly Thr Ile Leu Cys Ala Ala Glu Arg Ala Thr Gln Val Ala Leu
                325                 330                 335
Gln Ala Ile Gln Cys Leu Gly Gly Asn Gly Tyr Ile Asn Glu Tyr Ala
            340                 345                 350
Thr Gly Arg Leu Leu Arg Asp Ala Lys Leu Tyr Glu Ile Gly Ala Gly
        355                 360                 365
Thr Ser Glu Ile Arg Arg Ile Val Ile Gly Arg Glu Leu Phe Lys Glu
    370                 375                 380
Glu Glu Thr
385

<210> SEQ ID NO 112
<211> LENGTH: 1232
<212> TYPE: DNA
<213> ORGANISM: Artificial
<220> FEATURE:
<223> OTHER INFORMATION: Homo sapiens

<400> SEQUENCE: 112
ggtaccggat ccctaacagg aggaattaac catgggtccg gaatttgact ggcaggaccc    60
gctggtactg gaagagcagc tgaccactga cgaaatcctg atccgtgaca ccttccgtac   120
ttactgccag gaacgtctga tgccgcgcat tctgctggct aaccgtaacg aagttttcca   180
ccgtgaaatc atctctgaaa tgggtgaact gggtgttctg ggtccgacta tcaaaggtta   240
cggttgcgca ggcgtttctt ccgttgctta cggtctgctg gcgcgtgaac tggaacgcgt   300
tgactccggt taccgttctg caatgtccgt tcagtcctct ctggtaatgc acccaatcta   360
cgcttacggt tctgaagagc agcgtcagaa atatctgccg cagctggcga aggtgaact   420 gctgggttgc ttcggtctga ctgaaccgaa ctccggttct gacccgtcct ctatggaaac   480
tcgcgcacac tacaactctt ctaacaagtc ttacactctg aacggcacca aaacctggat   540

```
cactaactct ccgatggctg acctgttcgt tgtatgggct cgctgcgaag atggttgcat    600
ccgcggtttc ctgctggaaa aaggtatgcg tggtctgtct gcaccgcgta tccagggtaa    660
gttctctctg cgcgcttctg caactggtat gatcatcatg gacggtgttg aagttccgga    720
agaaaacgtt ctgccgggtg catcttctct gggtggtccg ttcggttgcc tgaacaacgc    780
gcgttacggt atcgcatggg gcgtactggg tgcttctgag ttctgcctgc acactgcacg    840
tcagtacgca ctggatcgca tgcagttcgg tgttccgctg gcgcgtaacc agctgattca    900
gaagaaactg gctgacatgc tgactgaaat cactctgggt ctgcacgctt gcctgcagct    960
gggtcgtctg aaagaccagg acaaagctgc accggaaatg gtttctctgc tgaagcgtaa   1020
caactgcggt aaagcgctgg atatcgctcg ccaggctcgc gacatgctgg gtggtaacgg   1080
tatctctgac gaataccacg ttatccgtca cgcgatgaac ctggaagctg ttaacaccta   1140
cgaaggtact cacgacatcc acgcgctgat cctgggtcgt gctatcaccg gtatccaggc   1200
tttcactgct tctaaagagc tctaataagc tt                                  1232

<210> SEQ ID NO 113
<211> LENGTH: 397
<212> TYPE: PRT
<213> ORGANISM: Homo sapiens

<400> SEQUENCE: 113

Met Gly Pro Glu Phe Asp Trp Gln Asp Pro Leu Val Leu Glu Glu Gln
1               5                   10                  15

Leu Thr Thr Asp Glu Ile Leu Ile Arg Asp Thr Phe Arg Thr Tyr Cys
            20                  25                  30

Gln Glu Arg Leu Met Pro Arg Ile Leu Leu Ala Asn Arg Asn Glu Val
        35                  40                  45

Phe His Arg Glu Ile Ile Ser Glu Met Gly Glu Leu Gly Val Leu Gly
    50                  55                  60

Pro Thr Ile Lys Gly Tyr Gly Cys Ala Gly Val Ser Ser Val Ala Tyr
65                  70                  75                  80

Gly Leu Leu Ala Arg Glu Leu Glu Arg Val Asp Ser Gly Tyr Arg Ser
                85                  90                  95

Ala Met Ser Val Gln Ser Ser Leu Val Met His Pro Ile Tyr Ala Tyr
            100                 105                 110

Gly Ser Glu Glu Gln Arg Gln Lys Tyr Leu Pro Gln Leu Ala Lys Gly
        115                 120                 125

Glu Leu Leu Gly Cys Phe Gly Leu Thr Glu Pro Asn Ser Gly Ser Asp
    130                 135                 140

Pro Ser Ser Met Glu Thr Arg Ala His Tyr Asn Ser Ser Asn Lys Ser
145                 150                 155                 160

Tyr Thr Leu Asn Gly Thr Lys Thr Trp Ile Thr Asn Ser Pro Met Ala
                165                 170                 175

Asp Leu Phe Val Val Trp Ala Arg Cys Glu Asp Gly Cys Ile Arg Gly
            180                 185                 190

Phe Leu Leu Glu Lys Gly Met Arg Gly Leu Ser Ala Pro Arg Ile Gln
        195                 200                 205

Gly Lys Phe Ser Leu Arg Ala Ser Ala Thr Gly Met Ile Ile Met Asp
    210                 215                 220

Gly Val Glu Val Pro Glu Glu Asn Val Leu Pro Gly Ala Ser Ser Leu
225                 230                 235                 240

Gly Gly Pro Phe Gly Cys Leu Asn Asn Ala Arg Tyr Gly Ile Ala Trp
                245                 250                 255
```

Gly Val Leu Gly Ala Ser Glu Phe Cys Leu His Thr Ala Arg Gln Tyr
                260                 265                 270

Ala Leu Asp Arg Met Gln Phe Gly Val Pro Leu Ala Arg Asn Gln Leu
            275                 280                 285

Ile Gln Lys Lys Leu Ala Asp Met Leu Thr Glu Ile Thr Leu Gly Leu
        290                 295                 300

His Ala Cys Leu Gln Leu Gly Arg Leu Lys Asp Gln Asp Lys Ala Ala
305                 310                 315                 320

Pro Glu Met Val Ser Leu Leu Lys Arg Asn Asn Cys Gly Lys Ala Leu
                325                 330                 335

Asp Ile Ala Arg Gln Ala Arg Asp Met Leu Gly Gly Asn Gly Ile Ser
            340                 345                 350

Asp Glu Tyr His Val Ile Arg His Ala Met Asn Leu Glu Ala Val Asn
        355                 360                 365

Thr Tyr Glu Gly Thr His Asp Ile His Ala Leu Ile Leu Gly Arg Ala
370                 375                 380

Ile Thr Gly Ile Gln Ala Phe Thr Ala Ser Lys Glu Thr
385                 390                 395

<210> SEQ ID NO 114
<211> LENGTH: 1784
<212> TYPE: DNA
<213> ORGANISM: Artificial
<220> FEATURE:
<223> OTHER INFORMATION: Homo sapiens

<400> SEQUENCE: 114

```
ggtaccggat ccctaacagg aggaattaat catgaccact ctggttatcg ctgaacacgc      60
taacgactct ctggcaccaa tcactctgaa caccatcact gcggcaactc gtctgggtgg     120
tgaagtttcc tgcctggttg ctggcaccaa gtgcgacaaa gttgctcagg acctgtgcaa     180
agtagcgggt atcgcgaaag ttctggtagc gcagcacgac gtttacaaag tctgctgcc      240
ggaagagctg actccgctga tcctggcaac tcagaagcag ttcaactaca ctcacatctg     300
tgcgggtgct tctgcattcg gtaaaaatct gctgccgcgc gttgctgcga aactggaagt     360
tgcaccgatt tctgacatca tcgctatcaa gtctccggat accttcgtac gtactatcta     420
cgctggtaac gcactgtgca ccgttaagtg cgacgaaaaa gttaaagtat tctctgtacg     480
tggtacttct ttcgacgctg cagcaacttc tggtggttct gcatcttctg aaaaagcatc     540
ttccacttct ccggttgaaa tctctgagtg gctggatcag aaactgacca gtctgaccg      600
tccggaactg actggcgcga agttgttgt ttctggtggt cgtggtctga atctggtga      660
aaacttcaaa ctgctgtacg acctggctga ccagctgcac gctgctgttg gtgcttctcg     720
cgctgctgtt gatgctggct tcgtaccgaa cgacatgcaa gttggtcaga ctggtaaaat     780
cgttgcaccg gaactgtaca tcgctgttgg tatctccggt gcgattcagc acctggcggg     840
tatgaaagac tccaaaacta tcgttgctat caacaaagac ccggaagcac cgatcttcca     900
ggttgctgac tacggtatcg ttgctgacct gttcaaagtt gttccggaaa tgactgaaat     960
cctgaagaag agtaataac tagtctaaca ggaggaatta accatggctg aactgcgcgt    1020
actggttgct gttaagcgcg ttatcgacta cgcagttaaa atccgcgtta agccggaccg    1080
tactggcgtt gttactgacg gtgttaaaca ctctatgaac ccgttctgcg aaatcgctgt    1140
tgaagaagcg gtacgtctga agagaagaa actggttaaa gaagttatcg ctgtttcctg    1200
cggtccggca cagtgccagg aaaccattcg tactgcactg gcgatgggcg cagaccgcgg    1260
```

| | |
|---|---|
| tatccacgtt gaagttccgc cagctgaagc agaacgtctg ggtccgctcc aggttgctcg | 1320 |
| cgtactggcg aaactggctg aaaaagaaaa agttgacctg gtactgctgg gtaagcaggc | 1380 |
| tatcgacgac gactgcaacc agactggtca gatgactgct ggcttcctgg actggccgca | 1440 |
| gggtactttc gcttctcagg taactctgga aggtgacaaa ctgaaagttg aacgtgaaat | 1500 |
| cgacggtggt ctggaaactc tgcgtctgaa actgccggca gttgttactg ctgatctgcg | 1560 |
| tctgaacgaa ccgcgttacg caactctgcc gaacattatg aaagcgaaga agaagaaaat | 1620 |
| cgaagttatc aagccgggcg aactgggtgt tgacctgact tctaaactgt ctgttatctc | 1680 |
| cgttgaagat ccgccgcagc gtactgctgg cgttaaagtt gaaaccactg aggatctggt | 1740 |
| agcgaaactg aaagaaatcg gtcgtatcga gctctaataa gctt | 1784 |

<210> SEQ ID NO 115
<211> LENGTH: 314
<212> TYPE: PRT
<213> ORGANISM: Homo sapiens

<400> SEQUENCE: 115

Met Thr Thr Leu Val Ile Ala Glu His Ala Asn Asp Ser Leu Ala Pro
1               5                   10                  15

Ile Thr Leu Asn Thr Ile Thr Ala Ala Thr Arg Leu Gly Gly Glu Val
            20                  25                  30

Ser Cys Leu Val Ala Gly Thr Lys Cys Asp Lys Val Ala Gln Asp Leu
        35                  40                  45

Cys Lys Val Ala Gly Ile Ala Lys Val Leu Val Ala Gln His Asp Val
    50                  55                  60

Tyr Lys Gly Leu Leu Pro Glu Glu Leu Thr Pro Leu Ile Leu Ala Thr
65                  70                  75                  80

Gln Lys Gln Phe Asn Tyr Thr His Ile Cys Ala Gly Ala Ser Ala Phe
                85                  90                  95

Gly Lys Asn Leu Leu Pro Arg Val Ala Ala Lys Leu Glu Val Ala Pro
            100                 105                 110

Ile Ser Asp Ile Ile Ala Ile Lys Ser Pro Asp Thr Phe Val Arg Thr
        115                 120                 125

Ile Tyr Ala Gly Asn Ala Leu Cys Thr Val Lys Cys Asp Glu Lys Val
    130                 135                 140

Lys Val Phe Ser Val Arg Gly Thr Ser Phe Asp Ala Ala Ala Thr Ser
145                 150                 155                 160

Gly Gly Ser Ala Ser Ser Glu Lys Ala Ser Ser Thr Ser Pro Val Glu
                165                 170                 175

Ile Ser Glu Trp Leu Asp Gln Lys Leu Thr Lys Ser Asp Arg Pro Glu
            180                 185                 190

Leu Thr Gly Ala Lys Val Val Ser Gly Gly Arg Gly Leu Lys Ser
        195                 200                 205

Gly Glu Asn Phe Lys Leu Leu Tyr Asp Leu Ala Asp Gln Leu His Ala
    210                 215                 220

Ala Val Gly Ala Ser Arg Ala Ala Val Asp Ala Gly Phe Val Pro Asn
225                 230                 235                 240

Asp Met Gln Val Gly Gln Thr Gly Lys Ile Val Ala Pro Glu Leu Tyr
                245                 250                 255

Ile Ala Val Gly Ile Ser Gly Ala Ile Gln His Leu Ala Gly Met Lys
            260                 265                 270

Asp Ser Lys Thr Ile Val Ala Ile Asn Lys Asp Pro Glu Ala Pro Ile

```
                275                 280                 285
Phe Gln Val Ala Asp Tyr Gly Ile Val Ala Asp Leu Phe Lys Val Val
    290                 295                 300
Pro Glu Met Thr Glu Ile Leu Lys Lys Lys
305                 310
```

<210> SEQ ID NO 116
<211> LENGTH: 255
<212> TYPE: PRT
<213> ORGANISM: Homo sapiens

<400> SEQUENCE: 116

```
Met Ala Glu Leu Arg Val Leu Val Ala Val Lys Arg Val Ile Asp Tyr
1               5                   10                  15
Ala Val Lys Ile Arg Val Lys Pro Asp Arg Thr Gly Val Val Thr Asp
                20                  25                  30
Gly Val Lys His Ser Met Asn Pro Phe Cys Glu Ile Ala Val Glu Glu
            35                  40                  45
Ala Val Arg Leu Lys Glu Lys Lys Leu Val Lys Glu Val Ile Ala Val
        50                  55                  60
Ser Cys Gly Pro Ala Gln Cys Gln Glu Thr Ile Arg Thr Ala Leu Ala
65                  70                  75                  80
Met Gly Ala Asp Arg Gly Ile His Val Glu Val Pro Pro Ala Glu Ala
                85                  90                  95
Glu Arg Leu Gly Pro Leu Gln Val Ala Arg Val Leu Ala Lys Leu Ala
            100                 105                 110
Glu Lys Glu Lys Val Asp Leu Val Leu Leu Gly Lys Gln Ala Ile Asp
        115                 120                 125
Asp Asp Cys Asn Gln Thr Gly Gln Met Thr Ala Gly Phe Leu Asp Trp
130                 135                 140
Pro Gln Gly Thr Phe Ala Ser Gln Val Thr Leu Glu Gly Asp Lys Leu
145                 150                 155                 160
Lys Val Glu Arg Glu Ile Asp Gly Gly Leu Glu Thr Leu Arg Leu Lys
                165                 170                 175
Leu Pro Ala Val Val Thr Ala Asp Leu Arg Leu Asn Glu Pro Arg Tyr
            180                 185                 190
Ala Thr Leu Pro Asn Ile Met Lys Ala Lys Lys Lys Ile Glu Val
        195                 200                 205
Ile Lys Pro Gly Asp Leu Gly Val Asp Leu Thr Ser Lys Leu Ser Val
        210                 215                 220
Ile Ser Val Glu Asp Pro Pro Gln Arg Thr Ala Gly Val Lys Val Glu
225                 230                 235                 240
Thr Thr Glu Asp Leu Val Ala Lys Leu Lys Glu Ile Gly Arg Ile
                245                 250                 255
```

<210> SEQ ID NO 117
<211> LENGTH: 316
<212> TYPE: PRT
<213> ORGANISM: Homo sapiens

<400> SEQUENCE: 117

```
Met Ser Ser Pro Gln Ala Pro Glu Asp Gly Gln Gly Cys Gly Asp Arg
1               5                   10                  15
Gly Asp Pro Pro Gly Asp Leu Arg Ser Val Leu Val Thr Thr Val Leu
                20                  25                  30
Asn Leu Glu Pro Leu Asp Glu Asp Leu Phe Arg Gly Arg His Tyr Trp
```

```
            35                  40                  45
Val Pro Ala Lys Arg Leu Phe Gly Gly Gln Ile Val Gly Gln Ala Leu
 50                  55                  60

Val Ala Ala Lys Ser Val Ser Glu Asp Val His Val His Ser Leu
 65                  70                  75                  80

His Cys Tyr Phe Val Arg Ala Gly Asp Pro Lys Leu Pro Val Leu Tyr
                     85                  90                  95

Gln Val Glu Arg Thr Arg Thr Gly Ser Ser Phe Ser Val Arg Ser Val
                100                 105                 110

Lys Ala Val Gln His Gly Lys Pro Ile Phe Ile Cys Gln Ala Ser Phe
                115                 120                 125

Gln Gln Ala Gln Pro Ser Pro Met Gln His Gln Phe Ser Met Pro Thr
130                 135                 140

Val Pro Pro Pro Glu Glu Leu Leu Asp Cys Glu Thr Leu Ile Asp Gln
145                 150                 155                 160

Tyr Leu Arg Asp Pro Asn Leu Gln Lys Arg Tyr Pro Leu Ala Leu Asn
                165                 170                 175

Arg Ile Ala Ala Gln Glu Val Pro Ile Glu Ile Lys Pro Val Asn Pro
                180                 185                 190

Ser Pro Leu Ser Gln Leu Gln Arg Met Glu Pro Lys Gln Met Phe Trp
                195                 200                 205

Val Arg Ala Arg Gly Tyr Ile Gly Glu Gly Asp Met Lys Met His Cys
210                 215                 220

Cys Val Ala Ala Tyr Ile Ser Asp Tyr Ala Phe Leu Gly Thr Ala Leu
225                 230                 235                 240

Leu Pro His Gln Trp Gln His Lys Val His Phe Met Val Ser Leu Asp
                245                 250                 255

His Ser Met Trp Phe His Ala Pro Phe Arg Ala Asp His Trp Met Leu
                260                 265                 270

Tyr Glu Cys Glu Ser Pro Trp Ala Gly Gly Ser Arg Gly Leu Val His
                275                 280                 285

Gly Arg Leu Trp Arg Gln Asp Gly Val Leu Ala Val Thr Cys Ala Gln
290                 295                 300

Glu Gly Val Ile Arg Val Lys Pro Gln Val Ser Glu
305                 310                 315
```

<210> SEQ ID NO 118
<211> LENGTH: 931
<212> TYPE: DNA
<213> ORGANISM: Artificial
<220> FEATURE:
<223> OTHER INFORMATION: Hyphomonas neptunium

<400> SEQUENCE: 118

```
ggtacctttt ttgggctaac aggaggaatt aaccatggcg aaagacccgg ttggcgatct      60
gctgactctg ctggatctgg aacgtctgga actggatctg ttccgcggtc agtctccgga     120
cgaagaagaa tctcagcgcg tattcggtgg tcaggttatc gctcagtctc tggttgctgc     180
ttaccgtact gtaccggacg accgtctgtg ccactctctg cactgctact catccgtcc     240 gggcgacccg tctgtaccaa tcatctacca ggttgaccac tctcgcgacg gtggttcttt     300
caccactcgt cgcgttgttg ctatccagca cggtaagcag attttcaacc tggcagcttc     360
tttccacgtt gttgaagatt cctggcacca ccagcacgaa atgccggaag ttgacccgcc     420
agaatccgta ggtgaccgta tcgagtggcg tcgtaaattc gctgaacagg ttccggaacg     480
```

```
tcaccgcggt cacttcctgc gcgaccgtcc ggttgaaatg cgtgaaatcg acccgctgga    540
cccgctgaaa ccggcaaaag cgtctgacca gcagaacctg tggttccgcg ttgctcgtcc    600
gatcgacgaa gcgccgtggc tgcaccactg cctgatggct tacgcttctg acatggcgct    660
gctgggtact ggtaaccgtc cgcacggtat ctcctggatg accggtgaac tgatgtccgc    720
atctctggat cacgcgatgt ggttccacgc accgactaaa ttcgacgagt ggcacctgta    780
ctctatggac tctccgtacg caggcggtgc acgttctttc aaccgcggtt ctatctacga    840
ctccaccggt cgtctggttg cttctgttgc tcaggaaggt ctgatgcgtc gcgttgaacg    900
taagccgcgt aaaagctaag gatccgagct c                                   931
```

<210> SEQ ID NO 119
<211> LENGTH: 294
<212> TYPE: PRT
<213> ORGANISM: Hyphomonas neptunium

<400> SEQUENCE: 119

```
Met Ala Lys Asp Pro Val Gly Asp Leu Leu Thr Leu Leu Asp Leu Glu
1               5                   10                  15

Arg Leu Glu Leu Asp Leu Phe Arg Gly Gln Ser Pro Asp Glu Glu Glu
            20                  25                  30

Ser Gln Arg Val Phe Gly Gly Gln Val Ile Ala Gln Ser Leu Val Ala
        35                  40                  45

Ala Tyr Arg Thr Val Pro Asp Asp Arg Leu Cys His Ser Leu His Cys
    50                  55                  60

Tyr Phe Ile Arg Pro Gly Asp Pro Ser Val Pro Ile Ile Tyr Gln Val
65                  70                  75                  80

Asp His Ser Arg Asp Gly Gly Ser Phe Thr Thr Arg Arg Val Val Ala
                85                  90                  95

Ile Gln His Gly Lys Gln Ile Phe Asn Leu Ala Ala Ser Phe His Val
            100                 105                 110

Val Glu Asp Ser Trp His His Gln His Glu Met Pro Glu Val Asp Pro
        115                 120                 125

Pro Glu Ser Val Gly Asp Arg Ile Glu Trp Arg Arg Lys Phe Ala Glu
    130                 135                 140

Gln Val Pro Glu Arg His Arg Gly His Phe Leu Arg Asp Arg Pro Val
145                 150                 155                 160

Glu Met Arg Glu Ile Asp Pro Leu Asp Pro Leu Lys Pro Ala Lys Ala
                165                 170                 175

Ser Asp Gln Gln Asn Leu Trp Phe Arg Val Ala Arg Pro Ile Asp Glu
            180                 185                 190

Ala Pro Trp Leu His His Cys Leu Met Ala Tyr Ala Ser Asp Met Ala
        195                 200                 205

Leu Leu Gly Thr Gly Asn Arg Pro His Gly Ile Ser Trp Met Thr Gly
    210                 215                 220

Glu Leu Met Ser Ala Ser Leu Asp His Ala Met Trp Phe His Ala Pro
225                 230                 235                 240

Thr Lys Phe Asp Glu Trp His Leu Tyr Ser Met Asp Ser Pro Tyr Ala
                245                 250                 255

Gly Gly Ala Arg Ser Phe Asn Arg Gly Ser Ile Tyr Asp Ser Thr Gly
            260                 265                 270

Arg Leu Val Ala Ser Val Ala Gln Glu Gly Leu Met Arg Arg Val Glu
        275                 280                 285

Arg Lys Pro Arg Lys Ser
```

<210> SEQ ID NO 120
<211> LENGTH: 1421
<212> TYPE: DNA
<213> ORGANISM: Artificial
<220> FEATURE:
<223> OTHER INFORMATION: Acinetobacter sp.

<400> SEQUENCE: 120

```
ggtacctttt ttgggctaac aggaggaatt aaccatgatc aacaagatca tcaacgatat      60
cgaaccgatt ctgaaatcta tcccagacgg ttctaccatc atgacttctg gcttcggtac     120
taccggtcag ccggaagcgc tgctggaagc gctgatcgac ttcgcaccga aagagctgac     180
tatcatcaac aacaacgctt cttccggtcc gaacggtctg actcagctgt tcactgctgg     240
tctggttaag aaactgatct gctcctaccc gaaatctatc tcttccaccg ttttcccgga     300
cctgtaccgc gctggtaaga tcgaactgga actggttccg cagggtaacc tggcttgccg     360
tatccaggca gctggcgcgg tctgggtgc agtattcact ccgactggtt acggtactaa     420
gatcgctgaa ggtaaagaaa ctcgtatcat caacggtaaa aactacgttc tggaatacc      480
gctggaagct gactacgcat tcatctacgc tgacaaagct gaccgctggg gtaacctgac     540
ttaccgtaaa gcggcacgta acttcggtcc gatcatggcg aaagcagcta aaccactat      600
tgctcaggtt aaccagactg ttgaactggg cgatctggac ccggaatgca tcatcactcc     660
gggtatcttc gtacagcacg ttgttcgtct gggtgacatc aaataatttt ttgggctaac     720
aggaggaatt aaccatgact attcagaagc gttctcgcga agatatcgct atcatgatcg     780
ctaaagacat cccggacggt tcttacgtta acctgggtat cggtctgccg actcacgttg     840
ctaaatatct gccgaaagac aaagaaatct tcctgcactc tgaaaacggt gttctggcat     900
tcggtccgcc gccagcagaa ggtgaagaag atcaggacct ggttaacgct ggtaaagagc     960
tggtaactct gctgtctggt ggttgcttca tgcaccacgg tgactccttc gacatcatgc    1020
gtggtggtca cctggatatc tgcgttatcg gtgcattcca ggttgcgctg aacggtgacc    1080
tggctaactg gcacaccggt aaagacgacg acgttccggc agtaggtggt gcaatggacc    1140
tggctgttgg tgcgaagcgt atcttcgttt acatggaaca caccaccaag aaaggtgaac    1200
cgaaaatcgt taagcacctg acttacccga tcaccggtga acagtgcgta gaccgtatct    1260
acactgacct gtgcaccatc gaactgaaag acggtcaggc ttacgttatc gaaatggttg    1320
acggtctgga tttcgacact ctgcaggcgc tgactgaatg cccgctgatc gaccactgca    1380
cctactcttc tctgattcag ctcagataag gatccgagct c                        1421
```

<210> SEQ ID NO 121
<211> LENGTH: 223
<212> TYPE: PRT
<213> ORGANISM: Acinetobacter sp.

<400> SEQUENCE: 121

```
Met Ile Asn Lys Ile Ile Asn Asp Ile Glu Pro Ile Leu Lys Ser Ile
1               5                   10                  15
Pro Asp Gly Ser Thr Ile Met Thr Ser Gly Phe Gly Thr Thr Gly Gln
            20                  25                  30
Pro Glu Ala Leu Leu Glu Ala Leu Ile Asp Phe Ala Pro Lys Glu Leu
        35                  40                  45
Thr Ile Ile Asn Asn Asn Ala Ser Ser Gly Pro Asn Gly Leu Thr Gln
    50                  55                  60
```

```
Leu Phe Thr Ala Gly Leu Val Lys Lys Leu Ile Cys Ser Tyr Pro Lys
 65                  70                  75                  80

Ser Ile Ser Ser Thr Val Phe Pro Asp Leu Tyr Arg Ala Gly Lys Ile
                 85                  90                  95

Glu Leu Glu Leu Val Pro Gln Gly Asn Leu Ala Cys Arg Ile Gln Ala
            100                 105                 110

Ala Gly Ala Gly Leu Gly Ala Val Phe Thr Pro Thr Gly Tyr Gly Thr
        115                 120                 125

Lys Ile Ala Glu Gly Lys Glu Thr Arg Ile Ile Asn Gly Lys Asn Tyr
    130                 135                 140

Val Leu Glu Tyr Pro Leu Glu Ala Asp Tyr Ala Phe Ile Tyr Ala Asp
145                 150                 155                 160

Lys Ala Asp Arg Trp Gly Asn Leu Thr Tyr Arg Lys Ala Ala Arg Asn
                165                 170                 175

Phe Gly Pro Ile Met Ala Lys Ala Ala Lys Thr Thr Ile Ala Gln Val
            180                 185                 190

Asn Gln Thr Val Glu Leu Gly Asp Leu Asp Pro Glu Cys Ile Ile Thr
        195                 200                 205

Pro Gly Ile Phe Val Gln His Val Val Arg Leu Gly Asp Ile Lys
    210                 215                 220

<210> SEQ ID NO 122
<211> LENGTH: 224
<212> TYPE: PRT
<213> ORGANISM: Acinetobacter sp.

<400> SEQUENCE: 122

Met Thr Ile Gln Lys Arg Ser Arg Glu Asp Ile Ala Ile Met Ile Ala
1               5                   10                  15

Lys Asp Ile Pro Asp Gly Ser Tyr Val Asn Leu Gly Ile Gly Leu Pro
            20                  25                  30

Thr His Val Ala Lys Tyr Leu Pro Lys Asp Lys Glu Ile Phe Leu His
        35                  40                  45

Ser Glu Asn Gly Val Leu Ala Phe Gly Pro Pro Ala Glu Gly Glu
    50                  55                  60

Glu Asp Gln Asp Leu Val Asn Ala Gly Lys Glu Leu Val Thr Leu Leu
65                  70                  75                  80

Ser Gly Gly Cys Phe Met His His Gly Asp Ser Phe Asp Ile Met Arg
                85                  90                  95

Gly Gly His Leu Asp Ile Cys Val Ile Gly Ala Phe Gln Val Ala Leu
            100                 105                 110

Asn Gly Asp Leu Ala Asn Trp His Thr Gly Lys Asp Asp Val Pro
        115                 120                 125

Ala Val Gly Gly Ala Met Asp Leu Ala Val Gly Ala Lys Arg Ile Phe
    130                 135                 140

Val Tyr Met Glu His Thr Thr Lys Lys Gly Glu Pro Lys Ile Val Lys
145                 150                 155                 160

His Leu Thr Tyr Pro Ile Thr Gly Glu Gln Cys Val Asp Arg Ile Tyr
                165                 170                 175

Thr Asp Leu Cys Thr Ile Glu Leu Lys Asp Gly Gln Ala Tyr Val Ile
            180                 185                 190

Glu Met Val Asp Gly Leu Asp Phe Asp Thr Leu Gln Ala Leu Thr Glu
        195                 200                 205

Cys Pro Leu Ile Asp His Cys Thr Tyr Ser Ser Leu Ile Gln Leu Arg
```

<210> SEQ ID NO 123
<211> LENGTH: 437
<212> TYPE: PRT
<213> ORGANISM: Clostridium kluyveri

<400> SEQUENCE: 123

Met Val Phe Lys Asn Trp Gln Asp Leu Tyr Lys Ser Lys Ile Val Ser
1               5                   10                  15

Ala Asp Glu Ala Val Ser Lys Val Ser Cys Gly Asp Ser Ile Ile Leu
            20                  25                  30

Gly Asn Ala Cys Gly Ala Ser Leu Thr Leu Leu Asp Ala Leu Ala Ala
        35                  40                  45

Asn Lys Glu Lys Tyr Lys Ser Val Lys Ile His Asn Leu Ile Leu Asn
    50                  55                  60

Tyr Lys Asn Asp Ile Tyr Thr Asp Pro Glu Ser Glu Lys Tyr Ile His
65                  70                  75                  80

Gly Asn Thr Phe Phe Val Ser Gly Gly Thr Lys Glu Ala Val Asn Cys
                85                  90                  95

Asn Arg Thr Asp Tyr Thr Pro Cys Phe Phe Tyr Glu Ile Pro Lys Leu
            100                 105                 110

Leu Lys Gln Lys Tyr Ile Asn Ala Asp Val Ala Phe Ile Gln Val Ser
        115                 120                 125

Lys Pro Asp Ser His Gly Tyr Cys Ser Phe Gly Val Ser Thr Asp Tyr
    130                 135                 140

Ser Gln Ala Met Val Gln Ser Ala Lys Leu Ile Ile Ala Glu Val Asn
145                 150                 155                 160

Asp Gln Met Pro Arg Val Leu Gly Asp Asn Phe Ile His Ile Ser Asp
                165                 170                 175

Met Asp Tyr Ile Val Glu Ser Ser Arg Pro Ile Leu Glu Leu Thr Pro
            180                 185                 190

Pro Lys Ile Gly Glu Val Glu Lys Thr Ile Gly Lys Tyr Cys Ala Ser
        195                 200                 205

Leu Val Glu Asp Gly Ser Thr Leu Gln Leu Gly Ile Gly Ala Ile Pro
    210                 215                 220

Asp Ala Val Leu Leu Phe Leu Lys Asp Lys Lys Asp Leu Gly Ile His
225                 230                 235                 240

Ser Glu Met Ile Ser Asp Gly Val Val Glu Leu Val Glu Ala Gly Val
                245                 250                 255

Ile Thr Asn Lys Lys Ser Leu His Pro Gly Lys Ile Ile Ile Thr
            260                 265                 270

Phe Leu Met Gly Thr Lys Lys Leu Tyr Asp Phe Ile Asn Asp Asn Pro
        275                 280                 285

Met Val Glu Gly Tyr Pro Val Asp Tyr Val Asn Asp Pro Lys Val Ile
    290                 295                 300

Met Gln Asn Ser Lys Met Val Cys Ile Asn Ser Cys Val Glu Val Asp
305                 310                 315                 320

Phe Thr Gly Gln Val Cys Ala Glu Ser Val Gly Phe Lys Gln Ile Ser
                325                 330                 335

Gly Val Gly Gly Gln Val Asp Tyr Met Arg Gly Ala Ser Met Ala Asp
            340                 345                 350

Gly Gly Lys Ser Ile Leu Ala Ile Pro Ser Thr Ala Ala Gly Gly Lys
        355                 360                 365

```
Ile Ser Arg Ile Val Pro Ile Leu Thr Glu Gly Ala Gly Val Thr Thr
370                 375                 380

Ser Arg Tyr Asp Val Gln Tyr Val Val Thr Glu Tyr Gly Ile Ala Leu
385                 390                 395                 400

Leu Lys Gly Lys Ser Ile Arg Glu Arg Ala Lys Glu Leu Ile Lys Ile
                405                 410                 415

Ala His Pro Lys Phe Arg Glu Glu Leu Thr Ala Gln Phe Glu Lys Arg
                420                 425                 430

Phe Ser Cys Lys Leu
                435

<210> SEQ ID NO 124
<211> LENGTH: 538
<212> TYPE: PRT
<213> ORGANISM: Clostridium kluyveri

<400> SEQUENCE: 124

Met Ser Lys Gly Ile Lys Asn Ser Gln Leu Lys Lys Asn Val Lys
1               5                   10                  15

Ala Ser Asn Val Ala Glu Lys Ile Glu Glu Lys Val Glu Lys Thr Asp
                20                  25                  30

Lys Val Val Glu Lys Ala Ala Glu Val Thr Glu Lys Arg Ile Arg Asn
                35                  40                  45

Leu Lys Leu Gln Glu Lys Val Val Thr Ala Asp Val Ala Ala Asp Met
50                  55                  60

Ile Glu Asn Gly Met Ile Val Ala Ile Ser Gly Phe Thr Pro Ser Gly
65                  70                  75                  80

Tyr Pro Lys Glu Val Pro Lys Ala Leu Thr Lys Lys Val Asn Ala Leu
                85                  90                  95

Glu Glu Glu Phe Lys Val Thr Leu Tyr Thr Gly Ser Ser Thr Gly Ala
                100                 105                 110

Asp Ile Asp Gly Glu Trp Ala Lys Ala Gly Ile Ile Glu Arg Arg Ile
                115                 120                 125

Pro Tyr Gln Thr Asn Ser Asp Met Arg Lys Lys Ile Asn Asp Gly Ser
130                 135                 140

Ile Lys Tyr Ala Asp Met His Leu Ser His Met Ala Gln Tyr Ile Asn
145                 150                 155                 160

Tyr Ser Val Ile Pro Lys Val Asp Ile Ala Ile Glu Ala Val Ala
                165                 170                 175

Ile Thr Glu Glu Gly Asp Ile Ile Pro Ser Thr Gly Ile Gly Asn Thr
                180                 185                 190

Ala Thr Phe Val Glu Asn Ala Asp Lys Val Ile Val Glu Ile Asn Glu
                195                 200                 205

Ala Gln Pro Leu Glu Leu Gly Met Ala Asp Ile Tyr Thr Leu Lys
                210                 215                 220

Asn Pro Pro Arg Arg Glu Pro Ile Pro Ile Val Asn Ala Gly Asn Arg
225                 230                 235                 240

Ile Gly Thr Thr Tyr Val Thr Cys Gly Ser Glu Lys Ile Cys Ala Ile
                245                 250                 255

Val Met Thr Asn Thr Gln Asp Lys Thr Arg Pro Leu Thr Glu Val Ser
                260                 265                 270

Pro Val Ser Gln Ala Ile Ser Asp Asn Leu Ile Gly Phe Leu Asn Lys
                275                 280                 285

Glu Val Glu Glu Gly Lys Leu Pro Lys Asn Leu Leu Pro Ile Gln Ser
                290                 295                 300
```

```
Gly Val Gly Ser Val Ala Asn Ala Val Leu Ala Gly Leu Cys Glu Ser
305                 310                 315                 320

Asn Phe Lys Asn Leu Ser Cys Tyr Thr Glu Val Ile Gln Asp Ser Met
                325                 330                 335

Leu Lys Leu Ile Lys Cys Gly Lys Ala Asp Val Val Ser Gly Thr Ser
            340                 345                 350

Ile Ser Pro Ser Pro Glu Met Leu Pro Glu Phe Ile Lys Asp Ile Asn
        355                 360                 365

Phe Phe Arg Glu Lys Ile Val Leu Arg Pro Gln Glu Ile Ser Asn Asn
370                 375                 380

Pro Glu Ile Ala Arg Arg Ile Gly Val Ile Ser Ile Asn Thr Ala Leu
385                 390                 395                 400

Glu Val Asp Ile Tyr Gly Asn Val Asn Ser Thr His Val Met Gly Ser
                405                 410                 415

Lys Met Met Asn Gly Ile Gly Gly Ser Gly Asp Phe Ala Arg Asn Ala
            420                 425                 430

Tyr Leu Thr Ile Phe Thr Thr Glu Ser Ile Ala Lys Lys Gly Asp Ile
        435                 440                 445

Ser Ser Ile Val Pro Met Val Ser His Val Asp His Thr Glu His Asp
450                 455                 460

Val Met Val Ile Val Thr Glu Gln Gly Val Ala Asp Leu Arg Gly Leu
465                 470                 475                 480

Ser Pro Arg Glu Lys Ala Val Ala Ile Ile Glu Asn Cys Val His Pro
                485                 490                 495

Asp Tyr Lys Asp Met Leu Met Glu Tyr Phe Glu Ala Cys Lys Ser
            500                 505                 510

Ser Gly Gly Asn Thr Pro His Asn Leu Glu Lys Ala Leu Ser Trp His
        515                 520                 525

Thr Lys Phe Ile Lys Thr Gly Ser Met Lys
530                 535

<210> SEQ ID NO 125
<211> LENGTH: 232
<212> TYPE: PRT
<213> ORGANISM: Pseudomonas fluorescens

<400> SEQUENCE: 125

Met Ala Gly Phe Asp Lys Arg Val Ala Ser Tyr Glu Glu Ala Leu Glu
1               5                   10                  15

Gly Leu Gln Asp Gly Met Thr Val Ile Ala Gly Gly Phe Gly Leu Cys
            20                  25                  30

Gly Ile Pro Glu Asn Leu Ile Ala Glu Ile Lys Arg Arg Gly Thr Arg
        35                  40                  45

Asp Leu Thr Val Val Ser Asn Asn Cys Gly Val Asp Gly Phe Gly Leu
    50                  55                  60

Gly Val Leu Leu Glu Asp Arg Gln Ile Ser Lys Val Ile Ala Ser Tyr
65                  70                  75                  80

Val Gly Glu Asn Ala Leu Phe Glu Lys Gln Leu Leu Ser Gly Glu Ile
                85                  90                  95

Glu Val Val Leu Thr Pro Gln Gly Thr Leu Ala Glu Lys Met Arg Ala
            100                 105                 110

Gly Gly Ala Gly Ile Pro Ala Phe Phe Thr Ala Thr Gly Val Gly Thr
        115                 120                 125

Pro Val Ala Asp Gly Lys Glu Thr Arg Glu Phe Lys Gly Arg Thr Tyr
```

```
                130                 135                 140
Leu Met Glu Glu Ser Ile Thr Gly Asp Phe Ala Ile Val Lys Gly Trp
145                 150                 155                 160

Lys Ala Asp His Phe Gly Asn Val Val Tyr Arg His Thr Ala Gln Asn
                165                 170                 175

Phe Asn Pro Leu Ala Ala Thr Ala Gly Lys Ile Thr Val Val Glu Val
            180                 185                 190

Glu Glu Ile Val Glu Pro Gly Glu Leu Asp Pro Thr Gln Ile His Thr
        195                 200                 205

Pro Gly Ile Tyr Val Asp Arg Val Ile Cys Gly Thr Phe Glu Lys Arg
    210                 215                 220

Ile Glu Gln Arg Thr Val Arg Lys
225                 230

<210> SEQ ID NO 126
<211> LENGTH: 219
<212> TYPE: PRT
<213> ORGANISM: Pseudomonas fluorescens

<400> SEQUENCE: 126

Met Ala Leu Thr Arg Glu Gln Met Ala Gln Arg Val Ala Arg Glu Leu
1               5                   10                  15

Gln Asp Gly Phe Tyr Val Asn Leu Gly Ile Gly Ile Pro Thr Leu Val
            20                  25                  30

Ala Asn Tyr Ile Pro Asp Gly Met Glu Val Met Leu Gln Ser Glu Asn
        35                  40                  45

Gly Leu Leu Gly Met Gly Ala Phe Pro Thr Glu Asp Glu Val Asp Ala
    50                  55                  60

Asp Met Ile Asn Ala Gly Lys Gln Thr Val Thr Ala Arg Ile Gly Ala
65                  70                  75                  80

Ser Ile Phe Ser Ser Ala Glu Ser Phe Ala Met Ile Arg Gly Gly His
                85                  90                  95

Ile Asp Leu Thr Val Leu Gly Ala Phe Glu Val Asp Val Gln Gly Asn
            100                 105                 110

Ile Ala Ser Trp Met Ile Pro Gly Lys Leu Val Lys Gly Met Gly Gly
        115                 120                 125

Ala Met Asp Leu Val Ala Gly Ala Glu Asn Ile Ile Val Thr Met Thr
    130                 135                 140

His Ala Ser Lys Asp Gly Glu Ser Lys Leu Leu Ser Arg Cys Ser Leu
145                 150                 155                 160

Pro Leu Thr Gly Ala Gln Cys Ile Lys Arg Val Leu Thr Asp Leu Ala
                165                 170                 175

Tyr Leu Glu Ile Glu Asn Gly Ala Phe Ile Leu Lys Glu Arg Ala Pro
            180                 185                 190

Gly Val Ser Val Glu Glu Ile Val Ser Lys Thr Ala Gly Lys Leu Ile
        195                 200                 205

Val Pro Asp His Val Pro Glu Met Gln Phe Ala
    210                 215

<210> SEQ ID NO 127
<211> LENGTH: 477
<212> TYPE: PRT
<213> ORGANISM: Acinetobacter sp.

<400> SEQUENCE: 127

Met Asn Tyr Pro Asn Ile Pro Leu Tyr Ile Asn Gly Glu Phe Leu Asp
```

```
                1               5                    10                   15
              His Thr Asn Arg Asp Val Lys Glu Val Phe Asn Pro Val Asn His Glu
                               20                   25                   30

Cys Ile Gly Leu Met Ala Cys Ala Ser Gln Ala Asp Leu Asp Tyr Ala
                               35                   40                   45

Leu Glu Ser Ser Gln Gln Ala Phe Leu Arg Trp Lys Lys Thr Ser Pro
                 50                            55                   60

Ile Thr Arg Ser Glu Ile Leu Arg Thr Phe Ala Lys Leu Ala Arg Glu
               65                   70                   75                   80

Lys Ala Ala Glu Ile Gly Arg Asn Ile Thr Leu Asp Gln Gly Lys Pro
                                    85                   90                   95

Leu Lys Glu Ala Ile Ala Glu Val Thr Val Cys Ala Glu His Ala Glu
                              100                  105                  110

Trp His Ala Glu Glu Cys Arg Arg Ile Tyr Gly Arg Val Ile Pro Pro
                              115                  120                  125

Arg Asn Pro Asn Val Gln Gln Leu Val Val Arg Glu Pro Leu Gly Val
                              130                  135                  140

Cys Leu Ala Phe Ser Pro Trp Asn Phe Pro Phe Asn Gln Ala Ile Arg
              145                  150                  155                  160

Lys Ile Ser Ala Ala Ile Ala Ala Gly Cys Thr Ile Ile Val Lys Gly
                                   165                  170                  175

Ser Gly Asp Thr Pro Ser Ala Val Tyr Ala Ile Ala Gln Leu Phe His
                              180                  185                  190

Glu Ala Gly Leu Pro Asn Gly Val Leu Asn Val Ile Trp Gly Asp Ser
                              195                  200                  205

Asn Phe Ile Ser Asp Tyr Met Ile Lys Ser Pro Ile Ile Gln Lys Ile
                 210                  215                  220

Ser Phe Thr Gly Ser Thr Pro Val Gly Lys Lys Leu Ala Ser Gln Ala
              225                  230                  235                  240

Ser Leu Tyr Met Lys Pro Cys Thr Met Glu Leu Gly Gly His Ala Pro
                                   245                  250                  255

Val Ile Val Cys Asp Asp Ala Asp Ile Asp Ala Ala Val Glu His Leu
                              260                  265                  270

Val Gly Tyr Lys Phe Arg Asn Ala Gly Gln Val Cys Val Ser Pro Thr
                              275                  280                  285

Arg Phe Tyr Val Gln Glu Gly Ile Tyr Lys Glu Phe Ser Glu Lys Val
                              290                  295                  300

Val Leu Arg Ala Lys Gln Ile Lys Val Gly Cys Gly Leu Asp Ala Ser
              305                  310                  315                  320

Ser Asp Met Gly Pro Leu Ala Gln Ala Arg Arg Met His Ala Met Gln
                                   325                  330                  335

Gln Ile Val Glu Asp Ala Val His Lys Gly Ser Lys Leu Leu Leu Gly
                              340                  345                  350

Gly Asn Lys Ile Ser Asp Lys Gly Asn Phe Phe Glu Pro Thr Val Leu
                              355                  360                  365

Gly Asp Leu Cys Asn Asp Thr Gln Phe Met Asn Asp Glu Pro Phe Gly
                 370                  375                  380

Pro Ile Ile Gly Leu Ile Pro Phe Asp Thr Ile Asp His Val Leu Glu
              385                  390                  395                  400

Glu Ala Asn Arg Leu Pro Phe Gly Leu Ala Ser Tyr Ala Phe Thr Thr
                              405                  410                  415

Ser Ser Lys Asn Ala His Gln Ile Ser Tyr Gly Leu Glu Ala Gly Met
                              420                  425                  430
```

Val Ser Ile Asn His Met Gly Leu Ala Leu Ala Glu Thr Pro Phe Gly
         435                 440                 445

Gly Ile Lys Asp Ser Gly Phe Gly Ser Glu Gly Gly Ile Glu Thr Phe
        450                 455                 460

Asp Gly Tyr Leu Arg Thr Lys Phe Ile Thr Gln Leu Asn
465                 470                 475

<210> SEQ ID NO 128
<211> LENGTH: 473
<212> TYPE: PRT
<213> ORGANISM: Brucella melitensis

<400> SEQUENCE: 128

Met Arg Ile Gly Lys Met Glu Met Gln Thr Arg Tyr Pro Asp Val Lys
1 5 10 15

Leu Phe Ile Asp Gly Thr Trp Arg Asp Gly Ser Arg Gly Glu Thr Ile
20 25 30

Glu Ile Phe Asn Pro Ala Thr Asp Glu Val Ile Gly His Ile Ala Arg
35 40 45

Ala Thr Thr Ala Asp Leu Asp Asp Ala Leu Ala Ala Val Asp Arg Gly
50 55 60

Phe Glu Ala Trp Ser Lys Val Ser Ala Phe Asp Arg Tyr Lys Ile Met
65 70 75 80

Arg Arg Ala Ala Asp Ile Phe Arg Ser Arg Gly Glu Glu Val Ala Arg
85 90 95

Leu Leu Thr Met Glu Gln Gly Lys Pro Leu Ala Glu Ala Arg Ile Glu
100 105 110

Ala Ala Ala Ala Cys Asp Leu Ile Asp Trp Phe Ala Glu Glu Ala Arg
115 120 125

Arg Ser Tyr Gly Arg Ile Val Pro Pro Arg Gln Ala Tyr Val Met Gln
130 135 140

Ala Glu Val Lys Glu Pro Val Gly Pro Val Ala Ala Phe Thr Pro Trp
145 150 155 160

Asn Phe Pro Ile Asn Gln Ala Val Arg Lys Ile Ser Ala Ala Leu Ala
165 170 175

Ala Gly Cys Ser Ile Leu Leu Lys Ala Ala Glu Asp Thr Pro Ala Ala
180 185 190

Pro Ala Glu Leu Val Arg Ala Phe Ala Glu Ala Gly Leu Pro Asp Gly
195 200 205

Ala Ile Asn Leu Val Tyr Gly Asp Pro Ala Glu Ile Ser Ala Tyr Leu
210 215 220

Ile Pro His Pro Val Ile Arg Lys Val Ser Phe Thr Gly Ser Thr Gln
225 230 235 240

Val Gly Lys Gln Leu Ala Ala Leu Ala Gly Leu His Met Lys Arg Val
245 250 255

Thr Met Glu Leu Gly Gly His Ala Pro Val Ile Ile Ala Ala Asp Ala
260 265 270

Asp Val Glu Gln Ala Ile Lys Val Val Ser Gly Ser Lys Phe Arg Asn
275 280 285

Ala Gly Gln Val Cys Ile Ser Pro Thr Arg Phe Leu Ile Glu Asn Ser
290 295 300

Val Tyr Asp Gln Val Val Glu Gly Met Ala Ala Tyr Ala Thr Ser Leu
305 310 315 320

Lys Val Gly Asp Gly Leu Glu Ala Gly Thr Thr Met Gly Pro Leu Val

```
                        325                 330                 335
Asn Ala Lys Arg Val Asn Ala Met Glu Arg Leu Val Gln Asp Ala Arg
            340                 345                 350
Glu His Lys Ala Arg Val Val Thr Gly Gly Glu Arg Ile Gly Asn Arg
            355                 360                 365
Gly Asn Phe Phe Glu Pro Thr Ile Leu Ala Asp Val Pro Arg Asp Ala
        370                 375                 380
Ala Ile Met Asn Glu Glu Pro Phe Gly Pro Val Ala Leu Leu Asn Arg
385                 390                 395                 400
Phe Asp Ala Leu Asp Glu Ala Leu Ser Glu Ala Asn Arg Leu Asn Tyr
                405                 410                 415
Gly Leu Ala Ala Tyr Ala Phe Thr Gly Ser Ser Ala Lys Ala Ala Arg
            420                 425                 430
Ile Ser Ser Thr Val Arg Ser Gly Met Ile Thr Ile Asn Gln Leu Arg
            435                 440                 445
Ser Gly Pro Ala Gly Ser Ala Leu Arg Arg Asp Gln Arg Phe Arg Leu
        450                 455                 460
Trp Asn Gly Arg Arg Cys Arg Arg Ala
465                 470

<210> SEQ ID NO 129
<211> LENGTH: 1371
<212> TYPE: DNA
<213> ORGANISM: Artificial
<220> FEATURE:
<223> OTHER INFORMATION: Pseudomonas aeruginosa

<400> SEQUENCE: 129
atgaacagcc aaatcaccaa cgccaagacc cgtgagtggc aggcgttgag ccgcgaccac    60
catctgccgc cgttcaccga ctacaagcag ttgaacgaga agggcgcgcg gatcatcacc   120
aaggccgaag gcgtctatat ctgggacagc gagggcaaca gatcctcga tgcgatggcc    180
ggcctctggt gcgtcaacgt cggctacggc gcgaggagc tggtccaggc cgccacccgg    240
cagatgcgcg agttgccgtt ctacaacctg ttcttccaga ccgccacccc gccggtggtc    300
gagctggcca aggcgatcgc cgacgtcgct ccggaaggca tgaaccacgt gttcttcacc    360
ggctccggct ccgaggccaa cgacaccgtg ctgcgtatgg tccgccacta ttgggcgacc    420
aagggccagc gcagaagaa agtggtgatc ggccgctgga acggctacca cggctccacc    480
gtcgccggcg tcagcctggg cggcatgaag gcgttgcatg agcagggtga tttccccatc    540
ccgggcatcg tccacatcgc ccagccctac tggtacggcg agggcggcga catgtcgccg    600
gacgagttcg gcgtctgggc cgccgagcag ttggagaaga agattctcga gtgggcgag    660
gaaaacgtcg ccgccttcat cgccgagccg atccagggcg ccggcggcgt gatcgtcccg    720
ccggacacct actggccgaa gatccgcgag atcctcgcca gtacgacat cctgttcatc    780
gccgacgaag tgatctgcgg cttcggccgt accggcgagt ggttcggcag ccagtactac    840
ggcaacgccc cggacctgat gccgatcgcc aagggcctca cctccggcta catccccatg    900
ggcgggggtgg tggtgcgcga cgagatcgtc gaagtgctca accagggcgg cgagttctac    960
cacggcttca cctattccgg tcacccggtg cggccgccgg tggccctgga gaacatccgc   1020
atcctgcgcg aagagaagat catcgagaag gtgaaggcgg aaacggcacc gtatttgcag   1080
aaacgctggc aggagctggc cgaccacccg ttggtgggcg aagcgcgcgg ggtcggcatg   1140
gtcgccgccc tggagctggt caagaacaag aagacccgcg agcgtttcac cgacaagggc   1200
```

-continued

```
gtcgggatgc tgtgccggga acattgtttc cgcaacggtt tgatcatgcg cgcggtgggc    1260
gacactatga ttatctcgcc gccgctggtg atcgatccgt cgcagatcga tgagttgatc    1320
accctggcgc gcaagtgcct cgatcagacc gccgccgccg tcctggcttg a             1371
```

<210> SEQ ID NO 130
<211> LENGTH: 456
<212> TYPE: PRT
<213> ORGANISM: Pseudomonas aeruginosa

<400> SEQUENCE: 130

| Met | Asn | Ser | Gln | Ile | Thr | Asn | Ala | Lys | Thr | Arg | Glu | Trp | Gln | Ala | Leu |
|---|---|---|---|---|---|---|---|---|---|---|---|---|---|---|---|
| 1 | | | | 5 | | | | | 10 | | | | | 15 | |

| Ser | Arg | Asp | His | His | Leu | Pro | Pro | Phe | Thr | Asp | Tyr | Lys | Gln | Leu | Asn |
| | | | 20 | | | | | 25 | | | | | 30 | | |

| Glu | Lys | Gly | Ala | Arg | Ile | Ile | Thr | Lys | Ala | Glu | Gly | Val | Tyr | Ile | Trp |
| | | | 35 | | | | | 40 | | | | | 45 | | |

| Asp | Ser | Glu | Gly | Asn | Lys | Ile | Leu | Asp | Ala | Met | Ala | Gly | Leu | Trp | Cys |
| | 50 | | | | | 55 | | | | | 60 | | | | |

| Val | Asn | Val | Gly | Tyr | Gly | Arg | Glu | Glu | Leu | Val | Gln | Ala | Ala | Thr | Arg |
| 65 | | | | | 70 | | | | | 75 | | | | | 80 |

| Gln | Met | Arg | Glu | Leu | Pro | Phe | Tyr | Asn | Leu | Phe | Phe | Gln | Thr | Ala | His |
| | | | | 85 | | | | | 90 | | | | | 95 | |

| Pro | Pro | Val | Glu | Leu | Ala | Lys | Ala | Ile | Ala | Asp | Val | Ala | Pro | Glu |
| | | | 100 | | | | | 105 | | | | | 110 | |

| Gly | Met | Asn | His | Val | Phe | Phe | Thr | Gly | Ser | Gly | Ser | Glu | Ala | Asn | Asp |
| | | | 115 | | | | | 120 | | | | | 125 | | |

| Thr | Val | Leu | Arg | Met | Val | Arg | His | Tyr | Trp | Ala | Thr | Lys | Gly | Gln | Pro |
| 130 | | | | | 135 | | | | | 140 | | | | | |

| Gln | Lys | Lys | Val | Val | Ile | Gly | Arg | Trp | Asn | Gly | Tyr | His | Gly | Ser | Thr |
| 145 | | | | | 150 | | | | | 155 | | | | | 160 |

| Val | Ala | Gly | Val | Ser | Leu | Gly | Gly | Met | Lys | Ala | Leu | His | Glu | Gln | Gly |
| | | | | 165 | | | | | 170 | | | | | 175 | |

| Asp | Phe | Pro | Ile | Pro | Gly | Ile | Val | His | Ile | Ala | Gln | Pro | Tyr | Trp | Tyr |
| | | | 180 | | | | | 185 | | | | | 190 | | |

| Gly | Glu | Gly | Gly | Asp | Met | Ser | Pro | Asp | Glu | Phe | Gly | Val | Trp | Ala | Ala |
| | | 195 | | | | | 200 | | | | | 205 | | | |

| Glu | Gln | Leu | Glu | Lys | Lys | Ile | Leu | Glu | Val | Gly | Glu | Glu | Asn | Val | Ala |
| 210 | | | | | 215 | | | | | 220 | | | | | |

| Ala | Phe | Ile | Ala | Glu | Pro | Ile | Gln | Gly | Ala | Gly | Gly | Val | Ile | Val | Pro |
| 225 | | | | | 230 | | | | | 235 | | | | | 240 |

| Pro | Asp | Thr | Tyr | Trp | Pro | Lys | Ile | Arg | Glu | Ile | Leu | Ala | Lys | Tyr | Asp |
| | | | | 245 | | | | | 250 | | | | | 255 | |

| Ile | Leu | Phe | Ile | Ala | Asp | Glu | Val | Ile | Cys | Gly | Phe | Gly | Arg | Thr | Gly |
| | | | 260 | | | | | 265 | | | | | 270 | | |

| Glu | Trp | Phe | Gly | Ser | Gln | Tyr | Tyr | Gly | Asn | Ala | Pro | Asp | Leu | Met | Pro |
| | | 275 | | | | | 280 | | | | | 285 | | | |

| Ile | Ala | Lys | Gly | Leu | Thr | Ser | Gly | Tyr | Ile | Pro | Met | Gly | Gly | Val | Val |
| | 290 | | | | | 295 | | | | | 300 | | | | |

| Val | Arg | Asp | Glu | Ile | Val | Glu | Val | Leu | Asn | Gln | Gly | Gly | Glu | Phe | Tyr |
| 305 | | | | | 310 | | | | | 315 | | | | | 320 |

| His | Gly | Phe | Thr | Tyr | Ser | Gly | His | Pro | Val | Ala | Ala | Val | Ala | Leu |
| | | | | 325 | | | | | 330 | | | | | 335 |

| Glu | Asn | Ile | Arg | Ile | Leu | Arg | Glu | Glu | Lys | Ile | Ile | Glu | Lys | Val | Lys |
| | | | 340 | | | | | 345 | | | | | 350 | | |

```
Ala Glu Thr Ala Pro Tyr Leu Gln Lys Arg Trp Gln Glu Leu Ala Asp
            355                 360                 365

His Pro Leu Val Gly Glu Ala Arg Gly Val Gly Met Val Ala Ala Leu
    370                 375                 380

Glu Leu Val Lys Asn Lys Lys Thr Arg Glu Arg Phe Thr Asp Lys Gly
385                 390                 395                 400

Val Gly Met Leu Cys Arg Glu His Cys Phe Arg Asn Gly Leu Ile Met
                405                 410                 415

Arg Ala Val Gly Asp Thr Met Ile Ile Ser Pro Pro Leu Val Ile Asp
                420                 425                 430

Pro Ser Gln Ile Asp Glu Leu Ile Thr Leu Ala Arg Lys Cys Leu Asp
            435                 440                 445

Gln Thr Ala Ala Val Leu Ala
            450                 455

<210> SEQ ID NO 131
<211> LENGTH: 70
<212> TYPE: DNA
<213> ORGANISM: Artificial
<220> FEATURE:
<223> OTHER INFORMATION: primer

<400> SEQUENCE: 131
ggggacaagt ttgtacaaaa aagcaggcta ggaggaatta accatgaaca gccaaatcac    60
caacgccaag                                                           70

<210> SEQ ID NO 132
<211> LENGTH: 49
<212> TYPE: DNA
<213> ORGANISM: Artificial
<220> FEATURE:
<223> OTHER INFORMATION: primer

<400> SEQUENCE: 132
ggggaccact ttgtacaaga aagctgggtt caagccagga cggcggcgg               49

<210> SEQ ID NO 133
<211> LENGTH: 1353
<212> TYPE: DNA
<213> ORGANISM: Artificial
<220> FEATURE:
<223> OTHER INFORMATION: Bacillus subtilis

<400> SEQUENCE: 133
atggagatga tggggatgga aaacattcag caaaatcagg gattaaagca aaaagatgag    60
caatttgtgt ggcatgccat gaagggagcg catcaagcgg acagcctgat agcccagaag   120
gccgaagggg cctgggtaac cgacacagac ggacgccgct atttggatgc gatgtccggt   180
ttgtggtgcg tcaacattgg ttacggcaga aaggagcttg cggaggctgc ctatgagcaa   240
ctaaaggagc tgccttacta cccgttaacg caaagtcacg cacccgcaat tcaactggcg   300
gaaaagctga atgaatggct tggcggcgat tatgttattt tttttccaa cagcggatcg   360 gaagcaaacg aaactgcttt taaaattgcc cgccagtacc atctgcaaaa cggcgaccac   420
agccgttata aattcatctc aagatatcgg gcataccacg caatacatt gggagcgctc   480 tcagctaccg acaggcgca gcggaaatat aaatacgagc ctttgagcca agggttcctg   540
catgcagctc cgccagatat ataccggaat cctgatgatg cagacacgct tgaaagcgca   600
aatgaaatcg accgcatcat gacatgggaa ttaagcgaaa cgattgccgg ggtcattatg   660
```

```
gagcccatca ttacaggcgg aggcatccta atgccgccgg acggatatat gaagaaggtg      720
gaggacattt gccggcgcca cggagcccct ttgatttgcg atgaagtgat ctgcgggttt      780
ggacggacag gtgagccgtt cgggtttatg cactacggtg tgaagcctga tatcattacg      840
atggcaaagg gaatcacaag cgcgtatctg ccattgtcag cgactgctgt gaaacgggac      900
attttcgaag cgtatcaggg ggaagctcct tatgaccgtt ccgccacgt gaacacgttc       960 ggcgaagcc cggctgcctg tgctttggcg ttgaaaaacc tgcaaattat ggaggacgaa      1020
cagctgattc agcgatcccg tgatcttgga gcaaagcttt taggtgagct tcaagctctg      1080
agagaacacc cggcagtcgg ggatgttaga ggaaaagggc tgctgatcgg aatcgaactc      1140
gtcaaagaca aattgactaa agagccggct gatgccgcca agtaaaccca gtggttgcg       1200 gcgtgcaaag aaaaagggct gatcatcggc aaaaacggcg atacagtcgc cggctacaac      1260
aatgtcatcc acgttgcgcc gccattttgc ctgacagaag aggacctttc ctttatcgtg      1320
aaaacggtga aagaaagctt tcaaacgata taa                                   1353
```

<210> SEQ ID NO 134
<211> LENGTH: 450
<212> TYPE: PRT
<213> ORGANISM: Bacillus subtilis

<400> SEQUENCE: 134

```
Met Glu Met Met Gly Met Glu Asn Ile Gln Gln Asn Gln Gly Leu Lys
1               5                   10                  15

Gln Lys Asp Glu Gln Phe Val Trp His Ala Met Lys Gly Ala His Gln
            20                  25                  30

Ala Asp Ser Leu Ile Ala Gln Lys Ala Glu Gly Ala Trp Val Thr Asp
        35                  40                  45

Thr Asp Gly Arg Arg Tyr Leu Asp Ala Met Ser Gly Leu Trp Cys Val
    50                  55                  60

Asn Ile Gly Tyr Gly Arg Lys Glu Leu Ala Glu Ala Tyr Glu Gln
65                  70                  75                  80

Leu Lys Glu Leu Pro Tyr Tyr Pro Leu Thr Gln Ser His Ala Pro Ala
                85                  90                  95

Ile Gln Leu Ala Glu Lys Leu Asn Glu Trp Leu Gly Gly Asp Tyr Val
            100                 105                 110

Ile Phe Phe Ser Asn Ser Gly Ser Glu Ala Asn Glu Thr Ala Phe Lys
        115                 120                 125

Ile Ala Arg Gln Tyr His Leu Gln Asn Gly Asp His Ser Arg Tyr Lys
    130                 135                 140

Phe Ile Ser Arg Tyr Arg Ala Tyr His Gly Asn Thr Leu Gly Ala Leu
145                 150                 155                 160

Ser Ala Thr Gly Gln Ala Gln Arg Lys Tyr Lys Tyr Glu Pro Leu Ser
                165                 170                 175

Gln Gly Phe Leu His Ala Ala Pro Pro Asp Ile Tyr Arg Asn Pro Asp
            180                 185                 190

Asp Ala Asp Thr Leu Glu Ser Ala Asn Glu Ile Asp Arg Ile Met Thr
        195                 200                 205

Trp Glu Leu Ser Glu Thr Ile Ala Gly Val Ile Met Glu Pro Ile Ile
    210                 215                 220

Thr Gly Gly Gly Ile Leu Met Pro Pro Asp Gly Tyr Met Lys Lys Val
225                 230                 235                 240

Glu Asp Ile Cys Arg Arg His Gly Ala Leu Leu Ile Cys Asp Glu Val
```

```
            245                 250                 255
Ile Cys Gly Phe Gly Arg Thr Gly Glu Pro Phe Gly Phe Met His Tyr
            260                 265                 270
Gly Val Lys Pro Asp Ile Ile Thr Met Ala Lys Gly Ile Thr Ser Ala
            275                 280                 285
Tyr Leu Pro Leu Ser Ala Thr Ala Val Lys Arg Asp Ile Phe Glu Ala
            290                 295                 300
Tyr Gln Gly Glu Ala Pro Tyr Asp Arg Phe Arg His Val Asn Thr Phe
305                 310                 315                 320
Gly Gly Ser Pro Ala Ala Cys Ala Leu Ala Leu Lys Asn Leu Gln Ile
                325                 330                 335
Met Glu Asp Glu Gln Leu Ile Gln Arg Ser Arg Asp Leu Gly Ala Lys
                340                 345                 350
Leu Leu Gly Glu Leu Gln Ala Leu Arg Glu His Pro Ala Val Gly Asp
                355                 360                 365
Val Arg Gly Lys Gly Leu Leu Ile Gly Ile Glu Leu Val Lys Asp Lys
370                 375                 380
Leu Thr Lys Glu Pro Ala Asp Ala Ala Lys Val Asn Gln Val Val Ala
385                 390                 395                 400
Ala Cys Lys Glu Lys Gly Leu Ile Ile Gly Lys Asn Gly Asp Thr Val
                405                 410                 415
Ala Gly Tyr Asn Asn Val Ile His Val Ala Pro Pro Phe Cys Leu Thr
                420                 425                 430
Glu Glu Asp Leu Ser Phe Ile Val Lys Thr Val Lys Glu Ser Phe Gln
                435                 440                 445
Thr Ile
450

<210> SEQ ID NO 135
<211> LENGTH: 1407
<212> TYPE: DNA
<213> ORGANISM: Artificial
<220> FEATURE:
<223> OTHER INFORMATION: Pseudomonas aeruginosa

<400> SEQUENCE: 135
atgaacgcaa gactgcacgc cacgtccccc ctcggcgacg ccgacctggt ccgtgccgac     60
caggcccact acatgcacgg ctaccacgtg ttcgacgacc accgcgtcaa cggctcgctg    120
aacatcgccg ccggcgacgg cgcctatatc tacgacaccg ccggcaaccg ctacctcgac    180
gcggtgggcg gcatgtggtg caccaacatc ggcctgggcg cgaggaaat ggctcgcacc    240
gtggccgagc agaccgcct gctggcctat tccaatccct tctgcgacat ggccaacccg    300
cgcgccatcg aactctgccg caagctcgcc gagctggccc ccggcgacct cgaccacgtg    360
ttcctcacca ccggcggttc caccgccgtg acaccgcga tccgcctcat gcactactac    420
cagaactgcc gcggcaagcg cgccaagaag cacgtcatca gcggatcaa cgcctaccac    480
ggctcgacct tcctcggcat gtcgctgggc ggcaagagcg ccgaccggcc ggccgagttc    540
gacttcctcg acgagcgcat ccaccacctc gcctgtccct attaccg cgctccggaa    600
gggctgggcg aagccgagtt cctcgatggc ctggtggaca gttcgaacg caagatcctc    660
gaactgggcg ccgaccgggt gggggcgttc atctccgagc cggtgttcgg ctccggcggc    720
gtgatcgtcc cgcccgcggg ctaccacagg cggatgtggg agctgtgcca gcgctacgac    780
gtgctgtaca tctccgacga agtggtgacc tccttcggcc gcctcggcca cttcttcgcc    840
```

```
agccaggcgg tgttcggcgt acagccggac atcatcctca ccgccaaggg cctcacctcc   900
ggctaccagc cgctgggcgc gtgcatcttc tcccggcgca tctgggaggt gatcgccgag   960
ccggacaagg gccgctgctt cagccatggt ttcacctact ccggccaccc ggtggcctgc  1020
gcggcggcgc tgaagaacat cgagatcatc gagcgcgagg gcttgctcgc ccacgccgac  1080
gaggtcggcc gctacttcga ggagcgcctg caaagcctcc gcgacctgcc catcgtcggc  1140
gacgtgcgcg gatgcgcttc atggcctgt gtcgagttcg tcgccgacaa ggcgagcaag  1200
gcgctgtttc cggaaagcct gaacatcggc gagtgggtcc acctgcgggc gcagaagcgc  1260
ggcctgctgg ttcgtccgat cgtccacctg aacgtgatgt cgccgccgct gatcctcacc  1320
cgcgaacagg tcgataccgt ggtccgggtg ctgcgcgaga gcatcgagga aaccgtggag  1380
gatcttgtcc gcgccggtca ccggtaa                                      1407
```

<210> SEQ ID NO 136
<211> LENGTH: 468
<212> TYPE: PRT
<213> ORGANISM: Pseudomonas aeruginosa

<400> SEQUENCE: 136

```
Met Asn Ala Arg Leu His Ala Thr Ser Pro Leu Gly Asp Ala Asp Leu
1               5                   10                  15

Val Arg Ala Asp Gln Ala His Tyr Met His Gly Tyr His Val Phe Asp
            20                  25                  30

Asp His Arg Val Asn Gly Ser Leu Asn Ile Ala Ala Gly Asp Gly Ala
        35                  40                  45

Tyr Ile Tyr Asp Thr Ala Gly Asn Arg Tyr Leu Asp Ala Val Gly Gly
    50                  55                  60

Met Trp Cys Thr Asn Ile Gly Leu Gly Arg Glu Glu Met Ala Arg Thr
65                  70                  75                  80

Val Ala Glu Gln Thr Arg Leu Leu Ala Tyr Ser Asn Pro Phe Cys Asp
                85                  90                  95

Met Ala Asn Pro Arg Ala Ile Glu Leu Cys Arg Lys Leu Ala Glu Leu
            100                 105                 110

Ala Pro Gly Asp Leu Asp His Val Phe Leu Thr Thr Gly Gly Ser Thr
        115                 120                 125

Ala Val Asp Thr Ala Ile Arg Leu Met His Tyr Tyr Gln Asn Cys Arg
    130                 135                 140

Gly Lys Arg Ala Lys Lys His Val Ile Thr Arg Ile Asn Ala Tyr His
145                 150                 155                 160

Gly Ser Thr Phe Leu Gly Met Ser Leu Gly Gly Lys Ser Ala Asp Arg
                165                 170                 175

Pro Ala Glu Phe Asp Phe Leu Asp Glu Arg Ile His His Leu Ala Cys
            180                 185                 190

Pro Tyr Tyr Tyr Arg Ala Pro Glu Gly Leu Gly Glu Ala Glu Phe Leu
        195                 200                 205

Asp Gly Leu Val Asp Glu Phe Glu Arg Lys Ile Leu Glu Leu Gly Ala
    210                 215                 220

Asp Arg Val Gly Ala Phe Ile Ser Glu Pro Val Phe Gly Ser Gly Gly
225                 230                 235                 240

Val Ile Val Pro Pro Ala Gly Tyr His Arg Arg Met Trp Glu Leu Cys
                245                 250                 255

Gln Arg Tyr Asp Val Leu Tyr Ile Ser Asp Glu Val Val Thr Ser Phe
            260                 265                 270
```

```
Gly Arg Leu Gly His Phe Phe Ala Ser Gln Ala Val Phe Gly Val Gln
            275                 280                 285
Pro Asp Ile Ile Leu Thr Ala Lys Gly Leu Thr Ser Gly Tyr Gln Pro
        290                 295                 300
Leu Gly Ala Cys Ile Phe Ser Arg Arg Ile Trp Glu Val Ile Ala Glu
305                 310                 315                 320
Pro Asp Lys Gly Arg Cys Phe Ser His Gly Phe Thr Tyr Ser Gly His
                325                 330                 335
Pro Val Ala Cys Ala Ala Ala Leu Lys Asn Ile Glu Ile Ile Glu Arg
            340                 345                 350
Glu Gly Leu Leu Ala His Ala Asp Glu Val Gly Arg Tyr Phe Glu Glu
        355                 360                 365
Arg Leu Gln Ser Leu Arg Asp Leu Pro Ile Val Gly Asp Val Arg Gly
    370                 375                 380
Met Arg Phe Met Ala Cys Val Glu Phe Val Ala Asp Lys Ala Ser Lys
385                 390                 395                 400
Ala Leu Phe Pro Glu Ser Leu Asn Ile Gly Glu Trp Val His Leu Arg
                405                 410                 415
Ala Gln Lys Arg Gly Leu Leu Val Arg Pro Ile Val His Leu Asn Val
            420                 425                 430
Met Ser Pro Pro Leu Ile Leu Thr Arg Glu Gln Val Asp Thr Val Val
        435                 440                 445
Arg Val Leu Arg Glu Ser Ile Glu Glu Thr Val Glu Asp Leu Val Arg
    450                 455                 460
Ala Gly His Arg
465

<210> SEQ ID NO 137
<211> LENGTH: 1335
<212> TYPE: DNA
<213> ORGANISM: Artificial
<220> FEATURE:
<223> OTHER INFORMATION: Pseudomonas aeruginosa

<400> SEQUENCE: 137
atgacaatga atgacgagcc gcagtcgagc agcctcgaca acttctggat gcccttcacc      60
gccaaccgcc agttcaaggc gcggccgcgc ctgctggaaa gcgccgaagg catccactat     120
atcgcccagg gcgggcgccg catcctcgac ggcaccgccg cctctggtg ctgcaatgcc     180 ggccacggcc ggcgcgagat cagcgaagcg gtgcccggc agatcgccac cctcgactac     240
gccccgccgt tccagatggg tcacccgctg ccgttcgaac tcgccgcgcg gctgacggaa     300
atcgccccgc cgagcctgaa caaagtattc ttcaccaact ccggctcgga atcggcggac     360
accgcgctga gatcgccct tgcctaccag cgcgccatcg ccagggcac ccgcacccgc     420 ctgatcggcc gcgaactggg ctaccacggg gtcggcttcg gcggcctgtc ggtaggcgt     480 atggtcaaca accgcaaggc cttctccgcc aacctgctgc gggggtcga ccacctgccg     540 cacaccctgg acgtcgcccg caacgccttc accgtcggcc tgcccgagca tggcgtggaa     600
aaggccgagg agctggaacg cctggtgacc ctgcacggcg ccgagaatat cgccgcggtg     660
atcgtcgagc cgatgtccgg ctcggccggc gtggtgctgc cgcccaaggg ctaccttcag     720
cggctgcgcg agataacccg caagcatggc atcctgctga tcttcgacga agtgatcacc     780
ggtttcggcc gcgtcggcga agccttcgcc gcgcagcgct ggggcgtcgt cccggacctg     840
ctgacctgcg ccaaggggct gaccaacggc agcatcccga tgggcgccgt attcgtcgac     900
```

-continued

```
gagaagatcc atgctgcctt catgcaaggc ccgcagggcg ccatcgagtt cttccacggc      960
tatacctatt ccggccatcc ggtagcctgc gccgccgccc tggcgaccct ggacatctac     1020
cgtcgcgacg acctgttcca gcgggccgtc gaactggaag gctactggca ggacgcgctg     1080
ttcagcctgc gcgacctgcc caacgtggtc gacatccgcg ccgtaggcct ggtcggcggc     1140
gtgcaactgg cgccgcacgc ggacggcccc ggcaagcgcg gctacgacgt cttcgagcgc     1200
tgcttctggg agcacgacct gatggtccgg gtgaccggcg acatcatcgc catgtcgccg     1260
ccgctgatca tcgacaagcc ccacatcgac cagatcgtcg agcgcctggc ccaggccatc     1320
cgcgccagcg tctga                                                     1335
```

<210> SEQ ID NO 138
<211> LENGTH: 444
<212> TYPE: PRT
<213> ORGANISM: Pseudomonas aeruginosa

<400> SEQUENCE: 138

```
Met Thr Met Asn Asp Glu Pro Gln Ser Ser Leu Asp Asn Phe Trp
1               5                   10                  15

Met Pro Phe Thr Ala Asn Arg Gln Phe Lys Ala Arg Pro Arg Leu Leu
            20                  25                  30

Glu Ser Ala Glu Gly Ile His Tyr Ile Ala Gln Gly Gly Arg Arg Ile
        35                  40                  45

Leu Asp Gly Thr Ala Gly Leu Trp Cys Cys Asn Ala Gly His Gly Arg
    50                  55                  60

Arg Glu Ile Ser Glu Ala Val Ala Arg Gln Ile Ala Thr Leu Asp Tyr
65                  70                  75                  80

Ala Pro Pro Phe Gln Met Gly His Pro Leu Pro Phe Glu Leu Ala Ala
                85                  90                  95

Arg Leu Thr Glu Ile Ala Pro Pro Ser Leu Asn Lys Val Phe Phe Thr
            100                 105                 110

Asn Ser Gly Ser Glu Ser Ala Asp Thr Ala Leu Lys Ile Ala Leu Ala
        115                 120                 125

Tyr Gln Arg Ala Ile Gly Gln Gly Thr Arg Thr Arg Leu Ile Gly Arg
    130                 135                 140

Glu Leu Gly Tyr His Gly Val Gly Phe Gly Gly Leu Ser Val Gly Gly
145                 150                 155                 160

Met Val Asn Asn Arg Lys Ala Phe Ser Ala Asn Leu Leu Pro Gly Val
                165                 170                 175

Asp His Leu Pro His Thr Leu Asp Val Ala Arg Asn Ala Phe Thr Val
            180                 185                 190

Gly Leu Pro Glu His Gly Val Glu Lys Ala Glu Glu Leu Glu Arg Leu
        195                 200                 205

Val Thr Leu His Gly Ala Glu Asn Ile Ala Ala Val Ile Val Glu Pro
    210                 215                 220

Met Ser Gly Ser Ala Gly Val Val Leu Pro Pro Lys Gly Tyr Leu Gln
225                 230                 235                 240

Arg Leu Arg Glu Ile Thr Arg Lys His Gly Ile Leu Leu Ile Phe Asp
                245                 250                 255

Glu Val Ile Thr Gly Phe Gly Arg Val Gly Glu Ala Phe Ala Ala Gln
            260                 265                 270

Arg Trp Gly Val Val Pro Asp Leu Leu Thr Cys Ala Lys Gly Leu Thr
        275                 280                 285

Asn Gly Ser Ile Pro Met Gly Ala Val Phe Val Asp Glu Lys Ile His
```

```
                290                 295                 300
Ala Ala Phe Met Gln Gly Pro Gln Gly Ala Ile Glu Phe Phe His Gly
305                 310                 315                 320

Tyr Thr Tyr Ser Gly His Pro Val Ala Cys Ala Ala Leu Ala Thr
                325                 330                 335

Leu Asp Ile Tyr Arg Arg Asp Asp Leu Phe Gln Arg Ala Val Glu Leu
                340                 345                 350

Glu Gly Tyr Trp Gln Asp Ala Leu Phe Ser Leu Arg Asp Leu Pro Asn
                355                 360                 365

Val Val Asp Ile Arg Ala Val Gly Leu Val Gly Val Gln Leu Ala
                370                 375                 380

Pro His Ala Asp Gly Pro Gly Lys Arg Gly Tyr Asp Val Phe Glu Arg
385                 390                 395                 400

Cys Phe Trp Glu His Asp Leu Met Val Arg Val Thr Gly Asp Ile Ile
                405                 410                 415

Ala Met Ser Pro Pro Leu Ile Ile Asp Lys Pro His Ile Asp Gln Ile
                420                 425                 430

Val Glu Arg Leu Ala Gln Ala Ile Arg Ala Ser Val
                435                 440
```

<210> SEQ ID NO 139
<211> LENGTH: 467
<212> TYPE: PRT
<213> ORGANISM: Escherichia coli

<400> SEQUENCE: 139

```
Met Asn Gln Gln Asp Ile Glu Gln Val Val Lys Ala Val Leu Leu Lys
1               5                   10                  15

Met Gln Ser Ser Asp Thr Pro Ser Ala Ala Val His Glu Met Gly Val
                20                  25                  30

Phe Ala Ser Leu Asp Asp Ala Val Ala Ala Lys Val Ala Gln Gln
                35                  40                  45

Gly Leu Lys Ser Val Ala Met Arg Gln Leu Ala Ile Ala Ala Ile Arg
                50                  55                  60

Glu Ala Gly Glu Lys His Ala Arg Asp Leu Ala Glu Leu Ala Val Ser
65                  70                  75                  80

Glu Thr Gly Met Gly Arg Val Glu Asp Lys Phe Ala Lys Asn Val Ala
                85                  90                  95

Gln Ala Arg Gly Thr Pro Gly Val Glu Cys Leu Ser Pro Gln Val Leu
                100                 105                 110

Thr Gly Asp Asn Gly Leu Thr Leu Ile Glu Asn Ala Pro Trp Gly Val
                115                 120                 125

Val Ala Ser Val Thr Pro Ser Thr Asn Pro Ala Ala Thr Val Ile Asn
                130                 135                 140

Asn Ala Ile Ser Leu Ile Ala Ala Gly Asn Ser Val Ile Phe Ala Pro
145                 150                 155                 160

His Pro Ala Ala Lys Lys Val Ser Gln Arg Ala Ile Thr Leu Leu Asn
                165                 170                 175

Gln Ala Ile Val Ala Ala Gly Gly Pro Glu Asn Leu Leu Val Thr Val
                180                 185                 190

Ala Asn Pro Asp Ile Glu Thr Ala Gln Arg Leu Phe Lys Phe Pro Gly
                195                 200                 205

Ile Gly Leu Leu Val Val Thr Gly Gly Glu Ala Val Val Glu Ala Ala
                210                 215                 220
```

Arg Lys His Thr Asn Lys Arg Leu Ile Ala Ala Gly Ala Gly Asn Pro
225                 230                 235                 240

Pro Val Val Val Asp Glu Thr Ala Asp Leu Ala Arg Ala Ala Gln Ser
            245                 250                 255

Ile Val Lys Gly Ala Ser Phe Asp Asn Ile Ile Cys Ala Asp Glu
            260                 265                 270

Lys Val Leu Ile Val Val Asp Ser Val Ala Asp Glu Leu Met Arg Leu
            275                 280                 285

Met Glu Gly Gln His Ala Val Lys Leu Thr Ala Glu Gln Ala Gln Gln
            290                 295                 300

Leu Gln Pro Val Leu Leu Lys Asn Ile Asp Glu Arg Gly Lys Gly Thr
305                 310                 315                 320

Val Ser Arg Asp Trp Val Gly Arg Asp Ala Gly Lys Ile Ala Ala Ala
            325                 330                 335

Ile Gly Leu Lys Val Pro Gln Glu Thr Arg Leu Leu Phe Val Glu Thr
            340                 345                 350

Thr Ala Glu His Pro Phe Ala Val Thr Glu Leu Met Met Pro Val Leu
            355                 360                 365

Pro Val Val Arg Val Ala Asn Val Ala Asp Ala Ile Ala Leu Ala Val
            370                 375                 380

Lys Leu Glu Gly Gly Cys His His Thr Ala Ala Met His Ser Arg Asn
385                 390                 395                 400

Ile Glu Asn Met Asn Gln Met Ala Asn Ala Ile Asp Thr Ser Ile Phe
            405                 410                 415

Val Lys Asn Gly Pro Cys Ile Ala Gly Leu Gly Leu Gly Gly Glu Gly
            420                 425                 430

Trp Thr Thr Met Thr Ile Thr Thr Pro Thr Gly Glu Gly Val Thr Ser
            435                 440                 445

Ala Arg Thr Phe Val Arg Leu Arg Arg Cys Val Leu Val Asp Ala Phe
            450                 455                 460

Arg Ile Val
465

<210> SEQ ID NO 140
<211> LENGTH: 532
<212> TYPE: PRT
<213> ORGANISM: Clostridium tetani

<400> SEQUENCE: 140

Met Glu Lys Tyr Asp Lys Asp Leu Tyr Ser Ile Gln Gln Ala Arg Asn
1               5                   10                  15

Leu Ala Arg Leu Gly Lys Val Ala Ala Asn Lys Ile Ala Asn Tyr Thr
            20                  25                  30

Glu Glu Gln Ile Asp Lys Ile Leu Arg Asn Met Val Arg Val Ala Glu
            35                  40                  45

Glu Asn Ala Val Ser Leu Ala Gln Met Ala Val Glu Glu Thr Gly Phe
        50                  55                  60

Gly Lys Val Glu Asp Lys Thr Tyr Lys Asn His Leu Ala Ala Thr Ile
65                  70                  75                  80

Leu Tyr Asp Ser Ile Lys Asp Met Lys Thr Ile Gly Val Ile Ser Glu
                85                  90                  95

Asp Lys Val Asn Lys Met Ile Glu Ile Ala Glu Pro Val Gly Leu Ile
            100                 105                 110

Met Gly Ile Val Pro Ser Thr Asn Pro Thr Ser Thr Ala Ile Phe Lys
            115                 120                 125

-continued

Ser Ile Ile Ala Ile Lys Ser Arg Asn Ala Ile Val Phe Ser Pro His
130                 135                 140

Pro Ala Ala Ala Lys Cys Thr Ile Arg Ala Val Glu Leu Met Arg Asp
145                 150                 155                 160

Ala Ala Ile Glu Ala Gly Ala Pro Glu Asp Ile Ile Ala Ser Leu Thr
                165                 170                 175

Asn Leu Thr Met Glu Ala Thr Asn Glu Leu Met Lys Asn Glu Asn Val
            180                 185                 190

Ser Leu Ile Ile Ala Thr Gly Gly Pro Gly Met Val Lys Ala Ala Tyr
        195                 200                 205

Ser Ser Gly Lys Pro Ala Ile Gly Val Gly Ala Gly Asn Ser Pro Ala
    210                 215                 220

Tyr Ile Glu Arg Thr Ala Asn Val Glu Lys Ala Ile Arg Asp Ile Ile
225                 230                 235                 240

Ser Ser Lys Ser Phe Asp Tyr Gly Thr Ile Cys Ala Ser Glu Gln Ser
                245                 250                 255

Ile Ile Cys Glu Glu Cys Asn His Asp Ala Val Val Glu Glu Leu Lys
            260                 265                 270

Lys Gln Gly Gly Tyr Phe Met Thr Ala Glu Glu Thr Glu Lys Val Cys
        275                 280                 285

Lys Leu Leu Phe Lys Asn Gly His Thr Met Asn Ala Lys Phe Val Gly
    290                 295                 300

Arg Ser Pro Gln Val Ile Ala Asn Ala Ala Gly Phe Thr Val Ser Glu
305                 310                 315                 320

Asp Ile Lys Val Leu Ile Gly Lys Gln Asn Gly Val Gly Asn Gly Asn
                325                 330                 335

Pro Leu Ser Phe Glu Lys Leu Thr Thr Val Leu Ala Phe Tyr Thr Val
            340                 345                 350

Lys Asp Trp His Glu Ala Cys Glu Leu Ser Ile Glu Leu Leu Gln Asn
        355                 360                 365

Gly Ile Gly His Thr Met Ser Ile His Thr Gln Asn Asp Asp Ile Val
    370                 375                 380

Met Glu Phe Ala Lys Lys Pro Ala Ser Arg Ile Leu Val Asn Thr Gly
385                 390                 395                 400

Gly Ser Gln Gly Gly Thr Gly Ala Ser Thr Gly Leu Lys Pro Ala Phe
                405                 410                 415

Thr Leu Gly Cys Gly Thr Trp Gly Gly Ser Ser Val Ser Glu Asn Val
            420                 425                 430

Thr Pro Glu His Leu Ile Asn Lys Lys Arg Val Ala Tyr Gly Leu Lys
        435                 440                 445

Asp Cys Ala Thr Leu Val Gln Asn Asp Pro Thr Phe Asn Cys Ile Lys
    450                 455                 460

Thr Ala Ser Asn Cys Arg Gly Val Lys Asn Gln Phe Met Asn Met Ser
465                 470                 475                 480

Pro Ala Gln Ile Ala Ala Ala Glu Val Leu Asn Lys Cys Asn Asp
                485                 490                 495

Tyr Ala Lys Asn Thr Gly Cys Ser Asn Glu Ser Lys Glu Lys Asp Ala
            500                 505                 510

Asn Asn Glu Glu Leu Leu Ser Leu Val Asn Gln Ile Val Ala Ala Met
        515                 520                 525

Lys Gly Ala Asn
    530

<210> SEQ ID NO 141
<211> LENGTH: 297
<212> TYPE: PRT
<213> ORGANISM: Burkholderia thailandensis

<400> SEQUENCE: 141

```
Met Lys Asn Lys Ser Ser Arg Thr Arg Val Ala Ile Leu Gly Ser Gly
1               5                   10                  15

Ser Ile Gly Leu Asp Leu Met Phe Lys Val Lys Ala Ser Glu His Phe
            20                  25                  30

Asp Leu Lys Phe Val Val Gly Arg His Ala Asn Ser Asp Gly Leu Lys
        35                  40                  45

Leu Ala Arg Ser Cys Asn Val Glu Thr Ser Ser Asp Gly Leu Asp Phe
    50                  55                  60

Leu Lys Glu Asn Glu Asp Ala Tyr Asp Leu Val Phe Asp Ala Thr Ser
65                  70                  75                  80

Ala Ala Ala His Lys Val Asn Asn Gly Phe Phe Ser Gly Ala Gly Lys
                85                  90                  95

Phe Val Ile Asp Leu Thr Pro Ala Lys Leu Gly Arg Leu Cys Val Pro
            100                 105                 110

Cys Ile Asn Leu Asp Asp Ile Gly Ala Glu Gln Asn Val Asn Leu Ile
        115                 120                 125

Thr Cys Gly Gly Gln Ala Ser Leu Pro Leu Ala Tyr Ala Leu Lys Gln
    130                 135                 140

Ala Val Asp Glu Ile Glu Tyr Leu Glu Val Val Ser Ala Ile Ala Ser
145                 150                 155                 160

Arg Ser Ala Gly Ile Ala Thr Arg Glu Asn Ile Asp Glu Tyr Met Thr
                165                 170                 175

Thr Thr Glu Tyr Ala Leu Ala Gln Phe Ser Gly Ala Lys Lys Thr Lys
            180                 185                 190

Ala Ile Leu Asn Ile Asn Pro Ala Glu Pro Gly Val Arg Met Gln Thr
        195                 200                 205

Thr Leu Tyr Ala His Ala Arg Tyr Arg Asp Phe Asp Arg Val Arg Ala
    210                 215                 220

Cys Val Ala Glu Met Val Glu Lys Val Arg Glu Tyr Val Pro Gly Tyr
225                 230                 235                 240

Arg Leu Val Val Glu Pro Ile Glu Ser Gln Gly Arg Ile Thr Ile Ser
                245                 250                 255

Leu Thr Val Arg Gly Arg Gly Asp Tyr Leu Pro Glu Tyr Ala Gly Asn
            260                 265                 270

Leu Asp Ile Ile Asn Cys Ala Ala Leu Ala Val Ala Ser His Arg His
        275                 280                 285

Ala Thr Ala Arg Leu Gly Ala Thr Gln
    290                 295
```

<210> SEQ ID NO 142
<211> LENGTH: 316
<212> TYPE: PRT
<213> ORGANISM: Pseudomonas putida

<400> SEQUENCE: 142

```
Met Thr Arg Lys Val Lys Ala Ala Ile Ile Gly Ser Gly Asn Ile Gly
1               5                   10                  15

Thr Asp Leu Met Ile Lys Ile Leu Arg His Gly Gln His Ile Glu Met
            20                  25                  30
```

```
Gly Ala Met Val Gly Ile Asp Pro Ala Ser Asp Gly Leu Ala Arg Ala
             35                  40                  45

Gln Arg Met Gly Val Ala Ile Thr His Glu Gly Val Glu Gly Leu Thr
 50                  55                  60

Arg Leu Pro Val Phe Asn Glu Ile Asp Val Val Phe Asp Ala Thr Ser
 65                  70                  75                  80

Ala Gly Ala His Val Lys Asn Glu Ala Leu Leu Arg Glu Arg Lys Pro
                 85                  90                  95

Gly Leu Arg Met Ile Asp Leu Thr Pro Ala Ala Ile Gly Pro Tyr Cys
            100                 105                 110

Ile Pro Val Val Asn Gly Asp Asp His Leu Asp Ala Thr Asn Val Asn
            115                 120                 125

Met Val Thr Cys Gly Gly Gln Ala Thr Ile Pro Met Val Ala Ala Val
130                 135                 140

Ser Arg Val Ala Lys Val His Tyr Ala Glu Ile Ile Ala Ser Ile Ser
145                 150                 155                 160

Ser Lys Ser Ala Gly Pro Gly Thr Arg Ala Asn Ile Asp Glu Phe Thr
                165                 170                 175

Glu Thr Thr Ser Lys Ala Ile Glu Val Val Gly Gly Ala Ala Lys Gly
            180                 185                 190

Lys Ala Ile Ile Val Leu Asn Pro Ala Glu Pro Pro Leu Met Met Arg
            195                 200                 205

Asp Thr Val Tyr Thr Leu Ser Asp Phe Ala Asp Ile Asp Gln Ile Glu
            210                 215                 220

Glu Ser Val Gln Arg Met Ala Asp Ala Val Gln Ala Tyr Val Pro Gly
225                 230                 235                 240

Tyr Arg Leu Lys Gln Arg Val Gln Phe Asp Arg Ile Glu Ala Asp Cys
                245                 250                 255

Pro Ile Arg Ile Pro Gly Val Gly Asp Arg Met Asn Gly Leu Lys Thr
            260                 265                 270

Ser Ile Phe Leu Glu Val Glu Gly Ala Ala His Tyr Leu Pro Ala Tyr
            275                 280                 285

Ala Gly Asn Leu Asp Ile Met Thr Ser Ala Ala Leu Arg Thr Ala Glu
            290                 295                 300

Lys Leu Ala Glu Arg Leu Leu Ala Ser Leu Val Ala
305                 310                 315

<210> SEQ ID NO 143
<211> LENGTH: 539
<212> TYPE: PRT
<213> ORGANISM: Burkholderia mallei

<400> SEQUENCE: 143

Met His Arg Gly Ala Ala Cys Trp His Gly Phe Gly Val Thr Asn Gly
 1                   5                  10                  15

Val Ala His Val Ala Arg Arg Ile Thr Asp Thr Asp Met Arg Gly Ala
                 20                  25                  30

Thr Met Asn His Ala Asp Met Gln His Leu Asn Ile Glu Phe Pro Tyr
             35                  40                  45

Arg Lys Gln Tyr Gly Asn Phe Ile Gly Gly Glu Trp Val Ala Pro Val
 50                  55                  60

Gly Gly Glu Tyr Phe Asp Asn Val Ser Pro Val Thr Gly Arg Pro Phe
 65                  70                  75                  80

Thr Ala Ile Pro Arg Ser Arg Glu Ala Asp Ile Glu Leu Ala Leu Asp
                 85                  90                  95
```

```
Ala Ala His Ala Ala Lys Ala Gly Trp Ala Ala Lys Gly Ala Ala Glu
            100                 105                 110
Arg Ala Asn Val Leu Leu Arg Ile Ala Asp Arg Met Glu Ala Asn Leu
        115                 120                 125
Thr Arg Leu Ala Val Ala Glu Thr Ile Asp Asn Gly Lys Pro Leu Arg
    130                 135                 140
Glu Thr Thr Ala Ala Asp Val Pro Leu Ala Ile Asp His Phe Arg Tyr
145                 150                 155                 160
Phe Ala Gly Cys Ile Arg Ala Gln Glu Gly Ser Ile Ala Asp Ile Gly
                165                 170                 175
Gly Asp Met Val Ala Tyr His Phe His Glu Pro Leu Gly Val Val Gly
            180                 185                 190
Gln Ile Ile Pro Trp Asn Phe Pro Leu Leu Met Ala Ala Trp Lys Leu
        195                 200                 205
Ala Pro Ala Leu Ala Ala Gly Asn Cys Val Val Leu Lys Pro Ala Glu
    210                 215                 220
Gln Thr Pro Ala Ser Ile Leu Val Phe Ala Glu Leu Ile Gln Asp Leu
225                 230                 235                 240
Leu Pro Pro Gly Val Leu Asn Ile Val Asn Gly Phe Gly Leu Glu Ala
                245                 250                 255
Gly Lys Pro Leu Ala Ser Ser Lys Arg Ile Ala Lys Ile Ala Phe Thr
            260                 265                 270
Gly Glu Thr Ser Thr Gly Arg Leu Ile Met Gln Tyr Ala Ser Glu Asn
        275                 280                 285
Leu Ile Pro Val Thr Leu Glu Leu Gly Gly Lys Ser Pro Asn Ile Phe
    290                 295                 300
Phe Ala Asp Val Met Asp Arg Asp Ser Tyr Phe Asp Lys Ala Leu
305                 310                 315                 320
Glu Gly Phe Ala Met Phe Ala Leu Asn Gln Gly Glu Val Cys Thr Cys
                325                 330                 335
Pro Ser Arg Ala Leu Val Glu Glu Ser Ile Tyr Asp Arg Phe Ile Glu
            340                 345                 350
Arg Ala Leu Lys Arg Val Glu Ala Ile Lys Gln Gly His Pro Leu Asp
        355                 360                 365
Ser Gln Thr Met Ile Gly Ala Gln Ala Ser Ala Glu Gln Leu Glu Lys
    370                 375                 380
Ile Leu Ser Tyr Ile Asp Ile Gly Arg Gly Glu Gly Ala Gln Cys Leu
385                 390                 395                 400
Thr Gly Gly Glu Arg Asn Val Leu Gly Gly Glu Leu Ala Glu Gly Tyr
                405                 410                 415
Tyr Val Lys Pro Thr Val Phe Arg Gly His Asn Lys Met Arg Ile Phe
            420                 425                 430
Gln Glu Glu Ile Phe Gly Pro Val Leu Ala Val Thr Thr Phe Lys Thr
        435                 440                 445
Glu Glu Glu Ala Leu Glu Ile Ala Asn Asp Thr Leu Tyr Gly Leu Gly
    450                 455                 460
Ala Gly Val Trp Thr Arg Asp Gly Asn Arg Ala Tyr Arg Phe Gly Arg
465                 470                 475                 480
Gly Ile Gln Ala Gly Arg Val Trp Thr Asn Cys Tyr His Ala Tyr Pro
                485                 490                 495
Ala His Ala Ala Phe Gly Gly Tyr Lys Gln Ser Gly Ile Gly Arg Glu
            500                 505                 510
```

Thr His Lys Met Met Leu Asp His Tyr Gln Gln Thr Lys Asn Leu Leu
                515                 520                 525

Val Ser Tyr Ser Glu Lys Pro Leu Gly Phe Phe
    530                 535

<210> SEQ ID NO 144
<211> LENGTH: 464
<212> TYPE: PRT
<213> ORGANISM: Salmonella typhimurium

<400> SEQUENCE: 144

Met Asn Thr Ser Glu Leu Glu Thr Leu Ile Arg Thr Ile Leu Ser Glu
1               5                   10                  15

Gln Leu Thr Thr Pro Ala Gln Thr Pro Val Gln Pro Gln Gly Lys Gly
            20                  25                  30

Ile Phe Gln Ser Val Ser Glu Ala Ile Asp Ala Ala His Gln Ala Phe
        35                  40                  45

Leu Arg Tyr Gln Gln Cys Pro Leu Lys Thr Arg Ser Ala Ile Ile Ser
    50                  55                  60

Ala Met Arg Gln Glu Leu Thr Pro Leu Leu Ala Pro Leu Ala Glu Glu
65                  70                  75                  80

Ser Ala Asn Glu Thr Gly Met Gly Asn Lys Glu Asp Lys Phe Leu Lys
                85                  90                  95

Asn Lys Ala Ala Leu Asp Asn Thr Pro Gly Val Glu Asp Leu Thr Thr
            100                 105                 110

Thr Ala Leu Thr Gly Asp Gly Gly Met Val Leu Phe Glu Tyr Ser Pro
        115                 120                 125

Phe Gly Val Ile Gly Ser Val Ala Pro Ser Thr Asn Pro Thr Glu Thr
130                 135                 140

Ile Ile Asn Asn Ser Ile Ser Met Leu Ala Ala Gly Asn Ser Ile Tyr
145                 150                 155                 160

Phe Ser Pro His Pro Gly Ala Lys Lys Val Ser Leu Lys Leu Ile Ser
                165                 170                 175

Leu Ile Glu Glu Ile Ala Phe Arg Cys Cys Gly Ile Arg Asn Leu Val
            180                 185                 190

Val Thr Val Ala Glu Pro Thr Phe Glu Ala Thr Gln Gln Met Met Ala
        195                 200                 205

His Pro Arg Ile Ala Val Leu Ala Ile Thr Gly Gly Pro Gly Ile Val
    210                 215                 220

Ala Met Gly Met Lys Ser Gly Lys Lys Val Ile Gly Ala Gly Ala Gly
225                 230                 235                 240

Asn Pro Pro Cys Ile Val Asp Glu Thr Ala Asp Leu Val Lys Ala Ala
                245                 250                 255

Glu Asp Ile Ile Asn Gly Ala Ser Phe Asp Tyr Asn Leu Pro Cys Ile
            260                 265                 270

Ala Glu Lys Ser Leu Ile Val Val Glu Ser Val Ala Glu Arg Leu Val
        275                 280                 285

Gln Gln Met Gln Thr Phe Gly Ala Leu Leu Leu Ser Pro Ala Asp Thr
    290                 295                 300

Asp Lys Leu Arg Ala Val Cys Leu Pro Glu Gly Gln Ala Asn Lys Lys
305                 310                 315                 320

Leu Val Gly Lys Ser Pro Ser Ala Met Leu Glu Ala Ala Gly Ile Ala
                325                 330                 335

Val Pro Ala Lys Ala Pro Arg Leu Leu Ile Ala Leu Val Asn Ala Asp
            340                 345                 350

```
Asp Pro Trp Val Thr Ser Glu Gln Leu Met Pro Met Leu Pro Val Val
        355                 360                 365

Lys Val Ser Asp Phe Asp Ser Ala Leu Ala Leu Ala Leu Lys Val Glu
        370                 375                 380

Glu Gly Leu His His Thr Ala Ile Met His Ser Gln Asn Val Ser Arg
385                 390                 395                 400

Leu Asn Leu Ala Ala Arg Thr Leu Gln Thr Ser Ile Phe Val Lys Asn
                405                 410                 415

Gly Pro Ser Tyr Ala Gly Ile Gly Val Gly Glu Gly Phe Thr Thr
                420                 425                 430

Phe Thr Ile Ala Thr Pro Thr Gly Glu Gly Thr Thr Ser Ala Arg Thr
        435                 440                 445

Phe Ala Arg Ser Arg Arg Cys Val Leu Thr Asn Gly Phe Ser Ile Arg
450                 455                 460

<210> SEQ ID NO 145
<211> LENGTH: 315
<212> TYPE: PRT
<213> ORGANISM: Rhodococcus sp.

<400> SEQUENCE: 145

Met Ser Thr Thr Lys Val Ala Val Ile Gly Ser Gly Asn Ile Gly Thr
1               5                   10                  15

Asp Leu Val Ile Lys Leu Glu Gln Val Ala Lys Asn Val Glu Ile Ala
                20                  25                  30

Val Leu Val Gly Ile Asp Pro Ala Ser Asp Gly Leu Ala Arg Ala Arg
            35                  40                  45

Arg Leu Gly Ile Ser Thr Val Asp Thr Gly Val Gln Gly Leu Ile Glu
    50                  55                  60

His Pro Glu Phe Asp Asp Ile Glu Ile Ile Phe Asp Ser Thr Ser Ala
65                  70                  75                  80

Lys Ala His Leu Thr Asn Ala Glu Ala Leu Arg Pro Tyr Gly Lys His
                85                  90                  95

Leu Ile Asp Leu Thr Pro Ala Ala Ile Gly Pro Tyr Val Val Pro Ala
            100                 105                 110

Val Asn Leu Asp Gln His Leu Gly Ala Pro Asp Val Asn Met Val Thr
        115                 120                 125

Cys Gly Gly Gln Ala Thr Ile Pro Ile Val Ala Ala Ile Ser Lys Val
    130                 135                 140

Thr Asp Val His Tyr Ala Glu Ile Val Ala Ser Ile Ala Ser Lys Ser
145                 150                 155                 160

Ala Gly Pro Gly Thr Arg Ala Asn Ile Asp Glu Phe Thr Glu Thr Thr
                165                 170                 175

Ala Lys Ala Ile Glu Glu Val Gly Gly Ala Ala His Gly Lys Ala Ile
            180                 185                 190

Ile Val Leu Asn Pro Ala Asp Pro Pro Leu Ile Met Arg Asp Thr Val
        195                 200                 205

Leu Ala Leu Val Ser Asn Pro Asp Gln Asp Ala Ile Arg Gln Ser Ile
    210                 215                 220

Thr Asp Met Val Ala Thr Val Ala Ala Tyr Val Pro Gly Tyr Arg Leu
225                 230                 235                 240

Lys Gln Asp Val Gln Phe Thr Glu Leu Gly Gly Ala Asp Thr Val Ala
                245                 250                 255

Thr Leu Thr Gly Gly Ala Asp Ile Gly Ser Pro Val Trp Lys Val Ser
```

```
            260                 265                 270

Val Phe Leu Glu Val Glu Gly Ala Ala His Tyr Leu Pro Ala Tyr Ala
        275                 280                 285

Gly Asn Leu Asp Ile Met Thr Ser Ala Ala Leu Gln Val Ala Glu Lys
    290                 295                 300

Leu Ala Glu Arg Thr Ala Leu Glu Ile Ala Arg
305                 310                 315

<210> SEQ ID NO 146
<211> LENGTH: 468
<212> TYPE: PRT
<213> ORGANISM: Clostridium beijerinckii

<400> SEQUENCE: 146

Met Asn Lys Asp Thr Leu Ile Pro Thr Thr Lys Asp Leu Lys Leu Lys
1               5                   10                  15

Thr Asn Val Glu Asn Ile Asn Leu Lys Asn Tyr Lys Asp Asn Ser Ser
            20                  25                  30

Cys Phe Gly Val Phe Glu Asn Val Glu Asn Ala Ile Asn Ser Ala Val
        35                  40                  45

His Ala Gln Lys Ile Leu Ser Leu His Tyr Thr Lys Glu Gln Arg Glu
    50                  55                  60

Lys Ile Ile Thr Glu Ile Arg Lys Ala Ala Leu Glu Asn Lys Glu Val
65                  70                  75                  80

Leu Ala Thr Met Ile Leu Glu Glu Thr His Met Gly Arg Tyr Glu Asp
                85                  90                  95

Lys Ile Leu Lys His Glu Leu Val Ala Lys Tyr Thr Pro Gly Thr Glu
            100                 105                 110

Asp Leu Thr Thr Thr Ala Trp Ser Gly Asp Asn Gly Leu Thr Val Val
        115                 120                 125

Glu Met Ser Pro Tyr Gly Val Ile Gly Ala Ile Thr Pro Ser Thr Asn
    130                 135                 140

Pro Thr Glu Thr Val Ile Cys Asn Ser Ile Gly Met Ile Ala Ala Gly
145                 150                 155                 160

Asn Ala Val Val Phe Asn Gly His Pro Gly Ala Lys Lys Cys Val Ala
                165                 170                 175

Phe Ala Ile Glu Met Ile Asn Lys Ala Ile Ile Ser Cys Gly Gly Pro
            180                 185                 190

Glu Asn Leu Val Thr Thr Ile Lys Asn Pro Thr Met Glu Ser Leu Asp
        195                 200                 205

Ala Ile Ile Lys His Pro Leu Ile Lys Leu Leu Cys Gly Thr Gly Gly
    210                 215                 220

Pro Gly Met Val Lys Thr Leu Leu Asn Ser Gly Lys Lys Ala Ile Gly
225                 230                 235                 240

Ala Gly Ala Gly Asn Pro Pro Val Ile Val Asp Asp Thr Ala Asp Ile
                245                 250                 255

Glu Lys Ala Gly Lys Ser Ile Ile Glu Gly Cys Ser Phe Asp Asn Asn
            260                 265                 270

Leu Pro Cys Ile Ala Glu Lys Glu Val Phe Val Phe Glu Asn Val Ala
        275                 280                 285

Asp Asp Leu Ile Ser Asn Met Leu Lys Asn Asn Ala Val Ile Ile Asn
    290                 295                 300

Glu Asp Gln Val Ser Lys Leu Ile Asp Leu Val Leu Gln Lys Asn Asn
305                 310                 315                 320
```

```
Glu Thr Gln Glu Tyr Phe Ile Asn Lys Lys Trp Val Gly Lys Asp Ala
                325                 330                 335

Lys Leu Phe Ser Asp Glu Ile Asp Val Glu Ser Pro Ser Asn Ile Lys
            340                 345                 350

Cys Ile Val Cys Glu Val Asn Ala Asn His Pro Phe Val Met Thr Glu
        355                 360                 365

Leu Met Met Pro Ile Leu Pro Ile Val Arg Val Lys Asp Ile Asp Glu
    370                 375                 380

Ala Val Lys Tyr Thr Lys Ile Ala Glu Gln Asn Arg Lys His Ser Ala
385                 390                 395                 400

Tyr Ile Tyr Ser Lys Asn Ile Asp Asn Leu Asn Arg Phe Glu Arg Glu
                405                 410                 415

Ile Asp Thr Thr Ile Phe Val Lys Asn Ala Lys Ser Phe Ala Gly Val
            420                 425                 430

Gly Tyr Glu Ala Glu Gly Phe Thr Thr Phe Thr Ile Ala Gly Ser Thr
        435                 440                 445

Gly Glu Gly Ile Thr Ser Ala Arg Asn Phe Thr Arg Gln Arg Arg Cys
    450                 455                 460

Val Leu Ala Gly
465

<210> SEQ ID NO 147
<211> LENGTH: 475
<212> TYPE: PRT
<213> ORGANISM: Bacillus thuringiensis

<400> SEQUENCE: 147

Met Thr Asn Lys Thr Asp Glu Lys Glu Val Gln Ala Met Val Asn Val
1               5                   10                  15

Val Ile Lys Asp Glu Asn Asp Val Gln Glu Val Val Asn Thr Leu Val
            20                  25                  30

Glu Asn Gly Lys Glu Ala Leu Lys Ala Leu Glu Ser Tyr Thr Gln Glu
        35                  40                  45

Gln Val Asp His Ile Val His Glu Met Ala Leu Ser Gly Leu Asp Gln
    50                  55                  60

His Met Pro Leu Ala Lys Met Ala Val Glu Glu Thr Gly Arg Gly Val
65                  70                  75                  80

Tyr Glu Asp Lys Cys Thr Lys Asn Ile Phe Ala Thr Glu Tyr Ile Trp
                85                  90                  95

His Ser Ile Lys Lys Asp Lys Thr Val Gly Ile Ile His Glu Asp Pro
            100                 105                 110

His Glu Glu Val Ile Glu Ile Ala Glu Pro Val Gly Val Val Ala Gly
        115                 120                 125

Val Thr Pro Val Thr Asn Pro Thr Ser Thr Thr Met Phe Lys Ala Ile
    130                 135                 140

Ile Ala Met Lys Thr Arg Asn Pro Ile Ile Phe Ala Phe His Pro Ser
145                 150                 155                 160

Ala Gln Gln Cys Ser Val Ala Ala Ala Lys Ile Leu Arg Asp Ala Ala
                165                 170                 175

Ile Arg Ala Gly Ala Pro Glu Asn Cys Ile Gln Trp Ile Glu Lys Pro
            180                 185                 190

Ser Val Glu Ala Thr Lys Arg Leu Met Asn His Glu Gly Val Ala Leu
        195                 200                 205

Val Leu Ala Thr Gly Gly Ala Gly Met Val Lys Ser Ala Tyr Ser Thr
    210                 215                 220
```

```
Gly Lys Pro Ala Leu Gly Val Gly Pro Gly Asn Val Pro Cys Tyr Leu
225                 230                 235                 240

Glu Lys Ser Ala His Val Lys Arg Ala Val Asn Asp Leu Ile Leu Ser
            245                 250                 255

Lys Thr Phe Asp Asn Gly Met Ile Cys Ala Ser Glu Gln Ala Ile Ile
        260                 265                 270

Val Asp Lys Glu Ile Tyr Asn Gly Val Lys Lys Glu Met Gln Asp Asn
    275                 280                 285

Asn Cys Tyr Phe Val Thr Glu Glu Arg Ile Lys Leu Glu Lys Leu
290                 295                 300

Val Ile Asn Glu Asn Thr Cys Ala Val Asn Ser Asp Ile Val Gly Lys
305                 310                 315                 320

Ser Ala His Tyr Ile Ala Ser Leu Val Ser Ile Lys Val Pro Glu Asp
                325                 330                 335

Thr Lys Ile Leu Val Ala Glu Ile Lys Gly Val Gly Ala Glu Tyr Pro
            340                 345                 350

Leu Ser Arg Glu Lys Leu Ser Pro Val Leu Ala Cys Ile Lys Ala Asn
        355                 360                 365

Ser Gln Glu Glu Gly Phe Lys Tyr Cys Glu Glu Met Leu Asn Leu Gly
    370                 375                 380

Gly Leu Gly His Ser Ala Val Ile His Ser Thr Asn Lys Glu Val Gln
385                 390                 395                 400

Lys Gln Phe Gly Leu Arg Met Lys Ala Cys Arg Leu Ile Val Asn Ser
                405                 410                 415

Pro Ser Ala Gln Gly Gly Ile Gly Asp Ile Tyr Asn Ala Phe Ile Pro
            420                 425                 430

Ser Leu Thr Leu Gly Cys Gly Ser Tyr Gly Lys Asn Ser Val Ser Gln
        435                 440                 445

Asn Val Thr Ala Thr His Ile Ile Asn Val Lys Arg Leu Ala Asn Ser
    450                 455                 460

Pro Asp Asn Met Arg Gly Phe Thr Ile Thr Thr
465                 470                 475

<210> SEQ ID NO 148
<211> LENGTH: 467
<212> TYPE: PRT
<213> ORGANISM: unknown
<220> FEATURE:
<223> OTHER INFORMATION: unclassified gamma proteobacterium protein

<400> SEQUENCE: 148

Met Ser Glu Ala Gln Ser Pro Ala Gln Glu Val Ala Glu Met Met Ser
1               5                   10                  15

Arg Ala Arg Ala Ala Gln Ala Gln Ile Ala Asp Tyr Thr Gln Glu Gln
            20                  25                  30

Val Asp Glu Leu Ile Thr Ala Met Val Tyr Ala Val Ala Arg Glu Asp
        35                  40                  45

Arg Ser Glu Glu Ile Ala Arg Phe Thr Val Glu Thr Gln Leu Gly
    50                  55                  60

Asn Tyr Glu Gly Lys Tyr Leu Lys Ile His Arg Lys Thr Arg Ala Thr
65                  70                  75                  80

Leu Met Asp Ile Ile Asp Asp Lys Ser Val Gly Val Ile Glu Glu Leu
                85                  90                  95

Pro Glu Arg Asn Ile Val Lys Ile Ala Lys Pro Val Gly Val Ile Gly
            100                 105                 110
```

```
Ala Leu Ser Pro Ser Thr Asn Pro Glu Ala Thr Pro Val Ile Lys Ala
            115                 120                 125

Ile Ser Ala Val Lys Gly Arg Asn Ala Ile Ile Val Ala Pro His Pro
    130                 135                 140

Arg Ala Lys Leu Thr Asn Lys Lys Ile Cys Asp Tyr Met Arg Glu Ala
145                 150                 155                 160

Leu Glu Leu Cys Gly Ala Pro Ala Asp Leu Val Gln Ser Ile Asp Val
                165                 170                 175

Pro Ser Leu Asp Lys Thr Asn Glu Leu Met Ala Gln Cys Asp Arg Val
            180                 185                 190

Leu Ala Thr Gly Gly Glu Ala Met Val Thr Ala Ala Tyr Ser Ser Gly
        195                 200                 205

Thr Pro Ala Leu Gly Val Gly Val Gly Asn Ala Val Ile Thr Val Asp
    210                 215                 220

Asp Thr Ala Asp Leu Asp Glu Ala Ala Glu Lys Ile Arg Ile Ser Lys
225                 230                 235                 240

Thr Leu Asp Leu Ala Ala Ser Cys Ser Ser Asp Asn Ser Val Leu Val
                245                 250                 255

Phe Glu Ser Val Tyr Asn Glu Leu Leu Glu Lys Leu Lys His Glu Gly
            260                 265                 270

Gly Phe Val Ile Glu Gly Asp Asp Lys Ala Lys Leu Gln Ser Val Ile
        275                 280                 285

Trp Glu Asp Asp His Leu Asn Ala Lys Ile Val Ala Gln His Ala Gln
    290                 295                 300

Thr Ile Cys Gly Gln Ala Gly Ile Asp Leu Pro Glu Gly Lys Ser Phe
305                 310                 315                 320

Leu Ile Val Pro Glu Thr Gly Ala Gly Ala Asp His Pro Phe Ser Gly
                325                 330                 335

Glu Lys Leu Thr Val Thr Met Ala Leu Tyr Lys Val Lys Asp Ile Asp
            340                 345                 350

Glu Ala Ile Glu Met Thr Asn Lys Ile Gln Ala Tyr Gln Gly Gln Gly
        355                 360                 365

His Ser Cys Gly Ile Tyr Ser Tyr Asn Asp Asp Asn Val Leu Lys Leu
    370                 375                 380

Ala Asp Ala Thr Arg Thr Ser Arg Val Met Val Asn Gln Pro Gln Ala
385                 390                 395                 400

Ala Ser Asn Ser Gly Asn Leu Trp Asn Gly Met Arg Gln Thr Phe Ser
                405                 410                 415

Leu Gly Cys Gly Ser Trp Gly Gly Asn Ser Ile Asn His Asn Ile Thr
            420                 425                 430

Trp Arg Asp Leu Ile Asn Glu Thr Trp Val Ser Lys Pro Leu Ala Thr
        435                 440                 445

Thr Lys Thr Ile Pro Ser Asp Glu Glu Leu Phe Gly Ala Val Met Ala
    450                 455                 460

Lys Phe Ser
465
```

ADIPATE (ESTER OR THIOESTER) SYNTHESIS

This application is a continuation of U.S. patent application Ser. No. 14/082,000, filed Nov. 15, 2013, which is a continuation of U.S. patent application Ser. No. 13/841,142, filed Mar. 15, 2013, which is a continuation of U.S. patent application Ser. No. 13/572,346, filed Aug. 10, 2012, now abandoned, which is a continuation of U.S. patent application Ser. No. 12/921,547, now issued U.S. Pat. No. 9,096,873, issued Aug. 4, 2015, which is a U.S. National Stage Application under 35 U.S.C. § 371 of International Patent Application No. PCT/NL2009/050115, filed Mar. 11, 2009, which claims the benefit of priority to European Patent Application No. 08152595.8, filed Mar. 11, 2008, the entire contents of which are each incorporated herein by reference.

SEQUENCE LISTING

The instant application contains a Sequence Listing which has been submitted in ASCII format via EFS-Web and is hereby incorporated by reference in its entirety. Said ASCII copy, created on Apr. 27, 2016, is named 12956-397-999_Sequence_Listing.txt and is 500,360 bytes in size.

BACKGROUND OF THE INVENTION

The present invention relates to a method for preparing an adipate ester or thioester. The invention further relates to a method for preparing adipic acid from said ester or thioester. Further the invention provides a number of methods for preparing an intermediate for said ester or thioester. Further the invention relates to a method for preparing 6-amino caproic acid (6-ACA), a method for preparing 5-formyl valeric acid (5-FVA), and a method for preparing caprolactam. Further, the invention relates to a host cell for use in a method according to the invention.

Adipic acid (hexanedioic acid) is inter alia used for the production of polyamide. Further, esters of adipic acid may be used in plasticisers, lubricants, solvent and in a variety of polyurethane resins. Other uses of adipic acid are as food acidulans, applications in adhesives, insecticides, tanning and dyeing. Known preparation methods include the oxidation of cyclohexanol or cyclohexanone or a mixture thereof (KA oil) with nitric acid.

Caprolactam is a lactam which may also be used for the production of polyamide, for instance nylon-6 or caprolactam-laurolactam copolymers (nylon-6,12). Various manners of preparing caprolactam from bulk chemicals are known in the art and include the preparation of caprolactam from cyclohexanone, toluene, phenol, cyclohexanol, benzene or cyclohexane.

The intermediate compounds, such as cyclohexanol, cyclohexanone or phenol, for preparing adipic acid or caprolactam are generally obtained from mineral oil. In view of a growing desire to prepare materials using more sustainable technology it would be desirable to provide a method wherein adipic acid or caprolactam is prepared from an intermediate compound that can be obtained from a biologically renewable source or at least from an intermediate compound that is converted into adipic acid or caprolactam using a biochemical method.

In U.S. Pat. No. 5,487,987, a method is described for the production of adipic acid, wherein use is made of a bacterial cell, wherein a carbon source is converted into 3-dehydroshikimate by the enzymes in the common pathway or aromatic amino acid biosynthesis of the bacterial cell, to produce cis, cis muconic acid, by the biocatalytic conversion of 3-dehydroshikimate. The cis, cis muconic acid is thereafter chemically reduced (using a platinum catalyst) to produce adipic acid. Thus, the final step requires chemical catalysis. It is further envisaged by the present inventors that the aromatic intermediates formed in the bacterial cell, may be toxic to the cell, likely requiring their concentration to be low in vivo as well as in the cell culture.

It is known to prepare caprolactam from 6-aminocaproic acid (6-ACA), e.g. as described in U.S. Pat. No. 6,194,572. As disclosed in WO 2005/068643, 6-ACA may be prepared biochemically by converting 6-aminohex-2-enoic acid (6-AHEA) in the presence of an enzyme having $\alpha,\beta$-enoate reductase activity. The 6-AHEA may be prepared from lysine, e.g. biochemically or by pure chemical synthesis. Although 6-ACA can be prepared via the reduction of 6-AHEA by the methods disclosed in WO 2005/068643, the inventors have found that—under the reduction reaction conditions—6-AHEA may spontaneously and substantially irreversibly cyclise to form an undesired side-product, notably $\beta$-homoproline. This cyclisation may be a bottleneck in the production of 6-ACA, and lead to a considerable loss in yield.

SUMMARY OF THE INVENTION

It is an object of the invention to provide a novel method for preparing adipic acid or caprolactam—which may, inter alia, be used for the preparation of polyamide—or an intermediate compound for adipic acid or caprolactam, that can serve as an alternative to known methods.

It is a further object to provide a novel method that would overcome one or more of the drawbacks mentioned above.

One or more further objects which may be solved in accordance with the invention will follow from the description, below.

The inventors have realised that adipate (or a ester or thioester thereof) can be produced from succinate (or a ester or thioester thereof). In particular, the inventors concluded that an adipate (thio)ester may be prepared from succinate (thio)ester and acetate (thio)ester via a sequence of specific reactions, e. g. similar to reverse beta-oxidation and fatty acid biosynthesis in living cells, as shown in FIG. 2. Herein, each R independently represents an activating group (facilitating the reaction), e.g. as described herein below. Each X independently represents an S or an O. ED/EDH$_2$ exemplify oxidised/reduced electron donors, for example NAD/NADH, NADP/NADPH, FAD/FADH$_2$, or oxidised ferredoxin/reduced ferredoxin. Actual transfer of electrons may occur directly or may be mediated by intermediate electron carriers such as coenzymes or electron transfer flavo proteins (ETF). Y—NH$_2$ refers to an amino donor, e.g. as described herein below.

Thus, the inventors came to the conclusion that it should be possible to biocatalytically prepare adipic acid (or a ester or thioester thereof) via a cascade of reactions from succinate (or a ester or thioester thereof) and acetate (or a ester or thioester thereof). Further, they realised that adipic acid may be converted biocatalytically into 5-formylpentanoic acid ('5-FVA', 5-formylvaleric acid), which is an intermediate for the preparation of 6-ACA, and that for this conversion a specific biocatalyst may be used.

Accordingly, the present invention relates to a method for preparing an adipate ester or thioester from a succinate ester or thioester, via a plurality of reactions, wherein at least one of the reactions is catalysed by a biocatalyst.

In particular, the invention relates to a method for preparing an adipate ester or adipate thioester, comprising converting a 2,3-dehydroadipate (IUPAC name: 5-carboxy-2-pentanoate) ester or 2,3-dehydroadipate thioester into the adipate ester or thioester in the presence of a biocatalyst.

When referred herein to carboxylic acids or carboxylates, e.g. 6-ACA, another amino acid, 5-FVA, adipic acid/adipate, succinic acid/succinate, acetic acid/acetate, these terms are meant to include the protonated carboxylic acid (free acid), the corresponding carboxylate (its conjugated base) as well as a salt thereof, unless specified otherwise. When referring herein to amino acids, e.g. 6-ACA, this term is meant to include amino acids in their zwitterionic form (in which the amino group is in the protonated and the carboxylate group is in the deprotonated form), the amino acid in which the amino group is protonated and the carboxylic group is in its neutral form, and the amino acid in which the amino group is in its neutral form and the carboxylate group is in the deprotonated form, as well as salts thereof.

When referred to ester or thioester of a carboxylic acid, e. g. adipate ester or thioester, acetate ester of thioester, succinate ester or thioester, these terms are meant to include any activating group, in particular any biological activating group, including coenzyme A (also referred to as CoA), phospho-pantetheine, which may be bound to an acyl or peptidyl carrier protein (ACP or PCP, respectively), N-acetyl-cysteamine, methyl-thio-glycolate, methyl-mercapto-propionate, ethyl-mercapto-propionate, methyl-mercapto-butyrate, methyl-mercapto-butyrate, mercaptopropionate and other esters or thioesters providing the same or a similar function. In case living cells are used as a biocatalyst, the ester or thioester, in particular CoA, may be produced by the used biocatalyst or originate from an organism also capable of producing a suitable enzyme for catalysing the reaction. CoA-ligase and CoA-transferases have been identified in many organisms and may provide the desired activated esters or thioesters.

DETAILED DESCRIPTION OF THE INVENTION

Figure 1:
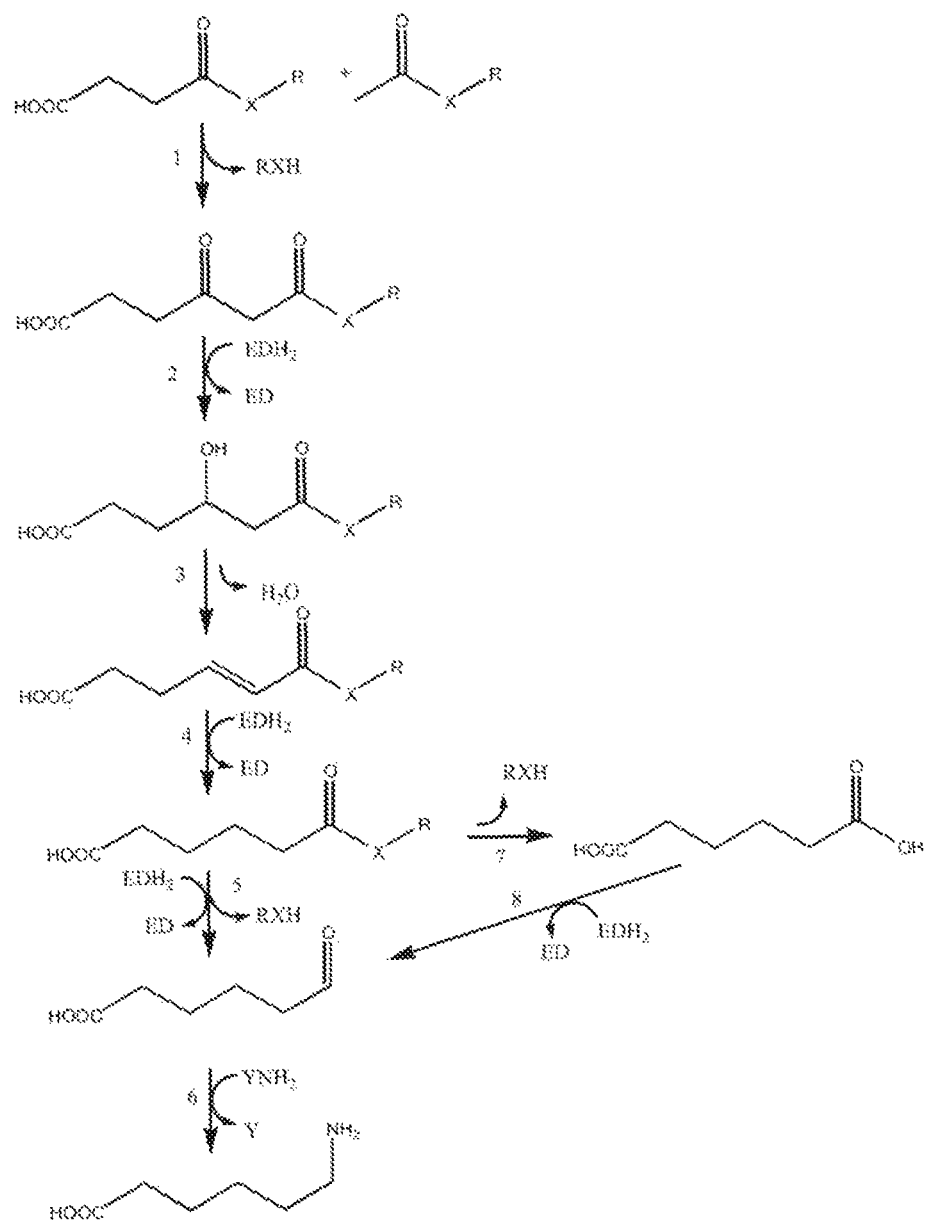
FIG. 1. The preparation of the adipate ester or thioester from the succinate ester or thioester.

The preparation of the adipate ester or thioester from the succinate ester or thioester may in particular comprise the following reaction steps (numbers between parentheses also correspond to FIG. 1):
(1) providing a succinate ester or thioester and reacting said ester or thioester with an acetate ester or thioester, thereby forming a 3-oxoadipate ester or thioester;
(2) hydrogenating the 3-oxo group of the 3-oxoadipate ester or thioester thereby forming a 3-hydroxyadipate ester or thioester;
(3) dehydrating the 3-hydroxyadipate ester or thioester thereby forming a 2,3-dehydroadipate ester or thioester; and
(4) hydrogenating of the C—C double bond of the 2,3-dehydroadipate ester or thioester, thereby forming an adipate ester or thioester.

The invention also relates to a method for preparing an intermediate compound, suitable for use in a method for preparing adipic acid, comprising carrying out one or more of said reactions steps 1-4, in the presence of a biocatalyst catalyzing such reaction step.

In an embodiment, the adipate ester or thioester is converted into 5-FVA (5).

If desired, the adipate ester or thioester can be converted into adipic acid. This may be accomplished by hydrolysing the ester bond or thioester bond (7), thereby forming adipic acid or by a transfer reaction, wherein 'the alcohol' or 'thiol' moiety (such as CoA) is transferred from the adipate ester or thioester to an acid different from adipic acid, thereby forming adipic acid and a (thio)ester of the acid different from adipic acid (7). If succinic acid or acetate is used as the different acid, this reaction may be advantageous in that the alcohol or thiol moiety, such as CoA may be recycled. E.g. adipyl-CoA+succinate or acetate may be converted (usually in the presence of a CoA transferase) to form succinyl-CoA or acetyl-CoA+adipic acid. The succinyl-CoA or acetyl-CoA may then be used as a starting compound in a method of the invention.

Adipic acid (or a ester or thioester thereof) may, e.g., be converted into 5-FVA (8).

In an embodiment, 5-FVA, obtained in a method of the invention is converted into 6-ACA (6). Thereafter, 6-ACA may be converted into caprolactam, e.g. in a manner known in the art per se.

In a further embodiment, adipic acid or caprolactam obtained in a method according to the invention is used for the preparation of polyamide.

The term "a" or "an" as used herein is defined as "at least one" unless specified otherwise.

When referring to a noun (e.g. a compound, an additive etc.) in the singular, the plural is meant to be included.

When referring to a compound of which several isomers exist (e.g. a cis and a trans isomer, an R and an S enantiomer), the compound in principle includes all enantiomers, diastereomers and cis/trans isomers of that compound that may be used in the particular method of the invention.

When an enzyme is mentioned with reference to an enzyme class (EC) between brackets, the enzyme class is a class wherein the enzyme is classified or may be classified, on the basis of the Enzyme Nomenclature provided by the Nomenclature Committee of the International Union of Biochemistry and Molecular Biology (NC-IUBMB), which nomenclature may be found at URL: chem-dot-qmul-dot-ac-dot-uk-forward slash-iubmb-forward slash-enzyme-forward slash. Other suitable enzymes that have not (yet) been classified in a specified class but may be classified as such, are meant to be included.

When referred herein to a protein by reference to a accession number, this number in particular is used to refer to a protein having a sequence as found in Uniprot on 11 Mar. 2008, unless specified otherwise.

The term "homologue" is used herein in particular for polynucleotides or polypeptides having a sequence identity of at least 30%, preferably at least 40%, more preferably at least 60%, more preferably at least 65%, more preferably at least 70%, more preferably at least 75%, more preferably at least 80%, in particular at least 85%, more in particular at least 90%, at least 91%, at least 92%, at least 93%, at least 94%, at least 95%, at least 96%, at least 97%, at least 98% or at least 99%. The term homologue is also meant to include nucleic acid sequences (polynucleotide sequences) which differ from another nucleic acid sequence due to the degeneracy of the genetic code and encode the same polypeptide sequence.

Sequence identity or similarity is herein defined as a relationship between two or more polypeptide sequences or two or more nucleic acid sequences, as determined by comparing the sequences. Usually, sequence identities or similarities are compared over the whole length of the sequences, but may however also be compared only for a part of the sequences aligning with each other. In the art, "identity" or "similarity" also means the degree of sequence relatedness between polypeptide sequences or nucleic acid sequences, as the case may be, as determined by the match between such sequences. Preferred methods to determine identity or similarity are designed to give the largest match between the sequences tested. In context of this invention a preferred computer program method to determine identity and similarity between two sequences includes BLASTP and BLASTN (Altschul, S. F. et al., J. Mol. Biol. 1990, 215, 403-410, publicly available from NCBI and other sources (BLAST Manual, Altschul, S., et al., NCBI NLM NIH Bethesda, Md. 20894). Preferred parameters for polypeptide sequence comparison using BLASTP are gap open 10.0, gap extend 0.5, Blosum 62 matrix. Preferred parameters for nucleic acid sequence comparison using BLASTN are gap open 10.0, gap extend 0.5, DNA full matrix (DNA identity matrix).

In a method of the invention, a biocatalyst is used, i.e. at least one reaction step in the method is catalysed by a biological material or moiety derived from a biological source, for instance an organism or a biomolecule derived there from. The biocatalyst may in particular comprise one or more enzymes. The biocatalyst may be used in any form. In an embodiment, one or more enzymes are used isolated from the natural environment (isolated from the organism it has been produced in), for instance as a solution, an emulsion, a dispersion, (a suspension of) freeze-dried cells, a lysate, or immobilised on a support. The use of an enzyme isolated from the organism it originates from may in particular be useful in view of an increased flexibility in adjusting the reaction conditions such that the reaction equilibrium is shifted to the desired side.

In an embodiment, one or more enzymes form part of a living organism (such as living whole cells). The enzymes may perform a catalytic function inside the cell. It is also possible that the enzyme may be secreted into a medium, wherein the cells are present.

Living cells may be growing cells, resting or dormant cells (e.g. spores) or cells in a stationary phase. It is also possible to use an enzyme forming part of a permeabilised cell (i.e. made permeable to a substrate for the enzyme or a precursor for a substrate for the enzyme or enzymes).

A biocatalyst used in a method of the invention may in principle be any organism, or be obtained or derived from any organism. The organism may be an eukaryote, a bacterium or an archea. In particular the organism may be selected from animals (including humans), plants, bacteria, archaea, yeasts and fungi.

Suitable bacteria may in particular be selected amongst the group of *Absidia, Achromobacter, Acinetobacter, Agrobacterium, Aeromonas, Alcaligenes, Arthrobacter, Arzoarcus, Azomonas, Azospirillum, Azotobacter, Bacillus, Beijerinckia, Bradyrhizobium, Burkholderia, Byssochlamys, Citrobacter, Clostridium, Comamonas, Corynebacterium, Deinococcus, Escherichia, Enterobacter, Flavobacterium, Fusobacterium, Gossypium, Klebsiella, Lactobacillus, Listeria, Megasphaera, Micrococcus, Mycobacterium, Norcadia, Porphyromonas, propionibacterium, Pseudomonas, Ralstonia, Rhizobium, Rhodopseudomonas, Rhodospirillum, Rodococcus, Roseburia, Shewanella, Streptomycetes, Xanthomonas, Xylella, Yersinia, Treponema, Vibrio, Streptococcus, Lactococcus, Zymomonas, Staphylococcus, Salmonella, Brucella, Microscilla.*

Suitable eukaryotes can be selected in particular from the group of fungi; metazoan; Viridiplantae (in particular *Arabidopsis* and *Chlamydomonadales*); Diplomonads (in particular *Giardiinae*); Entamoebidae (in particular *Entaboeba*); Euglenozoa (in particular *Euglena*); Pelobiontida (in particular *Mastigamoeba*); and Alveolata (in particular *Cryptosporidium*).

Suitable fungi in particular include fungi and yeasts selected amongst the group of *Rhizopus, Neurospora, Penicillium, Aspergillus, Piromyces, Trichosporon, Candida, Hansenula, Kluyveromyces, Saccharomyces, Rhodotorula, Schizosaccharomyces, Yarrowia* (such as *Yarrowia lypolytica*).

Suitable metazoan in particular include metazoan selected amongst the group of mammals (including human), more in particular selected from the group of Leporidae, Muridae, Suidae, Bovidae, hominidae. A biocatalyst can originate from any part of a metazoan, e.g. liver, pancreas, brain, kidney, heart or other organ. Suitable metazoan may also include in particular *Caenorhabditis* and *Drosophila*.

Organisms which in particular may provide a suitable biocatalyst for a specific reaction step are mentioned below, when describing specific reaction steps of a method of the invention.

It will be clear to the person skilled in the art that use can be made of a naturally occurring biocatalyst (wild type) or a mutant of a naturally occurring biocatalyst with suitable activity in a method according to the invention. Properties of a naturally occurring biocatalyst may be improved by biological techniques known to the skilled person in the art, such as e.g. molecular evolution or rational design. Mutants of wild-type biocatalysts can for example be made by modifying the encoding DNA of an organism capable of acting as a biocatalyst or capable of producing a biocatalytic moiety (such as an enzyme) using mutagenesis techniques known to the person skilled in the art (random mutagenesis, site-directed mutagenesis, directed evolution, gene recombination, etc.). In particular the DNA may be modified such that it encodes an enzyme that differs by at least one amino acid from the wild-type enzyme, so that it encodes an enzyme that comprises one or more amino acid substitutions, deletions and/or insertions compared to the wild-type, or such that the mutants combine sequences of two or more parent enzymes or by effecting the expression of the thus modified DNA in a suitable (host) cell. The latter may be achieved by methods known to the skilled person in the art such as codon optimisation or codon pair optimisation, e.g. based on a method as described in WO 2008/000632.

A mutant biocatalyst may have improved properties, for instance with respect to one or more of the following aspects: selectivity towards the substrate, activity, stability, solvent tolerance, pH profile, temperature profile, substrate profile, susceptibility to inhibition, cofactor utilisation and substrate-affinity. Mutants with improved properties can be identified by applying e.g. suitable high through-put screening or selection methods based on such methods known to the skilled person in the art.

The substrate specificity of enzymes acting on alkyl or alkyl esters or thioesters can be modified. Molecular evolution to create diversity followed by screening for desired mutants and/or rational engineering of substrate binding pockets may be utilised. Techniques to modify the substrate specificity of an enzyme used in a method of the invention may be based on those described in the art. For instance, rational engineering employing structural and sequence information to design specific mutations has been utilised to modify the substrate specificity of the acyl transferase domain 4 from the erythromycin polyketide synthase to accept alternative acyl donors. It has been shown that modifying the proposed substrate binding site resulted in a modified binding pocket able to accommodate alternative substrates resulting in a different product ratio (Reeves, C. D.; Murli, S.; Ashley, G. W.; Piagentini, M.; Hutchinson, C. R.; McDaniel, R. Biochemistry 2001, 40(51), 15464-15470). Both rational design and molecular evolution approaches have been used to alter the substrate specificity of the biocatalyst BM3 resulting in a large number of mutants capable of oxidizing a large variety of different alkenes, cycloalkenes, arenes and heteroarenes instead or in addition to the natural substrate of medium chain fatty acids (e.g. myristic acid) (Peters, M. W.; Meinhold, P.; Glieder, A.; Arnold, F. H. Journal of the American Chemical Society 2003, 125(44), 13442-13450; Appel, D.; Lutz-Wahl, S.; Fischer, P.; Schwaneberg, U.; Schmid, R. D. Journal of Biotechnology 2001, 88(2), 167-171 and references therein).

When referred to a biocatalyst, in particular an enzyme, from a particular source, recombinant biocatalysts, in particular enzymes, originating from a first organism, but actually produced in a (genetically modified) second organism, are specifically meant to be included as biocatalysts, in particular enzymes, from that first organism.

The Preparation of 3-Oxoadipate (Ester or Thioester) ('Reaction 1')

In an embodiment of the invention, 3-oxoadipate (ester or thioester) is prepared from succinate and acetate, which succinate and/or acetate which are usually provided with an activating group, in particular to yield an ester or a thioester, facilitating the reaction.

The 3-oxoadipate (ester of thioester) may be accomplished biocatalytically or chemically, in particular by a 'Claisen condensation', wherein an acetate ester or thioester and a succinate ester or thioester are coupled In a preferred method of the invention, the preparation comprises a biocatalytic reaction in the presence of a biocatalyst capable of catalysing an acyl-group transfer. An enzyme having such catalytic activity may therefore be referred to as an acyltransferase.

In a preferred method an acyl transfer takes place between two acyl thioesters or acyl esters. Preferred acyl thioesters are acetyl-CoA and succinyl-CoA. Preferably, the said biocatalyst is selective towards the said acyl thioesters.

The biocatalyst may in particular comprise an enzyme capable of acyl-group transfer selected from the group of acyltransferases (E.C. 2.3.1), preferably from the group of acetyl-CoA:acetyl-CoA C-acetyltransferases (EC 2.3.1.9), acyl-CoA:acetyl-CoA C-acyltransferases (EC 2.3.1.16) and succinyl-CoA:acetyl-CoA C-succinyltransferases (EC 2.3.1.174, also known as beta-ketoadipyl-CoA thiolases). Acyltransferase activity has for instance been described in beta-oxidation, fatty acid biosynthesis, polyketide biosynthesis, or butanoate metabolism in the KEGG (Kyoto Encyclopedia of Genes and Genomes) database.

An acyltransferase may in particular be an acyltransferase of an organism selected from the group of archae, bacteria and eukaryota.

In particular, the enzyme may originate from a microorganism that is able to degrade organic compounds comprising an aromatic or alicyclic ring structure, in particular a 5, 6 or 7 membered ring structure. The organic compound may optionally comprise one or more heteroatoms in the ring or as a substituent or a part of a substituent. For instance, the organic moiety may be an aromatic compound, in particular an aromatic comprising a six-membered ring. In particular the aromatic compound may be selected from the group of phenylacetate, benzoate, catechol, protocatechuate and gentisate. The organic compound may be a alicyclic compound, in particular a cyclic alcohol, such as cyclohexanol, a cyclic ketone, such as cyclohexanone, or a cycloalkane, such as cyclohexane. The organic compound may be a lactam, such as caprolactam. In an embodiment the enzyme originates from an organism capable of degrading a dicarboxylic acid (usually $C_6$-$C_{10}$), in particular a straight-chain saturated dicarboxylic acid, such as adipic acid.

In a further embodiment, the enzyme originates from an organism capable of synthesizing 3-keto-adipate e.g. as part of a secondary metabolite (e.g. malonomycin) are preferred, for instance, from Streptomycetes (in particular *Streptomyces rimosus*), from *Actinomycres*, from other Actinobacteria or other known secondary metabolite producers.

Preferred microorganism for providing a biocatalyst capable of catalysing the preparation of 3-oxoadipate (ester or thioester) further include *Acinetobacter* (in particular *Acinetobacter* sp. Strain ADP1 and *A. calcoaceticus*), *Agrobacterium* (in particular *A. tumefaciens*), *Alicaligenes* (in particular *Alicaligenes* strains D2 and *A. eutrophus*), *Arthrobacter, Arzoarcus* (in particular *A. evansii*), *Azomonas, Azotobacter, Bacillus* (in particular *B. halodurans*), *Beijerinckia, Bradyrhizobium, Burkholderia, Clostridia* (in particular *C. kluyveri, C. acetobutylicum, C. beijerinckii*), *Comamonas, Corynebacterium* (in particular *C. glutamicum* and *C. aurantiacum*), *E. coli, Enterobacter, Flavobacterium, Megasphera* (in particular *M. elsdenii*), *Norcadia, Pseudomonas* (in particular *P. putida, P. aeruginosa* and *Pseudomonas* sp. strain B13), *Ralstonia* (in particular *R. eutropha*), *Rhizobium, Rhodopseudomonas* (in particular *R. palustris*), *Rodococcus* (in particular *R. erythropolis, R. opacus,* and *Rodococcus* sp strain RHA1), *Aspergillus* (in particular *A. niger*), Euglenozoa (in particular *Euglena gracilis*), *Neurospora* (in particular *N. crassa*), *Penicillium* (in particular *P. chrysogenum*), *Rhodotorula, Saccharomyces, Trichosporon* (in particular *T. cutaneum*).

In a specific embodiment, the biocatalyst comprises an enzyme comprising an amino acid sequence as identified in any of the SEQUENCE ID's 1-13 or a homologue thereof.

The Preparation of 3-Hydroxyadipate (Ester or Thioester) ('Reaction 2')

In an embodiment, 3-hydroxyadipate (ester or thioester) is prepared from 3-oxoadipate (ester or thioester). Usually, the 3-oxoadipate is provided with an activating group, as indicated above.

In principle, the 3-hydroxyadipate (ester or thioester) may be prepared chemically, e.g. by selective hydrogenation of the 3-oxo group in 3-oxo-adipate (ester or thioester).

This reaction may particular be performed in the presence of a biocatalyst, catalysing this reaction step, in particular a biocatalyst that is capable of catalysing the reduction of an oxo group, in particular a carbonyl group to a hydroxy group.

In a specific embodiment, the 3-oxoadipate is present as its thioester with co-enzyme A (hereinafter, the thioester of 3-oxoadipate and co-enzyme A will be referred to as 3-oxoadipyl-CoA).

In a preferred method of the invention, the preparation comprises a biocatalytic reaction in the presence of a biocatalyst capable of catalysing the reduction of a 3-oxoacyl (ester or thioester) to a 3-hydroxyacyl (ester or thioester).

An enzyme having such catalytic activity may therefore be referred to as a 3-hydroxyacyl (ester or thioester) dehydrogenase. An enzyme having such catalytic activity toward the 3-hydroxyacyl CoA-thioester may therefore be referred to as a 3-hydroxyacyl-CoA dehydrogenase. Preferably, the said 3-hydroxyacyl-CoA dehydrogenase is selective towards the substrate 3-oxoadipyl-CoA.

An enzyme capable of catalysing the reduction of 3-oxoacyl (ester or thioester) to a 3-hydroxyacyl (ester or thioester) may in particular be selected from the group of dehydrogenases (E.C. 1.1.1), preferably from the group 3-hydroxyacyl-CoA dehydrogenase (EC 1.1.1.35 and EC 1.1.1.36), 3-hydroxybutanoyl-CoA dehydrogenase (EC 1.1.1.157), 3-hydroxypimeloyl-CoA dehydrogenase (EC 1.1.1.259) and long-chain-3-hydroxyacyl-CoA dehydrogenases (EC 1.1.1.211). The enzymes may use NADH or NADPH as cofactor. 3-Hydroxyacyl-CoA dehydrogenase activity has been described, for example, in fatty acid metabolism, polyketide biosynthesis, polyhydroxyalkanoate metabolism, butanoate metabolism, as well as degradation of aromatic compounds according to the KEGG (Kyoto Encyclopedia of Genes and Genomes) database.

In particular, microorganisms that are able to degrade an organic compound, as identified above (see 'reaction 1'), in particular an aromatic compound, an alicyclic compound or a dicarboxylic acid.

Other preferred organisms for providing a biocatalyst capable of catalysing the preparation of 3-hydroxyadipate (ester or thioester) include: *Acinetobacter* (in particular *Acinetobacter* sp. Strain ADP1 and *A. calcoaceticus*), *Alicaligenes* (in particular *Alicaligenes* strain D2 and *A. eutrophus*), *Arzoarcus* (in particular *A. evansii*), *Bacillus* (in particular *B. halodurans*), *Bordetella* (in particular *B. pertussis*), *Burkholderia* (in particular *B. pseudomallei* and *B. xenovorans*), *Corynebacterium* (in particular *C. glutamicum*, *C. aurantiacum* and *C. efficiens*), *Deinococcus* (in particular *D. radiodurans*), *E. coli*, *Flavobacterium*, *Klebsiella* (in particular *K. pneumonia*), *Pseudomonas* (in particular *P. putida* and *P. fluorescens*), *Rhodopseudomonas* (in particular *R. palustris*), *Rodococcus* (in particular *R. erythropolis*, *R. opacus*, and *Rodococcus* sp strain RHA1), *Aspergillus* (in particular *A. niger*), *Neurospora* (in particular *N. crassa*), *Penicillium* (in particular *P. chrysogenum*), *Saccharomyces* (in particular *S. cerevisiae*).

A suitable organism for providing an enzyme of EC1.1.1.35, acting on 3-ketohexanoyl-CoA may be from any organism including mammals, in particular mammals selected from the group of *Bos taurus*, *Rattus norvegicus*, *Sus scrofa*, and *Homo sapiens*.

At suitable biocatalyst involved in (anaerobic) fatty acid synthesis, polyketide biosynthesis or polyhydroxyalkanoate metabolism may be from any organism, in particular microorganisms including: *Clostridia* (in particular *C. acetobutylicum* and *C. kluyven*), Euglenozoa (in particular *Euglena gracilis*), *Megasphera* (in particular *Megasphera elsdenii*), *Raistonia* (in particular *Raistonia eutropha*), and *Zoogloea* (in particular *Zoogloea ramigera*).

In a specific embodiment, the biocatalyst (catalysing 'reaction 2') comprises an enzyme comprising an amino acid sequence as identified in any of the SEQUENCE ID's 15-26, 29 or a homologue thereof. It is envisaged that in particular an enzyme comprising an amino acid sequence according to SEQUENCE ID 26 may catalyse both 'reaction 2' and 'reaction 3'.

The Preparation of 2,3-Dehydro Adipate (Ester or Thioester) ('Reaction 3')

In an embodiment, 2,3-dehydro adipate (5-carboxy-2-pentenoate) (ester or thioester) is prepared from 3-hydroxyadipate (ester or thioester). Optionally, the 2,3-dehydro adipate and the 3-hydroxyadipate are coupled to a co-enzyme, ACP or another activating group, as indicated above.

In an embodiment of the invention, the 2,3-dehydro adipate (ester or thioester) is prepared by converting 3-hydroxyadipate (ester or thioester) chemically, e.g. by dehydration in a water free environment in the presence of e. g. sulphuric acid.

The 2,3-dehydro adipate may in particular be prepared from 3-hydroxyadipate using at least one biocatalyst.

A preferred biocatalyst is a biocatalyst that is capable of catalysing the dehydration of a 3-hydroxyacyl ester or thioester to a 2-enoyl ester or 2-enoyl thioester thereof.

In a specific embodiment, the 2,3-dehydro adipate is present as its thioester with co-enzyme A (hereinafter, the thioester of 2,3-dehydro adipate and co-enzyme A will be referred to as 5-carboxy-2-pentenoyl-CoA).

In a specific embodiment, the biocatalyst catalyses the dehydration of 3-hydroxyadipyl-CoA to 5-carboxy-2-pentenoyl-CoA.

In particular, the biocatalytic reaction may be carried out in the presence of a biocatalyst capable of catalysing the dehydration of a 3-hydroxyacyl (thio)ester to a 2,3-dehydroacyl thioester.

An enzyme having such catalytic activity may therefore be referred to as a 3-hydroxyacyl (ester or thioester) dehydratase. An enzyme having such catalytic activity toward the 3-hydroxyacyl CoA-thioester may therefore be referred to as a 3-hydroxyacyl-CoA dehydratase. Preferably, the said 3-hydroxyacyl-CoA dehydratase is selective towards the substrate 3-hydroxyadipyl-CoA.

An enzyme capable of catalysing the dehydration of 3-hydroxyacyl (ester or thioester) to a 2,3-dehydroacyl (ester or thioester) may in particular be selected from the group of hydrolyases (E.C. 4.2.1), preferably from the group of preferably from the group of enoyl-CoA hydratases (EC 4.2.1.17), 3-hydroxybutyryl-CoA dehydratases (EC 4.2.1.55) and long-chain-enoyl-CoA hydratases (EC 4.2.1.74). 3-Hydroxyacyl-CoA dehydratase activity has been described, for example, in fatty acid metabolism, polyketide synthesis, or butanoate metabolism, as well as degradation of aromatic compounds according to the KEGG database.

A 3-hydroxyacyl (ester or thioester) dehydratase may be a 3-hydroxyacyl (ester or thioester) dehydratase of an organism selected from the group of archaea, bacteria, and eukaryotes, for instance from the group of yeasts, fungi and mammals.

In particular, microorganisms that are able to degrade an organic compound, as identified above (see 'reaction 1'), in particular an aromatic compound, an alicyclic compound or a dicarboxylic acid, are preferred sources for a biocatalyst catalysing the preparation of 2,3-dehydro adipate (ester or thioester).

Microorganisms capable of degrading an aromatic compound, an alicyclic compound or a dicarboxylic acid include *Acinetobacter* (in particular *Acinetobacter* sp. strain ADP1 and *A. calcoaceticus*), *Alicaligenes* (in particular *Alicaligenes* D2), *Aspergillus* (in particular *A. niger*), *Azoarcus* (in particular *A. evansii*), *Bacillus* (in particular *B. halodurans*), *Corynebacterium* (in particular *C. glutamicum* and *C. aurantiacum*), *E. coli*, *Flavobacterium*, *Neurospora* (in particular *N. crassa*), *Penicillium* (in particular *P. chrysogenum*), *Pseudomonas* (in particular *P. putida* and *P. fluorescens*), *Rhodopseudomonas* (in particular *R. palustris*), *Rhodococcus* (in particular *Rhodococcus* sp strain RHA1).

A preferred organism for providing an enzyme of EC4.2.1.17, acting on 3-hydroxyhexanoyl-CoA includes an organism selected from the group of mammals and microorganisms. A suitable enzyme of EC4.2.1.17 from a mammal may in particular be from a mammal selected from the group of *Bos taurus, Homo sapiens, Rattus norvegicus*, and *Sus scrofa*. A suitable enzyme of EC4.2.1.17 from a microorganism may in particular be from a microorganism selected from the group of *Aeromonas* (in particular *A. caviae*), *Clostridium* (in particular *C. acetobutylicumi*), *Gossypium* (in particular *G. hirsutum*), *Rhodospirillum* (in particular *R. rubrumi*), and *Raistonia* (in particular *Raistonia eutropha*).

Preferred also are microorganisms capable of (anaerobic) fatty acid biosynthesis. Such micro-organisms include *Clostridia*, in particular (*C. acetobutylicum* and *C. kluyven*), Euglenozoa (in particular *Euglena gracilis, Megasphera* (in particular *M. elsdenii*), and *Saccharomyces* (in particular *S. cerevisiae*).

A suitable enzyme may in particular comprise an amino acid sequence according to any of the SEQUENCE ID's 14, 27, 28, 30-41, 92, or a homologue thereof The Preparation of Adipate (Ester or Thioester) from 2,3-Dehydro Adipate (Ester or Thioester) ('Reaction 4')

In an embodiment, adipate (ester or thioester) is prepared from 2,3-dehydro adipate (ester or thioester). Adipate (ester or thioester) may be prepared chemically from 2,3-dehydro adipate (ester or thioester), e.g. by selective hydrogenation of the $C_2$-$C_3$ doublebond, or biocatalytically.

Usually, the 2,3-dehydro adipate is provided with an activating group, as indicated above.

The adipate (ester or thioester) preferably is prepared from 2,3-dehydro adipate (ester or thioester) using at least one biocatalyst, catalysing the hydrogenation of the carbon-carbon double bond of 5-carboxy-2-pentenoate (ester or thioester).

In a preferred method of the invention, the preparation comprises a biocatalytic reaction in the presence of a biocatalyst capable of catalysing the reduction of a cis or a trans 2-enoyl (ester or thioester) to an acyl (ester or thioester). The biocatalyst may use a range of electron donors, for example, an electron donor selected from the group of NADH, NADPH, $FADH_2$ and reduced ferredoxin. The electrons may be transferred directly from the electron donor to the biocatalyst, or, alternatively, mediated, in particular by the so-called electron transfer flavoprotein (ETF). An enzyme having such catalytic activity may therefore be referred to as a 2-enoyl (ester or thioester) reductase (ER). An enzyme having such catalytic activity toward the 2-enoyl CoA-thioester may therefore be referred to as a 2-enoyl-CoA reductase. Preferably, the said 2-enoyl-CoA reductase is selective towards the substrate 2,3-dehydroadipyl-CoA.

An enzyme capable of catalysing the reduction of 2-enoyl (ester or thioester) may in particular be selected from the group of oxidoreductases (EC 1.3.1 and EC 1.3.99), preferably from the group of enoyl-CoA reductases EC 1.3.1.8, EC 1.3.1.38 and EC 1.3.1.44, from the group of enoyl-[acyl-carrier-protein] reductases EC 1.3.1.9, EC 1.3.1.10 and EC 1.3.1.39, and from the group butyryl-CoA dehydrogenase (EC 1.3.99.2), acyl-CoA dehydrogenase (1.3.99.3) and long-chain-acyl-CoA dehydrogenase (EC 1.3.99.13). Trans-2-enoyl (ester or thioester) reductase activity has been described, for example, in fatty acid metabolism, polyketide synthesis, butanoate metabolism and mitochondrial fatty acid biosynthesis according to the KEGG database.

An 2-enoyl (ester or thioester) reductase may in principle be obtained or derived from any organism. In particular the organism can be selected from bacteria, archaea, or eukariotes, such as from the group of yeasts, fungi, protists, plants and animals (including human).

In an embodiment, the organism may be selected from the following bacteria: *E. coli, Vibrio, Bacillus* (in particular *B. subtilis*), *Clostridia* (in particular *C. kluyveri, C. acetobutylicum, C. beijerinckii* and *C. perfringens*), *Streptomyces* (in particular *S. coelicolor* and *S. avermitilis*), *Pseudomonas* (in particular *P. putida* and *P. aeruginosa*), *Shewanella, Xanthomonas, Xylella, Yersinia, Treponema* (in particular *T. denticola*), *Aeromonas* (in particular *Aeromonas hydrophila*), *Microscilla* (in particular *Microscilla marina*), *Megasphera* (in particular *Megasphera elsdenii*), *Deinococcus* (in particular *Deinococcus radiourans*), *Yarrowia* (in particular *Y. lypolytica*) and *Eubacterium* (in particular *E. pyruvativorans*).

In an embodiment an 2-enoyl (ester or thioester) reductase is from an organism selected from the group of Euglenozoa, in particular *Euglena gracilis*)

In an embodiment an 2-enoyl (ester or thioester) reductase is from an organism selected from the group of *Saccharomyces* (in particular *S. cerevisiae*), *Kluyveromyces* (in particular *K. lactis*), *Schizosaccharomyces* (in particular *S. pombe*), *Candida* (in particular *C. tropicalis*)

In an embodiment an 2-enoyl (ester or thioester) reductase is from an organism selected from the group of *Aspergillus* (in particular *A. niger* and *A. nidulans*), and *Penicillium* (in particular *P. chrysogenum*).

In an embodiment an 2-enoyl (ester or thioester) reductase is from an organism selected from the group of *Arabidopsis* (in particular *A. thaliana*).

In an embodiment an 2-enoyl (ester or thioester) reductase is from an organism selected from the group of *Homo sapiens, Rattus norvegicus, Bos Taurus, Cavia* sp., *Caenorhabditis elegans*, and *Drosophila melanogaster.*

A suitable enzyme may in particular comprise an amino acid sequence according to any of the SEQUENCE ID's 42-67, 94, 96, 98, 100, 105, 107, 109, 111, 113, or a homologue thereof, in particular an amino acid sequence according to any of the SEQUENCE ID's 60, 63, 96, 100 or a homologue thereof. Exemplary nucleotide sequences encoding a suitable enzyme for catalysing 'reaction 4' are represented by 2-enoyl (ester or thioester) reductase 93, 95, 97, 99, 104, 106, 108, 110 and 112.

In an advantageous embodiment, in addition to the 2-enoyl (ester or thioester) reductase an ETF is used, which may be beneficial to the activity of said reductase. Such ETF may be obtained or derived from an organism from which a reductase can be obtained or derived, as identified above. In particular it may be obtained or derived from an organism of the same genus, more in particular of the same species, as the reductase that is used. Specific ETF's comprise a amino acid sequences represented by SEQUENCE ID's 102, 103, 115, 116. SEQUENCE ID's 101 and 114 represent nucleotide sequences encoding a specific ETF. Usually, such ETFs comprise two subunits (etfA and etfB) encoded by two different genes. These are generally used together to make the ETF protein active. E.g. the following combinations could be used: Sequence ID 102 with Sequence ID 103 or Sequence ID 116 with Sequence ID 115. The skilled person will be able to select other suitable ETF combinations, known in the art per se.

In an embodiment of the invention a biocatalyst not per se having a desired activity or substrate specificity may be modified by methods known in the art, e.g. by rational design or molecular evolution to create mutants able to catalyse the conversion of 2,3-dehydro adipate (ester or thioester) to adipate (ester or thioester) at a desirable rate or selectivity. Biocatalysts having activity with 2-enoyl-CoA derivatives with a chain length of 6, in particular such biocatalysts from *C. kluyveri*, *Bos taurus*, *Euglena gracilis*, *Cavia* sp., *S. cerevisiae*, *C. tropicalis*, *Homo sapiens*, and *E. pyruvativorans* are preferred.

The Preparation of Adipic Acid ('Reaction 7')

In accordance with the invention an adipate ester or thioester may be used to prepare adipic acid, by hydrolysis of the ester or thioester bond. This may be accomplished chemically, e.g. by chemical hydrolysis in the presence of acid or base or biocatalytically.

In a preferred method of the invention, the preparation comprises a biocatalytic reaction in the presence of a biocatalyst capable of catalysing the hydrolysis of an acyl (thio)ester.

An enzyme having such catalytic activity may therefore be referred to as an acyl (thio)ester hydrolase. An enzyme having such catalytic activity toward the acyl-CoA thioester may therefore be referred to as an acyl-CoA hydrolase. Preferably, the said acyl-CoA hydrolase is selective towards the substrate adipyl-CoA.

An enzyme capable of catalysing the hydrolysing an acyl (thio)ester may in particular be selected from the group of hydrolases (EC 3.1.2), preferably from the group of acyl-CoA hydrolase (EC 3.1.2.20), acetyl-CoA hydrolase (EC 3.1.2.1), long-chain fatty-acyl-CoA hydrolase (EC 3.1.2.2), succinyl-CoA hydrolase (EC 3.1.2.3) and acyl-[acyl-carrier-protein]-hydrolase (EC 3.1.2.14).

The biocatalyst may comprise an enzyme originating from any organism, including archaea, bacteria or eukaryotes.

In particular, the biocatalyst may comprise an enzyme of a bacterium selected from the group of *E. coli*, *Brucella*, (in particular *Brucella melitensis*), *Agrobacterium* (in particular *A. tumefaciens*), *Xanthomonas*, *Sinorhizobium* (in particular *Sinorhizobium meliloti*), *Mesorhizobium* (in particular *Mesorhizobium loti*), *Vibrio*, *Streptomyces* (in particular *S. coelicolor* and *S. avermitilis*), *Rhodopseudomonas* (in particular *Rhodopseudomonas palustris*), *Xylella*, *Yersinia*, *Pseudomonas* (in particular *P. putida* and *P. aeruginosa*), *Shewanella*, *Shigella*, *Salmonella*, *Corynebacterium*, *Mycobacterium*, *Hyphomonas* (in particular *Hyphomonas neptunium*) and *Propionibacterium*.

A suitable biocatalyst may in particular be found in a yeast selected from the group of *Saccharomyces* (in particular *Saccharomyces cerevisiae*) and *Kluyveromyces* (in particular *K. lactis*).

A suitable biocatalyst may in particular be found in a fungus selected from the group of *Aspergillus* (in particular *A. niger*, *A. fumigatus* and *A. nidulans*) and *Penicillium* (in particular *P. chrysogenum*).

In a further embodiment, the organism is selected from the group of *Arabidopsis* (in particular *A. thaliana*), Muridae (in particular *Rattus norvegicus*, *Mus musculus*), Bovidae (in particular *Bos taurus*, *Ovis aries*), *Homo sapiens*, and *Caenorhabditis* (in particular *Caenorhabditis elegans*).

In an embodiment of the invention a biocatalysts not per se having the desired activity or substrate specificity may be modified by methods known in the art, e.g. by rational design or molecular evolution, to create mutants able to efficiently convert an adipate ester or thioester to adipate. A biocatalyst having initial activity with a acyl-CoA derivative of a C4-C8 acid, preferably including dicarboxylic acids, are preferred. For instance a mutant may be created based on an acyl-CoA-thioesterase from *Mus musculus* (e.g. as given in Seq ID 73).

In a specific embodiment of the invention, the preparation comprises a biocatalytic reaction in the presence of a biocatalyst capable of catalysing the transfer of an activating group, in particular an ester or thio-ester, most particular CoA.

An enzyme having such catalytic activity may therefore be referred to as a CoA transferase. Preferably, the said CoA transferase is selective towards a dicarboxylic-CoA as CoA-donating substrate. More preferably, the said dicarboxylic-CoA is adipyl-CoA. Preferably, the said CoA transferase is selective towards or acetate as the CoA-accepting substrate.

An enzyme capable of catalysing the transfer of a CoA group may in particular be selected from the group of CoA transferases (EC 2.8.3), preferably from the group of dicarboxylic acid-CoA:dicarboxylic acid CoA transferase, adipate:succinyl-CoA CoA transferase, 3-oxoacid CoA-transferase (EC 2.8.3.5), 3-oxoadipate CoA-transferase (EC 2.8.3.6) and acetate CoA-transferase (EC 2.8.3.8).

A CoA transferase may in principle be obtained or derived from any organism. The organism may be bacteria, archaea or eukaryotes. In particular, organisms that are able to degrade dicarboxylic acids, in particular adipic acid, are preferred.

The organism may in particular be a bacterium selected from the group of *Acinetobacter* (in particular *Acinetobacter* strain ADP1, *A. calcoaceticus*), *Clostridium* (in particular *C. kluyveri*, *C. acetobutylicum* or *C. beijerinckii*), *Pseudomonas* (in particular *P. putida* and *P. fluorescens*), *Agrobacterium*, *Alcaligenes*, *Athrobacter*, *Azomonas*, *Azospirillum*, *Azotobacter*, *Bacillus*, *Beijerinckia*, *Bradyrhizobium*, *Burkholderia*, *Comamonas*, *Corynebacterium*, *Norcadia*, *Rhizobium*, *Rhodotorula*, *Rodococcus*, *Trichosporon*, and *Roseburia* sp., The organism may in particular be a yeast or fungus selected from the group of *Aspergillus* (in particular *A. niger*), *Penicillium* (in particular *P. chrysogenum*), and *Neurospora*.

In particular, a suitable CoA transferase may be obtained or derived from a species from the family of Hominidea, more in particular from *Homo sapiens*.

A suitable enzyme for reaction 7 may in particular comprise an amino acid sequence according to any of the SEQUENCE ID's 68-73, 85, 116, 117, 119-124 or a homologue thereof.

The preparation of adipic acid from a thioester may in particular be catalysed by a biocatalyst comprising an acyl-CoA hydrolase comprising an amino acid sequence according to any of the SEQUENCE ID's 68-73, 117, 119 or a homologue thereof.

The preparation of adipic acid from a thioester may in particular be catalysed by a biocatalyst comprising a CoA transferase comprising an amino acid sequence according to any of the SEQUENCE ID's 85, 121, 122, 123, 124, 125, 126 or a homologue thereof.

The CoA-transferase can be encoded by a single gene or by more than one gene. For instance, some CoA-transferases comprise two subunits encoded by two different genes. These are generally used together to make the CoA transferase protein active. E.g. the following combinations could be used: Sequence ID 121 with Sequence ID 122, or Sequence ID 125 with Sequence ID 126.

The Preparation of 5-FVA from an Adipate Ester or an Adipate Thioester ('Reaction 5')

In an embodiment, 5-formylpentanoate (5-FVA) is prepared from an adipate ester or an adipate thioester. This may be done chemically, or biocatalytically. The adipate may in particular be coupled to CoA or another activating group, as indicated above.

In particular, the present invention also provides a method for preparing 5-FVA from an adipate ester or an adipate thioester, in particular a method for preparing 5-FVA from adipyl-CoA thioester, in the presence of a biocatalyst capable of catalysing the reduction of an acyl ester or thioester to an aldehyde.

An enzyme having such catalytic activity may therefore be referred to as an aldehyde dehydrogenase. An enzyme having such catalytic activity toward an acyl ester or acyl thioester—for instance acyl-CoA thioester—may therefore be referred to as an aldehyde dehydrogenase (acetylating). Preferably, the biocatalyst—comprising an aldehyde dehydrogenase (acetylating)—is selective towards the substrate adipate-ester or thioester.

An enzyme capable of catalysing the reduction of an acyl (thio)ester may in particular be selected from the group of oxidoreductases (EC 1.2.1), preferably from the group of aldehyde dehydrogenases (acetylating) (EC 1.2.1.10), fatty acyl-CoA reductases (EC 1.2.1.42), long-chain-fatty-acyl-CoA reductases (EC 1.2.1.50), butanal dehydrogenases (EC 1.2.1.57) and succinate semialdehyde dehydrogenases (acetylating) (see e.g. Sohling et al. 1996. J Bacteriol. 178: 871-880)

An aldehyde dehydrogenase may in principle be obtained or derived from any organism. It is understood that the enzyme can also be obtained from metagenomic sources by direct isolation of the encoding nucleic acid and subsequent determination of activity in a heterologous host or by sequence homology found in the metagenomic DNA. The organism may be bacteria, archaea or eukaryotes. In particular the organism can be selected from bacteria, more in particular amongst the group of *E. coli*, *Clostridium* (in particular *C. kluyveri*, *C. beijerinckii*, *C. acetobutylicum*, *C. botylicum*, *C. tetani*, *C. perfringens* and *C. novyi*), *Porphyromonas gingivalis*, *Listeria*, *Propionibacterium* (in particular *P. freudenreichii*), *Enterococcus*, *Fusobacterium*, *Lactobacillus* (in particular *L. lactis*), *Bacillus* (in particular *B. thuringiensis*), *Burkholderia* (in particular *B. thailandensis* and *B. mallei*), *Pseudomonas* (in particular *P. putida*), *Rhodococcus* (in particular R. sp. RHA1) and *Salmonella* (in particular *S. typhimurium*). The organism can also be selected from eukaryotes, more in particular amongst the group of *Giardia* (in particular *G. lamblia*), *Entamoeba* (in particular *E. Histolytica*), *Mastigamoeba balamuthi*, *Chlamydomonas reinhardtii*, *Polytomella*, *Piromyces*, *Cryptosporidium*, and *Spironucleus barkhanus*.

A suitable dehydrogenase, may in particular comprise an amino acid sequence according to any of the SEQUENCE ID's 74-81, 139-148, or a homologue thereof.

In an embodiment of the invention a biocatalyst not per se having the desired activity or substrate specificity may be modified by methods known in the art, e.g. by rational design or molecular evolution, to create mutants able to convert adipate ester or thioester to 5-FVA. Biocatalysts having acylating aldehyde dehydrogenase activity with acyl-CoA derivatives with a chain length of 4-8, including but not limited to biocatalysts such as succinate semialdehyde dehydrogenase (acetylating) from *C. kluyveri* (Sequence ID 74) or *P. gingivialis* (Sequence ID 75) and butylaldehyde dehydrogenase (acetylating) from *C. acetobutylicum* (Sequence ID 80, 81) or *Propionibacterium freudenreichii* (Sequence ID 79) are preferred.

The Preparation of 5-FVA from Adipic Acid ('Reaction 8')

In accordance with the invention adipic acid may be used to prepare 5-FVA, by reduction of one of the carboxylic acid groups. This may be accomplished chemically, e.g. by selective chemical reduction optionally including protection of one carboxylic acid group or biocatalytically. In a preferred method of the invention, the preparation comprises a biocatalytic reaction in the presence of a biocatalyst capable of catalysing the reduction a carboxylic acid. The biocatalyst may use NADH or NADPH as electron donor.

An enzyme having such catalytic activity may therefore be referred to as an aldehyde dehydrogenase. Preferably, the said aldehyde dehydrogenase is selective towards the substrate adipate.

An enzyme capable of catalysing the reduction of a carboxylic acid may in particular be selected from the group of oxidoreductases (EC 1.2.1), preferably from the group of aldehyde dehydrogenase (EC 1.2.1.3, EC 1.2.1.4 and EC 1.2.1.5), malonate-semialdehyde dehydrogenase (EC 1.2.1.15), succinate-semialdehyde dehydrogenase (EC 1.2.1.16 and EC 1.2.1.24); glutarate-semialdehyde dehydrogenase (EC 1.2.1.20), aminoadipate semialdehyde dehydrogenase (EC 1.2.1.31), adipate semialdehyde dehydrogenase (EC 1.2.1.63), which may also be referred to as 6-oxohexanoate dehydrogenase. Adipate semialdehyde dehydrogenase activity has been described, for example, in the caprolactam degradation pathway in the KEGG database. In particular a 6-oxohexanoate dehydrogenase may be used. Examples of 6-oxohexanoate dehydrogenases are enzymes comprising a sequence as represented by SEQUENCE ID 127, 128 or a homologue thereof.

An aldehyde dehydrogenase may in principle be obtained or derived from any organism. The organism may be prokaryotic or eukaryotic. In particular the organism can be selected from bacteria, archaea, yeasts, fungi, protists, plants and animals (including human).

In an embodiment the bacterium is selected from the group of *Acinetobacter* (in particular *Acinetobacter* sp. NCIMB9871), *Ralstonia*, *Bordetella*, *Burkholderia*, *Methylobacterium*, *Xanthobacter*, *Sinorhizobium*, *Rhizobium*, *Nitrobacter*, *Brucella* (in particular *B. melitensis*), *Pseudomonas*, *Agrobacterium* (in particular *Agrobacterium tumefaciens*), *Bacillus*, *Listeria*, *Alcaligenes*, *Corynebacterium*, and *Flavobacterium*.

In an embodiment the organism is selected from the group of yeasts and fungi, in particular from the group of *Aspergillus* (in particular *A. niger* and *A. nidulans*) and *Penicillium* (in particular *P. chrysogenum*)

In an embodiment, the organism is a plant, in particular *Arabidopsis*, more in particular *A. thaliana*.

The Preparation of 6-ACA ('Reaction 6')

In an embodiment of the invention, 5-FVA is used to prepare 6-ACA.

In an embodiment, 6-ACA is obtained by hydrogenation over $PtO_2$ of 6-oximocaproic acid, prepared by reaction of 5-FVA and hydroxylamine. (see e.g. F. O. Ayorinde, E. Y. Nana, P. D. Nicely, A. S. Woods, E. O. Price, C. P. Nwaonicha *J. Am. Oil Chem. Soc.* 1997, 74, 531-538 for synthesis of the homologous 12-aminododecanoic acid).

6-ACA can be prepared in high yield by reductive amination of 5-FVA with ammonia over a hydrogenation catalyst, for example Ni on SiO2/Al2O3 support, as described for 9-aminononanoic acid (9-aminopelargonic acid) and 12-aminododecanoic acid (12-aminolauric acid) in EP-A 628 535 or DE 4 322 065.

In a further embodiment 6-ACA is biocatalytically prepared. In a preferred method, the preparation of 6-ACA from 5-FVA comprises an enzymatic reaction in the presence of an enzyme capable of catalysing a transamination reaction in the presence of an amino donor, selected from the group of aminotransferases (E.C. 2.6.1).

In general, a suitable aminotransferase has 6-ACA 6-aminotransferase activity, capable of catalysing the conversion of 5-FVA into 6-ACA.

The aminotransferase may in particular be selected amongst aminotransferases from a mammal; *Mercurialis*, in particular *Mercurialis perennis*, more in particular shoots of *Mercurialis perennis*; *Asplenium*, more in particular *Asplenium unilaterale* or *Asplenium septentrionale*; *Ceratonia*, more in particular *Ceratonia siliqua*; *Rhodobacter*, in particular *Rhodobacter sphaeroides*, *Staphylococcus*, in particular *Staphylococcus aureus*; *Vibrio*, in particular *Vibrio fluvialis*; *Pseudomonas*, in particular *Pseudomonas aeruginosa*; *Rhodopseusomonas*; *Bacillus*, in particular *Bacillus weihenstephanensis* and *Bacillus subtilis*; *Legionella*; *Nitrosomas*; *Neisseria*; or yeast, in particular *Saccharomyces cerevisiae*.

In case the enzyme is of a mammal, it may in particular originate from mammalian kidney, from mammalian liver, from mammalian heart or from mammalian brain. For instance a suitable enzyme may be selected amongst the group of β-aminoisobutyrate:α-ketoglutarate aminotransferase from mammalian kidney, in particular β-aminoisobutyrate:α-ketoglutarate aminotransferase from hog kidney; β-alanine aminotransferase from mammalian liver, in particular β-alanine aminotransferase from rabbit liver; aspartate aminotransferase from mammalian heart; in particular aspartate aminotransferase from pig heart; 4-amino-butyrate aminotransferase from mammalian liver, in particular 4-amino-butyrate aminotransferase from pig liver; 4-aminobutyrate aminotransferase from mammalian brain, in particular 4-aminobutyrate aminotransferase from human, pig, or rat brain; α-ketoadipate-glutamate aminotransferase from *Neurospora*, in particular α-ketoadipate:glutamate aminotransferase from *Neurospora crassa*; 4-amino-butyrate aminotransferase from *E. coli*, or α-aminoadipate aminotransferase from *Thermus*, in particular α-aminoadipate aminotransferase from *Thermus thermophilus*, and 5-aminovalerate aminotransferase from *Clostridium* in particular from *Clostridium aminovalericum*. A suitable 2-aminoadipate aminotransferase may e.g. be provided by *Pyrobaculum islandicum*.

In a specific embodiment, an aminotransferase is used comprising an amino acid sequence according to Sequence ID 82, Sequence ID 83, Sequence ID 84, Sequence ID 134, Sequence ID 136, Sequence 138, or a homologue of any of these sequences. Sequence ID's 86 (wild-type) and 88 (codon optimised) represent sequence encoding an enzyme represented by Sequence ID 82 (=87). Sequence ID's 89 (wild-type) and 91 (codon optimised) represent sequence encoding an enzyme represented by Sequence ID 83 (=90). Sequence ID 133, Sequence ID 135, Sequence 137 represent encoding sequences for Sequence ID 134, Sequence ID 136, Sequence 138, respectively.

In particular, the amino donor can be selected from the group of ammonia, ammonium ions, amines and amino acids. Suitable amines are primary amines and secondary amines. The amino acid may have a D- or L-configuration. Examples of amino donors are alanine, glutamate, isopropylamine, 2-aminobutane, 2-aminoheptane, phenylmethanamine, 1-phenyl-1-aminoethane, glutamine, tyrosine, phenylalanine, aspartate, β-aminoisobutyrate, β-alanine, 4-aminobutyrate, and α-aminoadipate.

In a further preferred embodiment, the method for preparing 6-ACA comprises a biocatalytic reaction in the presence of an enzyme capable of catalysing a reductive amination reaction in the presence of an ammonia source, selected from the group of oxidoreductases acting on the CH—NH$_2$ group of donors (EC 1.4), in particular from the group of amino acid dehydrogenases (E.C. 1.4.1). In general, a suitable amino acid dehydrogenase has 6-aminocaproic acid 6-dehydrogenase activity, catalysing the conversion of 5-FVA into 6-ACA or has α-aminopimelate 2-dehydrogenase activity, catalysing the conversion of AKP into AAP. In particular a suitable amino acid dehydrogenase be selected amongst the group of diaminopimelate dehydrogenases (EC 1.4.1.16), lysine 6-dehydrogenases (EC 1.4.1.18), glutamate dehydrogenases (EC 1.4.1.3; EC 1.4.1.4), and leucine dehydrogenases (EC 1.4.1.9).

In an embodiment, an amino acid dehydrogenase may be selected amongst an amino acid dehydrogenases classified as glutamate dehydrogenases acting with NAD or NADP as acceptor (EC 1.4.1.3), glutamate dehydrogenases acting with NADP as acceptor (EC 1.4.1.4), leucine dehydrogenases (EC 1.4.1.9), diaminopimelate dehydrogenases (EC 1.4.1.16), and lysine 6-dehydrogenases (EC 1.4.1.18).

An amino acid dehydrogenase may in particular originate from an organism selected from the group of *Corynebacterium*, in particular *Corynebacterium glutamicum*; *Proteus*, in particular *Proteus vulgaris*; *Agrobacterium*, in particular *Agrobacterium tumefaciens*; *Geobacillus*, in particular *Geobacillus stearothermophilus*; *Acinetobacter*, in particular *Acinetobacter* sp. ADP1; *Ralstonia*, in particular *Ralstonia solanacearum*; *Salmonella*, in particular *Salmonella typhimurium*; *Saccharomyces*, in particular *Saccharomyces cerevisiae*; *Brevibacterium*, in particular *Brevibacterium flavum*; and *Bacillus*, in particular *Bacillus sphaericus*, *Bacillus cereus* or *Bacillus subtilis*. For instance a suitable amino acid dehydrogenase may be selected amongst diaminopimelate dehydrogenases from *Bacillus*, in particular *Bacillus sphaericus*; diaminopimelate dehydrogenases from *Brevibacterium* sp.; diaminopimelate dehydrogenases from *Corynebacterium*, in particular diaminopimelate dehydrogenases from *Corynebacterium glutamicum*; diaminopimelate dehydrogenases from *Proteus*, in particular diaminopimelate dehydrogenase from *Proteus vulgaris*; lysine 6-dehydrogenases from *Agrobacterium*, in particular *Agrobacterium tumefaciens*, lysine 6-dehydrogenases from *Geobacillus*, in particular from *Geobacillus stearothermophilus*; glutamate dehydrogenases acting with NADH or NADPH as cofactor (EC 1.4.1.3) from *Acinetobacter*, in particular glutamate dehydrogenases from *Acinetobacter* sp. ADP1; glutamate dehydrogenases (EC 1.4.1.3) from *Ralstonia*, in particular glutamate dehydrogenases from *Ralstonia solanacearum*; glutamate dehydrogenases acting with NADPH as cofactor (EC 1.4.1.4) from *Salmonella*, in particular glutamate dehydrogenases from *Salmonella typhimurium*; glutamate dehydrogenases (EC 1.4.1.4) from *Saccharomyces*, in particular glutamate dehydrogenases from *Saccharomyces cerevisiae*; glutamate dehydrogenases (EC 1.4.1.4) from *Brevibacterium*, in particular glutamate dehydrogenases from *Brevibacterium flavum*; and leucine dehydrogenases from *Bacillus*, in particular leucine dehydrogenases from *Bacillus cereus* or *Bacillus subtilis*.

In an embodiment, 6-ACA prepared in a method of the invention is used for preparing caprolactam. Such method comprises cyclising the 6 amino-caproic acid, optionally in the presence of a biocatalyst.

Reaction conditions for any biocatalytic step in the context of the present invention may be chosen depending upon known conditions for the biocatalyst, in particular the enzyme, the information disclosed herein and optionally some routine experimentation.

In principle, the pH of the reaction medium used may be chosen within wide limits, as long as the biocatalyst is active under the pH conditions. Alkaline, neutral or acidic conditions may be used, depending on the biocatalyst and other factors. In case the method includes the use of a micro-organism, e.g. for expressing an enzyme catalysing a method of the invention, the pH is selected such that the micro-organism is capable of performing its intended function or functions. The pH may in particular be chosen within the range of four pH units below neutral pH and two pH units above neutral pH, i.e. between pH 3 and pH 9 in case of an essentially aqueous system at 25° C. A system is considered aqueous if water is the only solvent or the predominant solvent (>50 wt. %, in particular >90 wt. %, based on total liquids), wherein e.g. a minor amount (<50 wt. %, in particular <10 wt. %, based on total liquids) of alcohol or another solvent may be dissolved (e.g. as a carbon source) in such a concentration that micro-organisms which may be present remain active. In particular in case a yeast and/or a fungus is used, acidic conditions may be preferred, in particular the pH may be in the range of pH 3 to pH 8, based on an essentially aqueous system at 25° C. If desired, the pH may be adjusted using an acid and/or a base or buffered with a suitable combination of an acid and a base.

In principle, the incubation conditions can be chosen within wide limits as long as the biocatalyst shows sufficient activity and/or growth. This includes aerobic, micro-aerobic, oxygen limited and anaerobic conditions.

Anaerobic conditions are herein defined as conditions without any oxygen or in which substantially no oxygen is consumed by the biocatalyst, in particular a micro-organism, and usually corresponds to an oxygen consumption of less than 5 mmol/l·h, in particular to an oxygen consumption of less than 2.5 mmol/l·h, or less than 1 mmol/l·h.

Aerobic conditions are conditions in which a sufficient level of oxygen for unrestricted growth is dissolved in the medium, able to support a rate of oxygen consumption of at least 10 mmol/l·h, more preferably more than 20 mmol/l·h, even more preferably more than 50 mmol/l·h, and most preferably more than 100 mmol/l·h.

Oxygen-limited conditions are defined as conditions in which the oxygen consumption is limited by the oxygen transfer from the gas to the liquid. The lower limit for oxygen-limited conditions is determined by the upper limit for anaerobic conditions, i.e. usually at least 1 mmol/l·h, and in particular at least 2.5 mmol/l·h, or at least 5 mmol/l·h. The upper limit for oxygen-limited conditions is determined by the lower limit for aerobic conditions, i.e. less than 100 mmol/l·h, less than 50 mmol/l·h, less than 20 mmol/l·h, or less than to 10 mmol/l·h.

Whether conditions are aerobic, anaerobic or oxygen limited is dependent on the conditions under which the method is carried out, in particular by the amount and composition of ingoing gas flow, the actual mixing/mass transfer properties of the equipment used, the type of micro-organism used and the micro-organism density.

In principle, the temperature used is not critical, as long as the biocatalyst, in particular the enzyme, shows substantial activity. Generally, the temperature may be at least 0° C., in particular at least 15° C., more in particular at least 20° C. A desired maximum temperature depends upon the biocatalyst. In general such maximum temperature is known in the art, e.g. indicated in a product data sheet in case of a commercially available biocatalyst, or can be determined routinely based on common general knowledge and the information disclosed herein. The temperature is usually 90° C. or less, preferably 70° C. or less, in particular 50° C. or less, more in particular or 40° C. or less.

Further, solvents, additional reagents and further aids, e.g. cofactors (for instance FAD/FADH and/or NAD/NADH cofactor) may be chosen based on known reaction principles, to accomplish or accelerate a specific reaction and/or measures may be taken to shift the equilibrium to the desired side. In particular if a biocatalytic reaction is performed outside a host organism, a reaction medium comprising an organic solvent may be used in a high concentration (e.g. more than 50%, or more than 90 wt. %), in case an enzyme is used that retains sufficient activity in such a medium.

Succinate (ester or thioester) and acetate (ester or thioester) used in a method of the invention may in principle be obtained in any way.

Succinate is, e.g. naturally formed as an intermediate of the citric acid cycle (Krebs cycle) or an end product in cellular metabolism. Thus, it may be obtained from a renewable carbon source by using a suitable biocatalyst. Biocatalysts, in particular microorganisms, can be used for producing succinate from a suitable carbon source. The microorganism can be a prokaryote or a eukaryote. The microorganism may be recombinant or wild type.

In a recombinant microorganism, the metabolism may be altered to increase the yield and productivity of succinate on a suitable carbon source. Methods for increasing succinate production have been described for prokaryotes in Song and Lee, Enzyme and Microbial Technology, 2006, 39: 352-361. Succinate may also be produced in a eukaryote. In addition and alternatively, adaptive evolutionary can be applied, such as described in US application 2007/111294.

Succinate ester or thioester can be obtained from succinate in any way. In particular, succinate ester or thioester can be obtained from succinate by using a biocatalyst. In particular, succinyl-CoA can be obtained from succinate by using a biocatalyst comprising an enzyme selected from the group of acid thiol ligase (EC 6.2.1), preferably from the group of succinyl-CoA synthase (EC 6.2.1.4 and EC 6.2.1.5). In addition or alternatively, succinyl-CoA can be obtained from succinate by using a biocatalyst comprising an enzyme selected from the group of CoA transferases (EC 2.8.3) as specified for reaction 7.

Succinate ester or thioester can also be obtained from molecules other than succinate in any way. In particular, succinyl-CoA can be obtained from 2-oxoglutarate using a biocatalyst comprising a 2-oxoglutarate dehydrogenase complex. 2-Oxoglutarate dehydrogenase complex is a multi-enzyme complex participating in the TCA cycle, known to person skilled in the art. In addition or alternatively, succinyl-CoA can be obtained from 2-oxoglutarate using a biocatalyst comprising a 2-oxoglutarate:ferredoxin oxidoreductase (EC 1.2.7.3).

Acetate is a natural intermediate or end product in cellular metabolism. Thus, it may be obtained from a renewable carbon source by using a suitable biocatalyst. Biocatalysts, in particular microorganisms, can be used for producing succinate from a suitable carbon source. The microorganism can be a prokaryote or a eukaryote. The microorganism may be recombinant or wild type.

Acetate ester or thioester can be obtained from acetate in any way. In particular, acetyl-CoA can be obtained from acetate by using a biocatalyst comprising an enzyme selected from the group of acid thiol ligase (EC 6.2.1), preferably acetyl-CoA synthase (EC 6.2.1.1 and EC 6.2.1.13). In addition or alternatively, acetyl-CoA can be obtained from acetate using a biocatalyst comprising of an enzyme selected from the group of CoA transferases (EC 2.8.3) as specified for reaction 7.

Acetate ester or thioester can also be obtained from molecules other than acetate in any way. In particular, acetyl-CoA can be obtained from pyruvate using a biocatalyst comprising an enzyme selected from the group of pyruvate dehydrogenase complex, pyruvate dehydrogenase (NADP+) (EC 1.2.1.51), pyruvate formate lyase (EC 2.3.1.54) or a biocatalyst or enzyme effectively converting pyruvate to acetyl-CoA. Pyruvate dehydrogenase complex is a multi-enzyme complex converting pyruvate into acetyl-CoA, known to person skilled in the art.

Acetyl-CoA can also be obtained from acetaldehyde using a biocatalyst comprising an enzyme selected from the group of oxidoreductases (EC 1.2.1), preferably from the group of aldehyde dehydrogenases (acetylating) (EC 1.2.1.10), fatty acyl-CoA reductases (EC 1.2.1.42), butanal dehydrogenases (EC 1.2.1.57) and succinate semialdehyde dehydrogenases (acetylating) (as described in Sohling et al. 1996. J Bacteriol. 178: 871-880).

When the biocatalyst is a eukaryote, the supply of acetyl-CoA, preferably in the cytosolic compartment in the host cell, may be increased by overexpressing homologous and/or heterologous genes encoding enzymes that catalyze the conversion of a precursor molecule to acetyl-CoA. The precursor molecule may for example be acetate, as described by Shiba et al., Metabolic Engineering, 2007, 9: 160-8.

In an advantageous method of the invention, in particular a method for preparing 6-ACA, adipic acid or an intermediate compound for 6-ACA or adipic acid, use is made of a whole cell biotransformation of the substrate for 6-ACA, adipic acid or an intermediate thereof, comprising the use of a micro-organism wherein one or more enzymes catalysing any of the above reactions are produced, and a carbon source for the micro-organism.

The carbon source may in particular contain at least one compound selected from the group of monohydric alcohols, polyhydric alcohols, carboxylic acids, carbon dioxide, fatty acids, glycerides, including mixtures comprising any of said compounds. Suitable monohydric alcohols include methanol and ethanol, Suitable polyols include glycerol and carbohydrates. Suitable fatty acids or glycerides may in particular be provided in the form of an edible oil, preferably of plant origin.

In particular a carbohydrate may be used, because usually carbohydrates can be obtained in large amounts from a biologically renewable source, such as an agricultural product, for instance an agricultural waste-material. Preferably a carbohydrate is used selected from the group of glucose, fructose, sucrose, lactose, saccharose, starch, cellulose and hemi-cellulose. Particularly preferred are glucose, oligosaccharides comprising glucose and polysaccharides comprising glucose.

In a specific method of the invention, the method is a fermentation method. Such method may in particular, comprise contacting cells comprising a biocatalyst—optionally a host cell as described herein—with a fermentable carbon source, wherein the carbon source contains any of said compounds which are to be converted into the compound to be prepared or wherein the cells prepare the compound to be converted into the compound to be prepared from the carbon source.

A cell comprising one or more enzymes for catalysing a reaction step in a method of the invention can be constructed using molecular biological techniques, which are known in the art per se. For instance, if one or more biocatalysts are to be produced in a heterologous system, such techniques can be used to provide a vector which comprises one or more genes encoding one or more of said biocatalysts. A vector comprising one or more of such genes can comprise one or more regulatory elements, e.g. one or more promoters, which may be operably linked to a gene encoding an biocatalyst.

As used herein, the term "operably linked" refers to a linkage of polynucleotide elements (or coding sequences or nucleic acid sequence) in a functional relationship. A nucleic acid sequence is "operably linked" when it is placed into a functional relationship with another nucleic acid sequence. For instance, a promoter or enhancer is operably linked to a coding sequence if it affects the transcription of the coding sequence.

As used herein, the term "promoter" refers to a nucleic acid fragment that functions to control the transcription of one or more genes, located upstream with respect to the direction of transcription of the transcription initiation site of the gene, and is structurally identified by the presence of a binding site for DNA-dependent RNA polymerase, transcription initiation sites and any other DNA sequences, including, but not limited to transcription factor binding sites, repressor and activator protein binding sites, and any other sequences of nucleotides known to one of skilled in the art to act directly or indirectly to regulate the amount of transcription from the promoter. A "constitutive" promoter is a promoter that is active under most environmental and developmental conditions. An "inducible" promoter is a promoter that is active under environmental or developmental regulation. The term "homologous" when used to indicate the relation between a given (recombinant) nucleic acid or polypeptide molecule and a given host organism or host cell, is understood to mean that in nature the nucleic acid or polypeptide molecule is produced by a host cell or organisms of the same species, preferably of the same variety or strain.

The promoter that could be used to achieve the expression of the nucleotide sequences coding for an enzyme for use in a method of the invention such as described herein above may be native to the nucleotide sequence coding for the enzyme to be expressed, or may be heterologous to the nucleotide sequence (coding sequence) to which it is operably linked. Preferably, the promoter is homologous, i.e. endogenous to the host cell.

If a heterologous promoter (to the nucleotide sequence encoding for the enzyme of interest) is used, the heterologous promoter is preferably capable of producing a higher steady state level of the transcript comprising the coding sequence (or is capable of producing more transcript molecules, i.e. mRNA molecules, per unit of time) than is the promoter that is native to the coding sequence. Suitable promoters in this context include both constitutive and inducible natural promoters as well as engineered promoters, which are well known to the person skilled in the art.

A "strong constitutive promoter" is one which causes mRNAs to be initiated at high frequency compared to a native host cell. Examples of such strong constitutive promoters in Gram-positive micro-organisms include SP01-26, SP01-15, veg, pyc (pyruvate carboxylase promoter), and amyE.

Examples of inducible promoters in Gram-positive micro-organisms include, the IPTG inducible Pspac promoter, the xylose inducible PxylA promoter.

Examples of constitutive and inducible promoters in Gram-negative microorganisms include, tac, tet, trp-tet, lpp, lac, lpp-lac, lacIq, T7, T5, T3, gal, trc, ara ($P_{BAD}$), SP6, $\lambda\text{-}P_R$, and $\lambda\text{-}P_L$.

The term "heterologous" when used with respect to a nucleic acid (DNA or RNA) or protein refers to a nucleic acid or protein that does not occur naturally as part of the organism, cell, genome or DNA or RNA sequence in which it is present, or that is found in a cell or location or locations in the genome or DNA or RNA sequence that differ from that in which it is found in nature. Heterologous nucleic acids or proteins are not endogenous to the cell into which it is introduced, but has been obtained from another cell or synthetically or recombinantly produced. Generally, though not necessarily, such nucleic acids encode proteins that are not normally produced by the cell in which the DNA is transcribed or expressed. Similarly exogenous RNA encodes for proteins not normally expressed in the cell in which the exogenous RNA is present. Heterologous nucleic acids and proteins may also be referred to as foreign nucleic acids or proteins. Any nucleic acid or protein that one of skill in the art would recognize as heterologous or foreign to the cell in which it is expressed is herein encompassed by the term heterologous nucleic acid or protein.

A method according to the invention may be carried out using an organism, which may be a host organism, in particular a host micro-organism, or a wild-type microorganism. Accordingly, the invention also relates to a novel (host) cell, which may be a microorganism, comprising a biocatalyst capable of catalysing at least one reaction step in a method of the invention, preferably the cell is capable of producing an enzyme or a plurality of enzymes, whereby two or more reaction steps in a method of the invention are catalysed. The invention also relates to a novel vector comprising one or more genes encoding for one or more enzymes capable of catalysing at least one reaction step in a method of the invention.

In an embodiment, a cell or a vector is provided comprising a nucleic acid sequence, which may be recombinant, encoding an enzyme with 5-carboxy-2-pentenoyl ester or thioester hydrogenase activity, in particular 5-carboxy-2-pentenoyl hydrogenase activity.

Preferably, the cell further comprises at least one (recombinant vector comprising a) nucleic acid sequence encoding an enzyme selected from the group of enzymes capable of catalysing the conversion of an adipyl ester or thioester, in particular adipyl-Coa, into 5-FVA and enzymes catalysing the conversion of adipyl ester or thioester, in particular adipyl-Coa, into adipic acid.

In particular in an embodiment wherein the cell comprises an enzyme capable of catalysing the conversion of an adipyl ester or thioester into 5-FVA, the cell may advantageously comprise (a recombinant vector comprising) a nucleic acid sequence encoding an enzyme capable of catalysing the conversion of 5-FVA into 6-ACA. Such enzyme may in particular be an enzyme with 5-FVA aminotransferase activity.

In addition or alternatively, the (host) cell respectively vector comprises at least one of the following nucleic acid sequences:
- a nucleic acid sequence encoding an enzyme capable of catalysing the formation of 3-oxoadipyl ester or thioester by reacting a succinyl ester or thioester with an acetate ester or thioester;
- a nucleic acid sequence encoding an enzyme capable of catalysing the formation of a 3-hydroxyadipyl ester or thioester from a 3-oxoadipyl ester or thioester;
- a nucleic acid sequence encoding an enzyme capable of catalysing the formation of a 5-carboxy-2-pentenoyl ester or thioester from a 3-hydroxyadipyl ester or thioester;
- a nucleic acid sequence encoding an enzyme capable of catalysing the formation of a an adipyl ester or thioester from 5-carboxy-2-pentenoyl ester or thioester.

One or more suitable genes may in particular be selected amongst genes encoding an enzyme as mentioned herein above, more in particular amongst genes encoding an enzyme according to any of the Sequence ID's 1-67, 94, 96, 98, 100, 102, 103, 105, 107, 109, 111, 113, 115, 116 or a homologue thereof.

The host cell may be a prokaryote or an eukaryote. In particular the host cell can be selected from bacteria, archaea, yeasts, fungi, protists, plants and animals (including human).

In particular a host cell according to the invention may be selected from the group of genera consisting of *Aspergillus, Bacillus, Corynebacterium, Escherichia, Saccharomyces, Pseudomonas, Gluconobacter, Penicillium, Pichia*. In particular a host strain and, thus, a host cell may be selected from the group of *E. coli, Bacillus subtilis, Bacillus amyloliquefaciens, Corynebacterium glutamicum, Aspergillus niger, Penicillium chrysogenum, Pichia pastoris, Saccharomyces cerevisiae*.

Host cells able to produce short chain fatty acids such as succinate and/or acetate and/or esters or thio-esters thereof may be advantageous. Organisms capable thereof are generally present in the rumen of ruminants. In particular an organism able of coproduction of succinate and acetate or esters or thioesters thereof is preferred.

The microorganism may be recombinant or wild type. In particular, microorganisms capable of producing succinate include *E. coli, Actinobacillus* (in particular *A. succinogenes*), *Mannheimia* (in particular *M. succiniciproducens*), *Saccharomyces cerevisiae, Aspergillus* (in particular *A. niger*), *Penicillium* (in particular *P. chrysogenum* and *P. simplicissimum*) and other organisms mentioned in Kaemwich Jantama, M. J. Haupt, Spyros A. Svoronos, Xueli Zhang, J. C. Moore, K. T. Shanmugam, L. O. Ingram. Biotechnology and Bioengineering (2007) 99, 5: 1140-1153.

In particular, microorganisms capable of producing acetate include Enterobacteriaceae (in particular *E. coli, Salmonella*, and *Shigella*), acetic acid bacteria (Includes *Acetobacter* (in particular *Acetobacter aceti*), *Gluconobacter* (in particular *Gluconobacter oxidans*), *Acidomonas, Gluconacetobacter, Asaia, Kozakia, Swaminathania, Saccharibacter, Neoasaia, Granulibacter, Clostridium* (in particular *C. aceticum, C. thermoaceticum, C. thermoautotrophicum, C. formicoaceticum, C. kluyveri, C. propionicum*), *Megasphaera* (in particular *M. elsdenii*), *Acetobacterium* (In particular *A. woodii* and *A. wieringae*), *Lactobacillus* (in particular *L. plantarum, L. brevum*), *Bifidobacterium* (In particular *B. bifidum*), and *Leuconostoc*.

The invention further relates to a novel polypeptide, respectively to a nucleotide sequence encoding such polypeptide. In particular, the invention further relates to a polypeptide comprising an amino acid sequence according to any of the Sequence ID's 57, 68-72, 79, 85 and homologues thereof. In particular, the invention further relates to a polynucleotide encoding a polypeptide comprising an amino acid sequence according to any of the Sequence ID's 57, 68-72, 79, 85 and homologues thereof.

Next, the invention is illustrated by the following examples.

EXAMPLES

Example 1: General Methods

Molecular and Genetic Techniques

Standard genetic and molecular biology techniques are generally known in the art and have been previously described (Maniatis et al. 1982 "Molecular cloning: a laboratory manual". Cold Spring Harbor Laboratory, Cold Spring Harbor, N.Y.; Miller 1972 "Experiments in molecular genetics", Cold Spring Harbor Laboratory, Cold Spring Harbor; Sambrook and Russell 2001 "Molecular cloning: a laboratory manual" (3rd edition), Cold Spring Harbor Laboratory, Cold Spring Harbor Laboratory Press; F. Ausubel et al, eds., "Current protocols in molecular biology", Green Publishing and Wiley Interscience, New York 1987).

Plasmids and Strains pBAD/Myc-His C and pET21d were obtained from Invitrogen (Carlsbad, Calif., USA) and EMD Biosciences (Darmstadt, Germany) respectively. pF113 (a derivative of pJF119EH (Fürste, J. P., W. Pansegrau, R. Frank, H. Blocker, P. Scholz, M. Bagdasarian, and E. Lanka. 1986. Molecular cloning of the plasmid RP4 primase region in a multi-host-range tacP expression vector. Gene 48:119-131) which contains two NotI sites at positions 515 and 5176 respectively with the tac promoter being the start of the numbering), pACYC-tac (Krämer, M. (2000). Untersuchungen zum Einfluss erhöhter Bereitstellung von Erythrose-4-Phosphat and Phosphoenolpyruvat auf den Kohlenstofffluss in den Aromatenbiosyntheseweg von *Escherichia coli*. Berichte des Forschungszentrums Jülich, 3824. ISSN 0944-2952 (PhD Thesis, University of Düsseldorf) and pMS470 (Balzer, D.; Ziegelin, G.; Pansegrau, W.; Kruft, V.; Lanka, E. *Nucleic Acids Research* 1992, 20(8), 1851-1858) have been described previously. *E. coli* TOP10 (Invitrogen, Carlsbad, Calif., USA) was used for all cloning procedures. *E. coli* strains Top10 (Invitrogen, Carlsbad, Calif., USA), Rv308 (ATCC31608), Rv308ΔaraB, and BL21 A1 (Invitrogen, Carlsbad, Calif., USA) were used for protein expression.

Figure 2:
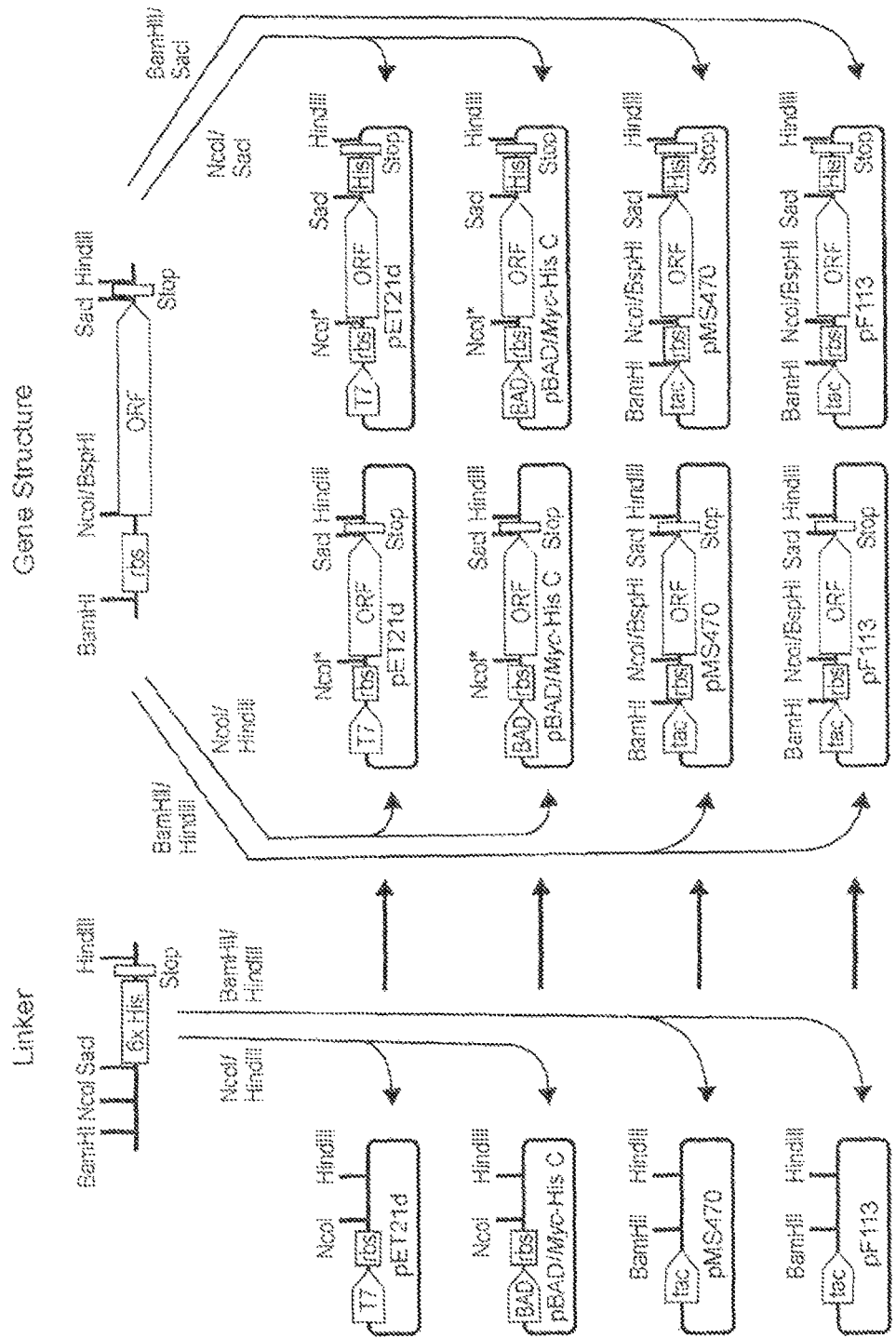
FIG. 2. Overall cloning strategy. Only relevant features and restriction sites are shown.

All vectors were adapted by inserting a common linker to allow an identical cloning strategy. The adaptation and general cloning scheme is shown in FIG. 2.

Media

2×TY medium (16 g/l tryptopeptone, 10 g/l yeast extract, 5 g/l NaCl) was used for growth of *E. coli*. Antibiotics (100 µg/ml ampicillin) were supplemented to maintain plasmids. For induction of gene expression arabinose (for pBAD derivatives), IPTG (for pMS470 and pF113 derivatives), and a combination of arabinose and IPTG (for pET21d derivatives in *E. coli* BL21-A1) were used at 0.005-0.2% (arabinose) and 0.1-0.5 mM (IPTG) final concentrations.

Identification of Plasmids

Plasmids carrying the different genes were identified by genetic, biochemical, and/or phenotypic means generally known in the art, such as resistance of transformants to antibiotics, PCR diagnostic analysis of transformant or purification of plasmid DNA, restriction analysis of the purified plasmid DNA or DNA sequence analysis.

HPLC-MS Analysis Method for the Determination of CoA-Derivatives

Adipyl-Coa and 6-carboxy-2,3-ene hexanoyl-CoA concentrations were determined by LC-MS. An Agilent SB-C18 2.1*50 mm column was used for separation with acetonitrile/water buffered with 750 mg/l octylammonium acetate (pH=7.5) as mobile phase. Flow was 300 µl/min and elution was done with a gradient (Start: 70% water, decrease to 58% in 3 min, step to 45%, further decrease to 20% in 1.5 min, followed by reequilibration of the column, in such a way that the total runtime was 7 min). A LTQ orbitrap was used in electrospray negative ionization mode, scanning from m/z 765-900. adipyl-Coa and 6-carboxy-2,3-ene hexanoyl-CoA eluted at 2.25 min and 2.5 min respectively. The selectivity of the method was enhanced by observing the accurate protonated molecules of the compounds requested (adipyl-Coa: 894.15123-894.16017, 6-carboxy-2,3-ene hexanoyl-CoA: 892.13437-892.14329). To determine concentrations a standard curve of synthetically prepared compounds was run to calculate a response factor for the respective ions. This was used to calculate the concentrations in unknown samples.

Adipate can be detected and quantified as described in Kippenberger, M.; Winterhalter, R.; Moortgat, G. K. *Anal. Bioanal. Chem.* 2008, 392(7-8), 1459-1470.

Example 2: 6-carboxy-2,3-ene-hexanoyl-CoA Reductase ACTIVITY Determination

Expression Constructs

Putative 6-carboxy-2,3-ene-hexanoyl-CoA reductases were selected from databases (Table 1).

Target genes encoding the selected proteins were codon pair optimized (using methodology described in WO08000632) and constructed synthetically (Geneart, Regensburg, Germany). Before optimization, targeting sequences (e.g secretion signals or peroxisomal/mitochondrial targeting sequences) were removed from the amino acid sequence. Such targeting sequences can be identified by bioinformatics tools well known in the art, such as described in Emanuelsson et al. 2007. Nature protocols, 2: 953-971). In the optimization procedure internal restriction sites were avoided and common restriction sites were introduced at the start and stop to allow cloning according to the strategy shown in FIG. 2. These modifications may result in minor changes to the respective protein sequences which are contemplated to not alter the properties of the respective protein in any way. Each ORF was preceded by a consensus ribosomal binding site and leader sequence to drive translation in pF113, pMS470 and pET21d. In pBAD translation initiation signals are provided by the vector. The target genes 'Adi4', Adi5', 'Adi8' and 'Adi 9' were cloned into all four plasmids both with and without read-through to the C-terminal His-tag provided by the linker sequence.

Protein Expression in *E. coli*

Starter cultures were grown overnight in 96-well plates with 200 µl medium/well. 40-160 µl were transferred to fresh 24-deep-well plates with 4 ml media. For pBAD constructs in *E. coli* TOP10 or *E. coli* Rv308ΔaraB this medium directly contained 0.005% arabinose for inductions. Plates were incubated on an orbital shaker (Infors, 550 rpm) at 25° C. After 4-6 h inducers were added (0.5 mM IPTG for pF113 and pMS470 in *E. coli* Rv308, *E. coli* BL21 or *E. coli* TOP10; 0.5 mM IPTG and 0.2% arabinose for pET21d in *E. coli* BL21A1) and plates were incubated for another 4-48 h until cells were collected by centrifugation.

Preparation of Cell Free Extract and His-Tag Purification

Cells from small scales growth (see previous paragraph) were harvested by centrifugation and the supernatant was discarded. The cell pellets formed during centrifugation were frozen at −20° C. for at least 16 h and then thawed on ice. 2 ml of freshly prepared lysis buffer (50 mM potassium phosphate pH7.5, 0.1 mg/ml DNAse I (Roche, Almere, NL), 2 mg/ml Lysozyme, 0.5 mM MgSO$_4$, 1 mM dithiothreitol, and protease inhibitors (Complete Mini EDTA-free Tablets™, Roche, Almere, NL, were used according to the manufacturers specification) were added to each well and cells were resuspended by vigorously vortexing the plate for 2-5 min. To achieve lysis, the plate was incubated at room temperature for 30 min. To remove cell debris, the plate was centrifuged at 4° C. and 6000 g for 20 min. The supernatant was transferred to a fresh plate and kept on ice until further use. For purification of His-tagged proteins His Multitrap HP filter plates (GE Healthcare bioscience AB, Uppsala, Sweden) were used according to the manufacturer's instructions.

Synthesis of Substrates

Substrate (J. R. Stern, A. del Campillo, J. Biol. Chem., 1956, 985. A. K. Das, M. D. Uhler, A. K. Hajra, J. Biol. Chem., 2000, 24333. H. Oku, N. Futamori, K. Masuda, Y. Shimabukuro, T. Omine, H. Iwasaki, Biosc. Biotech. Biochem., 2003, 2107. Elvidge et. al, J. Chem. Soc., 1953, 1793. F. Liu, H-Y. Zha, Z-J. Yao, J. Org. Chem., 2003, 6679-6684) and product (WO2004/106347) of the desired biochemical reaction and were synthesized by Syncom (Groningen, NL) according to published procedures.

Enzymatic Enoyl-CoA Assay

A reaction mixture was prepared comprising 50 mM potassium buffer (pH7.5), 0.7 mM NADH and NADPH each, and approximately 20 µM of the substrate 6-carboxylic 2,3-ene hexanoyl-CoA. 190 µl of the reaction mixture were dispensed into each well of 96-wellplates. The same way 10 µl of cell free extract prepared from the respective strain carrying the empty vector was used in control reactions. To start the reaction, 10 µl of the cell free extracts or purified protein were added, to each of the wells. Reaction mixtures were incubated at room temperature (20-25 C) for 15 min to 24 h with online monitoring of UV absorption at 340 nm. At the end reactions were stopped by adding an equal volume of MeOH and samples were centrifuged. Supernatant was transferred to a fresh plate and stored at −80 C until further analysis by HPLC-MS. adipyl-Coa was found as shown in Table 1.

TABLE 1 adipyl-CoA (amount is indicated by relative peak-area) found in the enzymatic assay.

| Biocatalyst | SeqID # | Modifications[1] | adipyl-CoA[2] |
|---|---|---|---|
| Adi4 | 63 | N-terminus 134 AA removed | 3266 |
| Adi5 | 96 | | 196031 |
| Adi8 | 60 | N-terminus 22 AA removed | 581859 |
| Adi9 | 100 | N-terminus 12 AA removed | 117077 |
| — (vector control) | | | 0 |

[1]If the resulting polypeptide after modification does not start with a methionine at the N-terminus, the resulting polypeptide is further modified by adding a methionine at the N-terminus.
[2]Results shown were obtained with E. coli BL21 containing the adi gene cloned in pMS470 after 20 h incubation. Positive results were also obtained with other expression vectors and host strains (such as pET21d in E. coli BL21-A1, pBAD/Myc-His C in E. coli Rv308 and pF113 in E. coli BL21) and different incubation periods (e.g. 2 h).

Example 3: Production of Adipate by a Heterologous Microorganism

Construction of an Adipate Biosynthetic Pathway

Figure 3:
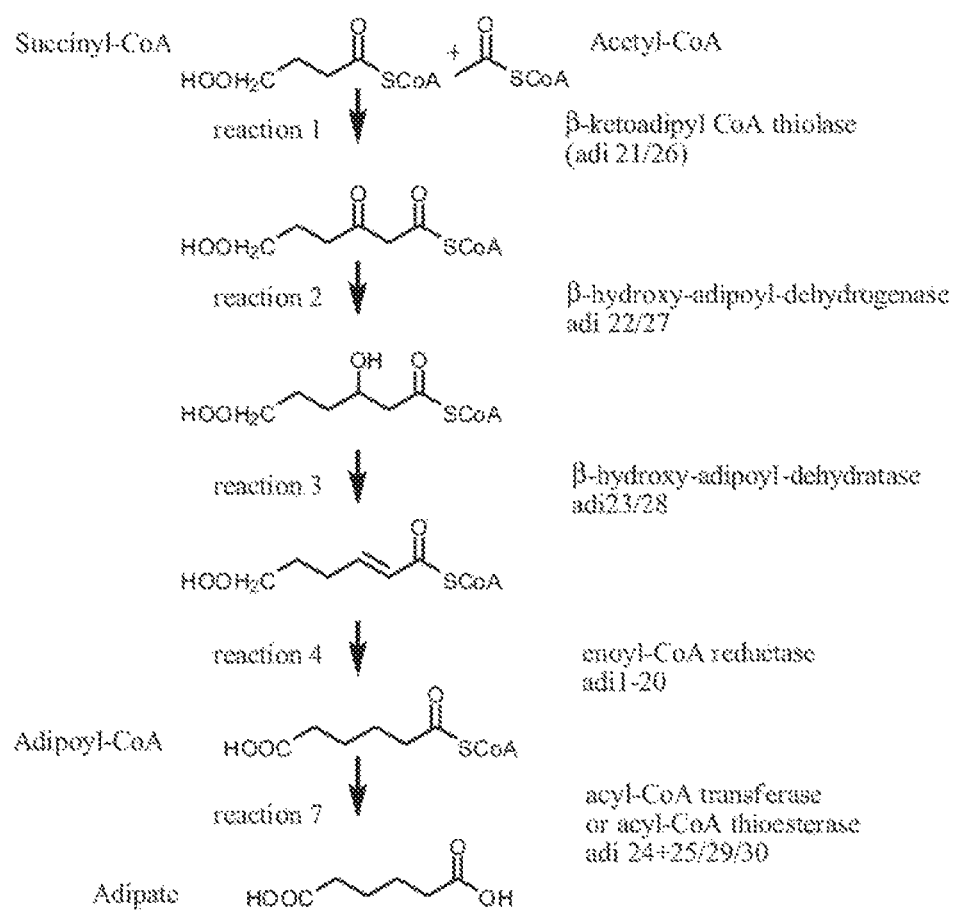
FIG. 3. Adipate biosynthetic pathway.
Figure 4:
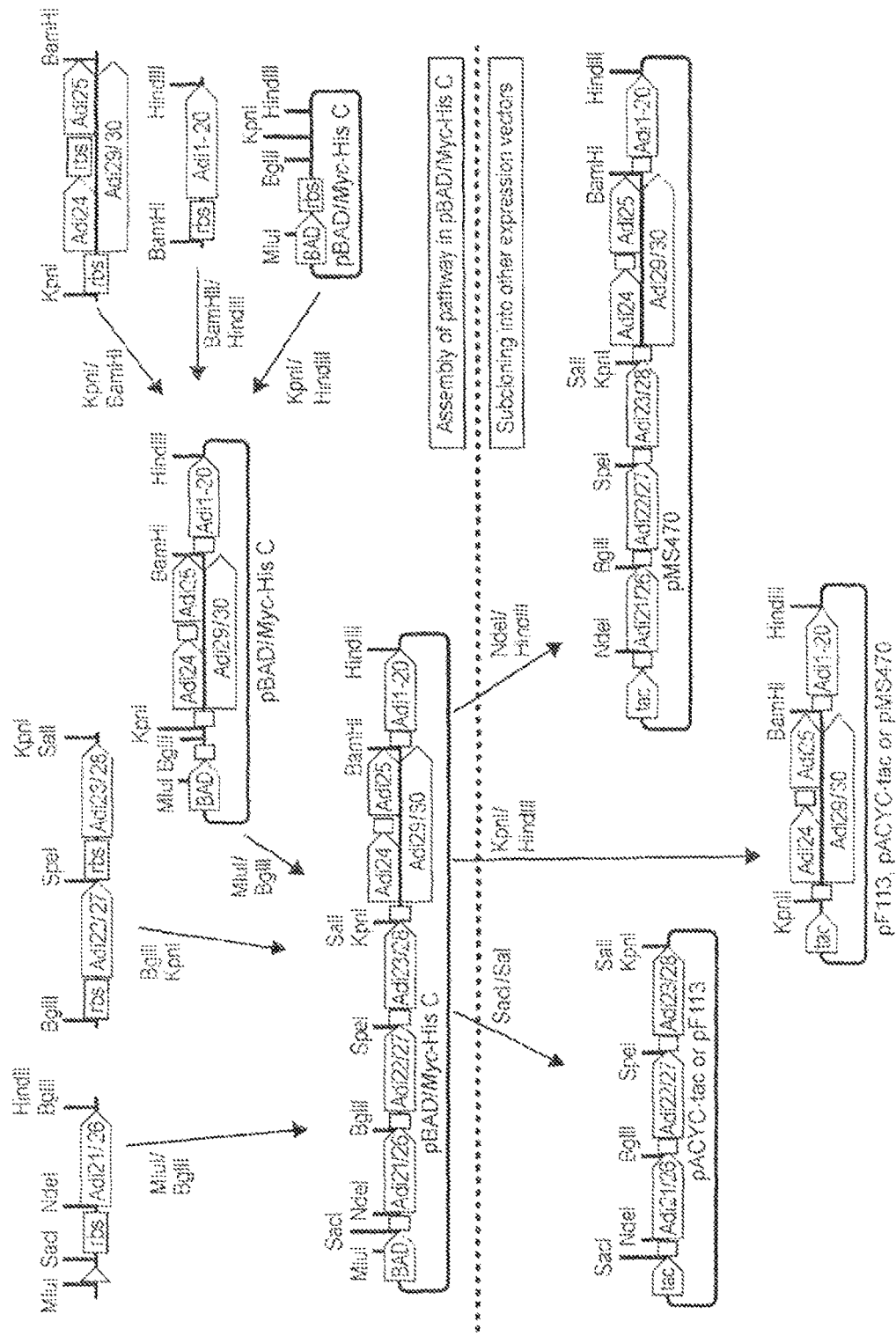
FIG. 4. Cloning strategy for assembly of adipate pathway.

A synthetic pathway was designed consisting of the enzymatic activities shown in FIG. 3. Enzymes encoding these activities were identified in databases. Target genes encoding these enzymes were codon pair optimized and constructed synthetically (Geneart, Regensburg, Germany). In the optimization procedure internal restriction sites, undesired targeting sequences (e.g secretion signals or peroxisomal targeting sequences) were removed and restriction sites were introduced at the start and stop to allow assembly of the pathway in expression vectors according to FIG. 4. These modifications may result in minor changes to the protein sequence which are contemplated to not alter the properties of the respective protein in any way. Each ORF was preceded by a consensus ribosomal binding site and leader sequence to drive translation.

For reactions 1, 2, and 3 the combinations of adi21+22+23 or adi26+27+28 were used. For reaction 7 adi29, adi30 or a combination of adi24+25 were used. For reaction 4 adi1-20 can be used with adi8, adi6, adi13+12.

TABLE 2

SeqIDs of the different Adi proteins.

| Protein | Seq ID # |
|---|---|
| Adi21 | 5 |
| Adi22 | 18 |
| Adi23 | 33 |
| Adi24 | 119 |
| Adi25 | 120 |
| Adi26 | 3 |
| Adi27 | 29 |
| Adi28 | 14 |
| Adi29 | 116 |
| Adi30 | 117 |

Construction of an Adipate Producing E. coli Strain

To construct adipate producing E. coli strains plasmids encoding a complete adipate pathway were transformed into the appropriate host strains for expression of the cloned genes. pMS470 constructs containing full pathways, were transformed into E. coli BL21, TOP10 and Rv308. pBAD/Myc-His C constructs were transformed into E. coli TOP10 and Rv308ΔaraB. Constructs in pF113 or pACYC-tac were transformed together with compatible pF113, pACYC-tac or pMS470 constructs in a way that the final strain contained a complete adipate pathway. These plasmids were co-transformed to E. coli TOP10, BL21, and Rv308.

Production of Adipate

For production of adipate, starter cultures were grown over night in 96-well plates with 200 µl medium at 30 C. 50 µl were transferred to a fresh plate 24-well plate with 4 ml medium and grown for 4-6 h at 25 C and then inducers to induce expression of the adipate pathway were added. Cultures were incubated for another 12 h-72 h at 25 C. Plates were centrifuged and samples prepared for LC-MS analysis. Supernatant was mixed 1:1 with MeOH to precipitate proteins and then directly analyzed. Metabolites from cells were extracted by resuspending the pellet in 1 ml Ethanol. The cell suspension was transferred to a tube with a screw top and heated in a boiling water bath for 3 min. After centrifugation the supernatant was transferred to a fresh tube and evaporated in a speed-vac. Dry samples were resuspended in 100 µl mobile phase prior to analysis.

Example 4: Preparation of 5-FVA from Adipyl-CoA

HPLC-MS Analysis Method for the Determination of 5-FVA

5-FVA was detected by selective reaction monitoring (SRM)-MS, measuring the transition m/z 129→83. Concentrations for 5-FVA were calculated by measuring the peak area of the 5-FVA peak eluting at approximately 6 min. Calibration was performed by using an external standard procedure. All the LC-MS experiments were performed on an Agilent 1200 LC system, consisting of a quaternary pump, autosampler and column oven, coupled with an Agilent 6410 QQQ triple quadrupole MS.

LC Conditions:
Column: 50×4.6 mm Nucleosil C18, 5 µm (Machery & Nagel) pre column coupled to a 250×4.6 mm id. Prevail C18, 5 µm (Alltech)
Column temperature: room temperature
Eluent: A: water containing 0.1% formic acid
B: acetonitrile containing 0.1% formic acid

| Gradient: | time (min) | % eluent B |
|---|---|---|
| | 0 | 10 |
| | 6 | 50 |
| | 6.1 | 10 |
| | 11 | 10 |

Flow: 1.2 ml/min, before entering the MS the flow is split 1:3
Injection volume: 2 µl
MS Conditions:
Ionisation: negative ion electrospray
 source conditions: ionspray voltage: 5 kV
 temperature: 350° C.
 fragmentor voltage and collision energy optimized
Scan mode: selective reaction mode: transition m/z 129→83
 Expression Constructs
 Putative adipyl-CoA-reductases were selected (SeqID 74, 75, 77, 79, 80, 139-148). Expression constructs are designed and prepared in the same way as described before in example 2 using pBAD/Myc-His C and pET21d.
 Protein Expression, Extraction and Purification
 All steps are carried out as described in example 2.
 Enzymatic Adipyl-CoA Reductase Assay
 A reaction mixture is prepared comprising 50 mM potassium buffer (pH7.5), 0.7 mM NADH and NADPH each, and 10 µM-10 mM of the substrate adipyl-CoA. 190 µl of the reaction mixture are dispensed into each well of 96-well-plates. Adipyl-CoA was prepared as described in example 2. To start the reaction, 10 µl of the cell free extracts or purified protein are added to each of the wells. The same way 10 µl of cell free extract prepared from the respective strain carrying the empty vector is used in control reactions. Reaction mixtures are incubated at room temperature (20-25 C) for 15 min-24 h with online monitoring of UV absorption at 340 nm. At the end reactions are stopped by adding an equal volume of MeOH and samples are centrifuged. Supernatant is transferred to a fresh plate and stored at −80 C until detection of 5-FVA by HPLC-MS. Measurement of 5-FVA demonstrates adipyl-CoA reductase activity of the selected enzymes.

Example 5: The Preparation of 6-ACA from 5-FVA

HPLC-MS Analysis for the Determination of 6-ACA
Calibration:
 The calibration was performed by an external calibration line of 6-ACA (m/z 132→m/z 114, Rt 7.5 min). All the LC-MS experiments were performed on an Agilent 1100, equipped with a quaternary pump, degasser, autosampler, column oven, and a single-quadrupole MS (Agilent, Waldbronn, Germany). The LC-MS conditions were:
Column: 50*4 Nucleosil (Mancherey-Nagel)+250×4.6 Prevail C18 (Alltech), both at room temperature (RT)
Eluent: A=0.1 (v/v) formic acid in ultrapure water
B=Acetonitrile (pa, Merck)
Flow: 1.0 ml/min, before entering the MS the flow was split 1:3

Gradient: The gradient was started at t=0 minutes with 100% (v/v) A, remaining for 15 minutes and changed within 15 minutes to 80% (v/v) B (t=30 minutes). From 30 to 31 minutes the gradient was kept at constant at 80% (v/v) B.
Injection volume: 5 µl
MS detection: ESI(+)-MS
 The electrospray ionization (ESI) was run in the positive scan mode with the following conditions; m/z 50-500, 50 V fragmentor, 0.1 m/z step size, 350° C. drying gas temperature, 10 L $N_2$/min drying gas, 50 psig nebuliser pressure and 2.5 kV capillary voltage.
Cloning of Target Genes
Design of Expression Constructs
 attB sites were added to all genes upstream of the ribosomal binding site and start codon and downstream of the stop codon to facilitate cloning using the Gateway technology (Invitrogen, Carlsbad, Calif., USA).
Gene Synthesis and Construction of Plasmids
 Synthetic genes were obtained from DNA2.0 and codon optimised for expression in *E. coli* according to standard procedures of DNA2.0. The aminotransferase genes from *Vibrio fluvialis* JS17 [SEQ ID No. 86] and *Bacillus weihenstephanensis* KBAB4 [SEQ ID No. 89] encoding the amino acid sequences of the *V. fluvialis* JS17 ω-aminotransferase [SEQ ID No. 82] and the *B. weihenstephanensis* KBAB4 aminotransferase (ZP_01186960) [SEQ ID No. 83], respectively, were codon optimised and the resulting sequences [SEQ ID No. 88] and [SEQ ID No. 91] were obtained by DNA synthesis.
 Cells provided with said genes are referred to herein below as *E. coli* TOP10/pBAD-Vfl_AT and *E. coli* TOP10/pBAD-Bwe_AT respectively
Cloning by PCR
 Various genes encoding a biocatalyst were amplified from genomic DNA by PCR using PCR Supermix High Fidelity (Invitrogen) according to the manufacturer's specifications
 PCR reactions were analysed by agarose gel electrophoresis and PCR products of the correct size were eluted from the gel using the QIAquick PCR purification kit (Qiagen, Hilden, Germany). Purified PCR products were cloned into pBAD/Myc-His-DEST expression vectors using the Gateway technology (Invitrogen) via the introduced attB sites and pDONR-zeo (Invitrogen) as entry vector as described in the manufacturer's protocols. The sequence of genes cloned by PCR was verified by DNA sequencing. This way the expression vectors, pBAD-Bsu_gi16077991_AT (comprising a gene as represented by Sequence ID 133, encoding peptide represented by Sequence ID 134), pBAD-Pae_gi9946143_AT (using primers as identified in sequence ID's 130 and 131), pBAD-Pae_gi9951072_AT (comprising a gene as represented by Sequence ID 135, encoding peptide represented by Sequence ID 136), pBAD-Pae_gi9951630_AT (comprising a gene as represented by Sequence ID 137, encoding peptide represented by Sequence ID 138) were obtained. The corresponding expression strains were obtained by transformation of chemically competent *E. coli* TOP10 (Invitrogen) with the pBAD constructs.
Enzymatic Reactions for Conversion of 5-Formylpentanoic Acid to 6-ACA
 Unless specified otherwise, a reaction mixture was prepared comprising 10 mM 5-formylpentanoic acid, 20 mM racemic α-methylbenzylamine, and 200 µM□ pyridoxal 5'-phosphate in 50 mM potassium phosphate buffer, pH 7.0. 100 µl of the reaction mixture were dispensed into each well of the well plates. To start the reaction, 20 µl of the cell free extracts were added, to each of the wells. Reaction mixtures were incubated on a shaker at 37° C. for 24 h. Furthermore, a chemical blank mixture (without cell free extract) and a biological blank (*E. coli* TOP10 with pBAD/Myc-His C) were incubated under the same conditions. Samples were analysed by HPLC-MS. The results are summarised in the following table.

TABLE 3

6-ACA formation from 5-FVA in the presence of aminotransferases

| Biocatalyst | 6-ACA concentration [mg/kg] |
|---|---|
| *E. coli* TOP10/pBAD-Vfl_AT | 43* |
| *E. coli* TOP10/pBAD-Pae_pBAD-Pae_gi_9946143 | 930 |
| *E. coli* TOP10/pBAD-Pae_AT | 25* |
| *E. coli* TOP10/pBAD-Bwe_AT | 24* |
| *E. coli* TOP10/pBAD-Bsu_gi16077991_AT | 288 |
| *E. coli* TOP10/pBAD-Pae_gi9951072_AT | 1087 |
| *E. coli* TOP10/pBAD-Pae_gi9951630_AT | 92 |
| *E. coli* TOP10 with pBAD/Myc-His C (biological blank) | 0.6 |
| None (chemical blank) | not detectable |

*method differed in that 10 μl cell free extract was used instead of 20 μl, the pyridoxal-5'-phosphate concentration was 50 μM instead of 200 μM and the reaction mixture volume in the wells was 190 μl instead of 100 μl It is shown that 6-ACA is formed from 5-FVA in the presence of an aminotransferase, and that *E. coli* is capable of catalysing this formation.

The invention claimed is:

1. A method for preparing an adipate ester or adipate thioester, comprising converting a 2,3-dehydroadipate ester or 2,3-dehydroadipate thioester into the adipate ester or thioester in the presence of a biocatalyst, wherein the biocatalyst comprises an enzyme, wherein said enzyme comprises the amino acid sequence of SEQ ID NO:60 or an amino acid sequence that has at least 90% sequence identity to SEQ ID NO:60, and wherein said enzyme catalyzes the conversion of 2,3-dehydroadipate ester or 2,3-dehydroadipate thioester into the adipate ester or thioester.

2. The method of claim 1, wherein said enzyme comprises an amino acid sequence that has at least 93% sequence identity to residues 23-386 of SEQ ID NO:60.

3. The method of claim 1, wherein said enzyme comprises an amino acid sequence that has at least 94% sequence identity to residues 23-386 of SEQ ID NO:60.

4. The method of claim 1, wherein said enzyme comprises an amino acid sequence that has at least 95% sequence identity to residues 23-386 of SEQ ID NO:60.

5. The method of claim 1, wherein said enzyme comprises an amino acid sequence that has at least 98% sequence identity to residues 23-386 of SEQ ID NO:60.

6. The method of claim 1, wherein said enzyme comprises an amino acid sequence that has at least 99% sequence identity to residues 23-386 of SEQ ID NO:60.

7. The method according to claim 1, wherein the enzyme comprises the amino acid sequence of SEQ ID NO:60.

8. The method according to claim 1, wherein said biocatalyst is a host cell comprising said enzyme.

9. The method according to claim 8, wherein said host cell is a microorganism.

10. The method according to claim 9, wherein said microorganism is a bacterium, yeast or fungi.

11. The method according to claim 9, wherein said microorganism is selected from the group consisting of *Escherichia coli, Bacillus subtilis, Bacillus amyloliquefaciens, Corynebacterium glutamicum, Aspergillus niger, Penicillium chrysogenum, Pichia pastoris*, and *Saccharomyces cerevisiae*.

12. The method according to claim 1, wherein said 2,3-dehydroadipate ester or 2,3-dehydroadipate thioester is prepared by converting a 3-hydroxyadipate ester or 3-hydroxyadipate thioester to 2,3-dehydroadipate ester or 2,3-dehydroxyadipate thioester, respectively.

13. The method according to claim 12, wherein said 3-hydroxyadipate ester or 3-hydroxyadipate thioester is biocatalytically converted in the presence of a biocatalyst comprising an enzyme capable of catalysing the dehydration of a 3-hydroxyacyl ester or 3-hydroxyacyl thioester to 2-enoyl ester or 2-enoyl thioester.

14. The method according to claim 13, wherein said enzyme capable of catalysing the dehydration of a 3-hydroxyacyl ester or 3-hydroxyacyl thioester to 2-enoyl ester or 2-enoyl thioester is selected from the group consisting of an enoyl-CoA hydratase, a 3-hydroxybutyryl-CoA dehydratase and a long-chain-enoyl-CoA hydratase.

15. The method according to claim 12, wherein said 3-hydroxyadipate ester or 3-hydroxyadipate thioester is prepared by converting a 3-oxoadipate ester or 3-oxoadipate thioester to said 3-hydroxyadipate ester or 3-hydroxyadipate thioester, respectively.

16. The method according to claim 15, wherein said 3-oxoadipate ester or 3-oxoadipate thioester is biocatalytically converted in the presence of a biocatalyst comprising an enzyme capable of catalysing the reduction of a carbonyl group to an alcohol group or capable of catalysing the reduction of a 3-oxoacyl ester or 3-oxoacyl thioester to 3-hydroxyacyl ester or 3-hydroxyacyl thioester.

17. The method according to claim 16, wherein said enzyme capable of catalyzing the reduction of a carbonyl group to an alcohol group or capable of catalyzing the reduction of a 3-oxoacyl ester or 3-oxoacyl thioester to 3-hydroxyacyl ester or 3-hydroxyacyl thioester is selected from the group consisting of a 3-hydroxyacyl-CoA dehydrogenase, a 3-hydroxybutanoyl-CoA dehydrogenase, a 3-hydroxypimeloyl-CoA dehydrogenase and a long-chain-3-hydroxyacyl-CoA dehydrogenase.

18. The method according to claim 15, wherein said 3-oxoadipate ester or 3-oxoadipate thioester is prepared by converting a succinate ester or succinate thioester and an acetate ester or acetate thioester to 3-oxoadipate ester or 3-oxoadipate thioester.

19. The method according to claim 18, wherein said 3-oxoadipate ester or 3-oxoadipate thioester is biocatalytically converted in the presence of a biocatalyst comprising an enzyme capable of acetyl-group transfer.

20. The method of claim 19, wherein said enzyme capable of acetyl-group transfer is selected from the group consisting of an acetyl-CoA:acetyl-CoA C-acetyltransferase, an acyl-CoA:acetyl-CoA C-acetyltransferase and an succinyl-CoA:acetyl-CoA C-succinyltransferase.

\* \* \* \* \*